(12) United States Patent
Kim et al.

(10) Patent No.: US 10,590,078 B2
(45) Date of Patent: Mar. 17, 2020

(54) SODIUM CHANNEL BLOCKERS

(71) Applicant: Daewoong Pharmaceutical Co., Ltd., Gyeonggi-do (KR)

(72) Inventors: Ji Duck Kim, Gyeonggi-do (KR); Hyung Geun Lee, Gyeonggi-do (KR); Inwoo Kim, Seoul (KR); Sun Ah Jun, Gyeonggi-do (KR); Myunggi Jung, Gyeonggi-do (KR); Hyo Shin Kim, Incheon (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 49 days.

(21) Appl. No.: 15/526,431

(22) PCT Filed: Feb. 11, 2016

(86) PCT No.: PCT/KR2016/001395
§ 371 (c)(1),
(2) Date: May 12, 2017

(87) PCT Pub. No.: WO2016/129933
PCT Pub. Date: Aug. 18, 2016

(65) Prior Publication Data
US 2018/0297948 A1    Oct. 18, 2018

(30) Foreign Application Priority Data

Feb. 11, 2015  (KR) .................. 10-2015-0021160

(51) Int. Cl.
| | |
|---|---|
| *A61K 31/437* | (2006.01) |
| *A61K 31/416* | (2006.01) |
| *A61K 31/4439* | (2006.01) |
| *C07D 209/10* | (2006.01) |
| *C07D 231/56* | (2006.01) |
| *C07D 401/04* | (2006.01) |
| *C07D 401/06* | (2006.01) |
| *C07D 403/04* | (2006.01) |
| *C07D 403/10* | (2006.01) |
| *C07D 417/04* | (2006.01) |
| *C07D 417/12* | (2006.01) |
| *C07D 417/14* | (2006.01) |
| *C07D 471/04* | (2006.01) |
| *C07D 403/12* | (2006.01) |
| *C07D 209/30* | (2006.01) |
| *C07D 209/42* | (2006.01) |
| *C07D 401/12* | (2006.01) |

(52) U.S. Cl.
CPC ......... *C07D 209/10* (2013.01); *C07D 209/30* (2013.01); *C07D 209/42* (2013.01); *C07D 231/56* (2013.01); *C07D 401/04* (2013.01); *C07D 401/06* (2013.01); *C07D 401/12* (2013.01); *C07D 403/04* (2013.01); *C07D 403/10* (2013.01); *C07D 403/12* (2013.01); *C07D 417/04* (2013.01); *C07D 417/12* (2013.01); *C07D 417/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 7,615,569 | B2 | 11/2009 | Fulp et al. |
| 7,799,822 | B2 | 9/2010 | Martinborough et al. |
| 7,947,707 | B2 | 5/2011 | Toyoshima et al. |
| 8,779,142 | B2 | 7/2014 | Kitade et al. |
| 9,212,139 | B2 | 12/2015 | Kyle et al. |
| 9,802,899 | B2 | 10/2017 | Heilmann et al. |
| 2010/0093703 | A1 | 4/2010 | Wagner et al. |
| 2010/0197655 | A1 | 8/2010 | Beaudoin et al. |
| 2012/0010183 | A1 | 1/2012 | Bell et al. |
| 2012/0238579 | A1 | 9/2012 | Besidki et al. |
| 2014/0243324 | A1 | 8/2014 | Bissonnette et al. |

FOREIGN PATENT DOCUMENTS

| | | |
|---|---|---|
| CN | 102115476 A | 7/2011 |
| EP | 2452940 A1 | 5/2012 |
| JP | 7-286107 | 10/1995 |

(Continued)

OTHER PUBLICATIONS

Li, Xianwei. Copper-Catalyzed Aerobic C(sp2)—H Functionalization for C—N Bond Formation: Synthesis of Pyrazoles and Indazoles. Journal of Organic Chemistry. 78, 2013, 3636-3646.*

(Continued)

*Primary Examiner* — Samantha L Shterengarts

(74) *Attorney, Agent, or Firm* — Marshall, Gerstein & Borun LLP

(57) ABSTRACT

The present invention relates to a compound having a blocking effect against sodium ion channels, particularly Nav1.7, a preparation method thereof and use thereof. The compound represented by the Formula 1 or a pharmaceutically acceptable salt, hydrate, solvate or isomer thereof can be effectively used in the prevention or treatment of pains, for example, acute pain, chronic pain, pain from nervous disease, postoperative pain, migraine, arthralgia, neuropathy, nerve injury, diabetic neuropathy, neuropathic disease, epilepsy, arrhythmia, myotonia, ataxia, multiple sclerosis, irritable bowel syndrome, urinary incontinence, visceral pain, depression, erythromelalgia, paroxysmal extreme pain disorder (PEPD).

20 Claims, No Drawings

(56) References Cited

FOREIGN PATENT DOCUMENTS

| JP | 2009-504741 A | 2/2009 |
| JP | 2009/524591 A | 7/2009 |
| JP | 2010-518149 A | 5/2010 |
| JP | 2013/530180 A | 7/2013 |
| JP | 2014-502266 A | 1/2014 |
| WO | WO-2004/014913 A2 | 2/2004 |
| WO | WO-2004/031159 A1 | 4/2004 |
| WO | WO-2006/042102 A2 | 4/2006 |
| WO | WO-2007/043401 A1 | 4/2007 |
| WO | WO-2007/046747 A1 | 4/2007 |
| WO | WO-2007/145922 A2 | 12/2007 |
| WO | WO-2008/004117 A1 | 1/2008 |
| WO | WO-2008/024978 A2 | 2/2008 |
| WO | WO-2008/0126901 A1 | 10/2008 |
| WO | WO-2011/004610 A1 | 1/2011 |
| WO | WO-2011/113798 A2 | 9/2011 |
| WO | WO-2011/158108 A2 | 12/2011 |
| WO | WO-2012/068406 A2 | 5/2012 |
| WO | WO-2012/095781 A1 | 7/2012 |
| WO | WO-2013/086229 A1 | 6/2013 |
| WO | WO-2013/177224 A1 | 11/2013 |
| WO | WO-2014/053450 A1 | 4/2014 |

OTHER PUBLICATIONS

Frayne, Gregory L. Investigation of the N-arylation of various substituted indoles using microwave-assisted technology. Tetrahedron Letters. 49 (2008) 7328-7329.*

Li et al., "Copper-Catalyzed Aerobic C(sp$^2$)-H Functionalization for C—N Bond Formation: Synthesis of Pyrazoles and Indazoles", The Journal of Organic Chemistry, 78, 2013, pp. 3636-3646.

Lebedev et al., "Synthesis of 1-Aryl-1H-indazoles via Palladium-Catalyzed Intramolecular Amination of Aryl Halides", Journal of Organic Chemistry, 70, 2005, pp. 596-602.

Cox et al., "An SCN9A Channelopathy Causes Congenital Inability to Experience Pain", Nature vol. 444, Dec. 14, 2006, pp. 894-898.

Fertleman et al., "SCN9A Mutations in Paroxysmal Extreme Pain Disorder: Allelic Variants Underlie Distinct Channel Defects and Phenotypes", Neuron 52, Dec. 7, 2006, pp. 767-774.

Dib-Hajj et al., "From Genes to Pain: Na$_v$ 1.7 and Human Pain Disorders", Trends in Neurosciences, vol. 30 No. 11, 2007, pp. 555-563.

International Search Report in International Application No. PCT/KR2016/001395 dated Aug. 2, 2016, 5 pages.

Notification of Transmittal of the International Search Report and Written Opinion in International Application No. PCT/KR2016/001395 dated Aug. 2, 2016.

Chemical Abstract Compounds, 2011-2014, 7 pages.

Stauffer et al., "New Aromatase Inhibitors From the 3-pyridyl Arylether and 1-aryl pyrrolo[2,3-c]pyridine Series", Bioorganic & Medicinal Chemistry Letters, 22, 2012, pp. 1860-1863.

Frayne et al., "Investigation of the N-arylation of Various Substituted Indoles Using Microwave-assisted Technology", Tetrahedron Letters 49, 2008, pp. 7328-7329.

Barta et al., "Novel Carbazole and Acyl-indole Antimitotics", Bioorganic & Medicinal Chemistry Letters 19, 2000, pp. 3078-3080.

Smith III et al., "A Novel and Selective Method for the N-arylation of Indoles Mediated by KF/Al$_2$O$_3$$^1$", Tetrahedron Letters, vol. 37, No. 3, 1996, pp. 299-302.

Zhang et al., "Indole Substituted Zinc Phthalocyanine: Improved Photosensitizing Ability and Modified Photooxidation Mechanism", Journal of Photochemistry and Photobiology A: Chemistry 225, 2011, pp. 117-124.

Song et al., "A Novel Synthesis of 2-Aryl-2H-indazoles via a Palladium-Catalyzed Intramolecular Amination Reaction", Organic Letters, vol. 2, No. 4, 2000, pp. 519-521.

Extended European Search Report in EP Application No. 16749473.1 dated Oct. 11, 2018, 15 pages.

* cited by examiner

SODIUM CHANNEL BLOCKERS

TECHNICAL FIELD

The present invention relates to a compound having a blocking effect against sodium ion channels, particularly Nav1.7, a preparation method thereof and the use thereof.

BACKGROUND OF ART

Voltage-gated sodium channels are found in all excitable cells including muscle cells and nerve cells of the central nervous system and peripheral nervous system. These sodium channels are essential in the initiation and propagation of electrical signals in the nervous system. Therefore, the sodium channels are appropriate and their suitable function is essential for normal function of the nerves. Ultimately, aberrant Nav channels play a critical role in a variety of diseases such as epilepsy, arrhythmia, myotonia, ataxia, multiple sclerosis, irritable bowel syndrome, urinary incontinence, visceral pain, depression, and pain. Currently, ten Nav channels are reported in Human (Nav1.1~1.9, Nax). Among them, four channels, Nav1.3, Nav1.7, Nav1.8, and Nav1.9, are known to be closely associated with the transmission of pain signals, and thus are recognized as important analgesic targets.

There are a total of ten types in the Nav channels found until now as summarized in Table 1 below. Among the ten channels, nine channels, Nav1.1~Nav1.9, form channels. Among them, Nav1.3, Nav1.6, Nav1.7, Nav1.8, and Nav1.9 are expressed in DRG.

TABLE 1

| Type | Gene | Distribution tissue | TTX IC-50 nM | Indication |
|---|---|---|---|---|
| Nav1.1 | SCN1A | CNS/PNS | 10 | pain, epilepsy, neurodegeneration |
| Nav1.2 | SCN2A | CNS | 10 | neurodegeneration, epilepsy |
| Nav1.3 | SCN3A | CNS | 15 | Pain, epilepsy |
| Nav1.4 | SCN4A | Sk. muscle | 25 | Myotonia |
| Nav1.5 | SCN5A | Heart | 2000 | Arrhythmia |
| Nav1.6 | SCN8A | CNS/PNS | 6 | Pain, movement disorder |
| Nav1.7 | SCN9A | PNS | 25 | Pain, neuroendocrine disorder |
| Nav1.8 | SCN10A | PNS | 50000 | Pain |
| Nav1.9 | SCN11A | PNS | 1000 | Pain |

In particular, Nav1.7 is known to be highly expressed mainly in DRG (dorsal root ganglia) and sympathetic ganglia. In DRG that are sensory ganglia, the Nav1.7 channel is expressed in A- or C-fiber neurons, but frequently distributed in small neurons having a deep connection with pains. In particular, 85% of DRG are present in cells defined as nociceptors. This fact indicates that Nav1.7 has a close connection with pains.

The fact that Nav1.7 channel has a close connection with pains is well demonstrated in the results of not only animal experiments, but also human disease experiments. The results of animal experiments indicated that, when inflammation occurs, the gene transcript of Nav1.7 significantly increases and the expression of proteins also increases. This increase in transcript is believed to be attributable to an increase in NGF. The increased expression of Nav1.7 is believed to be the direct cause of an increase in excitability of sensory cells. In particular, when the gene of the Nav1.7 channels is removed or reduced, inflammatory pains are greatly reduced. However, animal experiments do not indicate that the removal or reduction of the Nav1.7 channel gene reduces neuropathic pains. However, there are many evidences that Nav1.7 is involved in a neuropathic pain in humans.

Assay results for family lineage that feel severe pain or no pain give many answers to pain studies. In particular, these results directly indicate that Nav1.7 plays an important role in causing pains. Genetically, there are two types of diseases which cause severe pain. In the case of erythromelalgia (or erythermalgia) among these diseases, severe pain is sometimes felt for a few hours when the body is slightly warm or takes exercises. At this time, the skin may become red, and the hand, the foot or the face may swell. The results of genetic research indicated that SCN9A (the human gene name of Nav1.7) is present at chromosomal sites that are associated with diseases. Nine mutations of Nav1.7 were found until now. These mutations lower activation threshold or result in slow deactivation of the channel. Therefore, these mutations can easily generate action potential even upon depolarization of some neurons [see, Dib-Hajj, S D. et al., TrendsinNeurosci., 30, 555-563:(2007)].

In the case of paroxysmal extreme pain disorder (PEPD) that is another inherited disease, pain is felt through life and caused when the bowels are evacuated or the anal region is stimulated. In addition to pain, the leg becomes red. As is known in the art, in PEPD, eight mutations occur in Nav1.7. These mutations occur mainly in sites which cause inactivation. The Nav channel has an inactivation ball in the linker between domains III and IV, and a peptide receiving region in the linker between the S5 and S6 segments of domains III and IV. Interestingly, mutations that cause PEPD all occur in these two regions. It appears that these cause a problem in the inactivation of Nav1.7. As expected, these mutations cause a problem in the inactivation of Nav1.7, resulting in slow deactivation of the channels (see, Fertleman, C. R. et al., Neuron, 52, 767-774: (2006)]. Therefore, the amount of electric current that enters through the channels increases.

Still another inherited disease is congenital indifference to pain (CIP). This disease results from mutation of the Nav1.7 channel and is present in Pakistani and Chinese family lineages. Patients suffering from this disease feel no pain [see, Cox, J. J, et al., Nature, 444, 894-898 (2006)]. CIP causes the loss of function of the Nav1.7 channel. Particularly, a mutation in this channel inhibits the expression of this channel. Thus, this channel is not expressed (see, Cox, J. J. et al., Nature, 444, 894-898 (2006)]. Interestingly, the knock-out of Nav1.7 does not influence other sensations, but it influences the olfactory sensation. This fact directly indicates that Nav1.7 does not overlap with other channels in pain transmission and the function thereof is not compensated for by other Nav channels.

As shown above for the above diseases, when a mutation in the Nav1.7 channels causes a gain of function, severe pain is felt, and when it causes a loss of function, labor pain is felt. This is a good clinical example that directly shows that the Nav1.7 channel is the major cause of pain. Therefore, it is considered that an antagonist that inhibits this channel will naturally lead to a potent analgesic effect.

However, if the Nav1.7 channel antagonist inhibits a plurality of Nav channels including the Nav1.7 channel, it can show adverse effects of various CNS disturbances, such as blurring of vision, dizziness, vomiting and sedation. In particular, if it inhibits the Nav1.5 channel, it can lead to cardiac arrhythmia and heart failure, which threaten life. For these reasons, selective inhibition of the Nav1.7 channels is very important.

Pains can be largely classified into three types: acute pain, inflammatory pain, and neuropathic pain. Acute pain performs an important protective function of maintaining the safety of organisms from stimuli that may cause tissue damage. Therefore, this pain is usually temporary and intense. On the other hand, inflammatory pain can be longer lasting, and the intensity thereof further rapidly increases. Inflammatory pain is mediated by various substances that are released during inflammation, including substance P, histamine, acid, prostaglandin, bradykinin, CGRP, cytokines, ATP, and other substances. The third pain is neuropathic and includes a nerve injury or a nerve injury caused by viral infection. It causes reorganization of circuits with neuronal proteins to cause pathological "sensitization", which may result in chronic pain that is lasting for several years. This type of pain does not provide an advantage of adaptability and is particularly difficult to treat by current therapy.

In particular, neuropathic pain and incurable pain are great medical problems that have not been solved. Several hundred million patients are suffering from severe pain that is not well inhibited by current therapeutic methods. Drugs that are currently used for the treatment of pain include NSAIDS, COX-2 inhibitors, opioids, tricyclic antidepressants and anti-convulsions. Neuropathic pain is particularly difficult to treat, because it does not well respond to opioids until a high dose is reached. Currently, gabapentin is most widely used as a therapeutic agent against neuropathic pain, but it is effective for only 60% of the patients and is not greatly effective. This drug is generally safe, but is problematic in terms of sedative action at high doses.

Accordingly, studies on the discovery of a new regulator of the Nav1.7 channel and the use thereof for the treatment of acute pain, chronic pain, inflammatory pain and neuropathic pain have been actively conducted by many pharmaceutical companies including global pharmaceutical companies such as Merck, AstraZeneca (see, US2010-0197655; US2012-0010183; WO2013-086229; WO2013-177224; US2012-0238579; WO2007-145922).

Accordingly, the present inventors have conducted extensive studies to develop new compounds, and as a result, have found that compounds having chemical structures different from those of sodium channel blockers reported to date have excellent sodium channel blocking effects, thereby completing the present invention. In particular, the compounds of the present invention exhibit a higher affinity against Nav1.7 channels than the affinity against Nav1.5 channels. Advantageously, the compounds of the present invention do not exhibit little or no affinity against the Nav1.5 channels. Compounds falling within the scope of the present invention mainly have sodium channel inhibitory activity, but it is not excluded that products produced by a special in vivo environment or a metabolic process after adsorption of the compounds in vivo is likely to act as agonists and exhibit effective pharmacological activity.

DETAILED DESCRIPTION OF THE INVENTION

Technical Problem

It is an object of the present invention to provide compounds having blocking effects against sodium ion channels, particularly Nav1.7, a preparation method thereof and the use thereof.

Technical Solution

In order to achieve the above object, the present invention provides a compound represented by the following Chemical Formula 1 or a pharmaceutically acceptable salt thereof:

[Chemical Formula 1]

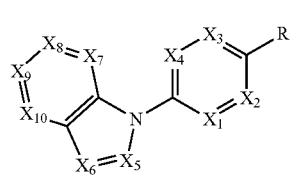

In the above Formula,
$X_1$ is C—$R_a$ or N, $X_2$ is C—$R_b$ or N, $X_3$ is C—$R_c$ or N, $X_4$ is C—$R_d$ or N,
$R_a$, $R_b$, $R_c$ and $R_d$ are each independently hydrogen, $C_{1-4}$ alkyl, $C_{3-6}$ cycloalkyl, $C_{1-4}$ alkoxy, $C_{6-10}$ aryl, 5-membered or 6-membered heteroaryl, halogen or cyano,
$X_5$ is CH, N or OH, $X_6$ is C—$R_e$ or N, $X_7$ is CH or N, $X_8$ is C—$R_f$ or N,
$R_e$ is hydrogen; $C_{1-4}$ alkyl; $C_{2-4}$ alkynyl which is unsubstituted or substituted with $C_{1-4}$ hydroxyalkyl; $C_{3-6}$ cycloalkyl; —COO—($C_{1-4}$ alkyl); —NHCO—($C_{1-4}$ alkyl); —CH═CH— (pyridinyl); amino; carboxy; cyano; halogen; morpholino; 5-membered or 6-membered heteroaryl which is unsubstituted or substituted with a substituent selected from the group consisting of $C_{1-4}$ alkyl, $C_{1-4}$ alkoxy, amino and halogen; phenyl which is unsubstituted or substituted with one to three substituents independently selected from the group consisting of $C_{1-4}$ alkyl, $C_{1-4}$ alkoxy, $C_{1-4}$ haloalkyl, $C_{1-4}$ haloalkoxy, halogen, amino, cyano and nitro; pyridin-2-onyl which is unsubstituted or substituted with $C_{1-4}$ alkyl; styryl which is unsubstituted or substituted with a substituent selected from the group consisting of $C_{1-4}$ haloalkyl and halogen; or tetrahydro-pyridinyl which is unsubstituted or substituted with —COO—($C_{1-4}$ alkyl),
$R_f$ is halogen, benzyloxy or phenyl,
$X_9$ is C—$R_g$ or N,
$R_g$ is hydrogen; $C_{1-4}$ alkyl; $C_{1-4}$ alkoxy which is unsubstituted or substituted with a substituent selected from the group consisting of $C_{3-6}$ cycloalkyl, phenyl, phenyl substituted with halogen, and naphthyl; $C_{1-4}$ haloalkyl; $C_{3-6}$ cycloalkyl; amino; halogen; hydroxy; nitro; phenylamino; benzyloxy which is unsubstituted or substituted with halogen; phenyl which is unsubstituted or substituted with one to three substituents independently selected from the group consisting of $C_{1-4}$ alkyl, $C_{1-4}$ alkoxy, $C_{1-4}$ haloalkyl, cyano, amino, nitro and halogen; 5-membered or 6-membered heteroaryl which is unsubstituted or substituted with one or two substituents independently selected from the group consisting of $C_{1-4}$ alkyl and halogen; or pyridinyloxy which is unsubstituted or substituted with halogen,
$X_{10}$ is C—$R_h$ or N,
$R_h$ is hydrogen, halogen or benzyloxy,
R is —CO—N($R_i$)—$SO_2$—$R_{ii}$, —$SO_2$—NH—$R_{iii}$, —CONH—$R_{iv}$, cyano, dihydrotriazolonyl, or tetrazolyl, $R_i$ is hydrogen; $C_{1-4}$ alkyl; naphthylmethyl; or benzyl which is unsubstituted or substituted with halogen;

$R_{ii}$ is $C_{1-4}$ alkyl or $N(C_{1-4}$ alkyl$)_2$, $R_{iii}$ is 5-membered or 6-membered heteroaryl which is unsubstituted or substituted with a substituent selected from the group consisting of $C_{1-4}$ alkyl and halogen; and $R_{iv}$ is hydrogen; —CO—($C_{1-4}$ alkyl); —NHCO—NH$_2$; or thiazolyl which is unsubstituted or substituted with a substituent selected from the group consisting of $C_{1-4}$ alkyl and —COO—($C_{1-4}$ alkyl).

Preferably, $X_1$ is C—$R_a$ or N, $X_2$ is CH, $X_3$ is C—$R_c$, and $X_4$ is CH.

Further, preferably, $R_a$, $R_b$, $R_c$ and $R_d$ are each independently hydrogen, fluoro, chloro or cyano.

Further, preferably, $X_1$ is C—Cl, $X_2$ is CH, $X_3$ is C—F, and $X_4$ is CH.

Further, preferably, the 5-membered or 6-membered heteroaryl of $R_e$ is pyrazolyl unsubstituted or substituted with $C_{1-4}$ alkyl; pyridinyl unsubstituted or substituted with a substituent selected from the group consisting of $C_{1-4}$ alkoxy and halogen; or thiazolyl unsubstituted or substituted with $C_{1-4}$ alkyl.

Further, preferably, $R_e$ is hydrogen; methyl; ethynyl substituted with hydroxyisopropyl; cyclopropyl; —COO-(methyl); —NHCO-(methyl); —CH=CH-(pyridinyl); amino; carboxy; cyano; bromo; chloro; morpholino; pyrazolyl unsubstituted or substituted with methyl; pyridinyl unsubstituted or substituted with a substituent selected from the group consisting of methoxy, fluoro and chloro; thiazolyl unsubstituted or substituted with methyl; phenyl unsubstituted or substituted with one to three substituents independently selected from the group consisting of methyl, methoxy, trifluoromethyl, trifluoromethoxy, fluoro, chloro, amino, cyano and nitro; pyridin-2-onyl unsubstituted or substituted with methyl; styryl unsubstituted or substituted with a substituent selected from the group consisting of trifluoromethyl, fluoro and chloro; or tetrahydropyridinyl unsubstituted or substituted with —COO-(tert-butyl).

Further, preferably, $R_i$ is hydrogen; methyl; naphthylmethyl; or benzyl substituted with fluoro, and $R_{ii}$ is methyl or dimethylamino.

Further, preferably, $R_{iv}$ is hydrogen; —CO-(methyl); —NHCO—NH$_2$; or thiazolyl unsubstituted or substituted with a substituent selected from the group consisting of methyl and —COO-(ethyl).

Further, preferably, $X_9$ is C—$R_g$ and $X_{10}$ is C—$R_h$.

Further, preferably, $X_9$ is C—$R_g$, and $R_g$ is hydrogen; isobutyl; methoxy, ethoxy or isobutoxy, which is unsubstituted or substituted with a substituent selected from the group consisting of cyclohexyl, phenyl, phenyl substituted with fluoro, and naphthyl; trifluoromethyl; cyclopropyl; amino; fluoro; chloro; bromo; hydroxy; nitro; phenylamino; benzyloxy unsubstituted or substituted with fluoro; phenyl unsubstituted or substituted with one or two substituents independently selected from the group consisting of methyl, methoxy, trifluoromethyl, cyano, fluoro and chloro; pyrazolyl substituted with methyl; pyridinyl unsubstituted or substituted with one or two substituents selected from the group consisting of fluoro and chloro; pyridinyloxy unsubstituted or substituted with fluoro; or pyrimidinyl.

Further, preferably, $X_{10}$ is C—$R_h$ and $R_h$ is hydrogen, chloro or benzyloxy.

Further, preferably, $X_5$ is N, $X_6$ is C—$R_e$, $X_7$ is CH, and $X_8$ is C—$R_f$, or $X_5$ is CH, $X_6$ is C—$R_e$, $X_7$ is N, and $X_8$ is C—$R_f$, or $X_5$ is CH, $X_6$ is C—$R_e$, $X_7$ is CH, and $X_8$ is C—$R_f$, or $X_5$ is N, $X_6$ is C—$R_e$, $X_7$ is N, $X_8$ is C—$R_f$, or $X_5$ is N, $X_6$ is C—$R_e$, $X_7$ is CH, and $X_8$ is N Further, preferably, $X_1$ is C—$R_a$ or N, $X_2$ is C—$R_b$, $X_3$ is C—$R_c$, $X_4$ is C—$R_d$, $X_5$ is N, $X_6$ is C—$R_e$, $X_7$ is CH, $X_8$ is C—$R_f$, $R_e$ is hydrogen; $C_{1-4}$ alkyl; $C_{2-4}$ alkyl unsubstituted or substituted with $C_{1-4}$ hydroxyalkyl; $C_{3-6}$ cycloalkyl; —COO—($C_{1-4}$ alkyl); —NHCO—($C_{1-4}$ alkyl); —CH=CH-(pyridinyl); amino; cyano; halogen; morpholino; 5-membered or 6-membered heteroaryl unsubstituted or substituted with a substituent selected from the group consisting of $C_{1-4}$ alkyl, $C_{1-4}$ alkoxy and halogen; phenyl unsubstituted or substituted with one to three substituents independently selected from the group consisting of $C_{1-4}$ alkyl, $C_{1-4}$ alkoxy, $C_{1-4}$ haloalkyl, $C_{1-4}$ haloalkoxy, halogen, amino, cyano and nitro; pyridin-2-onyl unsubstituted or substituted with $C_{1-4}$ alkyl; styryl unsubstituted or substituted with a substituents selected from the group consisting of $C_{1-4}$ haloalkyl and halogen; or tetrahydropyridinyl unsubstituted or substituted with —COO—($C_{1-4}$ alkyl), $X_9$ is C—$R_g$, $X_{10}$ is C—$R_h$, and $R_h$ is hydrogen or halogen.

Further, preferably, $X_1$ is C—$R_a$, $X_2$ is C—$R_b$, $X_3$ is C—$R_c$, and $X_4$ is C—$R_d$, $R_a$, $R_b$, $R_c$ and $R_d$ are each independently hydrogen or halogen, $X_5$ is CH, $X_6$ is C—$R_e$, $X_7$ is N, and $X_8$ is C—$R_f$, $R_e$ is halogen; or phenyl unsubstituted or substituted with one to three substituents independently selected from the group consisting of $C_{1-4}$ alkyl, $C_{1-4}$ alkoxy, $C_{1-4}$ haloalkyl, $C_{1-4}$ haloalkoxy, halogen, amino, cyano and nitro, $R_f$ is hydrogen, $X_9$ is C—$R_g$, $R_g$ is hydrogen, halogen, or phenyl unsubstituted or substituted with a substituent selected from the group consisting of $C_{1-4}$ alkoxy, $C_{1-4}$ haloalkyl, cyano and halogen, $X_{10}$ is C—$R_h$, $R_h$ is hydrogen, R is —CO—N($R_i$)—SO$_2$—$R_{ii}$, $R_i$ is hydrogen, and $R_{ii}$ is $C_{1-4}$ alkyl.

Further, preferably, $X_1$ is C—$R_a$ or N, $X_2$ is C—$R_b$, $X_3$ is C—$R_c$, $X_4$ is C—$R_d$, $R_a$, $R_b$, $R_c$ and $R_d$ are each independently hydrogen or halogen, $X_5$ is CH, $X_6$ is C—$R_e$, $X_7$ is CH, and $X_8$ is C—$R_f$, $R_e$ is carboxy; halogen; 5-membered or 6-membered heteroaryl unsubstituted or substituted with a substituent selected from the group consisting of $C_{1-4}$ alkyl, $C_{1-4}$ alkoxy and halogen; or phenyl unsubstituted or substituted with one to three substituents independently selected from the group consisting of $C_{1-4}$ alkyl, $C_{1-4}$ alkoxy, $C_{1-4}$ haloalkyl, $C_{1-4}$ haloalkoxy, halogen, amino, cyano and nitro, $R_f$ is hydrogen or benzyloxy, $X_9$ is C—$R_g$, $R_g$ is hydrogen; $C_{1-4}$ alkoxy unsubstituted or substituted with a substituent selected from the group consisting of $C_{3-6}$ cycloalkyl, phenyl, phenyl substituted with halogen, and naphthyl; halogen; hydroxy; or benzyloxy unsubstituted or substituted with halogen, $X_{10}$ is C—$R_h$,
R is —CO—N($R_i$)—$SO_2$—$R_{ii}$,
$R_i$ is hydrogen, and
$R_{ii}$ is $C_{1-4}$ alkyl.

Further, preferably,
$X_1$ is C—$R_a$, $X_2$ is C—$R_b$, $X_3$ is C—$R_c$, $X_4$ is C—$R_d$,
$R_a$, $R_b$, $R_c$ and $R_d$ are each independently hydrogen or halogen,
$X_5$ is N, $X_6$ is C—$R_e$, $X_7$ is N, $X_8$ is C—$R_f$,
$R_e$ is halogen,
$R_f$ is hydrogen,
$X_9$ is C—$R_g$,
$R_g$ is halogen,
$X_{10}$ is C—$R_h$,
$R_h$ is hydrogen,
R is —CO—N($R_i$)—$SO_2$—$R_{ii}$,
$R_i$ is hydrogen, and
$R_{ii}$ is $C_{1-4}$ alkyl.

Further, preferably,
$X_1$ is C—$R_a$, $X_2$ is C—$R_b$, $X_3$ is C—$R_c$, and $X_4$ is C—$R_d$,
$R_a$, $R_b$, $R_c$ and $R_d$ are each independently hydrogen or halogen,
$X_5$ is N, $X_6$ is C—$R_e$, $X_7$ is CH, $X_8$ is N,
$R_e$ is hydrogen or halogen;
$X_9$ is C—$R_g$,
$R_g$ is halogen,
$X_{10}$ is C—$R_h$,
$R_h$ is hydrogen,
R is —CO—N($R_i$)—$SO_2$—$R_{ii}$,
$R_i$ is hydrogen, and
$R_{ii}$ is $C_{1-4}$ alkyl.

The representative compounds represented by Chemical Formula 1 are as follows:
1) 5-chloro-4-(5-chloro-3-methyl-1H-indazol-1-yl)-2-fluoro-N-(methylsulfonyl)benzamide,
2) 5-chloro-4-(5-chloro-1H-indazol-1-yl)-2-fluoro-N-(methylsulfonyl)benzamide,
3) 5-chloro-4-(3,5-dichloro-1H-pyrazolo[3,4-b]pyridin-1-yl)-2-fluoro-N-(methylsulfonyl)benzamide,
4) 4-(3,5-dichloro-1H-indazol-1-yl)-2-fluoro-N-(methylsulfonyl)benzamide,
5) 4-(3-amino-5-chloro-1H-indazol-1-yl)-5-chloro-2-fluoro-N-(methylsulfonyl)benzamide,
6) 4-(3-acetamido-5-chloro-1H-indazol-1-yl)-5-chloro-2-fluoro-N-(methylsulfonyl)benzamide,
7) 5-chloro-4-(3,5-dichloro-1H-indazol-1-yl)-N—(N,N-dimethylsulfamoyl)-2-fluorobenzamide,
8) 3-chloro-4-(3,5-dichloro-1H-indazol-1-yl)-N-(methylsulfonyl)benzamide,
9) 5-chloro-4-(3,5-dichloro-1H-indazol-1-yl)-2-fluoro-N-(methylsulfonyl)benzamide,
10) 5-chloro-4-(5-chloro-1H-pyrazolo[3,4-c]pyridin-1-yl)-2-fluoro-N-(methylsulfonyl)benzamide,
11) 5-chloro-4-(3,5-dichloro-1H-pyrazolo[3,4-c]pyridin-1-yl)-2-fluoro-N-(methylsulfonyl)benzamide,
12) 4-(3-chloro-5-hydroxy-1H-indazol-1-yl)-N-(methylsulfonyl)benzamide,
13) 4-(5-amino-1H-indazol-1-yl)-5-chloro-2-fluoro-N-(methylsulfonyl)benzamide,
14) 5-chloro-2-fluoro-4-(3-methyl-5-nitro-1H-indazol-1-yl)-N-(methylsulfonyl)benzamide,
15) 5-chloro-4-(4-chloro-5-fluoro-1H-indazol-1-yl)-2-fluoro-N-(methylsulfonyl)benzamide,
16) 5-chloro-4-(3-chloro-5-hydroxy-1H-indazol-1-yl)-2-fluoro-N-(methylsulfonyl)benzamide,
17) 5-chloro-4-(3-chloro-5-fluoro-1H-indazol-1-yl)-2-fluoro-N-(methylsulfonyl)benzamide,
18) 5-chloro-4-(3-chloro-5-(trifluoromethyl)-1H-indazol-1-yl)-2-fluoro-N-(methylsulfonyl)benzamide,
19) 4-(3-bromo-5-chloro-1H-indazol-1-yl)-5-chloro-2-fluoro-N-(methylsulfonyl)benzamide,
20) 5-chloro-4-(3,5-dichloro-1H-pyrrolo[2,3-b]pyridin-1-yl)-2-fluoro-N-(methylsulfonyl)benzamide,
21) 4-(5-bromo-3-chloro-1H-indazol-1-yl)-5-chloro-2-fluoro-N-(methylsulfonyl)benzamide,
22) 4-(5-bromo-3-cyano-1H-indazol-1-yl)-5-chloro-2-fluoro-N-(methylsulfonyl)benzamide,
23) 5-chloro-4-(3-chloro-5-nitro-1H-indazol-1-yl)-2-fluoro-N-(methylsulfonyl)benzamide,
24) 5-chloro-4-(3-chloro-5-cyclopropyl-1H-indazol-1-yl)-2-fluoro-N-(methylsulfonyl)benzamide,
25) 5-chloro-4-(5-chloro-3-cyclopropyl-1H-indazol-1-yl)-2-fluoro-N-(methylsulfonyl)benzamide,
26) 5-chloro-4-(5-cyclopropyl-3-phenyl-1H-indazol-1-yl)-2-fluoro-N-(methylsulfonyl)benzamide,
27) 5-chloro-4-(3-chloro-5-(phenylamino)-1H-indazol-1-yl)-2-fluoro-N-(methylsulfonyl)benzamide,
28) 4-(5-(benzyloxy)-3-chloro-1H-indazol-1-yl)-5-chloro-2-fluoro-N-(methylsulfonyl)benzamide,
29) 4-(5-(benzyloxy)-4-chloro-1H-indazol-1-yl)-5-chloro-2-fluoro-N-(methylsulfonyl)benzamide,
30) 4-(5-(benzyloxy)-3-methyl-1H-indazol-1-yl)-5-chloro-2-fluoro-N-(methylsulfonyl)benzamide,
31) 5-chloro-4-(3,4-dichloro-5-((4-fluorobenzyl)oxy)-1H-indazol-1-yl)-2-fluoro-N-(methylsulfonyl)benzamide,
32) 5-chloro-4-(3,4-dichloro-5-((2-fluorobenzyl)oxy)-1H-indazol-1-yl)-2-fluoro-N-(methylsulfonyl)benzamide,
33) 5-chloro-4-(3-chloro-5-(1-phenylethoxy)-1H-indazol-1-yl)-2-fluoro-N-(methylsulfonyl)benzamide,
34) 5-chloro-4-(3-chloro-5-(cyclohexylmethoxy)-1H-indazol-1-yl)-2-fluoro-N-(methylsulfonyl)benzamide,
35) 5-chloro-4-(3-chloro-5-(naphthalen-2-ylmethoxy)-1H-indazol-1-yl)-2-fluoro-N-(methylsulfonyl)benzamide,
36) 5-chloro-4-(3-chloro-5-((4-fluorobenzyl)oxy)-1H-indazol-1-yl)-2-fluoro-N-(methylsulfonyl)benzamide,
37) 5-chloro-4-(3-chloro-5-((2-fluorobenzyl)oxy)-1H-indazol-1-yl)-2-fluoro-N-(methylsulfonyl)benzamide,
38) 5-chloro-4-(3-chloro-5-((3-fluorobenzyl)oxy)-1H-indazol-1-yl)-2-fluoro-N-(methylsulfonyl)benzamide,
39) 5-chloro-4-(3-chloro-5-(1-(4-fluorophenyl)ethoxy)-1H-indazol-1-yl)-2-fluoro-N-(methylsulfonyl)benzamide,
40) 5-chloro-4-(3-chloro-5-phenethoxy-1H-indazol-1-yl)-2-fluoro-N-(methylsulfonyl)benzamide,
41) 5-chloro-2-fluoro-4-(5-isobutoxy-1H-indazol-1-yl)-N-(methylsulfonyl)benzamide,
42) 5-chloro-4-(3-chloro-5-isobutoxy-1H-indazol-1-yl)-2-fluoro-N-(methylsulfonyl)benzamide,
43) 4-(5-(benzyloxy)-3-chloro-1H-indazol-1-yl)-5-chloro-N—(N,N-dimethylsulfamoyl)-2-fluorobenzamide,
44) 4-(5-(benzyloxy)-3-chloro-1H-indazol-1-yl)-3-chloro-N-(methylsulfonyl)benzamide,
45) 4-(6-(benzyloxy)-3-chloro-1H-indazol-1-yl)-5-chloro-2-fluoro-N-(methylsulfonyl)benzamide,
46) methyl 6-(benzyloxy)-1-(2-chloro-5-fluoro-4-((methylsulfonyl)carbamoyl)phenyl)-1H-indazole-3-carboxylate,
47) 5-chloro-4-(3-chloro-5-((6-fluoropyridin-3-yl)oxy)-1H-indazol-1-yl)-2-fluoro-N-(methylsulfonyl)benzamide,
48) 5-chloro-4-(5-chloro-3-phenyl-1H-indazol-1-yl)-2-fluoro-N-(methylsulfonyl)benzamide,
49) 5-chloro-4-(5-chloro-3-(pyridin-4-yl)-1H-indazol-1-yl)-2-fluoro-N-(methylsulfonyl)benzamide,
50) 5-chloro-4-(5-chloro-3-(pyridin-3-yl)-1H-indazol-1-yl)-2-fluoro-N-(methylsulfonyl)benzamide, 51) 5-chloro-4-(5-chloro-3-(5-chloropyridin-3-yl)-1H-indazol-1-yl)-2-fluoro-N-(methylsulfonyl)benzamide,
52) 5-chloro-4-(5-chloro-3-(m-tolyl)-1H-indazol-1-yl)-2-fluoro-N-(methylsulfonyl)benzamide,
53) 5-chloro-4-(5-chloro-3-(2-fluorophenyl)-1H-indazol-1-yl)-2-fluoro-N-(methylsulfonyl)benzamide,
54) 5-chloro-4-(5-chloro-3-(3-fluorophenyl)-1H-indazol-1-yl)-2-fluoro-N-(methylsulfonyl)benzamide,
55) 5-chloro-4-(5-chloro-3-(4-fluorophenyl)-1H-indazol-1-yl)-2-fluoro-N-(methylsulfonyl)benzamide,
56) 5-chloro-4-(5-chloro-3-(2,4-difluorophenyl)-1H-indazol-1-yl)-2-fluoro-N-(methylsulfonyl)benzamide,
57) 5-chloro-4-(5-chloro-3-(2-methoxypyridin-3-yl)-1H-indazol-1-yl)-2-fluoro-N-(methylsulfonyl)benzamide,
58) 5-chloro-4-(5-chloro-3-(2-methoxyphenyl)-1H-indazol-1-yl)-2-fluoro-N-(methylsulfonyl)benzamide,
59) 5-chloro-4-(5-chloro-3-(4-methoxyphenyl)-1H-indazol-1-yl)-2-fluoro-N-(methylsulfonyl)benzamide,
60) 5-chloro-4-(5-chloro-3-(2-cyanophenyl)-1H-indazol-1-yl)-2-fluoro-N-(methylsulfonyl)benzamide,
61) 5-chloro-4-(5-chloro-3-(3-cyanophenyl)-1H-indazol-1-yl)-2-fluoro-N-(methylsulfonyl)benzamide,
62) 5-chloro-4-(5-chloro-3-(4-cyanophenyl)-1H-indazol-1-yl)-2-fluoro-N-(methylsulfonyl)benzamide,
63) 5-chloro-4-(5-chloro-3-(2-(trifluoromethyl)phenyl)-1H-indazol-1-yl)-2-fluoro-N-(methylsulfonyl)benzamide,
64) 5-chloro-4-(5-chloro-3-(3-(trifluoromethyl)phenyl)-1H-indazol-1-yl)-2-fluoro-N-(methylsulfonyl)benzamide,
65) 5-chloro-4-(5-chloro-3-(4-(trifluoromethyl)phenyl)-1H-indazol-1-yl)-2-fluoro-N-(methylsulfonyl)benzamide,
66) 5-chloro-4-(5-chloro-3-(4-chloro-2-fluorophenyl)-1H-indazol-1-yl)-2-fluoro-N-(methylsulfonyl)benzamide,
67) 5-chloro-4-(5-chloro-3-(4-chlorophenyl)-1H-indazol-1-yl)-2-fluoro-N-(methylsulfonyl)benzamide,
68) 5-chloro-4-(5-chloro-3-(2-fluoropyridin-4-yl)-1H-indazol-1-yl)-2-fluoro-N-(methylsulfonyl)benzamide,
69) 5-chloro-4-(5-chloro-3-(5-chloro-2-fluorophenyl)-1H-indazol-1-yl)-2-fluoro-N-(methylsulfonyl)benzamide,
70) 5-chloro-4-(5-chloro-3-(3-cyano-4-fluorophenyl)-1H-indazol-1-yl)-2-fluoro-N-(methylsulfonyl)benzamide,
71) 5-chloro-4-(5-chloro-3-(2-chlorophenyl)-1H-indazol-1-yl)-2-fluoro-N-(methylsulfonyl)benzamide,
72) 5-chloro-4-(5-chloro-3-(3-chlorophenyl)-1H-indazol-1-yl)-2-fluoro-N-(methylsulfonyl)benzamide,
73) 5-chloro-4-(5-chloro-3-(3-chloro-5-fluorophenyl)-1H-indazol-1-yl)-2-fluoro-N-(methylsulfonyl)benzamide,
74) 5-chloro-4-(5-chloro-3-(2-chloro-4-fluorophenyl)-1H-indazol-1-yl)-2-fluoro-N-(methylsulfonyl)benzamide,
75) 5-chloro-4-(5-chloro-3-(3,4-difluorophenyl)-1H-indazol-1-yl)-2-fluoro-N-(methylsulfonyl)benzamide,
76) 5-chloro-4-(5-chloro-3-(2,5-difluorophenyl)-1H-indazol-1-yl)-2-fluoro-N-(methylsulfonyl)benzamide,
77) 5-chloro-4-(5-chloro-3-(3,4,5-trifluorophenyl)-1H-indazol-1-yl)-2-fluoro-N-(methylsulfonyl)benzamide,
78) 5-chloro-4-(5-chloro-3-(2-chloro-6-fluorophenyl)-1H-indazol-1-yl)-2-fluoro-N-(methylsulfonyl)benzamide,
79) 5-chloro-4-(5-chloro-3-(3-chloro-2-fluorophenyl)-1H-indazol-1-yl)-2-fluoro-N-(methylsulfonyl)benzamide,
80) 5-chloro-4-(5-chloro-3-(4-chloro-3-fluorophenyl)-1H-indazol-1-yl)-2-fluoro-N-(methylsulfonyl)benzamide,
81) 5-chloro-4-(5-chloro-3-(4-nitrophenyl)-1H-indazol-1-yl)-2-fluoro-N-(methylsulfonyl)benzamide,
82) 4-(3-(4-aminophenyl)-5-chloro-1H-indazol-1-yl)-5-chloro-2-fluoro-N-(methylsulfonyl)benzamide,
83) 5-chloro-4-(5-chloro-3-(4-(trifluoromethoxy)phenyl)-1H-indazol-1-yl)-2-fluoro-N-(methylsulfonyl)benzamide,
84) 5-chloro-2-fluoro-4-(5-isobutyl-3-phenyl-1H-indazol-1-yl)-N-(methylsulfonyl)benzamide,
85) 5-chloro-4-(3-(4-chlorophenyl)-5-cyclopropyl-1H-indazol-1-yl)-2-fluoro-N-(methylsulfonyl)benzamide,
86) 5-chloro-4-(5-chloro-3-morpholino-1H-indazol-1-yl)-2-fluoro-N-(methylsulfonyl)benzamide,
87) 5-chloro-4-(5-chloro-3-(1-methyl-1H-pyrazol-5-yl)-1H-indazol-1-yl)-2-fluoro-N-(methylsulfonyl)benzamide,
88) 5-chloro-4-(5-chloro-3-(1-methyl-1H-pyrazol-4-yl)-1H-indazol-1-yl)-2-fluoro-N-(methylsulfonyl)benzamide,
89) 5-chloro-4-(5-chloro-3-(1H-pyrazol-4-yl)-1H-indazol-1-yl)-2-fluoro-N-(methylsulfonyl)benzamide,
90) 5-chloro-4-(5-chloro-3-(1H-pyrazol-3-yl)-1H-indazol-1-yl)-2-fluoro-N-(methylsulfonyl)benzamide,
91) 5-chloro-4-(5-chloro-3-(2-methylthiazol-5-yl)-1H-indazol-1-yl)-2-fluoro-N-(methylsulfonyl)benzamide,
92) 4-(5-chloro-3-(2-methoxyphenyl)-1H-indazol-1-yl)-3-cyano-N-(methylsulfonyl)benzamide,
93) 4-(5-chloro-3-(4-methoxyphenyl)-1H-indazol-1-yl)-3-cyano-N-(methylsulfonyl)benzamide,
94) 4-(5-chloro-3-(2-cyanophenyl)-1H-indazol-1-yl)-3-cyano-N-(methylsulfonyl)benzamide,
95) 4-(5-chloro-3-(3-cyanophenyl)-1H-indazol-1-yl)-3-cyano-N-(methylsulfonyl)benzamide,
96) 4-(5-chloro-3-(4-cyanophenyl)-1H-indazol-1-yl)-3-cyano-N-(methylsulfonyl)benzamide,
97) 4-(5-chloro-3-(2-(trifluoromethyl)phenyl)-1H-indazol-1-yl)-3-cyano-N-(methylsulfonyl)benzamide,
98) 4-(5-chloro-3-(3-(trifluoromethyl)phenyl)-1H-indazol-1-yl)-3-cyano-N-(methylsulfonyl)benzamide,
99) 4-(5-chloro-3-(4-(trifluoromethyl)phenyl)-1H-indazol-1-yl)-3-cyano-N-(methylsulfonyl)benzamide,
100) 4-(5-chloro-3-(4-chloro-2-fluorophenyl)-1H-indazol-1-yl)-3-cyano-N-(methylsulfonyl)benzamide,
101) 4-(5-chloro-3-(4-fluorophenyl)-1H-indazol-1-yl)-3-cyano-N-(methylsulfonyl)benzamide,
102) 4-(5-chloro-3-(2-fluorophenyl)-1H-indazol-1-yl)-3-cyano-N-(methylsulfonyl)benzamide,
103) 4-(5-chloro-3-(3-fluorophenyl)-1H-indazol-1-yl)-3-cyano-N-(methylsulfonyl)benzamide,
104) 4-(5-chloro-3-(5-chloropyridin-3-yl)-1H-indazol-1-yl)-3-cyano-N-(methylsulfonyl)benzamide,
105) 4-(5-chloro-3-(2,4-difluorophenyl)-1H-indazol-1-yl)-3-cyano-N-(methylsulfonyl)benzamide,
106) 4-(5-chloro-3-(2-methoxypyridin-3-yl)-1H-indazol-1-yl)-3-cyano-N-(methylsulfonyl)benzamide,
107) 2-chloro-4-(5-chloro-3-(2-methoxyphenyl)-1H-indazol-1-yl)-5-fluoro-N-(methylsulfonyl)benzamide,
108) 2-chloro-4-(5-chloro-3-(4-methoxyphenyl)-1H-indazol-1-yl)-5-fluoro-N-(methylsulfonyl)benzamide,
109) 2-chloro-4-(5-chloro-3-(3-cyanophenyl)-1H-indazol-1-yl)-5-fluoro-N-(methylsulfonyl)benzamide,
110) 2-chloro-4-(5-chloro-3-(3-(trifluoromethyl)phenyl)-1H-indazol-1-yl)-5-fluoro-N-(methylsulfonyl)benzamide,
111) 2-chloro-4-(5-chloro-3-(4-(trifluoromethyl)phenyl)-1H-indazol-1-yl)-5-fluoro-N-(methylsulfonyl)benzamide,
112) 2-chloro-4-(5-chloro-3-(4-fluorophenyl)-1H-indazol-1-yl)-5-fluoro-N-(methylsulfonyl)benzamide,
113) 2-chloro-4-(5-chloro-3-(2-fluorophenyl)-1H-indazol-1-yl)-5-fluoro-N-(methylsulfonyl)benzamide,
114) 2-chloro-4-(5-chloro-3-(3-fluorophenyl)-1H-indazol-1-yl)-5-fluoro-N-(methylsulfonyl)benzamide,
115) 2-chloro-4-(5-chloro-3-(2,4-difluorophenyl)-1H-indazol-1-yl)-5-fluoro-N-(methylsulfonyl)benzamide, 116) 2-chloro-4-(5-chloro-3-(2-methoxypyridin-3-yl)-1H-indazol-1-yl)-5-fluoro-N-(methylsulfonyl)benzamide,
117) 4-(5-chloro-3-(2-methoxyphenyl)-1H-indazol-1-yl)-3-fluoro-N-(methylsulfonyl)benzamide,
118) 4-(5-chloro-3-(4-methoxyphenyl)-1H-indazol-1-yl)-3-fluoro-N-(methylsulfonyl)benzamide,
119) 4-(5-chloro-3-(3-cyanophenyl)-1H-indazol-1-yl)-3-fluoro-N-(methylsulfonyl)benzamide,
120) 4-(5-chloro-3-(4-cyanophenyl)-1H-indazol-1-yl)-3-fluoro-N-(methylsulfonyl)benzamide,
121) 4-(5-chloro-3-(3-(trifluoromethyl)phenyl)-1H-indazol-1-yl)-3-fluoro-N-(methylsulfonyl)benzamide,
122) 4-(5-chloro-3-(4-(trifluoromethyl)phenyl)-1H-indazol-1-yl)-3-fluoro-N-(methylsulfonyl)benzamide,
123) 4-(5-chloro-3-(4-fluorophenyl)-1H-indazol-1-yl)-3-fluoro-N-(methylsulfonyl)benzamide,
124) 4-(5-chloro-3-(2-fluorophenyl)-1H-indazol-1-yl)-3-fluoro-N-(methylsulfonyl)benzamide,
125) 4-(5-chloro-3-(3-fluorophenyl)-1H-indazol-1-yl)-3-fluoro-N-(methylsulfonyl)benzamide,
126) 4-(5-chloro-3-(4-chlorophenyl)-1H-indazol-1-yl)-3-fluoro-N-(methylsulfonyl)benzamide,
127) 4-(5-chloro-3-phenyl-1H-indazol-1-yl)-2-fluoro-N-(methylsulfonyl)benzamide,
128) 6-(5-chloro-3-(4-chloro-2-fluorophenyl)-1H-indazol-1-yl)-N-(methylsulfonyl)nicotinamide,
129) 5-chloro-4-(5-chloro-3-(3-hydroxy-3-methylbut-1-yn-1-yl)-1H-indazol-1-yl)-2-fluoro-N-(methylsulfonyl)benzamide,
130) 5-chloro-4-(5-chloro-3-(1-methyl-6-oxo-1,6-dihydropyridin-3-yl)-1H-indazol-1-yl)-2-fluoro-N-(methylsulfonyl)benzamide,
131) tert-butyl 4-(5-chloro-1-(2-chloro-5-fluoro-4-((methylsulfonyl)carbamoyl)phenyl)-1H-indazol-3-yl)-3,6-dihydropyridine-1(2H)-carboxylate,
132) 5-chloro-4-(5-chloro-3-(1,2,3,6-tetrahydropyridin-4-yl)-1H-indazol-1-yl)-2-fluoro-N-(methylsulfonyl)benzamide,
133) (E)-5-chloro-4-(5-chloro-3-styryl-1H-indazol-1-yl)-2-fluoro-N-(methylsulfonyl)benzamide,
134) (E)-5-chloro-4-(5-chloro-3-(2-(pyridin-2-yl)vinyl)-1H-indazol-1-yl)-2-fluoro-N-(methylsulfonyl)benzamide,
135) (E)-5-chloro-4-(5-chloro-3-(2-fluorostyryl)-1H-indazol-1-yl)-2-fluoro-N-(methylsulfonyl)benzamide,
136) (E)-5-chloro-4-(5-chloro-3-(2-chlorostyryl)-1H-indazol-1-yl)-2-fluoro-N-(methylsulfonyl)benzamide,
137) (E)-5-chloro-4-(5-chloro-3-(4-(trifluoromethyl)styryl)-1H-indazol-1-yl)-2-fluoro-N-(methylsulfonyl)benzamide,
138) 5-chloro-4-(5-chloro-3-(4-chloro-2-fluorophenyl)-1H-indazol-1-yl)-N—(N,N-dimethylsulfamoyl)-2-fluorobenzamide,
139) 5-chloro-4-(5-chloro-3-(4-chloro-2-fluorophenyl)-1H-indazol-1-yl)-2-fluoro-N-methyl-N-(methylsulfonyl)benzamide,
140) 5-chloro-4-(3-chloro-5-hydroxy-1H-indazol-1-yl)-2-fluoro-N-(methylsulfonyl)-N-(naphthalen-2-ylmethyl)benzamide,
141) 5-chloro-4-(3-chloro-5-hydroxy-1H-indazol-1-yl)-2-fluoro-N-(4-fluorobenzyl)-N-(methylsulfonyl)benzamide,
142) 5-chloro-4-(3-(4-chloro-2-fluorophenyl)-5-fluoro-1H-indazol-1-yl)-2-fluoro-N-(methylsulfonyl)benzamide,
143) 5-chloro-2-fluoro-4-(5-fluoro-3-(2-fluorophenyl)-1H-indazol-1-yl)-N-(methylsulfonyl)benzamide,
144) 5-chloro-4-(3-(2-chlorophenyl)-5-fluoro-1H-indazol-1-yl)-2-fluoro-N-(methylsulfonyl)benzamide,
145) 5-chloro-2-fluoro-4-(5-fluoro-3-(2-(trifluoromethyl)phenyl)-1H-indazol-1-yl)-N-(methylsulfonyl)benzamide,
146) 5-chloro-2-fluoro-4-(5-fluoro-3-(2-methoxyphenyl)-1H-indazol-1-yl)-N-(methylsulfonyl)benzamide,
147) 5-chloro-2-fluoro-4-(5-fluoro-3-(o-tolyl)-1H-indazol-1-yl)-N-(methylsulfonyl)benzamide,
148) 5-chloro-2-fluoro-4-(5-fluoro-3-(3-fluorophenyl)-1H-indazol-1-yl)-N-(methylsulfonyl)benzamide,
149) 5-chloro-4-(3-(3-chlorophenyl)-5-fluoro-1H-indazol-1-yl)-2-fluoro-N-(methylsulfonyl)benzamide,
150) 5-chloro-2-fluoro-4-(5-fluoro-3-(3-(trifluoromethyl)phenyl)-1H-indazol-1-yl)-N-(methylsulfonyl)benzamide,
151) 5-chloro-2-fluoro-4-(5-fluoro-3-(3-methoxyphenyl)-1H-indazol-1-yl)-N-(methylsulfonyl)benzamide,
152) 5-chloro-2-fluoro-4-(5-fluoro-3-(m-tolyl)-1H-indazol-1-yl)-N-(methylsulfonyl)benzamide,
153) 5-chloro-2-fluoro-4-(5-fluoro-3-(4-fluorophenyl)-1H-indazol-1-yl)-N-(methylsulfonyl)benzamide,
154) 5-chloro-4-(3-(4-chlorophenyl)-5-fluoro-1H-indazol-1-yl)-2-fluoro-N-(methylsulfonyl)benzamide,
155) 5-chloro-2-fluoro-4-(5-fluoro-3-(4-methoxyphenyl)-1H-indazol-1-yl)-N-(methylsulfonyl)benzamide,
156) 5-chloro-2-fluoro-4-(5-fluoro-3-(p-tolyl)-1H-indazol-1-yl)-N-(methylsulfonyl)benzamide,
157) 5-chloro-4-(3-(3-chloro-5-fluorophenyl)-5-fluoro-1H-indazol-1-yl)-2-fluoro-N-(methylsulfonyl)benzamide,
158) 5-chloro-4-(3-(2-chloro-4-fluorophenyl)-5-fluoro-1H-indazol-1-yl)-2-fluoro-N-(methylsulfonyl)benzamide,
159) 5-chloro-4-(3-(2,4-difluorophenyl)-5-fluoro-1H-indazol-1-yl)-2-fluoro-N-(methylsulfonyl)benzamide,
160) 5-chloro-4-(3-(2,5-difluorophenyl)-5-fluoro-1H-indazol-1-yl)-2-fluoro-N-(methylsulfonyl)benzamide,
161) 5-chloro-4-(3-(3,4-difluorophenyl)-5-fluoro-1H-indazol-1-yl)-2-fluoro-N-(methylsulfonyl)benzamide,
162) 5-chloro-4-(3-(2-chloro-6-fluorophenyl)-5-fluoro-1H-indazol-1-yl)-2-fluoro-N-(methylsulfonyl)benzamide,
163) 5-chloro-4-(3-(3-chloro-2-fluorophenyl)-5-fluoro-1H-indazol-1-yl)-2-fluoro-N-(methylsulfonyl)benzamide,
164) 5-chloro-4-(3-(4-chloro-3-fluorophenyl)-5-fluoro-1H-indazol-1-yl)-2-fluoro-N-(methylsulfonyl)benzamide,
165) 5-chloro-2-fluoro-4-(5-fluoro-3-(pyridin-3-yl)-1H-indazol-1-yl)-N-(methylsulfonyl)benzamide,
166) 5-chloro-4-(3-(3-cyanophenyl)-5-fluoro-1H-indazol-1-yl)-2-fluoro-N-(methylsulfonyl)benzamide,
167) 3-cyano-4-(5-fluoro-3-(pyridin-3-yl)-1H-indazol-1-yl)-N-(methylsulfonyl)benzamide,
168) 3-cyano-4-(3-(3-cyanophenyl)-5-fluoro-1H-indazol-1-yl)-N-(methylsulfonyl)benzamide,
169) 5-chloro-4-(3-(4-chloro-2-fluorophenyl)-5-methoxy-1H-indazol-1-yl)-2-fluoro-N-(methylsulfonyl)benzamide,
170) 5-chloro-4-(3-(3-chlorophenyl)-1H-indazol-1-yl)-2-fluoro-N-(methylsulfonyl)benzamide,
171) 5-chloro-2-fluoro-4-(3-(3-fluorophenyl)-1H-indazol-1-yl)-N-(methylsulfonyl)benzamide,
172) 5-chloro-2-fluoro-N-(methylsulfonyl)-4-(3-(3-(trifluoromethyl)phenyl)-1H-indazol-1-yl)benzamide,
173) 5-chloro-2-fluoro-N-(methylsulfonyl)-4-(3-(o-tolyl)-1H-indazol-1-yl)benzamide,
174) 5-chloro-2-fluoro-4-(3-(2-methoxyphenyl)-1H-indazol-1-yl)-N-(methylsulfonyl)benzamide,
175) 5-chloro-4-(3-(2-chloro-4-fluorophenyl)-1H-indazol-1-yl)-2-fluoro-N-(methylsulfonyl)benzamide,
176) 5-chloro-4-(3-(2,4-difluorophenyl)-1H-indazol-1-yl)-2-fluoro-N-(methylsulfonyl)benzamide, 177) 5-chloro-2-fluoro-4-(3-(4-fluoropyridin-3-yl)-1H-indazol-1-yl)-N-(methylsulfonyl)benzamide,
178) 5-chloro-2-fluoro-N-(methylsulfonyl)-4-(3-(4-(trifluoromethyl)phenyl)-1H-indazol-1-yl)benzamide,
179) 5-chloro-2-fluoro-4-(3-(4-fluorophenyl)-1H-indazol-1-yl)-N-(methylsulfonyl)benzamide,
180) 5-chloro-2-fluoro-N-(methylsulfonyl)-4-(3-(pyridin-3-yl)-1H-indazol-1-yl)benzamide,
181) 5-chloro-4-(3-(3-cyanophenyl)-1H-indazol-1-yl)-2-fluoro-N-(methylsulfonyl)benzamide,
182) 3-cyano-N-(methylsulfonyl)-4-(3-(pyridin-3-yl)-1H-indazol-1-yl)benzamide,
183) 3-cyano-4-(3-(3-cyanophenyl)-1H-indazol-1-yl)-N-(methylsulfonyl)benzamide,
184) 5-chloro-4-(3-(4-chloro-2-fluorophenyl)-1H-indazol-1-yl)-2-fluoro-N-(methylsulfonyl)benzamide,
185) 5-chloro-4-(5-chloro-3-(4-fluorophenyl)-1H-pyrrolo[2,3-b]pyridin-1-yl)-2-fluoro-N-(methylsulfonyl)benzamide,
186) 5-chloro-4-(5-chloro-3-(2,4-difluorophenyl)-1H-pyrrolo[2,3-b]pyridin-1-yl)-2-fluoro-N-(methylsulfonyl)benzamide,
187) 5-chloro-4-(5-chloro-3-(4-cyanophenyl)-1H-pyrrolo[2,3-b]pyridin-1-yl)-2-fluoro-N-(methylsulfonyl)benzamide,
188) 5-chloro-4-(5-chloro-3-(4-(trifluoromethyl)phenyl)-1H-pyrrolo[2,3-b]pyridin-1-yl)-2-fluoro-N-(methylsulfonyl)benzamide,
189) 5-chloro-4-(5-chloro-3-(4-chloro-2-fluorophenyl)-1H-pyrrolo[2,3-b]pyridin-1-yl)-2-fluoro-N-(methylsulfonyl)benzamide,
190) 5-chloro-4-(5-chloro-3-(3-fluorophenyl)-1H-pyrrolo[2,3-b]pyridin-1-yl)-2-fluoro-N-(methylsulfonyl)benzamide,
191) 5-chloro-4-(5-chloro-3-(2-fluorophenyl)-1H-pyrrolo[2,3-b]pyridin-1-yl)-2-fluoro-N-(methylsulfonyl)benzamide,
192) 5-chloro-4-(5-chloro-3-(3-(trifluoromethyl)phenyl)-1H-pyrrolo[2,3-b]pyridin-1-yl)-2-fluoro-N-(methylsulfonyl)benzamide,
193) 5-chloro-4-(5-chloro-3-(2-(trifluoromethyl)phenyl)-1H-pyrrolo[2,3-b]pyridin-1-yl)-2-fluoro-N-(methylsulfonyl)benzamide,
194) 5-chloro-4-(5-chloro-3-(3-cyanophenyl)-1H-pyrrolo[2,3-b]pyridin-1-yl)-2-fluoro-N-(methylsulfonyl)benzamide,
195) 5-chloro-4-(5-chloro-3-(4-chlorophenyl)-1H-pyrrolo[2,3-b]pyridin-1-yl)-2-fluoro-N-(methylsulfonyl)benzamide,
196) 5-chloro-4-(5-chloro-3-(4-methoxyphenyl)-1H-pyrrolo[2,3-b]pyridin-1-yl)-2-fluoro-N-(methylsulfonyl)benzamide,
197) 5-chloro-4-(5-chloro-3-(2-chloro-4-fluorophenyl)-1H-pyrrolo[2,3-b]pyridin-1-yl)-2-fluoro-N-(methylsulfonyl)benzamide,
198) 5-chloro-4-(5-chloro-3-(2-chlorophenyl)-1H-pyrrolo[2,3-b]pyridin-1-yl)-2-fluoro-N-(methylsulfonyl)benzamide,
199) 5-chloro-4-(5-chloro-3-(4-fluoro-2-methoxyphenyl)-1H-pyrrolo[2,3-b]pyridin-1-yl)-2-fluoro-N-(methylsulfonyl)benzamide,
200) 5-chloro-4-(5-chloro-3-(4-fluoro-2-methylphenyl)-1H-pyrrolo[2,3-b]pyridin-1-yl)-2-fluoro-N-(methylsulfonyl)benzamide,
201) 5-chloro-4-(3-(4-chloro-2-fluorophenyl)-5-fluoro-1H-pyrrolo[2,3-b]pyridin-1-yl)-2-fluoro-N-(methylsulfonyl)benzamide,
202) 5-chloro-4-(3-(2-chloro-4-fluorophenyl)-5-fluoro-1H-pyrrolo[2,3-b]pyridin-1-yl)-2-fluoro-N-(methylsulfonyl)benzamide,
203) 5-chloro-4-(3-(2,4-difluorophenyl)-5-fluoro-1H-pyrrolo[2,3-b]pyridin-1-yl)-2-fluoro-N-(methylsulfonyl)benzamide,
204) 5-chloro-4-(3-(4-chlorophenyl)-5-fluoro-1H-pyrrolo[2,3-b]pyridin-1-yl)-2-fluoro-N-(methylsulfonyl)benzamide,
205) 5-chloro-2-fluoro-4-(5-fluoro-3-(4-(trifluoromethyl)phenyl)-1H-pyrrolo[2,3-b]pyridin-1-yl)-N-(methylsulfonyl)benzamide,
206) 5-chloro-2-fluoro-4-(5-fluoro-3-(4-fluorophenyl)-1H-pyrrolo[2,3-b]pyridin-1-yl)-N-(methylsulfonyl)benzamide,
207) 5-chloro-4-(3-(2-chlorophenyl)-5-fluoro-1H-pyrrolo[2,3-b]pyridin-1-yl)-2-fluoro-N-(methylsulfonyl)benzamide,
208) 5-chloro-4-(3-(3-chlorophenyl)-5-fluoro-1H-pyrrolo[2,3-b]pyridin-1-yl)-2-fluoro-N-(methylsulfonyl)benzamide,
209) 5-chloro-4-(3-(2,4-dichlorophenyl)-5-fluoro-1H-pyrrolo[2,3-b]pyridin-1-yl)-2-fluoro-N-(methylsulfonyl)benzamide,
210) 5-chloro-4-(3-(4-chloro-3-fluorophenyl)-5-fluoro-1H-pyrrolo[2,3-b]pyridin-1-yl)-2-fluoro-N-(methylsulfonyl)benzamide,
211) 5-chloro-4-(3-(3-chloro-2-fluorophenyl)-5-fluoro-1H-pyrrolo[2,3-b]pyridin-1-yl)-2-fluoro-N-(methylsulfonyl)benzamide,
212) 5-chloro-2-fluoro-4-(5-fluoro-3-(4-fluoro-2-methylphenyl)-1H-pyrrolo[2,3-b]pyridin-1-yl)-N-(methylsulfonyl)benzamide,
213) 5-chloro-2-fluoro-4-(3-(2-fluorophenyl)-1H-pyrrolo[2,3-b]pyridin-1-yl)-N-(methylsulfonyl)benzamide,
214) 5-chloro-2-fluoro-4-(3-(3-fluorophenyl)-1H-pyrrolo[2,3-b]pyridin-1-yl)-N-(methylsulfonyl)benzamide,
215) 5-chloro-2-fluoro-N-(methylsulfonyl)-4-(3-(m-tolyl)-1H-pyrrolo[2,3-b]pyridin-1-yl)benzamide,
216) 5-chloro-2-fluoro-N-(methylsulfonyl)-4-(3-(2-(trifluoromethyl)phenyl)-1H-pyrrolo[2,3-b]pyridin-1-yl)benzamide,
217) 5-chloro-2-fluoro-N-(methylsulfonyl)-4-(3-(3-(trifluoromethyl)phenyl)-1H-pyrrolo[2,3-b]pyridin-1-yl)benzamide,
218) 5-chloro-2-fluoro-N-(methylsulfonyl)-4-(3-(4-(trifluoromethyl)phenyl)-1H-pyrrolo[2,3-b]pyridin-1-yl)benzamide,
219) 5-chloro-4-(3-(5-chloro-2-fluorophenyl)-1H-pyrrolo[2,3-b]pyridin-1-yl)-2-fluoro-N-(methylsulfonyl)benzamide,
220) 5-chloro-4-(3-(3-chloro-5-fluorophenyl)-1H-pyrrolo[2,3-b]pyridin-1-yl)-2-fluoro-N-(methylsulfonyl)benzamide,
221) 5-chloro-4-(3-(3-chlorophenyl)-1H-pyrrolo[2,3-b]pyridin-1-yl)-2-fluoro-N-(methylsulfonyl)benzamide,
222) 5-chloro-4-(3-(3-chloro-2-fluorophenyl)-1H-pyrrolo[2,3-b]pyridin-1-yl)-2-fluoro-N-(methylsulfonyl)benzamide,
223) 5-chloro-4-(3-(4-chloro-3-fluorophenyl)-1H-pyrrolo[2,3-b]pyridin-1-yl)-2-fluoro-N-(methylsulfonyl)benzamide,
224) 5-chloro-4-(3-(4-chlorophenyl)-1H-pyrrolo[2,3-b]pyridin-1-yl)-2-fluoro-N-(methylsulfonyl)benzamide,
225) 5-chloro-4-(3-(2-chlorophenyl)-1H-pyrrolo[2,3-b]pyridin-1-yl)-2-fluoro-N-(methylsulfonyl)benzamide, 226) 5-chloro-2-fluoro-4-(3-(4-fluorophenyl)-1H-pyrrolo[2,3-b]pyridin-1-yl)-N-(methylsulfonyl)benzamide,
227) 5-chloro-4-(3-(4-chloro-2-fluorophenyl)-1H-pyrrolo[2,3-b]pyridin-1-yl)-2-fluoro-N-(methylsulfonyl)benzamide,
228) 5-chloro-4-(3-(2-chloro-4-fluorophenyl)-1H-pyrrolo[2,3-b]pyridin-1-yl)-2-fluoro-N-(methylsulfonyl)benzamide,
229) 5-chloro-4-(3-(2,4-difluorophenyl)-1H-pyrrolo[2,3-b]pyridin-1-yl)-2-fluoro-N-(methylsulfonyl)benzamide,
230) 5-chloro-4-(3-chloro-5-phenyl-1H-indazol-1-yl)-2-fluoro-N-(methylsulfonyl)benzamide,
231) 5-chloro-4-(3-chloro-5-(pyridin-3-yl)-1H-indazol-1-yl)-2-fluoro-N-(methylsulfonyl)benzamide,
232) 5-chloro-4-(3-chloro-5-(pyridin-4-yl)-1H-indazol-1-yl)-2-fluoro-N-(methylsulfonyl)benzamide,
233) 5-chloro-4-(3-chloro-5-(m-tolyl)-1H-indazol-1-yl)-2-fluoro-N-(methylsulfonyl)benzamide,
234) 5-chloro-4-(3-chloro-5-(2-fluorophenyl)-1H-indazol-1-yl)-2-fluoro-N-(methylsulfonyl)benzamide,
235) 5-chloro-4-(3-chloro-5-(3-fluorophenyl)-1H-indazol-1-yl)-2-fluoro-N-(methylsulfonyl)benzamide,
236) 5-chloro-4-(3-chloro-5-(4-fluorophenyl)-1H-indazol-1-yl)-2-fluoro-N-(methylsulfonyl)benzamide,
237) 5-chloro-4-(3-chloro-5-(2-cyanophenyl)-1H-indazol-1-yl)-2-fluoro-N-(methylsulfonyl)benzamide,
238) 5-chloro-4-(3-chloro-5-(5-cyano-2-fluorophenyl)-1H-indazol-1-yl)-2-fluoro-N-(methylsulfonyl)benzamide,
239) 5-chloro-4-(3-chloro-5-(3-cyano-4-fluorophenyl)-1H-indazol-1-yl)-2-fluoro-N-(methylsulfonyl)benzamide,
240) 5-chloro-4-(3-chloro-5-(4-cyanophenyl)-1H-indazol-1-yl)-2-fluoro-N-(methylsulfonyl)benzamide,
241) 5-chloro-4-(3-chloro-5-(pyrimidin-5-yl)-1H-indazol-1-yl)-2-fluoro-N-(methylsulfonyl)benzamide,
242) 5-chloro-4-(3-chloro-5-(5-chloropyridin-3-yl)-1H-indazol-1-yl)-2-fluoro-N-(methylsulfonyl)benzamide,
243) 5-chloro-4-(3-chloro-5-(2,4-difluorophenyl)-1H-indazol-1-yl)-2-fluoro-N-(methylsulfonyl)benzamide,
244) 5-chloro-4-(3-chloro-5-(2-fluoropyridin-3-yl)-1H-indazol-1-yl)-2-fluoro-N-(methylsulfonyl)benzamide,
245) 5-chloro-4-(3-chloro-5-(6-fluoropyridin-3-yl)-1H-indazol-1-yl)-2-fluoro-N-(methylsulfonyl)benzamide,
246) 5-chloro-4-(3-chloro-5-(2,6-difluoropyridin-3-yl)-1H-indazol-1-yl)-2-fluoro-N-(methylsulfonyl)benzamide,
247) 5-chloro-4-(3-chloro-5-(4-chloro-2-fluorophenyl)-1H-indazol-1-yl)-2-fluoro-N-(methylsulfonyl)benzamide,
248) 5-chloro-4-(3-chloro-5-(4-methoxyphenyl)-1H-indazol-1-yl)-2-fluoro-N-(methylsulfonyl)benzamide,
249) 5-chloro-4-(3-chloro-5-(3-(trifluoromethyl)phenyl)-1H-indazol-1-yl)-2-fluoro-N-(methylsulfonyl)benzamide,
250) 5-chloro-4-(3-chloro-5-(2-(trifluoromethyl)phenyl)-1H-indazol-1-yl)-2-fluoro-N-(methylsulfonyl)benzamide,
251) 5-chloro-4-(3-chloro-5-(4-(trifluoromethyl)phenyl)-1H-indazol-1-yl)-2-fluoro-N-(methylsulfonyl)benzamide,
252) 5-chloro-4-(3-chloro-5-(2-chlorophenyl)-1H-indazol-1-yl)-2-fluoro-N-(methylsulfonyl)benzamide,
253) 5-chloro-4-(3-chloro-5-(4-chloro-2-methylphenyl)-1H-indazol-1-yl)-2-fluoro-N-(methylsulfonyl)benzamide,
254) 5-chloro-4-(3-chloro-5-(5-chloro-2-fluorophenyl)-1H-indazol-1-yl)-2-fluoro-N-(methylsulfonyl)benzamide,
255) 5-chloro-4-(3-chloro-5-(4-chlorophenyl)-1H-indazol-1-yl)-2-fluoro-N-(methylsulfonyl)benzamide,
256) 5-chloro-4-(3-chloro-5-(1-methyl-1H-pyrazol-5-yl)-1H-indazol-1-yl)-2-fluoro-N-(methylsulfonyl)benzamide,
257) 5-chloro-4-(3-chloro-5-(4-fluorophenyl)-1H-pyrrolo[2,3-b]pyridin-1-yl)-2-fluoro-N-(methylsulfonyl)benzamide,
258) 5-chloro-4-(3-chloro-5-(4-cyanophenyl)-1H-pyrrolo[2,3-b]pyridin-1-yl)-2-fluoro-N-(methylsulfonyl)benzamide,
259) 5-chloro-4-(3-chloro-5-(4-chlorophenyl)-1H-pyrrolo[2,3-b]pyridin-1-yl)-2-fluoro-N-(methylsulfonyl)benzamide,
260) 5-chloro-4-(3-chloro-5-(4-methoxyphenyl)-1H-pyrrolo[2,3-b]pyridin-1-yl)-2-fluoro-N-(methylsulfonyl)benzamide,
261) 5-chloro-4-(3-chloro-5-(4-(trifluoromethyl)phenyl)-1H-pyrrolo[2,3-b]pyridin-1-yl)-2-fluoro-N-(methylsulfonyl)benzamide,
262) 5-chloro-4-(3-chloro-5-(3-fluorophenyl)-1H-pyrrolo[2,3-b]pyridin-1-yl)-2-fluoro-N-(methylsulfonyl)benzamide,
263) 5-chloro-4-(3-chloro-6-phenyl-1H-indazol-1-yl)-2-fluoro-N-(methylsulfonyl)benzamide,
264) 5-chloro-4-(3,5-diphenyl-1H-indazol-1-yl)-2-fluoro-N-(methylsulfonyl)benzamide,
265) 5-chloro-1-(2-chloro-5-fluoro-4-((methylsulfonyl)carbamoyl)phenyl)-1H-indole-3-carboxylic acid,
266) 5-chloro-4-(3,5-dichloro-1H-indol-1-yl)-2-fluoro-N-(methylsulfonyl)benzamide,
267) 5-chloro-4-(3,4-dichloro-5-hydroxy-1H-indol-1-yl)-2-fluoro-N-(methylsulfonyl)benzamide,
268) 5-chloro-4-(3-chloro-5-methoxy-1H-indol-1-yl)-2-fluoro-N-(methylsulfonyl)benzamide,
269) 4-(5-(benzyloxy)-3-chloro-1H-indol-1-yl)-5-chloro-2-fluoro-N-(methylsulfonyl)benzamide,
270) 4-(4-(benzyloxy)-3-chloro-1H-indol-1-yl)-5-chloro-2-fluoro-N-(methylsulfonyl)benzamide,
271) 4-(6-(benzyloxy)-3-chloro-1H-indol-1-yl)-5-chloro-2-fluoro-N-(methylsulfonyl)benzamide,
272) 5-chloro-4-(5-chloro-3-(4-chlorophenyl)-1H-indol-1-yl)-2-fluoro-N-(methylsulfonyl)benzamide,
273) 5-chloro-4-(5-chloro-3-(6-chloropyridin-3-yl)-1H-indol-1-yl)-2-fluoro-N-(methylsulfonyl)benzamide,
274) 6-(5-chloro-3-(4-chlorophenyl)-1H-indol-1-yl)-N-(methylsulfonyl)nicotinamide,
275) 6-(5-chloro-3-(4-fluorophenyl)-1H-indol-1-yl)-N-(methylsulfonyl)nicotinamide,
276) 5-chloro-4-(3-chloro-5-phenyl-1H-indazol-1-yl)-2-fluoro-N-(thiazol-4-yl)benzenesulfonamide,
277) 5-chloro-4-(5-chloro-3-methyl-1H-indazol-1-yl)-2-fluoro-N-(thiazol-4-yl)benzenesulfonamide,
278) 4-(3-chloro-5-(trifluoromethyl)-1H-indazol-1-yl)-3-cyano-N-(thiazol-4-yl)benzenesulfonamide,
279) 4-(3-chloro-5-(trifluoromethyl)-1H-indazol-1-yl)-2,5-difluoro-N-(thiazol-4-yl)benzenesulfonamide,
280) 5-chloro-4-(3-chloro-5-(trifluoromethyl)-1H-indazol-1-yl)-2-fluoro-N-(thiazol-4-yl)benzenesulfonamide,
281) 4-(3-chloro-5-(trifluoromethyl)-1H-indazol-1-yl)-2,5-difluoro-N-(1,2,4-thiadiazol-5-yl)benzenesulfonamide,
282) 5-chloro-4-(5-chloro-3-(1-methyl-1H-pyrazol-5-yl)-1H-indazol-1-yl)-2-fluoro-N-(thiazol-4-yl)benzenesulfonamide, 283) 5-chloro-4-(5-chloro-3-(1-methyl-1H-pyrazol-5-yl)-1H-indazol-1-yl)-2-fluoro-N-(1,2,4-thiadiazol-5-yl)benzenesulfonamide,
284) 5-chloro-4-(5-chloro-3-(1H-pyrazol-4-yl)-1H-indazol-1-yl)-2-fluoro-N-(thiazol-4-yl)benzenesulfonamide,
285) 5-chloro-2-fluoro-4-(5-(1-methyl-1H-pyrazol-5-yl)-1H-indazol-1-yl)-N-(thiazol-4-yl)benzenesulfonamide,
286) 5-chloro-4-(3-chloro-5-(1-methyl-1H-pyrazol-5-yl)-1H-indazol-1-yl)-2-fluoro-N-(thiazol-4-yl)benzenesulfonamide,
287) 5-chloro-4-(5-chloro-3-(4-chloro-2-fluorophenyl)-1H-indazol-1-yl)-2-fluoro-N-(thiazol-4-yl)benzenesulfonamide,
288) 5-chloro-4-(5-chloro-3-(4-chloro-2-fluorophenyl)-1H-indazol-1-yl)-2-fluorobenzonitrile,
289) 5-chloro-3-(4-chloro-2-fluorophenyl)-1-(2-chloro-5-fluoro-4-(1H-tetrazol-5-yl)phenyl)-1H-indazole,
290) 2-(5-chloro-4-(5-chloro-3-(4-chloro-2-fluorophenyl)-1H-indazol-1-yl)-2-fluorobenzoyl)hydrazine-1-carboxamide,
291) 5-(5-chloro-4-(5-chloro-3-(4-chloro-2-fluorophenyl)-1H-indazol-1-yl)-2-fluorophenyl)-2,4-dihydro-3H-1,2,4-triazol-3-one,
292) 5-chloro-4-(5-chloro-3-(4-chloro-2-fluorophenyl)-1H-indazol-1-yl)-2-fluorobenzamide,
293) N-acetyl-5-chloro-4-(5-chloro-3-(4-chloro-2-fluorophenyl)-1H-indazol-1-yl)-2-fluorobenzamide,
294) 5-chloro-4-(5-chloro-3-(4-chloro-2-fluorophenyl)-1H-indazol-1-yl)-2-fluoro-N-(thiazol-2-yl)benzamide,
295) 5-chloro-4-(5-chloro-3-(4-chloro-2-fluorophenyl)-1H-indazol-1-yl)-2-fluoro-N-(5-methylthiazol-2-yl)benzamide, and
296) ethyl 2-(5-chloro-4-(5-chloro-3-(4-chloro-2-fluorophenyl)-1H-indazol-1-yl)-2-fluorobenzamido)thiazole-5-carboxylate.

In addition, as an example, the present invention provides a method for preparing a compound represented by Formula 1 as shown in the following Reaction Scheme 1:

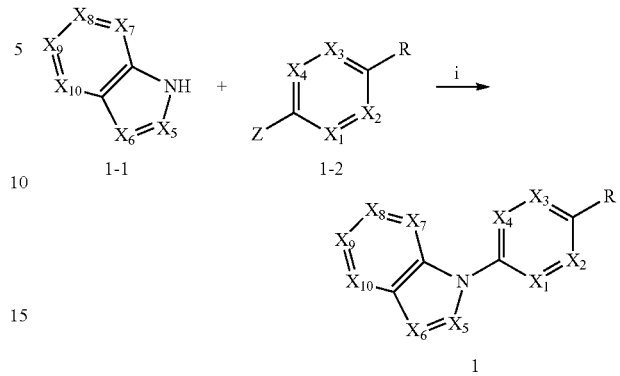

(In the above Scheme 1, $X_1$ to $X_{10}$ and R are as defined above, and Z is halogen. Preferably, Z is fluoro.)

In the reaction shown in the Reaction Scheme 1, a compound represented by Formula 1-1 is allowed to react with a compound represented by Formula 1-2. The reaction is preferably carried out in the presence of cesium carbonate at room temperature to elevated temperature, and the solvent for the reaction is preferably dimethylformamide.

Further, as an example, if $X_6$ in the Formula 1 is C—$R_e$, there is provided a method for preparing a compound represented by Formula 2 as shown in Reaction Scheme 2 below:

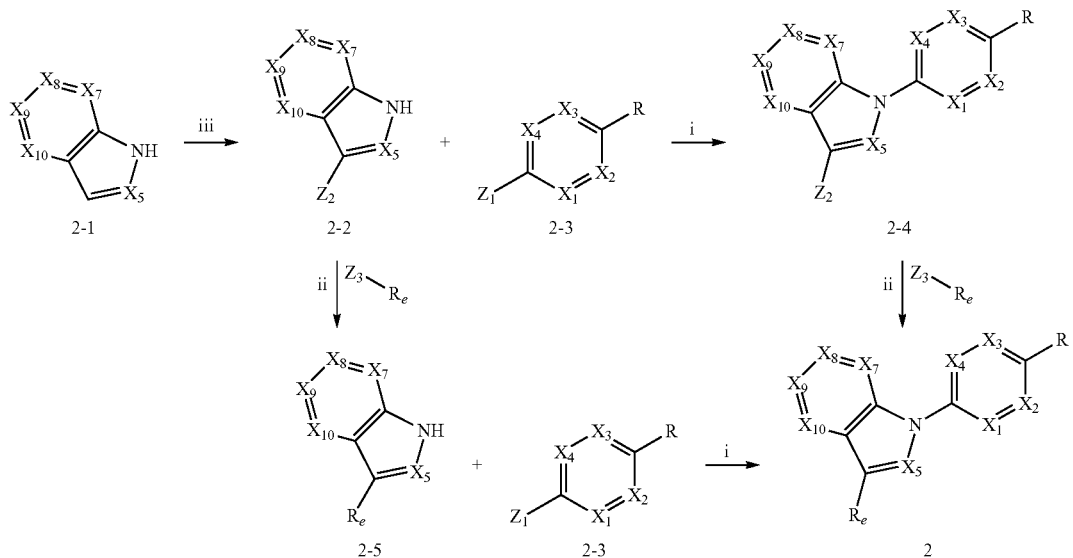

(In the above Scheme 2, $X_1$ to $X_5$, $X_7$ to $X_{10}$, R and $R_e$ are as defined above, $Z_1$ and $Z_2$ are halogen, preferably $Z_1$ is fluoro and $Z_2$ is bromo or iodo. $Z_3$ is metal or boron group.)

The above step iii refers to a step of preparing a compound represented by Formula 2-2 from a compound represented by Formula 2-1. The above reaction is carried out preferably in the presence of N-halogen succinimide or sodium hypochlorite at 0° C. to room temperature, and dibenzoyl peroxide can be used as an additive. A solvent for the reaction is preferably tetrahydrofuran, methylene chloride, and dimethylformamide.

In accordance with the above steps i and ii, it is possible to prepare the compounds represented by Formula 2-4 or Formula 2-5 as intermediates. Step i is the same as described in the Reaction Scheme 1, and step ii is carried out preferably under basic conditions at 50° C. to 180° C. in the presence of unsubstituted or substituted metal or boron group suitable for cross-coupling, and a solvent for the reaction is preferably dioxane, tetrahydrofuran, dimethylformamide, and dimethyl sulfoxide.

Further, as an example, when $X_9$ in Formula 1 is C—$R_g$, there is provided a method for preparing a compound represented by Formula 3 as shown in the Reaction Scheme 3 below.

intermediate in the preparation of the compound represented by Formula 1, or a pharmaceutically acceptable salt or solvate thereof.

The compounds represented by Formula 1 according to the present invention include, in addition to pharmaceutically acceptable salts thereof, possible solvates and hydrates that may be prepared therefrom, as well as all possible stereoisomers. The solvates, hydrates and stereoisomers of the compounds represented by Formula 1 can prepared from the compounds represented by Formula 1 using conventional methods.

Further, the compounds represented by Formula 1 according to the present invention may be prepared in a crystalline or non-crystalline form. When the compound represented by Formula 1 is prepared in a crystalline form, it may optionally be hydrated or solvated. The present invention includes in its

[Reaction Scheme 3]

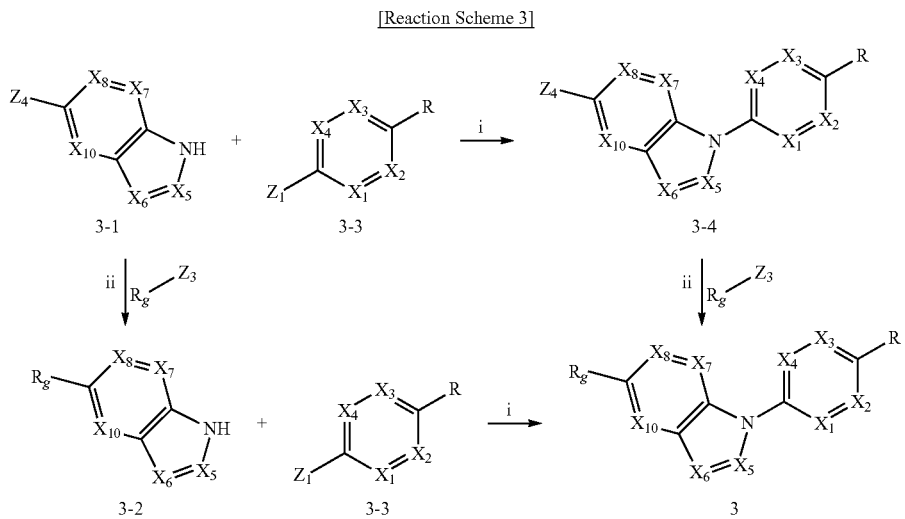

(In the above Scheme 3, R, $X_1$ to $X_9$ and $X_{10}$ are as defined above, $Z_1$ and $Z_4$ are halogen, preferably $Z_1$ is fluoro, $Z_4$ is bromo or iodo. $Z_3$ is metal or boron group. $R_g$ is alkyl, cycloalkyl, 5-membered or 6-membered heteroaryl, phenyl, preferably $R_g$ is phenyl.)

In accordance with the above steps i and ii, it is possible to prepare compounds represented by Formula 3-2 or Formula 3-4 as intermediates. Step i is the same as described in the Reaction Scheme 1, and step ii is carried out preferably under basic conditions at 50° C. to 180° C. in the presence of unsubstituted or substituted metal or boron group and palladium suitable for cross-coupling, and a solvent for the reaction is preferably dioxane, tetrahydrofuran, dimethylformamide, and dimethyl sulfoxide.

In addition, a pharmaceutically acceptable metal salt of the compound represented by Formula 1 can be obtained using a base by a conventional method. For example, a pharmaceutically acceptable metal salt of the compound represented by Formula 1 can be obtained by dissolving the compound represented by Formula 1 in an excess of an alkali metal hydroxide or alkaline earth metal hydroxide solution, filtering out undissolved compound salt, and then evaporating and drying the filtrate. Herein, the metal salt prepared is particularly preferably a sodium salt, a potassium salt or a calcium salt. These metal salts may be reacted with a suitable salt (e.g., nitrate).

A pharmaceutically unacceptable salt or solvate of the compound represented by Formula 1 may be used as an scope stoichiometric hydrates of the compounds represented by Formula 1 as well as compounds containing variable amounts of water. Solvates of the compounds represented by Formula 1 according to the present invention include all stoichiometric solvates and non-stoichiometric solvates.

The present invention provides a pharmaceutical composition for preventing or treating diseases useful for a blocking activity against sodium ion channels, comprising the compound represented by Formula 1 or a pharmaceutically acceptable salt, hydrate, solvate or isomer thereof as an active ingredient. Herein, the diseases are selected from the group consisting of acute pain, chronic pain, neuropathic pain, postoperative pain, migraine, arthralgia, neuropathy, nerve injury, diabetic neuropathy, neuropathic disease, epilepsy, arrhythmia, myotonia, ataxia, multiple sclerosis, irritable bowel syndrome, urinary incontinence, visceral pain, depression, erythromelalgia, paroxysmal extreme pain disorder (PEPD), and the like.

The pharmaceutical composition according to the present invention can be formulated in oral or parenteral dosage forms in accordance with standard pharmaceutical practices. These formulations may contain, in addition to the active ingredient, additives such as a pharmaceutically acceptable carrier, adjuvant or diluent. Examples of suitable carriers include, but are not limited to, physiological saline, polyethylene glycol, ethanol, vegetable oil, isopropyl myristate or the like, and examples of suitable diluents include, but are not limited to, lactose, dextrose, sucrose, mannitol, sorbitol, cellulose and/or glycine or the like. In addition, the compounds of the present invention can be dissolved in oil, propylene glycol or other solvents which are typically used in the preparation of injectable solutions. Further, the compounds of the present invention may be formulated into ointment or cream for topical application.

Hereinafter, the formulation methods and excipients will be described, but the invention are not limited to these examples.

The pharmaceutical dosage forms of the compounds of the present invention can also be used in the form of a pharmaceutically acceptable salt or solvate thereof and they can be used alone or in combination with other pharmaceutically active compounds, as well as in appropriate association.

The compounds of the present invention can be formulated into injections by dissolving, suspending or emulsifying the compounds in aqueous solvents such as common physiological saline or 5% dextrine, or in non-aqueous solvents such as synthetic fatty acid glycerides, higher fatty acid esters or propylene glycol. The formulation of the present invention may include conventional additives such as solubilizers, isotonic agents, suspending agents, emulsifying agents, stabilizers and preservatives.

The preferred dose of the compounds according to the present invention varies depending on patient's condition and weight, the severity of the disease, the form of drug, and the route and duration of administration, but it may be suitably selected by those skilled in the art. However, to achieve the desired effects, the compounds of the present invention may be administered at a daily dose of 0.0001 to 100 mg/kg (body weight), and preferably 0.001 to 100 mg/kg (body weight). The compounds of the present invention may be administrated by an oral or parenteral route in a single dose or multiple doses daily.

The compounds according to the present invention may be contained in an amount of 0.001 to 99% by weight and preferably 0.01 to 60% by weight, depending on the mode of administration.

The pharmaceutical composition according to the present invention may be administered to mammals, including rats, mice, domestic animals and humans by a variety of routes. All routes of administration may be contemplated, and for example, the composition can be administered orally, rectally or by intravenous, intramuscular, subcutaneous, intrauterine epidural or intracerbroventricular injection.

Advantageous Effects

As described above, the compound represented by Formula 1 or a pharmaceutically acceptable salt, hydrate, solvate or isomer thereof according to the present invention can be effectively used in the prevention or treatment of pains, for example, acute pain, chronic pain, neuropathic pain, postoperative pain, migraine, arthralgia, neuropathy, nerve injury, diabetic neuropathy, neuropathic disease, epilepsy, arrhythmia, myotonia, ataxia, multiple sclerosis, irritable bowel syndrome, urinary incontinence, visceral pain, depression, erythromelalgia, paroxysmal extreme pain disorder (PEPD).

DETAILED DESCRIPTION OF THE EMBODIMENTS

Hereinafter, the present invention will be described in more detail with reference to the following examples. However, it is to be understood that these examples are for illustrative purposes and are not intended to limit the scope of the present invention.

Example 1) Preparation of (5-chloro-4-(5-chloro-3-methyl-1H-indazol-1-yl)-2-fluoro-N-(methylsulfonyl)benzamide

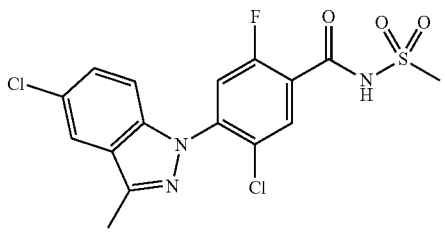 [SMILES: Cc1nn(-c2cc(F)c(C(=O)NS(C)(=O)=O)cc2Cl)c2ccc(Cl)cc12]

0.2 g (1.2 mmol) of 5-chloro-3-methyl-1H-indazole was dissolved in 10 mL of anhydrous N,N-dimethylformamide to which 0.78 g (2.4 mmol) of cesium carbonate and 0.32 g (1.2 mmol) of 5-chloro-2,4-difluoro-N-(methylsulfonyl)benzamide were added. The reaction mixture was stirred at 150° C. for 1 hour, and the organic layer was separated, treated with magnesium sulfate, filtered and then concentrated under reduced pressure. The residue was separated by column chromatography to give 0.15 g (30% yield) of the title compound.

1H NMR (MeOD) δ: 7.84 (s, 1H), 7.82-7.81 (d, 1H), 7.45-7.43 (d, 2H), 7.30-7.28 (d, 1H), 3.30 (s, 3H), 2.60 (s, 3H)

Example 6) Preparation of 4-(3-acetamido-5-chloro-1H-indazol-1-yl)-5-chloro-2-fluoro-N-(methylsulfonyl)benzamide

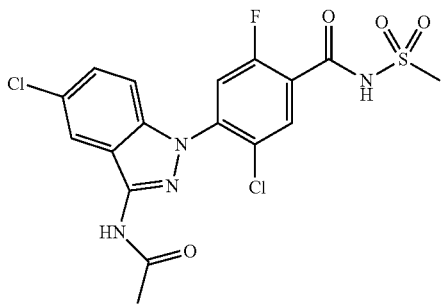 [SMILES: CC(=O)Nc1nn(-c2cc(F)c(C(=O)NS(C)(=O)=O)cc2Cl)c2ccc(Cl)cc12]

0.1 g (0.24 mmol) of 4-(3-amino-5-chloro-1H-indazol-1-yl)-5-chloro-2-fluoro-N-(methylsulfonyl)benzamide was dissolved in 5 mL of anhydrous tetrahydrofuran to which 0.018 g (0.24 mmol) of acetyl chloride was added. The reaction mixture was stirred at room temperature for 2 hours, and the organic layer was separated, treated with magnesium sulfate, filtered and then concentrated under reduced pressure. The residue was separated by column chromatography to give 0.033 g (30% yield) of the title compound.

1H NMR (MeOD) δ: 7.80-7.99 (d, 1H), 7.64-7.62 (d, 1H), 7.40-7.38 (d, 1H), 7.28-7.27 (d, 2H), 3.15 (s, 3H), 2.25 (s, 3H)

Example 24) Preparation of 5-chloro-4-(3-chloro-5-cyclopropyl-1H-indazol-1-yl)-2-fluoro-N-(methylsulfonyl)benzamide

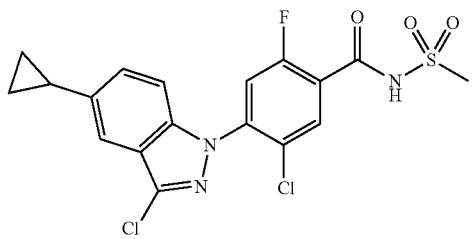 [SMILES: CS(=O)(=O)NC(=O)c1cc(Cl)c(-n2nc(Cl)c3cc(C4CC4)ccc32)cc1F]

25 mL of tetrahydrofuran was added to 1.0 g (7.0 mmol) of zinc(II) chloride under nitrogen conditions to which 4.0 mL (7.0 mmol, 1.7 M tetrahydrofuran) of cyclopropyl magnesium bromide was added, followed by stirring at room temperature for 30 minutes. The reaction mixture was added to 0.4 g (1.72 mmol) of 5-bromo-3-chloro-1H-indazole under nitrogen conditions, and then reacted with microwave reactor at 100° C. for 10 minutes. The organic layer was separated and concentrated under reduced pressure. The residue was separated by column chromatography to give 0.24 g (80% yield) of 3-chloro-5-cyclopropyl-1H-indazole.

1H NMR (MeOD) δ: 7.36 (d, 1H), 7.29 (s, 1H), 7.18 (d, 1H), 2.00 (m, 1H), 0.95 (d, 2H), 0.68 (d, 2H)

0.10 g (18% yield) of the title compound was prepared in the same manner as described in Example 1, except that 3-chloro-5-cyclopropyl-1H-indazole was used instead of 5-chloro-3-methyl-1H-indazole.

1H NMR (MeOH) δ: 8.01 (d, 1H), 7.44 (s, 2H), 7.31 (d, 1H), 7.23 (d, 1H), 3.21 (s, 3H), 2.00 (m, 1H), 1.02 (d, 2H), 0.76 (d, 2H)

Example 26) Preparation of 5-chloro-4-(5-cyclopropyl-3-phenyl-1H-indazol-1-yl)-2-fluoro-N-(methylsulfonyl)benzamide

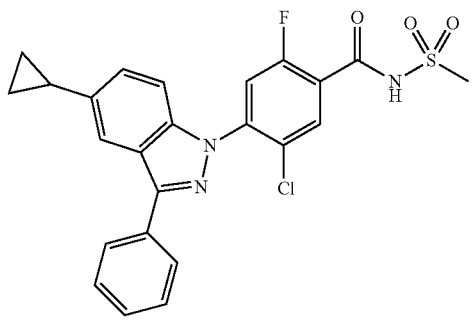 [SMILES: CS(=O)(=O)NC(=O)c1cc(Cl)c(-n2nc(-c3ccccc3)c3cc(C4CC4)ccc32)cc1F]

0.24 g (1.24 mmol) of 3-chloro-5-cyclopropyl-1H-indazole was dissolved in 4 mL of 1,4-dioxane and 2 mL of distilled water to which 0.40 g (3.72 mmol) of sodium carbonate, 0.14 g (0.12 mmol) of tetrakis(triphenyl phosphine)palladium(0) and 0.17 g (1.84 mmol) of phenylboronic acid were added. The reaction mixture was reacted with microwave reactor at 180° C. for 15 minutes, and the organic layer was separated, treated with magnesium sulfate, filtered and then concentrated under reduced pressure. The residue was separated by column chromatography to give 0.2 g (70% yield) of 5-cyclopropyl-3-phenyl-1H-indazole.

1H NMR (MeOD) δ: 7.89 (d, 2H), 7.69 (s, 1H), 7.50 (t, 2H), 7.42 (dd, 1H), 7.16 (d, 1H), 2.05 (m, 1H), 0.96 (d, 2H), 0.70 (d, 2H)

0.05 g (12% yield) of the title compound was prepared in the same manner as described in Example 1, except that 5-cyclopropyl-3-phenyl-1H-indazole was used instead of 5-chloro-3-methyl-1H-indazole.

1H NMR (MeOH) δ: 8.05 (d, 1H), 7.98 (d, 3H), 7.79 (s, 1H), 7.56 (t, 2H), 7.48 (t, 2H), 7.26 (s, 2H), 3.20 (s, 3H), 2.12 (m, 1H), 1.01 (d, 2H), 0.77 (d, 2H)

Example 28) Preparation of 4-(5-(benzyloxy)-3-chloro-1H-indazol-1-yl)-5-chloro-2-fluoro-N-(methylsulfonyl)benzamide

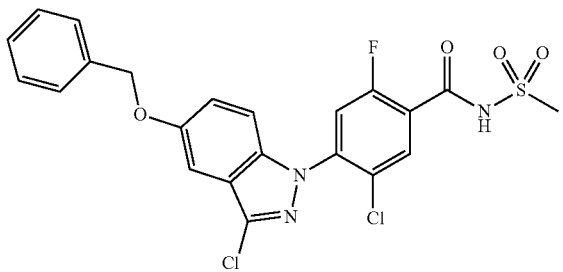 [SMILES: CS(=O)(=O)NC(=O)c1cc(Cl)c(-n2nc(Cl)c3cc(OCc4ccccc4)ccc32)cc1F]

0.50 g (2.23 mmol) of 5-(benzyloxy)-1H-indazole was dissolved in 100 mL of anhydrous tetrahydrofuran to which 0.30 g (2.23 mmol) of N-chlorosuccinimide was added. The reaction mixture was stirred at room temperature for 5 hours, and the organic layer was separated, treated with magnesium sulfate, filtered and then concentrated under reduced pressure. The residue was separated by column chromatography to give 0.40 g (69% yield) of 5-(benzyloxy)-3-chloro-1H-indazole.

1H NMR (MeOD) δ: 7.48-7.46 (d, 2H), 7.42 (d, 1H), 7.38 (t, 2H), 7.32 (d, 1H), 7.20-7.17 (m, 1H), 7.08 (s, 1H), 5.12 (s, 2H)

0.15 g (20% yield) of the title compound was prepared in the same manner as described in Example 1, except that 5-(benzyloxy)-3-chloro-1H-indazole was used instead of 5-chloro-3-methyl-1H-indazole.

1H NMR (MeOD) δ: 8.01-8.00 (d, 1H), 7.49-7.47 (d, 2H), 7.41-7.37 (m, 3H), 7.33 (t, 1H), 7.27 (s, 2H), 7.19 (s, 1H), 5.17 (s, 2H), 3.16 (s, 3H)

Example 29) Preparation of 4-(5-(benzyloxy)-4-chloro-1H-indazol-1-yl)-5-chloro-2-fluoro-N-(methylsulfonyl)benzamide

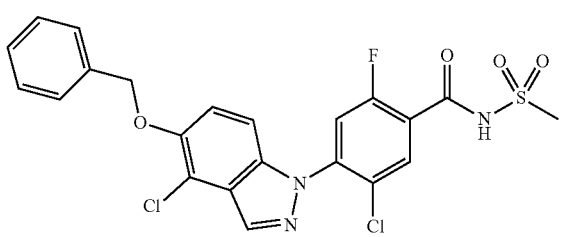 [SMILES: CS(=O)(=O)NC(=O)c1cc(Cl)c(-n2ncc3c(Cl)c(OCc4ccccc4)ccc32)cc1F]

0.50 g (2.96 mmol) of 4-chloro-1H-indazol-5-ol was dissolved in 100 mL of anhydrous tetrahydrofuran to which 0.82 g (5.92 mmol) of potassium carbonate and 0.62 g (3.55 mmol) of (bromomethyl) benzene were added. The reaction mixture was stirred at room temperature for 5 hours, and the organic layer was separated, treated with magnesium sulfate, filtered and then concentrated under reduced pressure. The residue was separated by column chromatography to give 0.46 g (60% yield) of 5-(benzyloxy)-4-chloro-1H-indazole.

1H NMR (MeOD) δ: 7.48 (d, 2H), 7.39-7.31 (m, 3H), 7.20 (d, 1H), 7.02 (d, 1H), 6.91 (s, 1H), 5.13 (s, 2H)

0.25 g (30% yield) of the title compound was prepared in the same manner as described in Example 1, except that 5-(benzyloxy)-4-chloro-1H-indazole was used instead of 5-chloro-3-methyl-1H-indazole.

1H NMR (MeOD) δ: 8.29 (s, 1H), 8.02-8.00 (d, 1H), 7.50-7.49 (d, 2H), 7.45-7.36 (m, 4H), 7.32-7.31 (d, 1H), 7.25-7.23 (d, 1H), 5.23 (s, 2H), 3.20 (s, 3H)

Example 31) Preparation of 5-chloro-4-(3,4-dichloro-5-((4-fluorobenzyl)oxy)-1H-indazol-1-yl)-2-fluoro-N-(methylsulfonyl) benzamide

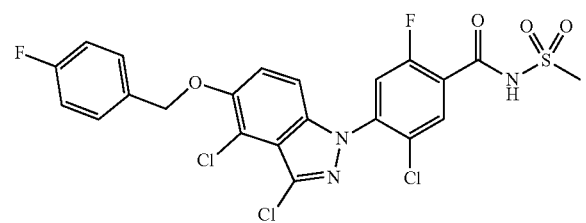 [SMILES: CS(=O)(=O)NC(=O)c1cc(Cl)c(-n2nc(Cl)c3c(Cl)c(OCc4ccc(F)cc4)ccc32)cc1F]

0.5 g (2.96 mmol) of 4-chloro-1H-indazol-5-ol was dissolved in 100 mL of anhydrous tetrahydrofuran to which 0.40 g (2.96 mmol) of N-chlorosuccinimide was added. The reaction mixture was stirred at room temperature for 5 hours, and the organic layer was separated, treated with magnesium sulfate, filtered and then concentrated under reduced pressure. The residue was separated by column chromatography to give 0.4 g (66% yield) of 3,4-dichloro-1H-indazol-5-ol.

1H NMR (MeOD) δ: 7.54 (d, 1H), 7.45 (d, 1H)

0.5 g (2.46 mmol) of 3,4-dichloro-1H-indazol-5-ol was dissolved in 100 mL of anhydrous tetrahydrofuran to which 0.68 g (4.92 mmol) of potassium carbonate and 0.55 g (2.95 mmol) of (bromomethyl) benzene were added. The reaction mixture was stirred at room temperature for 5 hours, and the organic layer was separated, treated with magnesium sulfate, filtered and then concentrated under reduced pressure. The residue was separated by column chromatography to give 0.5 g (65% yield) of 3,4-dichloro-5-((4-fluorobenzyl)oxy)-1H-indazole.

1H NMR (MeOD) δ: 8.00-7.99 (d, 1H), 7.89-7.86 (t, 2H), 7.54-7.51 (t, 2H), 7.47-7.45 (d, 1H), 7.42-7.40 (d, 1H), 7.23-7.21 (d, 1H), 7.13-7.09 (t, 3H), 5.20 (s, 2H), 3.12 (s, 3H)

0.25 g (28% yield) of the title compound was prepared in the same manner as described in Example 1, except that 3,4-dichloro-5-((4-fluorobenzyl)oxy)-1H-indazole was used instead of 5-chloro-3-methyl-1H-indazole.

1H NMR (MeOD) δ: 8.00-7.99 (d, 1H), 7.89-7.86 (t, 2H), 7.54-7.51 (t, 2H), 7.47-7.45 (d, 1H), 7.42-7.40 (d, 1H), 7.23-7.21 (d, 1H), 7.13-7.09 (t, 3H), 5.20 (s, 2H), 3.12 (s, 3H)

Example 47) Preparation of 5-chloro-4-(3-chloro-5-((6-fluoropyridin-3-yl)oxy)-1H-indazol-1-yl)-2-fluoro-N-(methylsulfonyl)benzamide

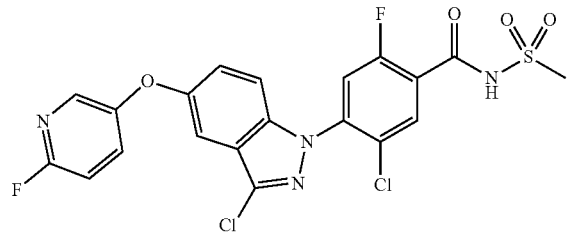 [SMILES: CS(=O)(=O)NC(=O)c1cc(Cl)c(-n2nc(Cl)c3cc(Oc4ccc(F)nc4)ccc32)cc1F]

0.70 g (2.61 mmol) of tert-butyl-3-chloro-5-hydroxy-indole-1-carboxylate was dissolved in 10 mL of N,N-dimethylformamide to which 0.55 g (3.12 mmol) of 5-bromo-2-fluoropyridine and 0.31 g (7.83 mmol) of sodium hydride (60%) were added. The reaction mixture was stirred at 150° C. for 3 hours, and the organic layer was separated, treated with magnesium sulfate, filtered and then concentrated under reduced pressure. The residue was separated by column chromatography to give 0.24 g (35% yield) of 3-chloro-5-((6-fluoropyridin-3-yl)-1H-indazole.

1H NMR (MeOD) δ: 8.17 (d, 1H), 7.94 (dd, 1H), 7.56 (d, 1H), 7.38 (m, 1H), 7.24 (dd, 1H), 6.96 (d, 1H)

0.20 g (0.76 mmol) of 3-chloro-5-((6-fluoropyridin-3-yl)oxy)-1H-indazole was dissolved in 20 mL of dimethylsulfoxide to which 0.25 g (0.91 mmol) of 5-chloro-2,4-difluoro-N-(methylsulfonyl)benzamide and 0.74 g (2.28 mmol) of cesium carbonate were added. The reaction mixture was stirred at 100° C. for 18 hours and then extracted with ethylacetate/distilled water. The organic layer was separated and then concentrated under reduced pressure. The residue was separated by column chromatography to give 0.17 g (43.7% yield) of the title compound.

1H NMR (MeOD) δ: 8.19 (s, 1H), 8.02 (d, 1H), 7.97 (d, 1H), 7.51 (s, 1H), 7.45 (d, 1H), 7.41 (m, 1H), 7.35 (m, 1H), 7.01 (d, 1H), 3.14 (s, 3H)

Example 48) Preparation of 5-chloro-4-(5-chloro-3-phenyl-1H-indazol-1-yl)-2-fluoro-N-(methylsulfonyl)benzamide

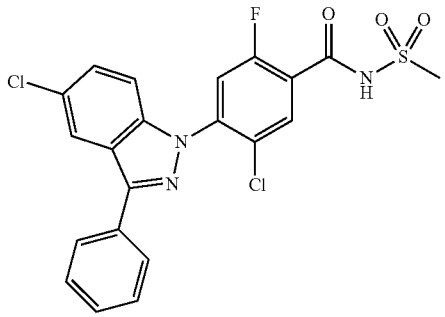 [SMILES: CS(=O)(=O)NC(=O)c1cc(Cl)c(-n2nc(-c3ccccc3)c3cc(Cl)ccc32)cc1F]

0.5 g (2.16 mmol) of 3-bromo-5-chloro-1H-indazole was dissolved in 4 mL of 1,4-dioxane and 2 mL of distilled water to which 0.68 g (6.48 mmol) of sodium carbonate, 0.25 g (0.21 mmol) of tetrakis(triphenyl phosphine)palladium(0) and 0.39 g (3.24 mmol) of phenylboronic acid were added.

After reacting with microwave reactor at 150° C. for 30 minutes, the organic layer was separated, treated with magnesium sulfate, filtered and then concentrated under reduced pressure. The residue was separated by column chromatography to give 0.4 g (81% yield) of 5-chloro-3-phenyl-1H-indazole.

1H NMR (MeOD) δ: 7.93 (s, 1H), 7.86 (d, 2H), 7.52-7.47 (m, 3H), 7.41-7.34 (m, 2H)

0.2 g (0.87 mmol) of 5-chloro-3-phenyl-1H-indazole was dissolved in 10 mL of anhydrous N,N-dimethylformamide to which 0.57 g (1.74 mmol) of cesium carbonate and 0.23 g (0.87 mmol) of 5-chloro-2,4-difluoro-N-(methylsulfonyl)benzamide were added. The reaction mixture was stirred at 150° C. for 1 hour, and the organic layer was separated, treated with magnesium sulfate, filtered and then concentrated under reduced pressure. The residue was separated by column chromatography to give 0.1 g (24% yield) of the title compound.

1H NMR (MeOD) δ: 8.09 (s, 1H), 8.06-8.04 (d, 1H), 7.99-7.97 (d, 2H), 7.58-7.54 (t, 2H), 7.51-7.48 (m, 3H), 7.38-7.37 (d, 1H), 3.14 (s, 3H)

Example 86) Preparation of 5-chloro-4-(5-chloro-3-morpholino-1H-indazol-1-yl)-2-fluoro-N-(methylsulfonyl)benzamide

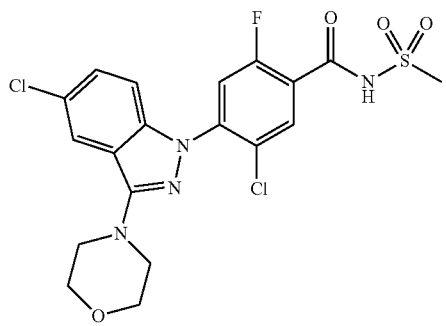 [SMILES: CS(=O)(=O)NC(=O)c1cc(Cl)c(-n2nc(N3CCOCC3)c3cc(Cl)ccc32)cc1F]

5.0 g (22.0 mmol) of 3-bromo-5-chloro-1H-indazole was dissolved in 10 mL of anhydrous tetrahydrofuran to which 2.6 g (65.0 mmol) of sodium hydride (60%) and 5.6 g (65.0 mmol) of morpholine were added. The reaction mixture was stirred at 150° C. for 12 hours, and the organic layer was separated, treated with magnesium sulfate, filtered and then concentrated under reduced pressure. The residue was separated by column chromatography to give 2.0 g (39% yield) of 4-(5-chloro-1H-indazol-3-yl) morpholine.

1H NMR (MeOD) δ: 8.26 (d, 1H), 8.14 (s, 1H), 7.63 (d, 1H), 3.70 (m, 4H), 3.22 (m, 4H)

0.70 g (17% yield) of the title compound was prepared in the same manner as described in Example 1, except that 4-(5-chloro-1H-indazol-3-yl)morpholine was used instead of 5-chloro-3-methyl-1H-indazole.

1H NMR (MeOD) δ: 8.38 (s, 1H), 7.74 (s, 1H), 7.42 (d, 1H), 7.31 (d, 1H), 7.04 (s, 1H), 3.88 (t, 4H), 3.20 (t, 4H), 3.16 (s, 3H)

Example 129) Preparation of 5-chloro-4-(5-chloro-3-(3-hydroxy-3-methylbut-1-yn-1-yl)-1H-indazol-1-yl)-2-fluoro-N-(methylsulfonyl)benzamide

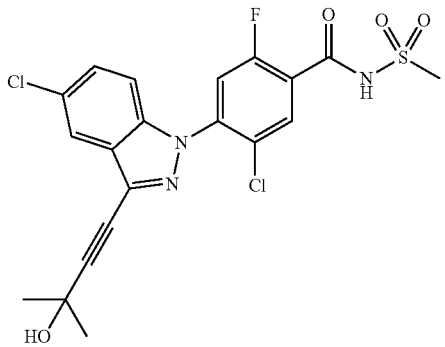 [SMILES: CC(C)(O)C#Cc1nn(-c2cc(F)c(C(=O)NS(C)(=O)=O)cc2Cl)c2ccc(Cl)cc12]

0.30 g (1.1 mmol) of 5-chloro-3-iodo-1H-indazole was dissolved in 2 mL of ethanol to which 0.12 g (0.11 mmol, 10 wt %) of palladium carbon, 0.3 mL (2.2 mmol) of tetraethylamine, 0.11 g (0.431 mmol) of triphenylphosphine, 0.02 g (0.11 mmol) of copper(I) iodide and 0.13 mL (1.1 mmol) of 2-methylbut-3-yn-2-ol were added, followed by stirring at 50° C. for 18 hours. The reaction mixture was filtered through diatomaceous earth and concentrated. The resulting residue was separated by column chromatography to give 0.15 g (65% yield) of 4-(5-chloro-1H-indazol-3-yl)-2-methylbut-3-yn-2-ol.

1H NMR (MeOD) δ: 7.71 (s, 1H), 7.50 (d, 1H), 7.36 (d, 1H), 1.63 (s, 6H)

0.05 g (16% yield) of the title compound was prepared in the same manner as described in Example 1, except that 4-(5-chloro-1H-indazol-3-yl)-2-methylbut-3-yn-2-ol was used instead of 5-chloro-3-methyl-1H-indazole.

1H NMR (MeOH) δ: 8.02 (d, 1H), 7.83 (s, 1H), 7.50 (t, 2H), 7.36 (d, 1H), 3.20 (s, 3H), 1.65 (s, 6H)

Example 133) Preparation of (E)-5-chloro-4-(5-chloro-3-styryl-1H-indazol-1-yl)-2-fluoro-N-(methylsulfonyl)benzamide

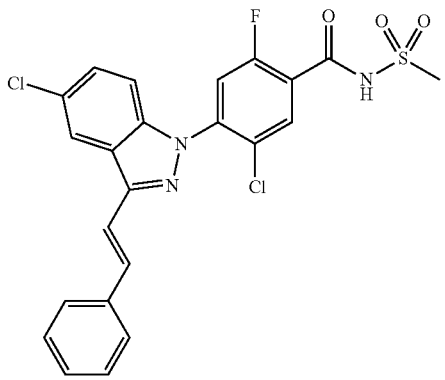 [SMILES: CS(=O)(=O)NC(=O)c1cc(Cl)c(-n2nc(/C=C/c3ccccc3)c3cc(Cl)ccc32)cc1F]

0.50 g (1.4 mmol) of 5-chloro-3-iodo-1-(tetrahydro-2H-pyran-2-yl)-1H-indazole was dissolved in 10 mL of N,N-dimethylformamide to which 0.3 mL (1.6 mmol) of styrene, 0.013 g (0.069 mmol) of palladium(II) chloride, 0.4 mL (2.76 mmol) of N,N-diisopropylethylamine and 0.04 g (0.14 mmol) of tri-o-tolyl phosphine were added. The reaction mixture was stirred at 100° C. for 18 hours, and the organic layer was separated, treated with magnesium sulfate, filtered and then concentrated under reduced pressure. The residue was dissolved in 10 mL of methylene chloride to which 0.70 g (2.1 mmol) of p-toluenesulfonic acid monohydrate was added and stirred at room temperature for 3 hours. The residue concentrated under reduced pressure was separated by column chromatography to give 0.28 g (80% yield) of (E)-5-chloro-3-styryl-1H-indazole.

1H NMR (MeOD) δ: 8.06 (d, 1H), 7.61 (d, 2H), 7.49 (d, 1H), 7.45-7.35 (m, 5H), 7.27 (t, 1H)

0.10 g (18% yield) of the title compound was prepared in the same manner as described in Example 1, except that (E)-5-chloro-3-styryl-1H-indazol was used instead of 5-chloro-3-methyl-1H-indazole.

1H NMR (MeOH) δ: 8.22 (d, 1H), 8.04 (d, 1H), 7.68 (d, 2H), 7.61 (s, 1H), 7.49 (m, 3H), 7.40 (m, 2H), 7.32 (m, 2H), 3.21 (s, 3H)

Example 140) Preparation of 5-chloro-4-(3-chloro-5-hydroxy-1H-indazol-1-yl)-2-fluoro-N-(methylsulfonyl)-N-(naphthalen-2-ylmethyl)benzamide

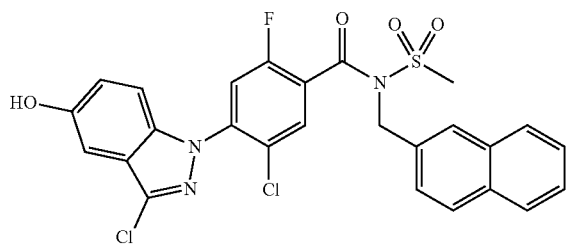 [SMILES: CS(=O)(=O)N(Cc1ccc2ccccc2c1)C(=O)c1cc(Cl)c(-n2nc(Cl)c3cc(O)ccc32)cc1F]

0.2 g (0.48 mmol) of 5-chloro-4-(3-chloro-5-hydroxy-1H-indazol-1-yl)-2-fluoro-N-(methylsulfonyl)benzamide was dissolved in 5 mL of anhydrous tetrahydrofuran to which 0.066 g (0.48 mmol) of potassium carbonate and 0.1 g (0.48 mmol) of 2-(bromomethyl)naphthalene were added. The reaction mixture was stirred at room temperature for 3 hours, and the organic layer was separated, treated with magnesium sulfate, filtered and then concentrated under reduced pressure. The residue was separated by column chromatography to give 0.1 g (45% yield) of the title compound.

1H NMR (MeOD) δ: 8.22-8.20 (d, 1H), 7.96 (s, 1H), 7.90-7.87 (m, 3H), 7.60-7.58 (d, 1H), 7.52-7.48 (m, 3H), 7.22-7.20 (d, 1H), 7.11-7.09 (d, 1H), 6.99 (s, 1H), 5.58 (s, 2H), 3.30 (s, 3H)

Example 185) Preparation of 5-chloro-4-(5-chloro-3-(4-fluorophenyl)-1H-pyrrolo[2,3-b]pyridin-1-yl)-2-fluoro-N-(methylsulfonyl) benzamide

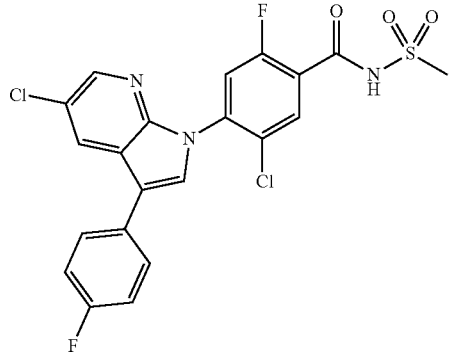 [SMILES: CS(=O)(=O)NC(=O)c1cc(Cl)c(-n2cc(-c3ccc(F)cc3)c3cc(Cl)cnc32)cc1F]

0.30 g (1.97 mmol) of 5-chloro-1H-pyrrolo[2,3-b]pyridine was dissolved in 10 mL of methylene chloride to which 0.38 g (2.16 mmol) of N-bromosuccinimide and 0.52 g (2.16 mmol) of dibenzoyl peroxide were added, followed by stirring at room temperature for 18 hours. The precipitated crystals were filtered and then washed with methylene chloride to give 0.24 g (52.0% yield) of 3-bromo-5-chloro-1H-pyrrolo[2,3-b]pyridine.

1H NMR (DMSO) δ: 12.32 (br s, 1H), 8.28 (m, 1H), 7.91 (m, 1H), 7.82 (m, 1H)

0.24 g (1.02 mmol) of 3-bromo-5-chloro-1H-pyrrolo[2,3-b]pyridine and 0.25 g (0.93 mmol) of 5-chloro-2,4-difluoro-N-(methylsulfonyl)benzamide were dissolved in 10 mL of dimethylsulfoxide to which 0.71 g (2.18 mmol) of cesium carbonate was added, followed by stirring at 100° C. for 18 hours. The reaction solution was extracted with ethyl acetate/distilled water. The organic layer was separated and concentrated under reduced pressure. The residue was separated by column chromatography to give 0.23 g (51.4% yield) of 4-(3-bromo-5-chloro-1H-pyrrolo[2,3-b]pyridin-1-yl)-2-fluoro-N-(methylsulfonyl)benzamide.

1H NMR (DMSO) δ: 12.32 (br s, 1H), 8.36 (m, 1H), 8.20 (s, 1H), 8.12 (d, 1H), 8.05 (d, 1H), 7.88 (d, 1H), 3.37 (s, 3H)

0.2 g (0.42 mmol) of 4-(3-bBromo-5-chloro-1H-pyrrolo[2,3-b]pyridin-1-yl)-2-fluoro-N-(methylsulfonyl)benzamide was dissolved in 10 mL of 1,4-dioxane to which 0.07 g (0.50 mmol) of (4-fluorophenyl)boronic acid, 0.049 g (0.042 mmol) of tetrakis(triphenylphosphine)palladium(0) and 0.13 g (1.26 mmol) of sodium carbonate were dissolved in 0.25 mL of distilled water and added. After reacting with microwave reactor at 120° C. for 15 minutes, the reaction solution was extracted with ethyl acetate/distilled water and the organic layer was concentrated under reduced pressure. The residue was separated by column chromatography to give 0.11 g (50.5% yield) of the title compound.

1H NMR (MeOD) δ: 8.33 (m, 1H), 8.27 (m, 1H), 8.02 (d, 1H), 7.91 (s, 1H), 7.73 (m, 2H), 7.58 (d, 1H), 7.23 (t, 2H), 3.26 (s, 3H)

Example 234) Preparation of 5-chloro-4-(3-chloro-5-(2-fluorophenyl)-1H-indazol-1-yl)-2-fluoro-N-(methylsulfonyl)benzamide

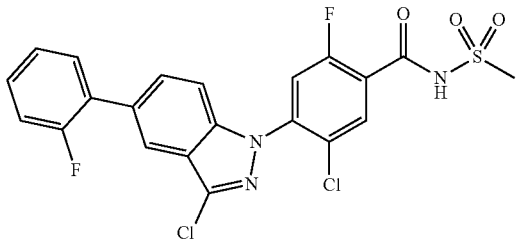 [SMILES: CS(=O)(=O)NC(=O)c1cc(Cl)c(-n2nc(Cl)c3cc(-c4ccccc4F)ccc32)cc1F]

0.7 g (3.6 mmol) of 5-bromo-3-chloro-1H-indazole was dissolved in 12 mL of acetonitrile to which 0.54 g (3.9 mmol) of N-chlorosuccinimide was added, followed by stirring at 65° C. for 3 hours. The reaction mixture was washed with 1N sodium hydroxide and saturated sodium chloride, extracted with ethyl acetate and concentrated under reduced pressure. The resulting residue was crystallized with ethyl acetate/methanol to give 0.4 g (48.7% yield) of 5-bromo-3-chloro-1H-indazole.

1H NMR (MeOD) δ: 7.83 (s, 1H), 7.54 (d, 1H), 7.46 (d, 1H)

0.14 g (0.60 mmol) of 5-bromo-1H-indazole was dissolved in 4 mL of 1,4-dioxane to which 0.084 g (0.60 mmol) of (2-fluorophenyl)boronic acid, 0.070 g (0.06 mmol) of tetrakis(triphenylphosphine)palladium(0) and 0.19 g (1.80 mmol) of sodium carbonate were dissolved in 1.0 mL of distilled water and added. After reacting with microwave reactor at 120° C. for 15 minutes, the organic layer was separated, treated with magnesium sulfate, filtered and then concentrated under reduced pressure. The residue was separated by column chromatography to give 0.11 g (74.2% yield) of 3-chloro-5-(2-fluorophenyl)-1H-indazole.

1H NMR (MeOD) δ: 7.80 (s, 1H), 7.69 (m, 3H), 7.58 (m, 1H), 7.19 (t, 2H)

0.25 g (1.0 mmol) of 3-chloro-5-(2-fluorophenyl)-1H-indazole and 0.25 g (0.9 mmol) of 5-chloro-2,4-difluoro-N-(methylsulfonyl)benzamide were dissolved in 10 mL of dimethyl sulfoxide to which 0.90 g (3.0 mmol) of cesium carbonate was added, followed by stirring at 100° C. for 18 hours. The organic layer was separated, treated with magnesium sulfate, filtered, and then concentrated under reduced pressure. The residue was separated by column chromatography to give 0.10 g (22.0% yield) of the title compound.

1H NMR (MeOD) δ: 8.06-8.04 (d, 1H), 7.91 (s, 1H), 7.77-7.75 (d, 1H), 7.59-7.56 (m, 2H), 7.46-7.45 (d, 1H), 7.42-7.40 (m, 1H), 7.32-7.29 (t, 1H), 7.26-7.22 (m, 1H), 3.30 (s, 3H)

Example 257) Preparation of 5-chloro-4-(3-chloro-5-(4-fluorophenyl)-1H-pyrrolo[2,3-b]pyridin-1-yl)-2-fluoro-N-(methylsulfonyl) benzamide

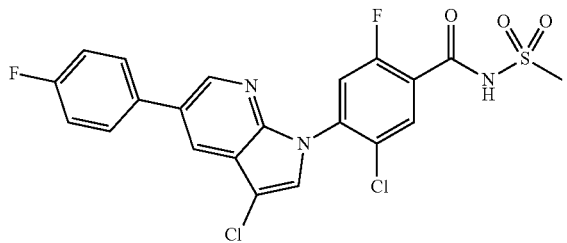 [SMILES: CS(=O)(=O)NC(=O)c1cc(Cl)c(-n2cc(Cl)c3cc(-c4ccc(F)cc4)cnc32)cc1F]

0.50 g (2.54 mmol) of 5-bromo-1H-pyrrolo[2,3-b]pyridine was dissolved in 10 mL of N,N-dimethylformamide to which 0.37 g (2.79 mmol) of N-chlorosuccinimide and 0.38 g (2.79 mmol) of dibenzoyl peroxide were added, followed by stirring at room temperature for 18 hours. After extracting with ethyl acetate/distilled water, the organic layer was concentrated under reduced pressure. The residue was separated by column chromatography to give 0.50 g (85.0% yield) of 5-bromo-3-chloro-1H-pyrrolo[2,3-b]pyridine.

1H NMR (DMSO) δ: 12.24 (br s, 1H), 8.35 (s, 1H), 8.14 (s, 1H), 8.03 (d, 1H), 7.81 (m, 1H), 7.77 (s, 1H), 7.64 (t, 1H)

0.14 g (0.60 mmol) of 5-bromo-3-chloro-1H-pyrrolo[2,3-b]pyridine was dissolved in 3 mL of N,N-dimethylformamide to which 0.13 g (0.50 mmol) of 5-chloro-2,4-difluoro-N-(methylsulfonyl)benzamide and 0.49 g (1.50 mmol) of cesium carbonate were added, followed by stirring at 100° C. for 18 hours. After extracting with ethyl acetate/distilled water, the organic layer was concentrated under reduced pressure. The residue was separated by column chromatography to give 0.15 g (52.0% yield) of 4-(5-bromo-3-chloro-1H-pyrrolo[2,3-b]pyridin-1-yl)-5-chloro-2-fluoro-N-(methylsulfonyl)benzamide.

1H NMR (MeOD) δ: 8.38 (m, 1H), 8.25 (m, 1H), 8.00 (d, 1H), 7.78 (s, 1H), 7.62 (d, 1H), 3.36 (s, 3H)

0.20 g (0.41 mmol) of 4-(5-bromo-3-chloro-1H-pyrrolo[2,3-b]pyridin-1-yl)-5-chloro-2-fluoro-N-(methylsulfonyl)benzamide was dissolved in 10 mL of 1,4-dioxane to which 70.0 mg (0.49 mmol) of (4-fluorophenyl) boronic acid, 48.0 mg (0.041 mmol) of tetrakis(triphenylphosphine)palladium (0) and 132.0 mg (1.23 mmol) of sodium carbonate were dissolved in distilled water (2.5 mL) and added. After reacting with microwave reactor at 120° C. for 15 minutes, the reaction solution was extracted with ethyl acetate/distilled water. The organic layer was then concentrated under reduced pressure. The residue was separated by column chromatography to give 0.13 g (63.9% yield) of the title compound.

1H NMR (MeOD) δ: 8.54 (m, 1H), 8.23 (m, 1H), 8.02 (d, 1H), 7.72 (m, 3H), 7.55 (m, 1H), 7.24 (m, 2H), 3.24 (s, 3H)

Example 274) Preparation of 6-(5-chloro-3-(4-chlorophenyl)-1H-indol-1-yl)-N-(methylsulfonyl)nicotinamide

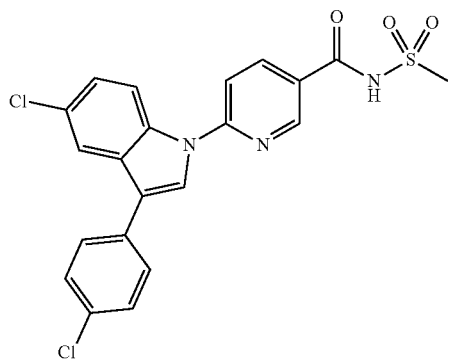 [SMILES: CS(=O)(=O)NC(=O)c1ccc(-n2cc(-c3ccc(Cl)cc3)c3cc(Cl)ccc32)nc1]

1.0 g (6.6 mmol) of 5-chloro-1H-indole and 0.93 g (16.5 mmol) of potassium hydroxide were dissolved in 10 mL of N,N-dimethylformamide to which 1.84 g (7.3 mmol) of iodine was added dropwise, followed by stirring at room temperature for 1 hour. The reaction mixture was washed with distilled water and saturated sodium thiosulfate solution, extracted with ethyl acetate and concentrated under reduced pressure to give 1.5 g (82% yield) of 5-chloro-3-iodo-1H-indole.

1H NMR (MeOD) δ: 7.83 (s, 1H), 7.54 (d, 1H), 7.46 (d, 1H)

0.20 g (0.72 mmol) of 5-chloro-3-iodo-1H-indole was dissolved in 4 mL of acetone to which 0.50 g (3.6 mmol) of potassium carbonate, 0.016 g (0.072 mmol) of palladium acetate, 0.044 g (1.44 mmol) of tri(o-tolyl)phosphine and 2 mL of distilled water were added. The reaction mixture was stirred at 90° C. for 3 hours and then extracted with ethyl acetate/distilled water. The organic layer was separated and then concentrated under reduced pressure. The residue was separated by column chromatography to give 0.12 g (63.6% yield) of 5-chloro-3-(4-chlorophenyl)-1H-indole.

1H NMR (MeOD) δ: 7.77 (d, 1H), 7.61 (m, 2H), 7.54 (s, 1H), 7.40 (m, 3H), 7.13 (dd, 1H)

0.20 g (0.76 mmol) of 5-chloro-3-(4-chlorophenyl)-1H-indole was dissolved in 20 mL of dimethyl sulfoxide to which 0.26 g (0.92 mmol) of 6-bromo-N-(methylsulfonyl) nicotinamide and 0.74 g (2.28 mmol) of cesium carbonate was added. The reaction mixture was stirred at 100° C. for 18 hours and extracted with ethyl acetate/distilled water. The organic layer was then separated and concentrated under reduced pressure. The residue was separated by column chromatography to give 0.14 g (40.0% yield) of the title compound.

1H NMR (MeOD) δ: 9.15 (s, 1H), 8.51 (d, 1H), 8.19 (s, 1H), 7.82 (s, 1H), 7.72 (m, 3H), 7.50 (m, 2H), 7.32 (m, 1H), 3.14 (s, 3H)

Example 290) Preparation of 2-(5-chloro-4-(5-chloro-3-(4-chloro-2-fluorophenyl)-1H-indazol-1-yl)-2-fluorobenzoyl)hydrazine-1-carboxamide

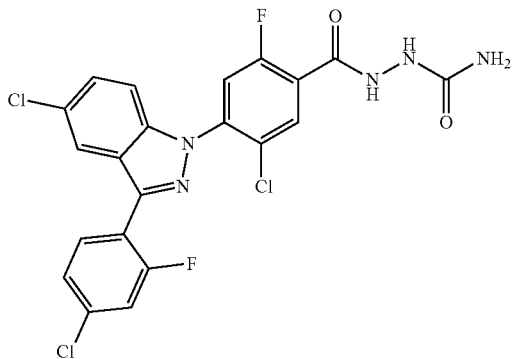 [SMILES: NC(=O)NNC(=O)c1cc(Cl)c(-n2nc(-c3ccc(Cl)cc3F)c3cc(Cl)ccc32)cc1F]

0.50 g (1.78 mmol) of 5-chloro-3-(4-chloro-2-fluorophenyl)-1H-indazole was dissolved in 10 mL of N,N-dimethylformamide to which 1.16 g (3.56 mmol) of cesium carbonate and 0.36 g (1.78 mmol) of methyl 5-chloro-2,4-difluoro benzoic acid were added, followed by stirring at 80° C. for 18 hours. The organic layer was separated, treated with magnesium sulfate, filtered and then concentrated under reduced pressure. The residue was separated by column chromatography and concentrated under reduced pressure to which 10 mL of 5M sodium hydroxide solution was added, followed by stirring at 100° C. for 24 hours. The reaction product was adjusted to pH 6-7 with 1M hydrochloric acid, extracted with ethyl acetate and dried. The residue was crystallized with methylene chloride to give 0.30 g (yield: 50%) of 5-chloro-4-(5-chloro-3-(4-chloro-2-fluorophenyl)-1H-indazol-1-yl)-2-fluorobenzoic acid.

0.3 g (0.661 mmol) of 5-chloro-4-(5-chloro-3-(4-chloro-2-fluorophenyl)-1H-indazol-1-yl)-2-fluoro benzoic acid was dissolved in 10 mL of thionyl chloride and then stirred at 100° C. for 24 hours. Then, the reaction product was concentrated under reduced pressure, and the resulting residue was dissolved in 10 mL of methylene chloride to which 0.05 mL (0.42 mmol) of triethylamine and 0.03 g (0.32 mmol) of semicarbazide hydrochloride were added, followed by stirring at room temperature for 18 hours and then concentrated under reduced pressure. The resulting residue was separated by column chromatography to give 0.05 g (46% yield) of the title compound.

1H NMR (DMSO) δ: 7.89 (m, 2H), 7.77 (s, 1H), 7.68 (d, 1H), 7.58-7.52 (m, 2H), 7.47 (d, 1H), 7.43 (d, 1H)

Example 291) Preparation of 5-(5-chloro-4-(5-chloro-3-(4-chloro-2-fluorophenyl)-1H-indazol-1-yl)-2-fluorophenyl)-2,4-dihydro-3H-1,2,4-triazol-3-one

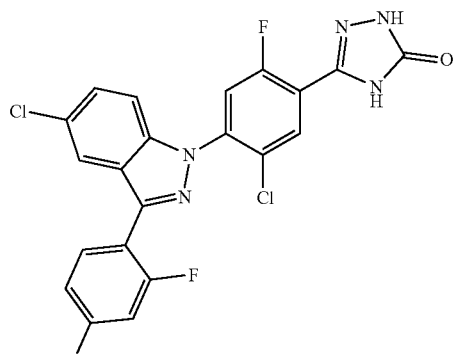

0.02 g (0.039 mmol) of 2-(5-chloro-4-(5-chloro-3-(4-chloro-2-fluorophenyl)-1H-indazol-1-yl)-2-fluorobenzoyl)hydrazine-1-carboxamide was dissolved in 5 mL of 1N sodium hydroxide and then stirred at 100° C. for 18 hours. The reaction product was washed with water, extracted with ethyl acetate and then concentrated under reduced pressure. The resulting residue was separated by column chromatography to give 0.02 g (79% yield) of the title compound.

1H NMR (DMSO) δ: 7.89 (m, 2H), 7.73 (d, 1H), 7.70 (d, 1H), 7.52 (d, 2H), 7.48 (d, 1H), 7.42 (d, 1H)

Example 292) Preparation of 5-chloro-4-(5-chloro-3-(4-chloro-2-fluorophenyl)-1H-indazol-1-yl)-2-fluorobenzamide

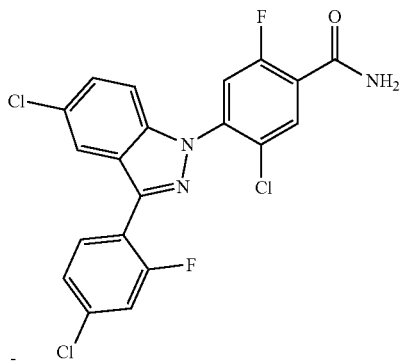 [SMILES: NC(=O)c1cc(Cl)c(-n2nc(-c3ccc(Cl)cc3F)c3cc(Cl)ccc32)cc1F]

0.20 g (0.42 mmol) of 5-chloro-4-(5-chloro-3-(4-chloro-2-fluorophenyl)-1H-indazol-1-yl)-2-fluorobenzoyl was dissolved in 10 mL of methylene chloride and 2 mL of distilled water to which 0.10 g of ammonium chloride and 0.08 g of sodium hydroxide were added, followed by stirring at room temperature for 18 hours. The reaction product was concentrated under reduced pressure. The resulting residue was separated by column chromatography to give 0.16 g (83% yield) of the title compound.

1H NMR (DMSO) δ: 8.00 (d, 1H), 7.93-7.88 (m, 3H), 7.71 (d, 1H), 7.56 (d, 1H), 7.48 (d, 2H)

Example 293) Preparation of N-acetyl-5-chloro-4-(5-chloro-3-(4-chloro-2-fluorophenyl)-1H-indazol-1-yl)-2-fluorobenzamide

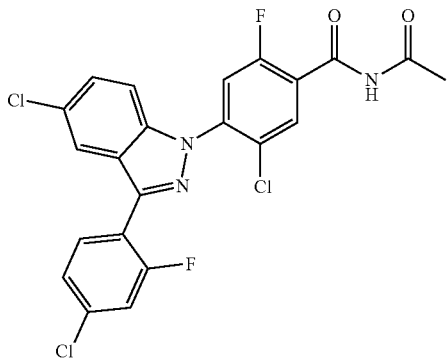 [SMILES: CC(=O)NC(=O)c1cc(Cl)c(-n2nc(-c3ccc(Cl)cc3F)c3cc(Cl)ccc32)cc1F]

0.40 g (0.90 mmol) of 5-chloro-4-(5-chloro-3-(4-chloro-2-fluorophenyl)-1H-indazol-1-yl)-2-fluorobenzamide was dissolved in 6 mL of tetrahydrofuran to which 0.20 g (60%, 1.30 mmol) of sodium hydride and 0.30 mL (1.30 mmol) of acetic anhydride were added. The reaction mixture was stirred at room temperature for 6 hours, washed with water, extracted with ethyl acetate and then concentrated under reduced pressure. The resulting residue was separated by column chromatography to give 0.20 g (45% yield) of the title compound.

1H NMR (MeOD) δ: 8.02 (d, 1H), 7.87 (m, 2H), 7.67 (d, 1H), 7.53 (d, 1H), 7.48 (d, 1H), 7.41 (d, 2H), 2.39 (s, 3H)

Example 294) Preparation of 5-chloro-4-(5-chloro-3-(4-chloro-2-fluorophenyl)-1H-indazol-1-yl)-2-fluoro-N-(thiazol-2-yl)benzamide

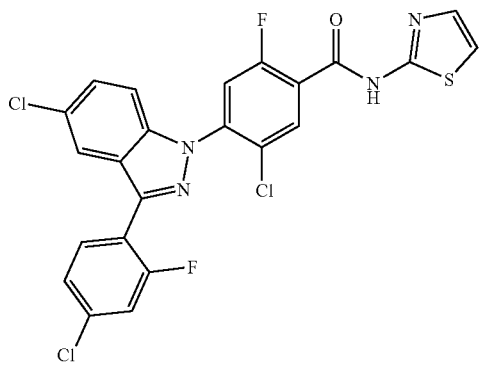 [SMILES: O=C(Nc1nccs1)c1cc(Cl)c(-n2nc(-c3ccc(Cl)cc3F)c3cc(Cl)ccc32)cc1F]

1.0 g (1.1 mmol) of 5-chloro-4-(5-chloro-3-(4-chloro-2-fluorophenyl)-1H-indazol-1-yl)-2-fluoro benzoic acid was dissolved in 30 mL of methylene chloride to which 3.3 g (1.65 mmol) of N-(3-dimethylaminopropyl)-N'-ethylcarbodiimide hydrochloride and 0.46 g (1.98 mmol) of N-hydroxy-succinimide were added, followed by stirring at room temperature for 18 hours. The reaction product was washed with water, dried over anhydrous magnesium sulfate and then concentrated under reduced pressure. The resulting residue was dissolved in 10 mL of methylene chloride to which 0.30 g (2.70 mmol) of 2-aminothiazole and 2.0 mL (3.6 mmol) of triethylamine were added, followed by stirring at room temperature for 18 hours. The precipitated reaction product was filtered to give 0.80 g (82% yield) of the title compound.

1H NMR (DMSO-D6) δ: 12.91 (br, 1H), 8.21 (d, 1H), 7.99 (d, 1H), 7.93-7.89 (m, 2H), 7.71 (m, 1H), 7.60 (m, 2H), 7.52 (m, 2H), 7.33 (s, 1H)

The compounds of the following examples were prepared by the methods similar to the preparation methods of the above-mentioned examples, except that the starting materials were suitably replaced to fit the structures of the compounds to be prepared with reference to Reaction Schemes 1 to 3 in the specification.

Example 2) Preparation of 5-chloro-4-(5-chloro-1H-indazol-1-yl)-2-fluoro-N-(methylsulfonyl)benzamide

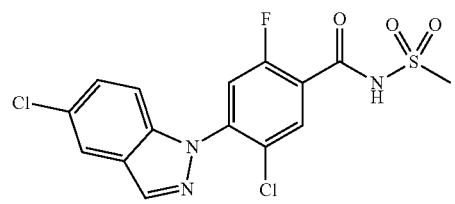 [SMILES: CS(=O)(=O)NC(=O)c1cc(Cl)c(-n2ncc3cc(Cl)ccc32)cc1F]

1H NMR (500 MHz, MeOD) δ: 8.30 (s, 1H), 7.90 (s, 1H), 7.85-7.84 (d, 1H), 7.50-7.45 (m, 2H), 7.36-7.35 (d, 2H), 3.30 (s, 3H)

Example 3) Preparation of 5-chloro-4-(3,5-dichloro-1H-pyrazolo[3,4-b]pyridin-1-yl)-2-fluoro-N-(methylsulfonyl)benzamide

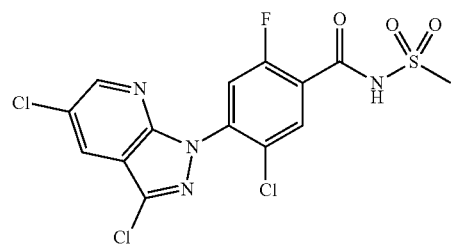 [SMILES: CS(=O)(=O)NC(=O)c1cc(Cl)c(-n2nc(Cl)c3cc(Cl)cnc32)cc1F]

1H NMR (500 MHz, MeOD) δ: 8.71 (s, 1H), 8.05 (d, 1H), 7.88 (s, 1H), 7.60 (d, 1H), 3.24 (s, 3H)

Example 4) Preparation of 4-(3,5-dichloro-1H-indazol-1-yl)-2-fluoro-N-(methylsulfonyl)benzamide

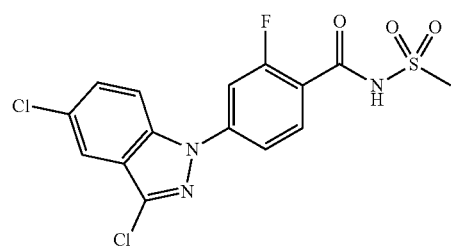 [SMILES: CS(=O)(=O)NC(=O)c1ccc(-n2nc(Cl)c3cc(Cl)ccc32)cc1F]

1H NMR (500 MHz, CDCl₃) δ: 8.05 (d, 1H), 7.90 (dd, 1H), 7.77 (m, 2H), 7.52 (m, 2H), 3.27 (s, 3H)

Example 5) Preparation of 4-(3-amino-5-chloro-1H-indazol-1-yl)-5-chloro-2-fluoro-N-(methylsulfonyl)benzamide

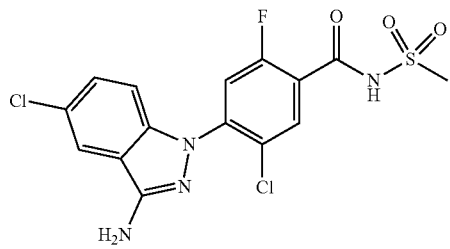 [SMILES: CS(=O)(=O)NC(=O)c1cc(Cl)c(-n2nc(N)c3cc(Cl)ccc32)cc1F]

1H NMR (500 MHz, DMSO) δ: 7.90-7.89 (d, 1H), 7.63-7361 (d, 1H), 7.31-7.24 (m, 2H), 7.16-7.14 (m, 1H), 5.96 (—NH2, bs, 2H), 2.95 (s, 3H)

Example 7) Preparation of 5-chloro-4-(3,5-dichloro-1H-indazol-1-yl)-N—(N,N-dimethylsulfamoyl)-2-fluorobenzamide

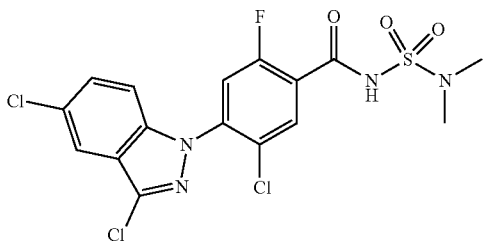 [SMILES: CN(C)S(=O)(=O)NC(=O)c1cc(Cl)c(-n2nc(Cl)c3cc(Cl)ccc32)cc1F]

1H NMR (500 MHz, CDCl3) δ: 8.24 (d, 1H), 7.73 (s, 1H), 7.42 (d, 1H), 7.35 (d, 1H), 7.16 (d, 1H), 2.96 (s, 6H)

Example 8) Preparation of 3-chloro-4-(3,5-dichloro-1H-indazol-1-yl)-N-(methylsulfonyl)benzamide

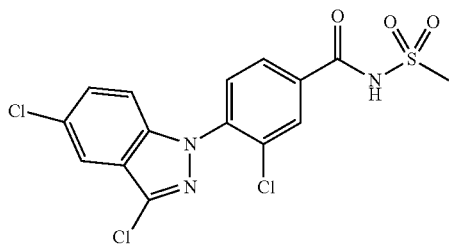 [SMILES: CS(=O)(=O)NC(=O)c1ccc(-n2nc(Cl)c3cc(Cl)ccc32)c(Cl)c1]

1H NMR (500 MHz, CDCl3) δ: 8.14 (d, 1H), 8.01 (d, 1H), 7.91 (d, 1H), 7.65 (d, 1H), 7.40 (d, 1H), 6.97 (d, 1H), 3.21 (s, 3H)

Example 9) Preparation of 5-chloro-4-(3,5-dichloro-1H-indazol-1-yl)-2-fluoro-N-(methylsulfonyl)benzamide

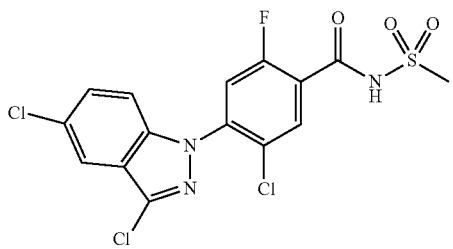 [SMILES: CS(=O)(=O)NC(=O)c1cc(Cl)c(-n2nc(Cl)c3cc(Cl)ccc32)cc1F]

1H NMR (500 MHz, MeOD) δ: 8.03-8.02 (d, 1H), 7.78 (s, 1H), 7.53-7.49 (m, 2H), 7.36-7.34 (d, 1H), 3.20 (s, 3H)

Example 10) Preparation of 5-chloro-4-(5-chloro-1H-pyrazolo[3,4-c]pyridin-1-yl)-2-fluoro-N-(methylsulfonyl)benzamide

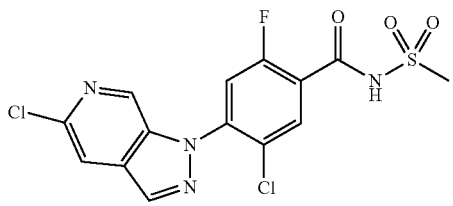 [SMILES: CS(=O)(=O)NC(=O)c1cc(Cl)c(-n2ncc3cc(Cl)ncc32)cc1F]

1H NMR (500 MHz, MeOD) δ: 8.65 (s, 1H), 8.41 (s, 1H), 8.05-8.04 (d, 1H), 7.93 (s, 1H), 7.51-7.49 (d, 1H), 3.13 (s, 3H)

Example 11) Preparation of 5-chloro-4-(3,5-dichloro-1H-pyrazolo[3,4-c]pyridin-1-yl)-2-fluoro-N-(methylsulfonyl)benzamide

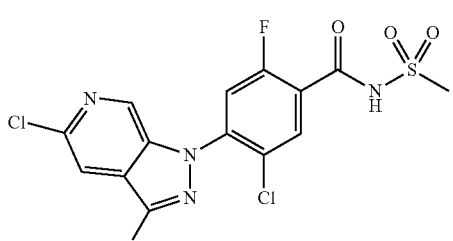

1H NMR (500 MHz, MeOD) δ: 8.61 (s, 1H), 8.35 (s, 1H), 8.01 (d, 1H), 7.57 (d, 1H), 3.24 (s, 3H)

Example 12) Preparation of 4-(3-chloro-5-hydroxy-1H-indazol-1-yl)-N-(methylsulfonyl)benzamide

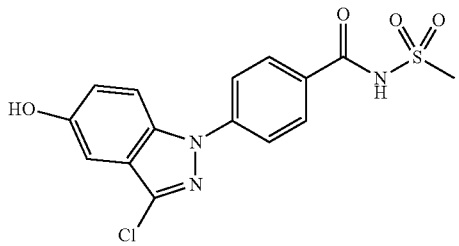 [SMILES: CS(=O)(=O)NC(=O)c1ccc(-n2nc(Cl)c3cc(O)ccc32)cc1]

1H NMR (500 MHz, MeOD) δ: 8.12 (s, 1H), 7.94-7.83 (t, 1H), 7.81-7.79 (d, 1H), 7.72-7.70 (d, 1H), 7.65-7.63 (d, 1H), 7.13-7.10 (m, 2H), 3.30 (s, 3H)

Example 13) Preparation of 4-(5-amino-1H-indazol-1-yl)-5-chloro-2-fluoro-N-(methylsulfonyl)benzamide

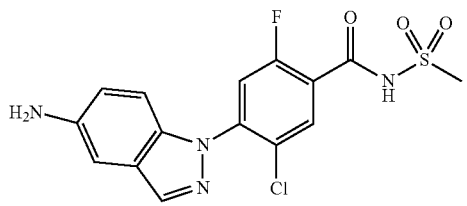 [SMILES: CS(=O)(=O)NC(=O)c1cc(Cl)c(-n2ncc3cc(N)ccc32)cc1F]

1H NMR (500 MHz, MeOD) δ: 8.10 (s, 1H), 8.01-8.00 (d, 1H), 7.39-7.37 (d, 1H), 7.17-7.13 (m, 2H), 7.06-7.04 (m, 1H), 3.21 (s, 3H)

Example 14) Preparation of 5-chloro-2-fluoro-4-(3-methyl-5-nitro-1H-indazol-1-yl)-N-(methylsulfonyl)benzamide

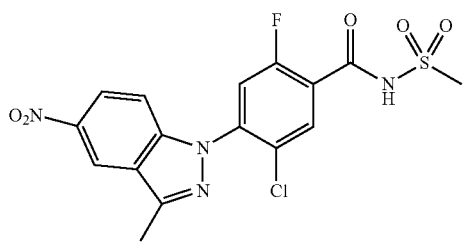 [SMILES: Cc1nn(-c2cc(F)c(C(=O)NS(C)(=O)=O)cc2Cl)c2ccc([N+](=O)[O-])cc12]

1H NMR (500 MHz, MeOD) δ: 8.84 (s, 1H), 8.35 (dd, 1H), 8.04 (d, 1H), 7.52 (d, 1H), 7.44 (d, 1H), 3.25 (s, 3H), 2.71 (s, 1H)

Example 15) Preparation of 5-chloro-4-(4-chloro-5-fluoro-1H-indazol-1-yl)-2-fluoro-N-(methylsulfonyl)benzamide

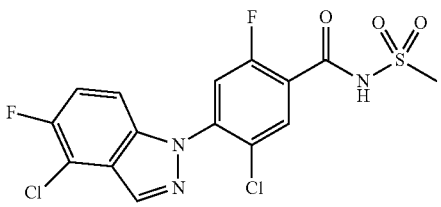 [SMILES: CS(=O)(=O)NC(=O)c1cc(Cl)c(-n2ncc3c(Cl)c(F)ccc32)cc1F]

1H NMR (500 MHz, MeOD) δ: 8.38 (s, 1H), 8.03-8.02 (d, 1H), 7.47-7.45 (d, 1H), 7.42-7.39 (t, 1H), 7.32-7.30 (m, 1H), 3.17 (s, 3H)

Example 16) Preparation of 5-chloro-4-(3-chloro-5-hydroxy-1H-indazol-1-yl)-2-fluoro-N-(methylsulfonyl)benzamide

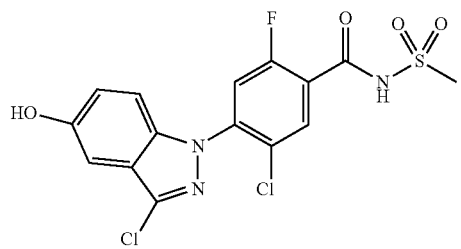 [SMILES: CS(=O)(=O)NC(=O)c1cc(Cl)c(-n2nc(Cl)c3cc(O)ccc32)cc1F]

1H NMR (500 MHz, CDCl$_3$) δ: 8.21-8.20 (d, 1H), 7.36-7.34 (d, 1H), 7.18-7.16 (d, 1H), 7.10-7.08 (d, 1H), 7.04 (s, 1H), 6.97 (s, 1H), 3.48 (s, 3H)

Example 17) Preparation of 5-chloro-4-(3-chloro-5-fluoro-1H-indazol-1-yl)-2-fluoro-N-(methylsulfonyl)benzamide

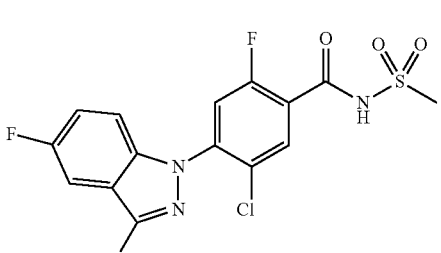

1H NMR (500 MHz, MeOD) δ: 8.03-8.02 (d, 1H), 7.50-7.45 (m, 2H), 7.39-7.38 (d, 2H), 3.22 (s, 3H)

Example 18) Preparation of 5-chloro-4-(3-chloro-5-(trifluoromethyl)-1H-indazol-1-yl)-2-fluoro-N-(methylsulfonyl)benzamide

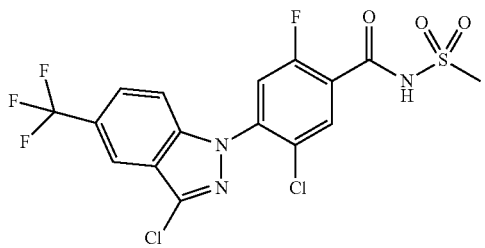 [SMILES: CS(=O)(=O)NC(=O)c1cc(Cl)c(-n2nc(Cl)c3cc(C(F)(F)F)ccc32)cc1F]

1H NMR (500 MHz, MeOD) δ: 8.15 (s, 1H), 8.04 (d, 1H), 7.81 (d, 1H), 7.55 (m, 2H), 3.21 (s, 3H)

Example 19) Preparation of 4-(3-bromo-5-chloro-1H-indazol-1-yl)-5-chloro-2-fluoro-N-(methylsulfonyl)benzamide

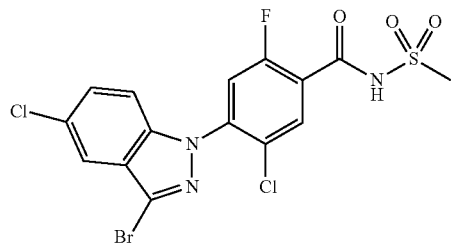 [SMILES: CS(=O)(=O)NC(=O)c1cc(Cl)c(-n2nc(Br)c3cc(Cl)ccc32)cc1F]

1H NMR (500 MHz, CDCl$_3$) δ: 8.32 (d, 1H), 7.69 (s, 1H), 7.45 (m, 2H), 7.19 (d, 1H), 3.43 (s, 3H)

Example 20) Preparation of 5-chloro-4-(3,5-dichloro-1H-pyrrolo[2,3-b]pyridin-1-yl)-2-fluoro-N-(methylsulfonyl)benzamide

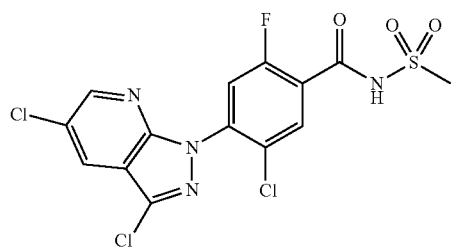 [SMILES: CS(=O)(=O)NC(=O)c1cc(Cl)c(-n2nc(Cl)c3cc(Cl)cnc32)cc1F]

1H NMR (500 MHz, MeOD) δ: 8.29-8.28 (d, 1H), 8.09 (d, 1H), 8.00 (d, 1H), 7.77 (s, 1H), 7.53-7.51 (d, 1H), 3.24 (s, 3H)

Example 21) Preparation of 4-(5-bromo-3-chloro-1H-indazol-1-yl)-5-chloro-2-fluoro-N-(methylsulfonyl)benzamide

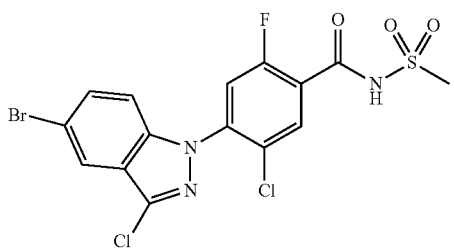

1H NMR (500 MHz, MeOD) δ: 8.05-8.04 (d, 1H), 7.96 (s, 1H), 7.66-7.64 (m, 1H), 7.49-7.47 (d, 1H), 7.32-7.30 (d, 1H), 3.27 (s, 3H)

Example 22) Preparation of 4-(5-bromo-3-cyano-1H-indazol-1-yl)-5-chloro-2-fluoro-N-(methylsulfonyl)benzamide

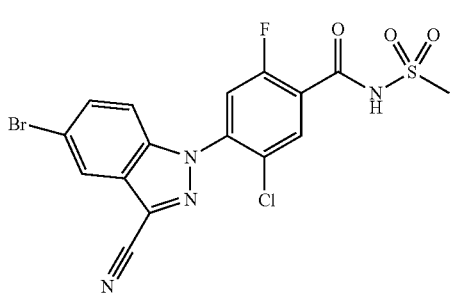 [SMILES: CS(=O)(=O)NC(=O)c1cc(Cl)c(-n2nc(C#N)c3cc(Br)ccc32)cc1F]

1H NMR (500 MHz, MeOD) δ: 8.77 (d, 1H), 8.42 (dd, 1H), 8.03 (d, 1H), 7.55 (dd, 2H), 3.18 (s, 3H)

Example 23) Preparation of 5-chloro-4-(3-chloro-5-nitro-1H-indazol-1-yl)-2-fluoro-N-(methylsulfonyl)benzamide

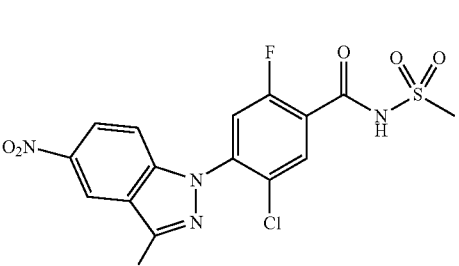

1H NMR (500 MHz, MeOD) δ: 8.16 (d, 1H), 8.05 (d, 1H), 7.73 (dd, 1H), 7.59 (d, 1H), 7.45 (d, 1H), 3.22 (s, 3H)

Example 25) Preparation of 5-chloro-4-(5-chloro-3-cyclopropyl-1H-indazol-1-yl)-2-fluoro-N-(methylsulfonyl)benzamide

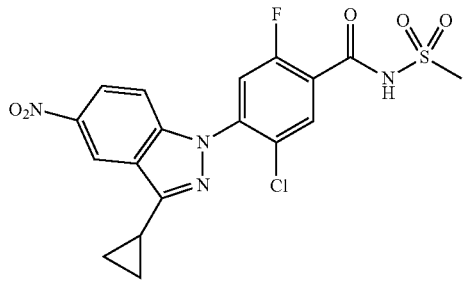 [SMILES: CS(=O)(=O)NC(=O)c1cc(Cl)c(-n2nc(C3CC3)c3cc([N+](=O)[O-])ccc32)cc1F]

1H NMR (500 MHz, MeOD) δ: 8.00 (d, 1H), 7.90 (s, 1H), m (7.42, 2H), 7.25 (m, 1H), 3.26 (s, 3H), 2.32 (m, 1H), 1.10 (m, 4H)

Example 27) Preparation of 5-chloro-4-(3-chloro-5-(phenylamino)-1H-indazol-1-yl)-2-fluoro-N-(methylsulfonyl)benzamide

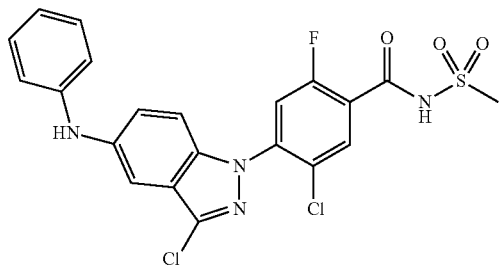 [SMILES: CS(=O)(=O)NC(=O)c1cc(Cl)c(-n2nc(Cl)c3cc(Nc4ccccc4)ccc32)cc1F]

1H NMR (500 MHz, MeOD) δ: 8.09 (s, 1H), 8.06-8.04 (d, 1H), 7.99-7.97 (d, 2H), 7.58-7.54 (t, 2H), 7.51-7.48 (m, 3H), 7.38-7.37 (d, 1H), 3.14 (s, 3H)

Example 30) Preparation of 4-(5-(benzyloxy)-3-methyl-1H-indazol-1-yl)-5-chloro-2-fluoro-N-(methylsulfonyl)benzamide

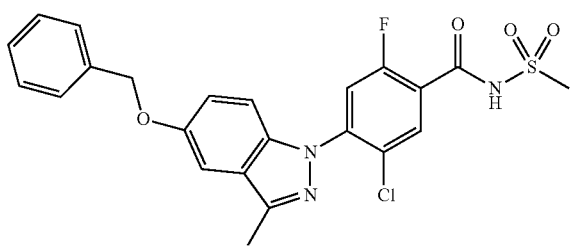 [SMILES: Cc1nn(-c2cc(F)c(C(=O)NS(C)(=O)=O)cc2Cl)c2ccc(OCc3ccccc3)cc12]

1H NMR (500 MHz, MeOD) δ: 8.01 (d, 1H), 7.49 (d, 2H), 7.41-7.37 (m, 3H), 7.32 (d, 1H), 7.29 (s, 1H), 7.22 (s, 2H), 5.17 (s, 2H), 3.25 (s, 3H), 2.58 (s, 3H),

Example 32) Preparation of 5-chloro-4-(3,4-dichloro-5-((2-fluorobenzyl)oxy)-1H-indazol-1-yl)-2-fluoro-N-(methylsulfonyl)benzamide

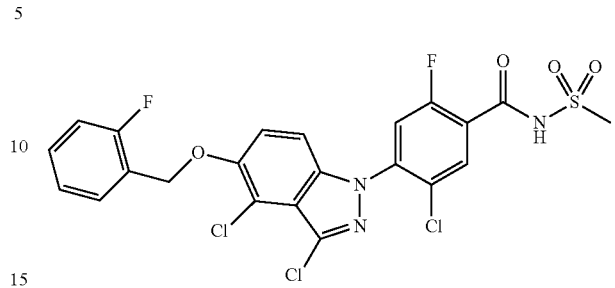

1H NMR (500 MHz, MeOD) δ: 8.01-8.00 (d, 1H), 7.60-7.57 (t, 1H), 7.48-7.42 (dd, 2H), 7.38-7.37 (d, 1H), 7.24-7.19 (m, 2H), 7.15-7.11 (m, 1H), 5.25 (s, 2H), 3.14 (s, 3H)

Example 33) Preparation of 5-chloro-4-(3-chloro-5-(1-phenylethoxy)-1H-indazol-1-yl)-2-fluoro-N-(methylsulfonyl)benzamide

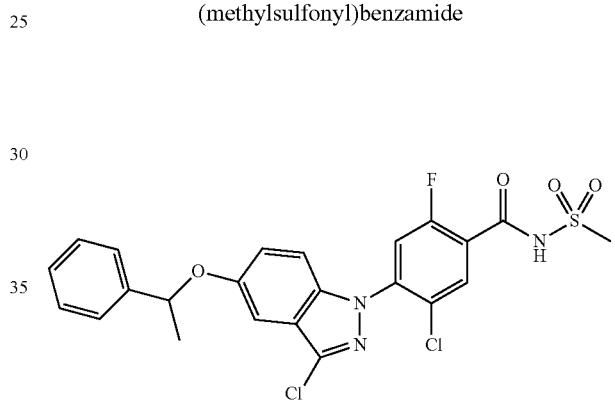

1H NMR (500 MHz, MeOD) δ: 8.00-7.98 (d, 1H), 7.45-7.40 (t, 3H), 7.35-7.32 (t, 2H), 7.26-7.20 (m, 3H), 6.97 (s, 1H), 5.48-5.47 (q, 1H), 3.23 (s, 3H), 1.65-1.64 (d, 3H)

Example 34) Preparation of 5-chloro-4-(3-chloro-5-(cyclohexylmethoxy)-1H-indazol-1-yl)-2-fluoro-N-(methylsulfonyl)benzamide

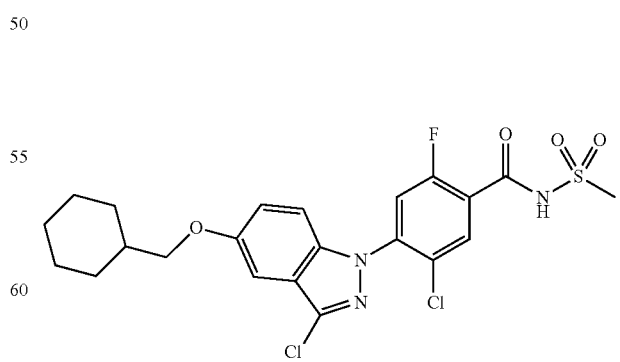

1H NMR (500 MHz, MeOD) δ: 8.01-7.99 (d, 1H), 7.39-7.37 (d, 1H), 7.25-7.24 (d, 1H), 7.19-7.17 (d, 1H), 7.06 (s, 1H), 3.87-3.86 (d, 2H), 3.13 (s, 3H)

Example 35) Preparation of 5-chloro-4-(3-chloro-5-(naphthalen-2-ylmethoxy)-1H-indazol-1-yl)-2-fluoro-N-(methylsulfonyl)benzamide

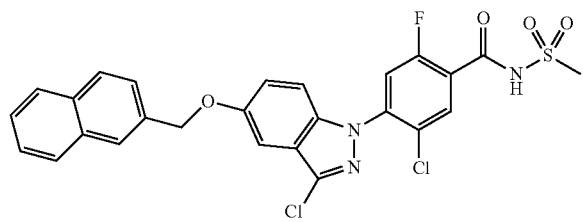 [SMILES: CS(=O)(=O)NC(=O)c1cc(Cl)c(-n2nc(Cl)c3cc(OCc4ccc5ccccc5c4)ccc32)cc1F]

1H NMR (500 MHz, MeOD) δ: 8.01-8.00 (d, 1H), 7.97 (s, 1H), 7.91-7.87 (m, 3H), 7.62-7.60 (d, 1H), 7.50-7.48 (t, 2H), 7.41-7.39 (d, 1H), 7.34-7.27 (m, 3H), 5.35 (s, 2H), 3.15 (s, 3H)

Example 36) Preparation of 5-chloro-4-(3-chloro-5-((4-fluorobenzyl)oxy)-1H-indazol-1-yl)-2-fluoro-N-(methylsulfonyl)benzamide

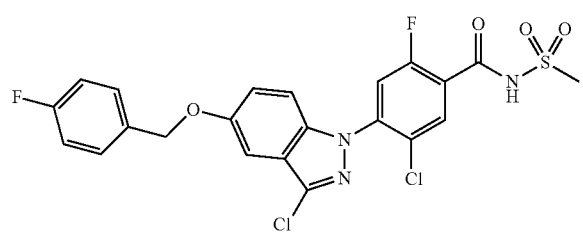

1H NMR (500 MHz, MeOD) δ: 8.02-8.00 (d, 1H), 7.52-7.49 (m, 2H), 7.39-7.37 (d, 1H), 7.26 (s, 1H), 7.20 (s, 1H), 7.13-7.10 (t, 2H), 5.14 (s, 2H), 3.13 (s, 3H)

Example 37) Preparation of 5-chloro-4-(3-chloro-5-((2-fluorobenzyl)oxy)-1H-indazol-1-yl)-2-fluoro-N-(methylsulfonyl)benzamide

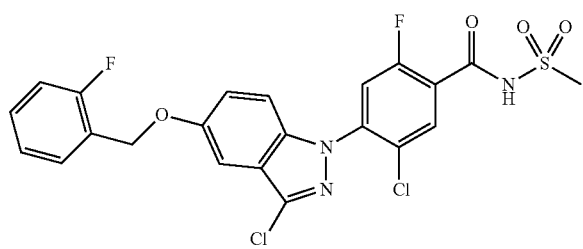 [SMILES: CS(=O)(=O)NC(=O)c1cc(Cl)c(-n2nc(Cl)c3cc(OCc4ccccc4F)ccc32)cc1F]

1H NMR (500 MHz, MeOD) δ: 8.02-8.00 (d, 1H), 7.58-7.55 (t, 1H), 7.43-7.38 (m, 2H), 7.28-7.13 (m, 5H), 5.23 (s, 2H), 3.18 (s, 3H)

Example 38) Preparation of 5-chloro-4-(3-chloro-5-((3-fluorobenzyl)oxy)-1H-indazol-1-yl)-2-fluoro-N-(methylsulfonyl)benzamide 1H NMR (500 MHz, MeOD) δ: 8.02-8.00 (d, 1H), 7.41-7.38 (t, 2H), 7.31-7.25 (m, 4H), 7.23 (s, 1H), 7.07-7.04 (t, 1H), 5.20 (s, 2H), 3.15 (s, 3H)

Example 39) Preparation of 5-chloro-4-(3-chloro-5-(1-(4-fluorophenyl)ethoxy)-1H-indazol-1-yl)-2-fluoro-N-(methylsulfonyl)benzamide 1H NMR (500 MHz, MeOD) δ: 8.00-7.99 (d, 1H), 7.47-7.44 (m, 2H), 7.39-7.38 (d, 1H), 7.21 (s, 2H), 7.08-7.04 (t, 2H), 6.98 (s, 1H), 5.50-5.49 (q, 1H), 3.30 (d, 3H), 3.20 (s, 3H)

Example 40) Preparation of 5-chloro-4-(3-chloro-5-phenethoxy-1H-indazol-1-yl)-2-fluoro-N-(methylsulfonyl)benzamide 1H NMR (500 MHz, MeOD) δ: 8.01 (d, 1H), 7.37 (d, 1H), 7.33-7.28 (m, 4H), 7.22-7.17 (m, 3H), 7.08 (s, 1H), 4.28 (t, 2H), 3.13 (s, 3H), 3.12 (t, 2H)

Example 41) Preparation of 5-chloro-2-fluoro-4-(5-isobutoxy-1H-indazol-1-yl)-N-(methylsulfonyl)benzamide

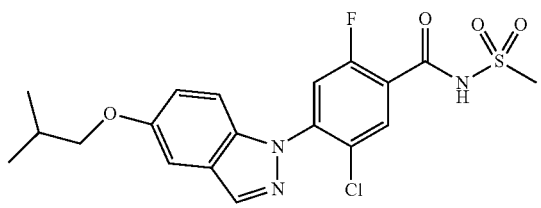 [SMILES: CC(C)COc1ccc2c(cnn2-c2cc(F)c(C(=O)NS(C)(=O)=O)cc2Cl)c1]

1H NMR (500 MHz, MeOD) δ: 8.20 (s, 1H), 8.03-8.02 (d, 1H), 7.44-7.42 (d, 1H), 7.25-7.24 (d, 2H), 7.15-7.13 (d, 1H), 3.82-8.30 (d, 2H), 3.25 (s, 3H), 2.12-2.09 (q, 1H), 1.07-1.06 (d, 6H)

Example 42) Preparation of 5-chloro-4-(3-chloro-5-isobutoxy-1H-indazol-1-yl)-2-fluoro-N-(methylsulfonyl)benzamide

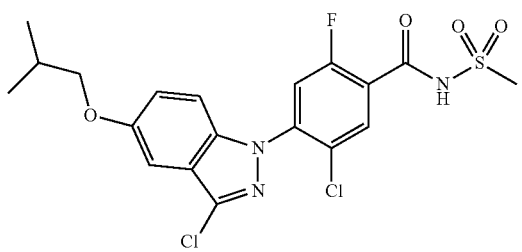 [SMILES: CC(C)COc1ccc2c(c1)c(Cl)nn2-c1cc(F)c(C(=O)NS(C)(=O)=O)cc1Cl]

1H NMR (500 MHz, MeOD) δ: 8.02-8.00 (d, 1H), 7.42-7.40 (d, 1H), 7.25-7.23 (d, 1H), 7.20-7.18 (t, 1H), 7.07 (s, 1H), 3.83-3.82 (d, 2H), 3.17 (s, 3H), 2.13-2.08 (q, 1H), 1.07-1.06 (d, 6H)

Example 43) Preparation of 4-(5-(benzyloxy)-3-chloro-1H-indazol-1-yl)-5-chloro-N—(N,N-dimethylsulfamoyl)-2-fluorobenzamide

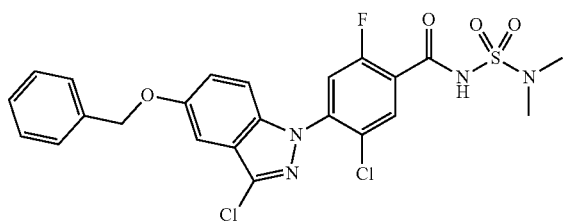 [SMILES: CN(C)S(=O)(=O)NC(=O)c1cc(Cl)c(-n2nc(Cl)c3cc(OCc4ccccc4)ccc32)cc1F]

1H NMR (500 MHz, CDCl₃) δ: 8.82 (d, 1H), 7.46 (m, 2H), 7.40 (m, 2H), 7.35 (m, 2H), 7.22 (m, 1H), 7.16 (m, 1H), 7.13 (m, 1H), 2.99 (s, 6H)

Example 44) Preparation of 4-(5-(benzyloxy)-3-chloro-1H-indazol-1-yl)-3-chloro-N-(methylsulfonyl)benzamide

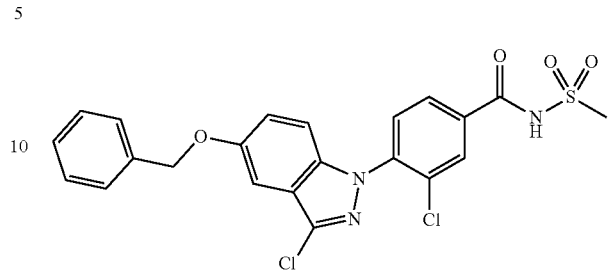

1H NMR (500 MHz, CDCl₃) δ: 8.15 (s, 1H), 8.01 (s, 1H), 7.91 (d, 1H), 7.41 (m, 2H), 7.36 (m, 2H), 7.31 (m, 1H), 7.08 (m, 1H), 7.04 (m, 1H), 6.99 (m, 1H), 3.27 (s, 3H)

Example 45) Preparation of 4-(6-(benzyloxy)-3-chloro-1H-indazol-1-yl)-5-chloro-2-fluoro-N-(methylsulfonyl)benzamide

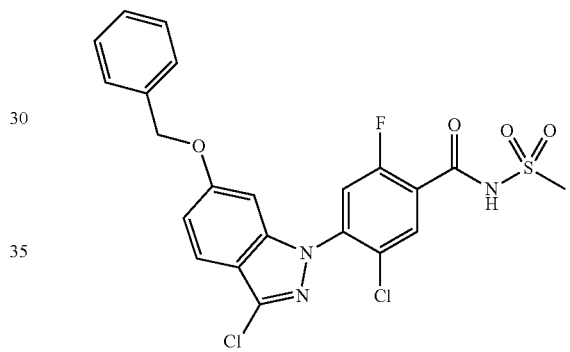

1H NMR (500 MHz, MeOD) δ: 8.66 (s, 1H), 8.01 (d, 1H), 7.71 (d, 1H), 7.58 (d, 1H), 7.50 (d, 2H), 7.38 (t, 2H), 7.31 (t, 1H), 7.19 (d, 1H), 5.30 (s, 2H), 3.14 (s, 3H)

Example 46) Preparation of methyl 6-(benzyloxy)-1-(2-chloro-5-fluoro-4-((methylsulfonyl)carbamoyl)phenyl)-1H-indazole-3-carboxylate

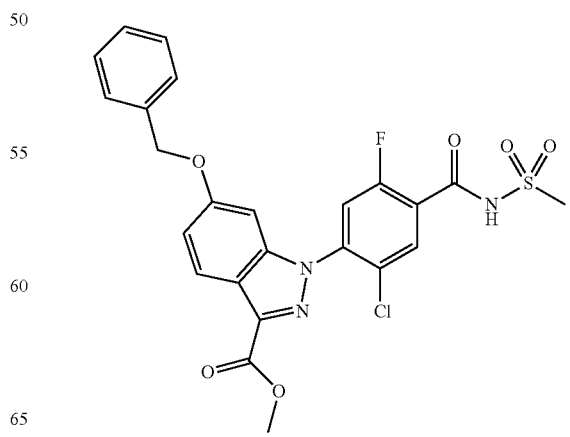

1H NMR (500 MHz, MeOD) δ: 8.09 (d, 1H), 8.03 (d, 1H), 7.49 (d, 1H), 7.43-7.42 (m, 2H), 7.38-7.30 (m, 2H), 7.14 (d, 1H), 7.12 (d, 1H), 6.81 (d, 1H), 5.11 (s, 2H), 4.02 (s, 3H), 3.21 (s, 3H)

Example 49) Preparation of 5-chloro-4-(5-chloro-3-(pyridin-4-yl)-1H-indazol-1-yl)-2-fluoro-N-(methylsulfonyl)benzamide

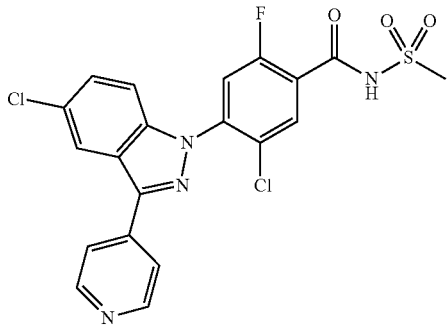 [SMILES: CS(=O)(=O)NC(=O)c1cc(Cl)c(-n2nc(-c3ccncc3)c3cc(Cl)ccc32)cc1F]

1H NMR (500 MHz, MeOD) δ: 8.71-8.70 (d, 2H), 8.26 (s, 1H), 8.11-8.10 (d, 2H), 8.06-8.04 (d, 1H), 7.56-7.52 (m, 2H), 7.44-7.42 (d, 1H), 3.15 (s, 3H)

Example 50) Preparation of 5-chloro-4-(5-chloro-3-(pyridin-3-yl)-1H-indazol-1-yl)-2-fluoro-N-(methylsulfonyl)benzamide

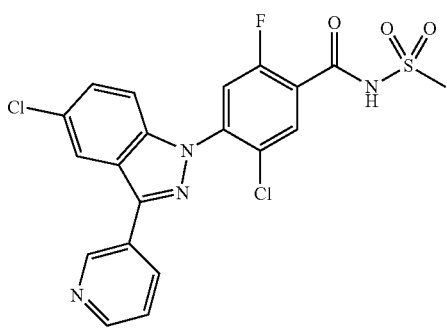 [SMILES: CS(=O)(=O)NC(=O)c1cc(Cl)c(-n2nc(-c3cccnc3)c3cc(Cl)ccc32)cc1F]

1H NMR (500 MHz, MeOD) δ: 9.19 (s, 1H), 8.64-8.64 (d, 1H), 8.49-8.47 (d, 1H), 8.16 (s, 1H), 8.06-8.04 (d, 1H), 7.65-7.63 (t, 1H), 7.55-7.53 (d, 2H), 7.43-7.42 (d, 1H), 3.17 (s, 3H)

Example 51) Preparation of 5-chloro-4-(5-chloro-3-(5-chloropyridin-3-yl)-1H-indazol-1-yl)-2-fluoro-N-(methylsulfonyl)benzamide

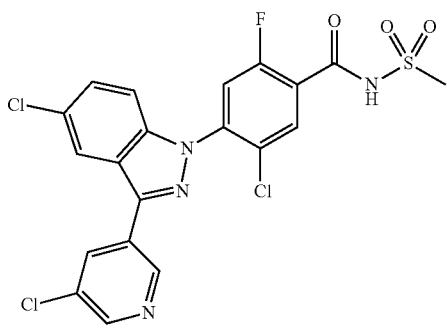 [SMILES: CS(=O)(=O)NC(=O)c1cc(Cl)c(-n2nc(-c3cncc(Cl)c3)c3cc(Cl)ccc32)cc1F]

1H NMR (500 MHz, MeOD) δ: 9.13 (s, 1H), 8.65 (s, 1H), 8.48 (s, 1H), 8.06-8.04 (d, 1H), 7.97 (s, 1H), 7.55-7.52 (t, 2H), 7.44-7.42 (d, 1H), 3.15 (s, 3H)

Example 52) Preparation of 5-chloro-4-(5-chloro-3-(m-tolyl)-1H-indazol-1-yl)-2-fluoro-N-(methylsulfonyl)benzamide

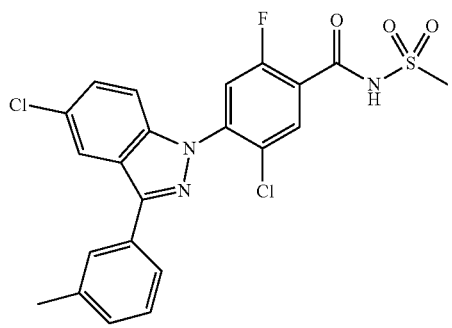 [SMILES: Cc1cccc(-c2nn(-c3cc(F)c(C(=O)NS(C)(=O)=O)cc3Cl)c3ccc(Cl)cc23)c1]

1H NMR (500 MHz, MeOD) δ: 8.06 (s, 1H), 7.78-7.75 (m, 2H), 7.55-7.49 (dd, 2H), 7.44 (s, 1H), 7.38-7.36 (d, 1H), 7.31 (s, 1H), 3.23 (s, 3H), 2.46 (s, 3H)

Example 53) Preparation of 5-chloro-4-(5-chloro-3-(2-fluorophenyl)-1H-indazol-1-yl)-2-fluoro-N-(methylsulfonyl)benzamide

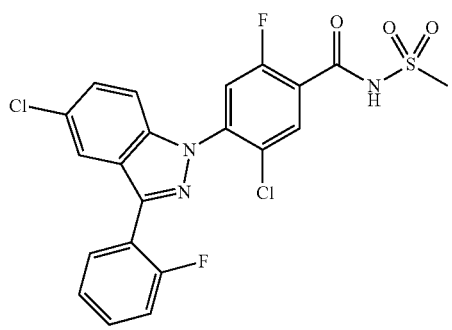 [SMILES: CS(=O)(=O)NC(=O)c1cc(Cl)c(-n2nc(-c3ccccc3F)c3cc(Cl)ccc32)cc1F]

1H NMR (500 MHz, MeOD) δ: 8.07-8.06 (d, 1H), 7.85 (s, 2H), 7.62-7.60 (d, 1H), 7.52-7.50 (m, 2H), 7.41-7.35 (m, 3H), 3.28 (s, 3H)

Example 54) Preparation of 5-chloro-4-(5-chloro-3-(3-fluorophenyl)-1H-indazol-1-yl)-2-fluoro-N-(methylsulfonyl)benzamide

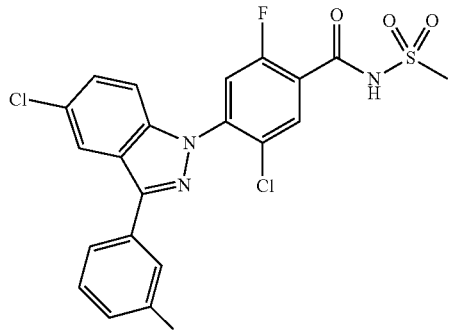

1H NMR (500 MHz, MeOD) δ: 8.11 (s, 1H), 8.06-8.04 (d, 1H), 7.84-7.83 (d, 1H), 7.73-7.71 (d, 1H), 7.60-7.56 (m, 1H), 7.52-7.50 (d, 2H), 7.40-7.38 (d, 1H), 7.23-7.20 (t, 1H), 3.17 (s, 3H)

Example 55) Preparation of 5-chloro-4-(5-chloro-3-(4-fluorophenyl)-1H-indazol-1-yl)-2-fluoro-N-(methylsulfonyl)benzamide

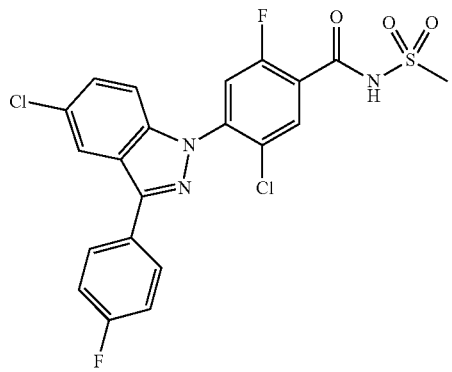 [SMILES: CS(=O)(=O)NC(=O)c1cc(Cl)c(-n2nc(-c3ccc(F)cc3)c3cc(Cl)ccc32)cc1F]

1H NMR (500 MHz, MeOD) δ: 8.10 (s, 1H), 8.06-8.01 (m, 3H), 7.59-7.57 (d, 1H), 7.52-7.50 (d, 1H), 7.40-7.38 (d, 1H), 7.32-7.28 (t, 2H), 3.28 (s, 3H)

Example 56) Preparation of 5-chloro-4-(5-chloro-3-(2,4-difluorophenyl)-1H-indazol-1-yl)-2-fluoro-N-(methylsulfonyl)benzamide

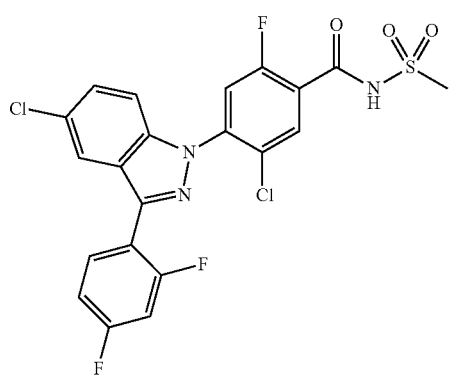 [SMILES: CS(=O)(=O)NC(=O)c1cc(Cl)c(-n2nc(-c3ccc(F)cc3F)c3cc(Cl)ccc32)cc1F]

1H NMR (500 MHz, MeOD) δ: 8.06-8.05 (d, 1H), 7.89-7.84 (m, 2H), 7.60-7.58 (d, 1H), 7.52-7.50 (d, 1H), 7.41-7.39 (d, 1H), 7.25-7.21 (t, 1H), 7.19-7.15 (t, 1H), 3.27 (s, 3H)

Example 57) Preparation of 5-chloro-4-(5-chloro-3-(2-methoxypyridin-3-yl)-1H-indazol-1-yl)-2-fluoro-N-(methylsulfonyl)benzamide

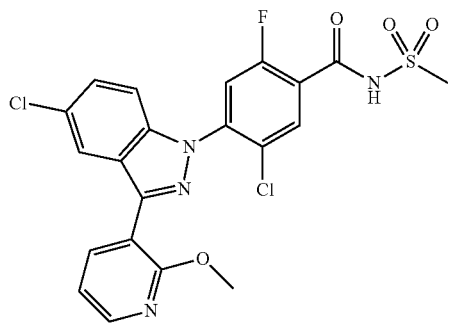 [SMILES: COc1ncccc1-c1nn(-c2cc(F)c(C(=O)NS(C)(=O)=O)cc2Cl)c2ccc(Cl)cc12]

1H NMR (500 MHz, MeOD) δ: 8.30 (s, 1H), 8.07-8.05 (t, 1H), 7.83 (s, 1H), 7.58-7.56 (d, 1H), 7.49-7.48 (d, 1H), 7.38-7.36 (d, 1H), 7.14-7.12 (t, 1H), 4.04 (s, 3H), 3.25 (s, 3H)

Example 58) Preparation of 5-chloro-4-(5-chloro-3-(2-methoxyphenyl)-1H-indazol-1-yl)-2-fluoro-N-(methylsulfonyl)benzamide

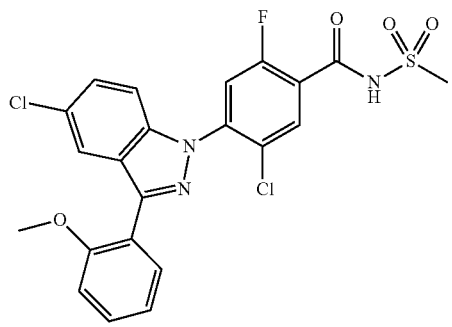

1H NMR (500 MHz, MeOD) δ: 8.06-8.05 (d, 1H), 7.73 (s, 1H), 7.63-7.57 (dd, 2H), 7.52-7.45 (m, 2H), 7.36-7.34 (d, 1H), 7.22-7.20 (d, 1H), 7.12-7.09 (t, 1H), 3.89 (s, 3H), 3.28 (s, 3H)

Example 59) Preparation of 5-chloro-4-(5-chloro-3-(4-methoxyphenyl)-1H-indazol-1-yl)-2-fluoro-N-(methylsulfonyl)benzamide

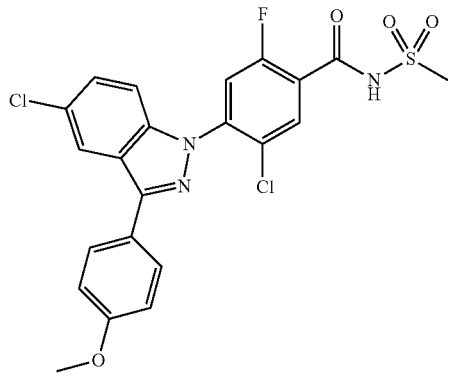 [SMILES: COc1ccc(-c2nn(-c3cc(F)c(C(=O)NS(C)(=O)=O)cc3Cl)c3ccc(Cl)cc23)cc1]

1H NMR (500 MHz, MeOD) δ: 8.07-8.04 (t, 2H), 7.92-7.90 (d, 2H), 7.49-7.47 (d, 2H), 7.36-7.34 (d, 1H), 7.12-7.11 (d, 2H), 3.88 (s, 3H), 3.16 (s, 3H)

Example 60) Preparation of 5-chloro-4-(5-chloro-3-(2-cyanophenyl)-1H-indazol-1-yl)-2-fluoro-N-(methylsulfonyl)benzamide

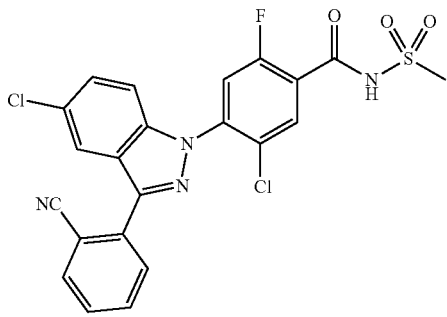 [SMILES: CS(=O)(=O)NC(=O)c1cc(Cl)c(-n2nc(-c3ccccc3C#N)c3cc(Cl)ccc32)cc1F]

1H NMR (500 MHz, MeOD) δ: 8.04-8.03 (d, 1H), 7.81 (s, 1H), 7.77-7.76 (d, 1H), 7.73-7.72 (d, 1H), 7.68-7.64 (t, 1H), 7.60-7.58 (d, 1H), 7.50-7.46 (t, 2H), 7.38-7.36 (d, 1H), 3.13 (s, 3H)

Example 61) Preparation of 5-chloro-4-(5-chloro-3-(3-cyanophenyl)-1H-indazol-1-yl)-2-fluoro-N-(methylsulfonyl)benzamide

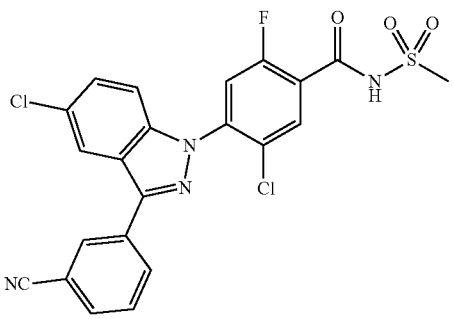 [SMILES: CS(=O)(=O)NC(=O)c1cc(Cl)c(-n2nc(-c3cccc(C#N)c3)c3cc(Cl)ccc32)cc1F]

1H NMR (500 MHz, MeOD) δ: 8.35-8.32 (d, 2H), 8.16 (s, 1H), 8.06-8.04 (d, 1H), 7.83-7.82 (d, 1H), 7.76-7.73 (t, 1H), 7.53-7.51 (d, 2H), 7.42-7.40 (d, 1H), 3.16 (s, 3H)

Example 62) Preparation of 5-chloro-4-(5-chloro-3-(4-cyanophenyl)-1H-indazol-1-yl)-2-fluoro-N-(methylsulfonyl)benzamide

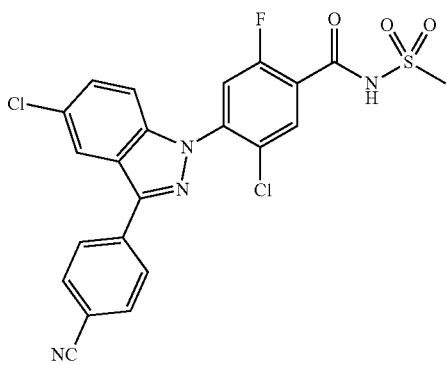 [SMILES: CS(=O)(=O)NC(=O)c1cc(Cl)c(-n2nc(-c3ccc(C#N)cc3)c3cc(Cl)ccc32)cc1F]

1H NMR (500 MHz, MeOD) δ: 8.23-8.21 (d, 2H), 8.18 (s, 1H), 8.05-8.04 (d, 1H), 7.92-7.90 (d, 2H), 7.53-7.52 (d, 2H), 7.41-7.40 (d, 1H), 3.16 (s, 3H)

Example 63) Preparation of 5-chloro-4-(5-chloro-3-(2-(trifluoromethyl)phenyl)-1H-indazol-1-yl)-2-fluoro-N-(methylsulfonyl)benzamide

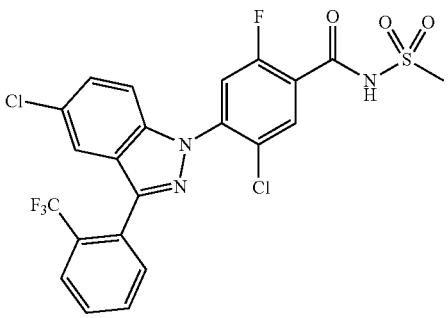

1H NMR (500 MHz, MeOD) δ: 8.06-8.05 (d, 1H), 7.95-7.93 (d, 1H), 7.81-7.80 (d, 1H), 7.75-7.69 (m, 2H), 7.55 (s, 1H), 7.52-7.51 (d, 2H), 7.43-7.41 (d, 1H), 3.28 (s, 3H)

Example 64) Preparation of 5-chloro-4-(5-chloro-3-(3-(trifluoromethyl)phenyl)-1H-indazol-1-yl)-2-fluoro-N-(methylsulfonyl)benzamide

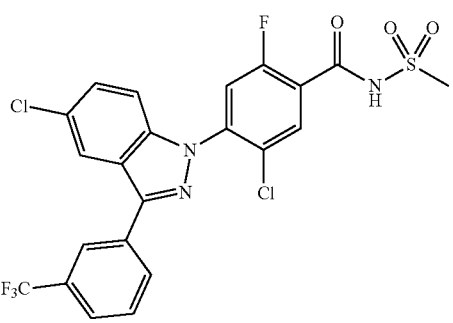 [SMILES: CS(=O)(=O)NC(=O)c1cc(Cl)c(-n2nc(-c3cccc(C(F)(F)F)c3)c3cc(Cl)ccc32)cc1F]

1H NMR (500 MHz, MeOD) δ: 8.27-8.26 (d, 2H), 8.07 (s, 1H), 8.06 (d, 1H), 7.78 (s, 2H), 7.61-7.60 (d, 1H), 7.54-7.52 (d, 1H), 7.43-7.41 (d, 1H), 3.27 (s, 3H)

Example 65) Preparation of 5-chloro-4-(5-chloro-3-(4-(trifluoromethyl)phenyl)-1H-indazol-1-yl)-2-fluoro-N-(methylsulfonyl)benzamide

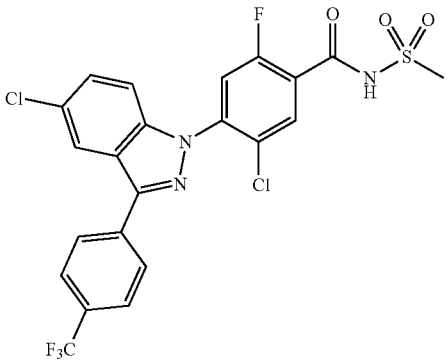 [SMILES: CS(=O)(=O)NC(=O)c1cc(Cl)c(-n2nc(-c3ccc(C(F)(F)F)cc3)c3cc(Cl)ccc32)cc1F]

1H NMR (500 MHz, MeOD) δ: 8.23-8.21 (d, 2H), 8.18 (s, 1H), 8.06-8.05 (d, 1H), 7.57-7.52 (m, 2H), 7.42-7.40 (d, 1H), 3.21 (s, 3H)

Example 66) Preparation of 5-chloro-4-(5-chloro-3-(4-chloro-2-fluorophenyl)-1H-indazol-1-yl)-2-fluoro-N-(methylsulfonyl)benzamide

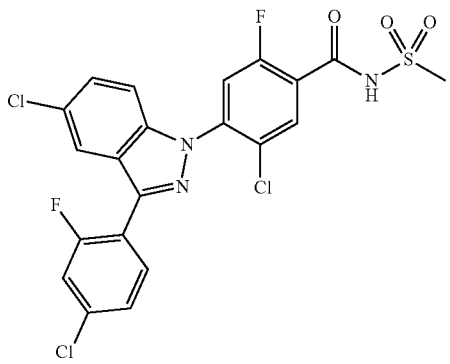 [SMILES: CS(=O)(=O)NC(=O)c1cc(Cl)c(-n2nc(-c3ccc(Cl)cc3F)c3cc(Cl)ccc32)cc1F]

1H NMR (500 MHz, MeOD) δ: 8.06-8.05 (d, 1H), 7.87-7.85 (d, 2H), 7.57-7.56 (d, 1H), 7.51-7.46 (m, 2H), 7.40-7.39 (d, 2H), 3.23 (s, 3H)

Example 67) Preparation of 5-chloro-4-(5-chloro-3-(4-chlorophenyl)-1H-indazol-1-yl)-2-fluoro-N-(methylsulfonyl)benzamide

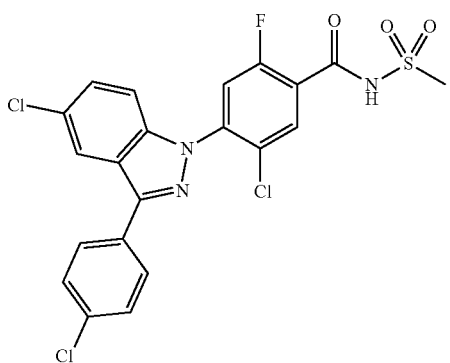 [SMILES: CS(=O)(=O)NC(=O)c1cc(Cl)c(-n2nc(-c3ccc(Cl)cc3)c3cc(Cl)ccc32)cc1F]

1H NMR (500 MHz, MeOD) δ: 8.11 (s, 1H), 8.05-8.04 (d, 1H), 8.01-7.99 (d, 2H), 7.58-7.56 (d, 2H), 7.51-7.50 (d, 2H), 7.39-7.38 (d, 1H), 3.16 (s, 3H)

Example 68) Preparation of 5-chloro-4-(5-chloro-3-(2-fluoropyridin-4-yl)-1H-indazol-1-yl)-2-fluoro-N-(methylsulfonyl)benzamide

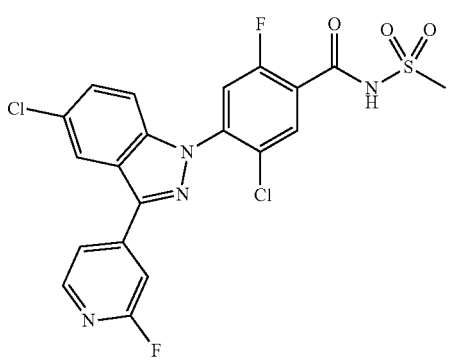 [SMILES: CS(=O)(=O)NC(=O)c1cc(Cl)c(-n2nc(-c3ccnc(F)c3)c3cc(Cl)ccc32)cc1F]

1H NMR (500 MHz, MeOD) δ: 8.37-8.36 (d, 1H), 8.26 (s, 1H), 8.06-8.05 (d, 1H), 8.00-7.99 (m, 1H), 7.71 (s, 1H), 7.59-7.55 (t, 2H), 7.45-7.43 (d, 1H), 3.21 (s, 3H)

Example 69) Preparation of 5-chloro-4-(5-chloro-3-(5-chloro-2-fluorophenyl)-1H-indazol-1-yl)-2-fluoro-N-(methylsulfonyl)benzamide

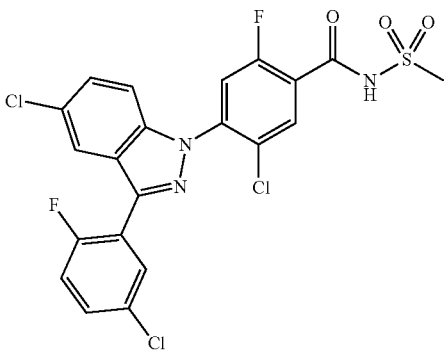 [SMILES: CS(=O)(=O)NC(=O)c1cc(Cl)c(-n2nc(-c3cc(Cl)ccc3F)c3cc(Cl)ccc32)cc1F]

1H NMR (500 MHz, MeOD) δ: 8.06 (d, 1H), 7.85 (s, 2H), 7.56-7.50 (m, 3H), 7.41-7.35 (m, 2H), 3.18 (s, 3H)

Example 70) Preparation of 5-chloro-4-(5-chloro-3-(3-cyano-4-fluorophenyl)-1H-indazol-1-yl)-2-fluoro-N-(methylsulfonyl)benzamide

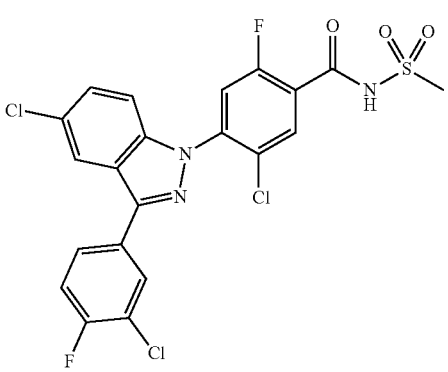 [SMILES: CS(=O)(=O)NC(=O)c1cc(Cl)c(-n2nc(-c3ccc(F)c(Cl)c3)c3cc(Cl)ccc32)cc1F]

1H NMR (500 MHz, MeOD) δ: 8.39 (d, 2H), 8.16 (s, 1H), 8.04 (d, 1H), 7.58-7.49 (m, 3H), 7.41 (d, 1H), 3.14 (s, 3H)

Example 71) Preparation of 5-chloro-4-(5-chloro-3-(2-chlorophenyl)-1H-indazol-1-yl)-2-fluoro-N-(methylsulfonyl)benzamide

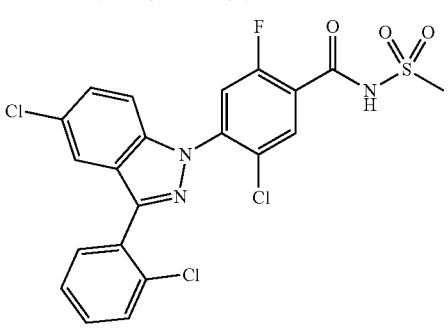 [SMILES: CS(=O)(=O)NC(=O)c1cc(Cl)c(-n2nc(-c3ccccc3Cl)c3cc(Cl)ccc32)cc1F]

1H NMR (500 MHz, MeOD) δ: 8.04 (d, 1H), 7.66-7.63 (m, 3H), 7.50-7.49 (d, 4H), 7.40 (d, 1H), 3.13 (s, 3H)

Example 72) Preparation of 5-chloro-4-(5-chloro-3-(3-chlorophenyl)-1H-indazol-1-yl)-2-fluoro-N-(methylsulfonyl)benzamide

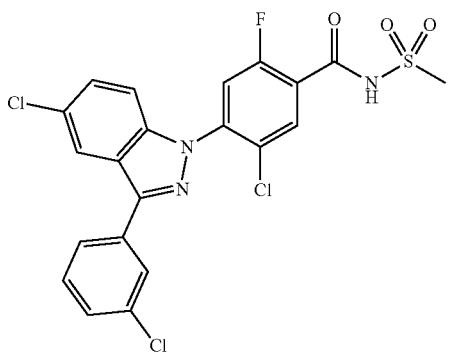 [SMILES: CS(=O)(=O)NC(=O)c1cc(Cl)c(-n2nc(-c3cccc(Cl)c3)c3cc(Cl)ccc32)cc1F]

1H NMR (500 MHz, MeOD) δ: 8.09-7.93 (m, 4H), 7.57-7.47 (m, 4H), 7.39 (d, 1H), 3.17 (s, 3H)

Example 73) Preparation of 5-chloro-4-(5-chloro-3-(3-chloro-5-fluorophenyl)-1H-indazol-1-yl)-2-fluoro-N-(methylsulfonyl)benzamide

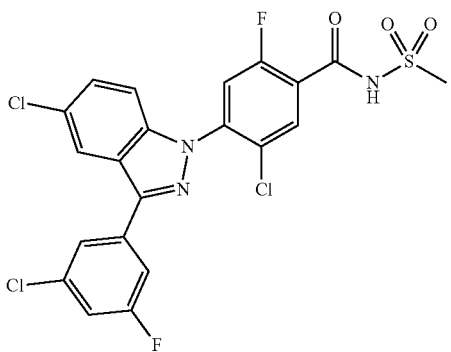 [SMILES: CS(=O)(=O)NC(=O)c1cc(Cl)c(-n2nc(-c3cc(F)cc(Cl)c3)c3cc(Cl)ccc32)cc1F]

1H NMR (500 MHz, MeOD) δ: 8.10 (s, 1H), 8.04 (d, 1H), 7.85 (s, 1H), 7.71 (d, 1H), 7.51-7.47 (m, 2H), 7.41 (d, 1H), 7.32 (d, 1H), 3.14 (s, 3H)

Example 74) Preparation of 5-chloro-4-(5-chloro-3-(2-chloro-4-fluorophenyl)-1H-indazol-1-yl)-2-fluoro-N-(methylsulfonyl)benzamide

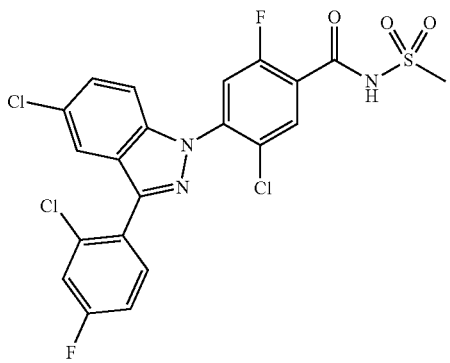 [SMILES: CS(=O)(=O)NC(=O)c1cc(Cl)c(-n2nc(-c3ccc(F)cc3Cl)c3cc(Cl)ccc32)cc1F]

1H NMR (500 MHz, MeOD) δ: 8.05 (d, 1H), 7.71-7.68 (m, 2H), 7.51-7.47 (m, 3H), 7.40 (d, 1H), 7.29-7.26 (m, 1H), 3.15 (s, 3H)

Example 75) Preparation of 5-chloro-4-(5-chloro-3-(3,4-difluorophenyl)-1H-indazol-1-yl)-2-fluoro-N-(methylsulfonyl)benzamide

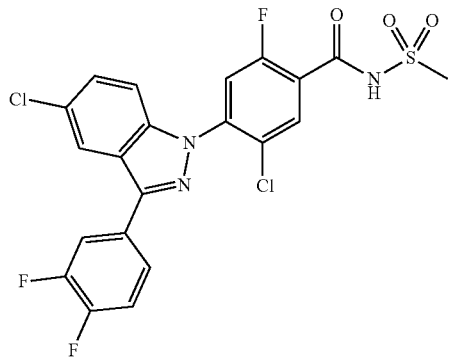 [SMILES: CS(=O)(=O)NC(=O)c1cc(Cl)c(-n2nc(-c3ccc(F)c(F)c3)c3cc(Cl)ccc32)cc1F]

1H NMR (500 MHz, MeOD) δ: 8.05 (s, 2H), 7.53-7.29 (m, 3H), 7.18-7.16 (m, 1H), 7.04-7.00 (m, 2H), 3.18 (s, 3H)

Example 76) Preparation of 5-chloro-4-(5-chloro-3-(2,5-difluorophenyl)-1H-indazol-1-yl)-2-fluoro-N-(methylsulfonyl)benzamide

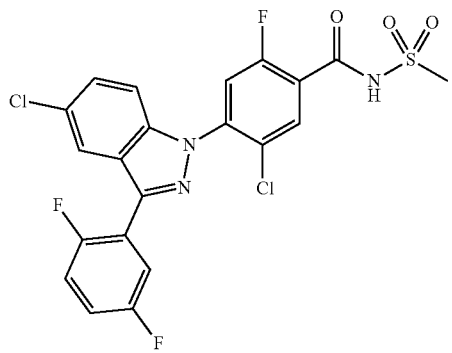

1H NMR (500 MHz, MeOD) δ: 8.05 (d, 1H), 7.86 (s, 1H), 7.58-7.49 (m, 3H), 7.39 (d, 2H), 7.27 (s, 1H), 3.15 (s, 3H)

Example 77) Preparation of 5-chloro-4-(5-chloro-3-(3,4,5-trifluorophenyl)-1H-indazol-1-yl)-2-fluoro-N-(methylsulfonyl)benzamide

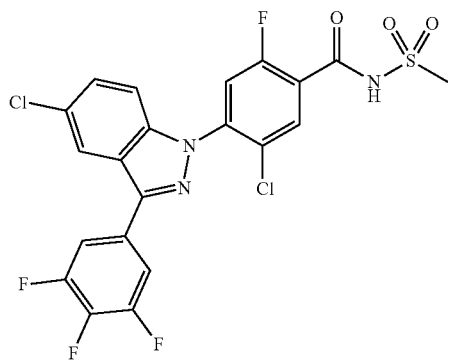 [SMILES: CS(=O)(=O)NC(=O)c1cc(Cl)c(-n2nc(-c3cc(F)c(F)c(F)c3)c3cc(Cl)ccc32)cc1F]

1H NMR (500 MHz, MeOD) δ: 8.14 (d, 1H), 8.04 (d, 1H), 7.81-7.78 (m, 2H), 7.54-7.50 (m, 2H), 7.40 (d, 1H), 3.16 (s, 3H)

Example 78) Preparation of 5-chloro-4-(5-chloro-3-(2-chloro-6-fluorophenyl)-1H-indazol-1-yl)-2-fluoro-N-(methylsulfonyl)benzamide

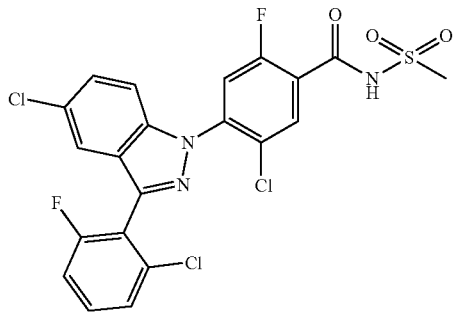 [SMILES: CS(=O)(=O)NC(=O)c1cc(Cl)c(-n2nc(-c3c(F)cccc3Cl)c3cc(Cl)ccc32)cc1F]

1H NMR (500 MHz, MeOD) δ: 8.05 (d, 1H), 7.58-7.41 (m, 6H), 7.30 (t, 1H), 3.14 (s, 3H)

Example 79) Preparation of 5-chloro-4-(5-chloro-3-(3-chloro-2-fluorophenyl)-1H-indazol-1-yl)-2-fluoro-N-(methylsulfonyl)benzamide

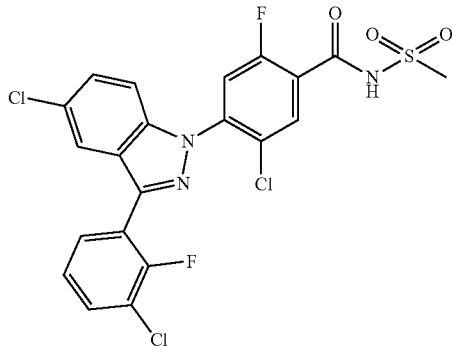 [SMILES: CS(=O)(=O)NC(=O)c1cc(Cl)c(-n2nc(-c3cccc(Cl)c3F)c3cc(Cl)ccc32)cc1F]

1H NMR (500 MHz, MeOD) δ: 8.06 (d, 1H), 7.82-7.76 (m, 2H), 7.62-7.31 (m, 5H), 3.16 (s, 3H)

Example 80) Preparation of 5-chloro-4-(5-chloro-3-(4-chloro-3-fluorophenyl)-1H-indazol-1-yl)-2-fluoro-N-(methylsulfonyl)benzamide

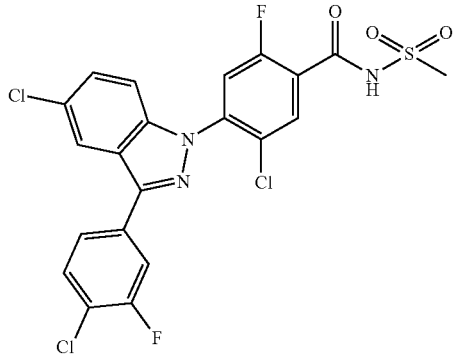 [SMILES: CS(=O)(=O)NC(=O)c1cc(Cl)c(-n2nc(-c3ccc(Cl)c(F)c3)c3cc(Cl)ccc32)cc1F]

1H NMR (500 MHz, MeOD) δ: 8.11 (s, 1H), 8.05 (d, 1H), 7.86-7.81 (m, 2H), 7.65 (t, 1H), 7.50 (t, 2H), 7.37 (d, 1H), 3.18 (s, 3H)

Example 81) Preparation of 5-chloro-4-(5-chloro-3-(4-nitrophenyl)-1H-indazol-1-yl)-2-fluoro-N-(methylsulfonyl)benzamide

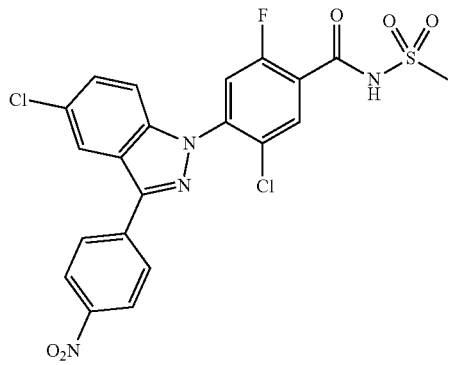 [SMILES: CS(=O)(=O)NC(=O)c1cc(Cl)c(-n2nc(-c3ccc([N+](=O)[O-])cc3)c3cc(Cl)ccc32)cc1F]

1H NMR (500 MHz, MeOD) δ: 8.40 (t, 2H), 8.27 (t, 2H), 8.20 (d, 1H), 8.05 (d, 1H), 7.52 (d, 2H), 7.40 (dd, 1H), 3.15 (s, 3H)

Example 82) Preparation of 4-(3-(4-aminophenyl)-5-chloro-1H-indazol-1-yl)-5-chloro-2-fluoro-N-(methylsulfonyl)benzamide

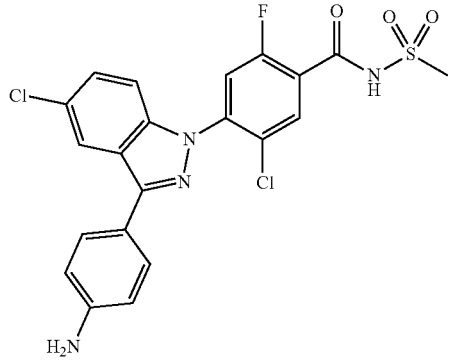

1H NMR (500 MHz, MeOD) δ: 8.04 (m, 2H), 7.70 (d, 2H), 7.46 (t, 2H), 7.31 (d, 1H), 6.86 (d, 2H), 3.17 (s, 3H)

Example 83) Preparation of 5-chloro-4-(5-chloro-3-(4-(trifluoromethoxy)phenyl)-1H-indazol-1-yl)-2-fluoro-N-(methylsulfonyl)benzamide

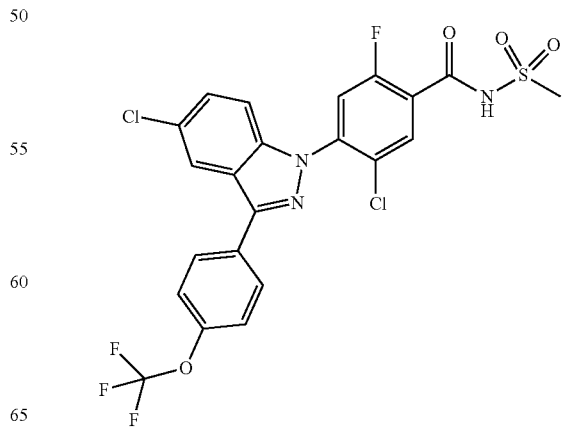

1H NMR (500 MHz, MeOD) δ: 8.14-8.11 (m, 3H), 8.05 (d, 1H), 7.55 (d, 1H), 7.53 (d, 1H), 7.49 (dd, 2H), 7.41 (d, 1H), 3.21 (s, 3H)

Example 84) Preparation of 5-chloro-2-fluoro-4-(5-isobutyl-3-phenyl-1H-indazol-1-yl)-N-(methylsulfonyl)benzamide

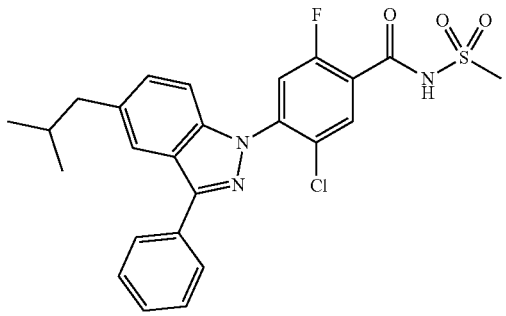 [SMILES: CC(C)Cc1ccc2c(c1)c(-c1ccccc1)nn2-c1cc(F)c(C(=O)NS(C)(=O)=O)cc1Cl]

1H NMR (500 MHz, MeOD) δ: 8.05 (d, 1H), 7.98 (d, 2H), 7.57 (s, 1H), 7.55 (t, 2H), 7.47 (m, 2H), 7.36 (d, 1H), 7.28 (d, 1H), 3.20 (s, 3H), 2.66 (d, 2H), 2.01 (s, 1H), 0.95 (d, 6H)

Example 85) Preparation of 5-chloro-4-(3-(4-chlorophenyl)-5-cyclopropyl-1H-indazol-1-yl)-2-fluoro-N-(methylsulfonyl)benzamide

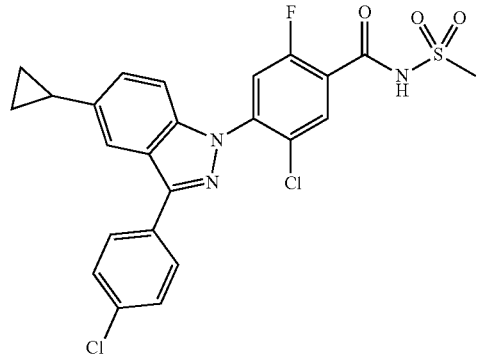 [SMILES: CS(=O)(=O)NC(=O)c1cc(Cl)c(-n2nc(-c3ccc(Cl)cc3)c3cc(C4CC4)ccc32)cc1F]

1H NMR (500 MHz, MeOD) δ: 8.04 (d, 1H), 8.00 (d, 2H), 7.79 (s, 1H), 7.56 (d, 2H), 7.50 (d, 1H), 7.27 (s, 2H), 3.23 (s, 3H), 2.12 (m, 1H), 1.02 (d, 2H), 0.78 (d, 2H)

Example 87) Preparation of 5-chloro-4-(5-chloro-3-(1-methyl-1H-pyrazol-5-yl)-1H-indazol-1-yl)-2-fluoro-N-(methylsulfonyl)benzamide

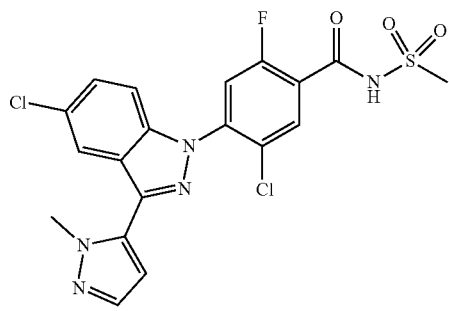 [SMILES: Cn1nccc1-c1nn(-c2cc(F)c(C(=O)NS(C)(=O)=O)cc2Cl)c2ccc(Cl)cc12]

1H NMR (500 MHz, MeOD) δ: 8.05-8.04 (d, 1H), 8.00 (s, 1H), 7.65 (s, 1H), 7.54-7.52 (m, 2H), 7.45-7.43 (d, 1H), 6.96 (s, 1H), 4.20 (s, 3H), 3.14 (s, 3H)

Example 88) Preparation of 5-chloro-4-(5-chloro-3-(1-methyl-1H-pyrazol-4-yl)-1H-indazol-1-yl)-2-fluoro-N-(methylsulfonyl)benzamide

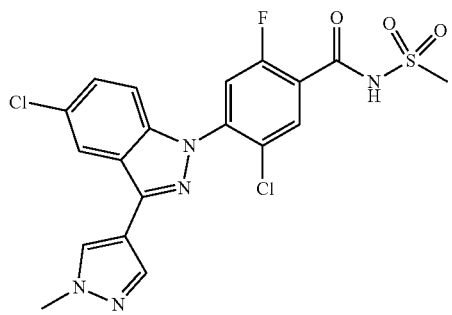 [SMILES: Cn1cc(-c2nn(-c3cc(F)c(C(=O)NS(C)(=O)=O)cc3Cl)c3ccc(Cl)cc23)cn1]

1H NMR (500 MHz, CDCl₃) δ: 8.43 (d, 1H), 8.08 (d, 1H), 7.98 (d, 1H), 7.92 (d, 1H), 7.56 (s, 1H), 7.44 (dd, 1H), 7.20 (dd, 1H), 4.10 (s, 3H), 3.43 (s, 3H)

Example 89) Preparation of 5-chloro-4-(5-chloro-3-(1H-pyrazol-4-yl)-1H-indazol-1-yl)-2-fluoro-N-(methylsulfonyl)benzamide

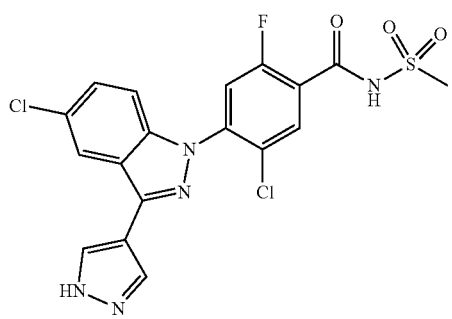 [SMILES: CS(=O)(=O)NC(=O)c1cc(Cl)c(-n2nc(-c3cn[nH]c3)c3cc(Cl)ccc32)cc1F]

1H NMR (500 MHz, CDCl₃) δ: 8.40 (d, 1H), 8.05 (d, 1H), 7.88 (d, 1H), 7.85 (d, 1H), 7.60 (s, 1H), 7.42 (dd, 1H), 7.25 (dd, 1H), 3.39 (s, 3H)

Example 90) Preparation of 5-chloro-4-(5-chloro-3-(1H-pyrazol-3-yl)-1H-indazol-1-yl)-2-fluoro-N-(methylsulfonyl)benzamide

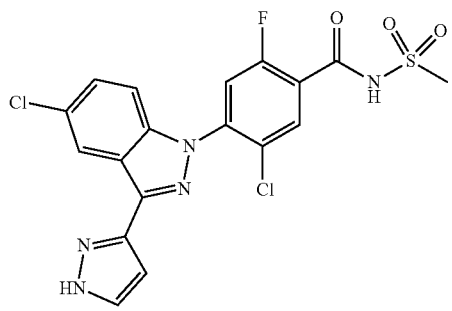 [SMILES: CS(=O)(=O)NC(=O)c1cc(Cl)c(-n2nc(-c3cc[nH]n3)c3cc(Cl)ccc32)cc1F]

1H NMR (500 MHz, CDCl₃) δ: 8.44 (d, 1H), 8.36 (d, 1H), 7.74 (d, 1H), 7.68 (d, 1H), 7.55 (d, 1H), 7.47 (d, 1H), 6.98 (d, 1H), 3.49 (s, 3H)

Example 91) Preparation of 5-chloro-4-(5-chloro-3-(2-methylthiazol-5-yl)-1H-indazol-1-yl)-2-fluoro-N-(methylsulfonyl)benzamide

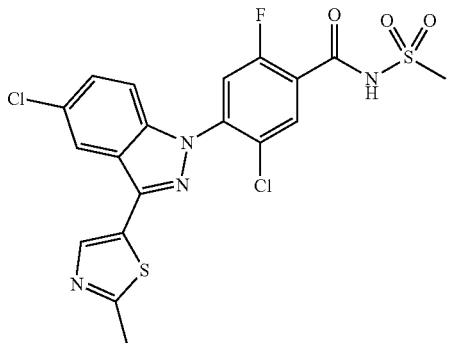 [SMILES: Cc1ncc(-c2nn(-c3cc(F)c(C(=O)NS(C)(=O)=O)cc3Cl)c3ccc(Cl)cc23)s1]

1H (500 MHz, MeOD) δ: 8.32 (d, 1H), 8.15 (d, 1H), 8.03 (d, 1H), 7.75 (s, 1H), 7.60 (d, 1H), 7.35 (d, 1H), 3.27 (s, 3H), 2.54 (s, 3H)

Example 92) Preparation of 4-(5-chloro-3-(2-methoxyphenyl)-1H-indazol-1-yl)-3-cyano-N-(methylsulfonyl)benzamide

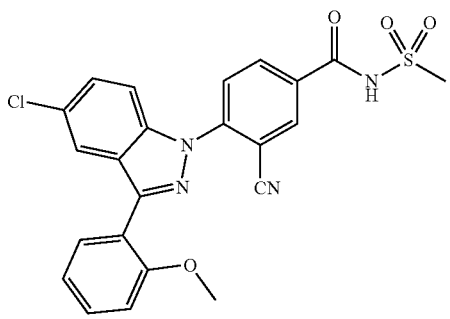 [SMILES: COc1ccccc1-c1nn(-c2ccc(C(=O)NS(C)(=O)=O)cc2C#N)c2ccc(Cl)cc12]

1H NMR (500 MHz, MeOD) δ: 8.58 (s, 1H), 8.47 (d, 1H), 7.90 (d, 1H), 7.77-7.67 (m, 3H), 7.51-7.49 (m, 2H), 7.21 (d, 1H), 7.10 (t, 1H), 3.16 (s, 3H)

Example 93) Preparation of 4-(5-chloro-3-(4-methoxyphenyl)-1H-indazol-1-yl)-3-cyano-N-(methylsulfonyl)benzamide

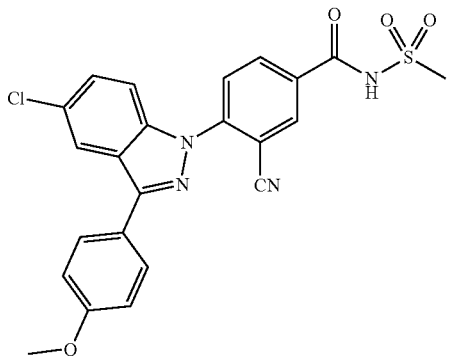 [SMILES: COc1ccc(-c2nn(-c3ccc(C(=O)NS(C)(=O)=O)cc3C#N)c3ccc(Cl)cc23)cc1]

1H NMR (500 MHz, MeOD) δ: 8.59 (s, 1H), 8.48 (d, 1H), 7.97 (d, 3H), 7.87 (d, 1H), 7.72 (d, 1H), 7.54 (d, 1H), 7.12 (d, 2H), 3.13 (s, 3H)

Example 94) Preparation of 4-(5-chloro-3-(2-cyanophenyl)-1H-indazol-1-yl)-3-cyano-N-(methylsulfonyl)benzamide

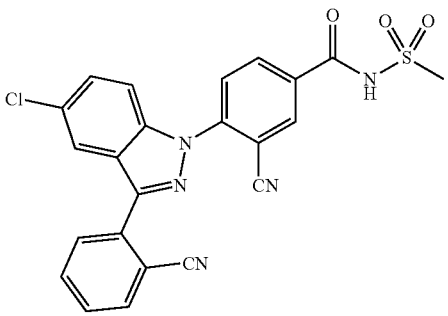 [SMILES: CS(=O)(=O)NC(=O)c1ccc(-n2nc(-c3ccccc3C#N)c3cc(Cl)ccc32)c(C#N)c1]

1H NMR (500 MHz, MeOD) δ: 8.58 (s, 1H), 8.49 (d, 1H), 7.88-7.51 (m, 8H), 3.13 (s, 3H)

Example 95) Preparation of 4-(5-chloro-3-(3-cyanophenyl)-1H-indazol-1-yl)-3-cyano-N-(methylsulfonyl)benzamide

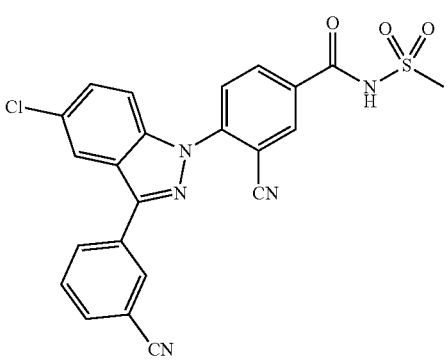 [SMILES: CS(=O)(=O)NC(=O)c1ccc(-n2nc(-c3cccc(C#N)c3)c3cc(Cl)ccc32)c(C#N)c1]

1H NMR (500 MHz, MeOD) δ: 8.60 (s, 1H), 8.50 (d, 1H), 8.38 (d, 2H), 8.19 (s, 1H), 7.91-7.75 (m, 4H), 7.58 (d, 1H), 3.13 (s, 3H)

Example 96) Preparation of 4-(5-chloro-3-(4-cyanophenyl)-1H-indazol-1-yl)-3-cyano-N-(methylsulfonyl)benzamide

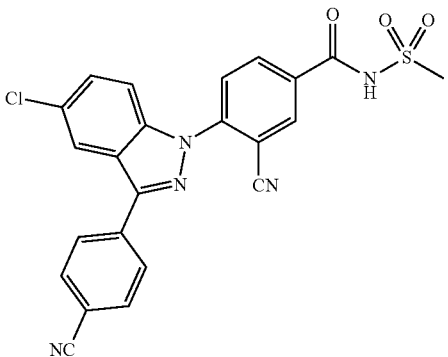 [SMILES: CS(=O)(=O)NC(=O)c1ccc(-n2nc(-c3ccc(C#N)cc3)c3cc(Cl)ccc32)c(C#N)c1]

1H NMR (500 MHz, MeOD) δ: 8.60 (s, 1H), 8.50 (d, 1H), 8.28-8.22 (m, 3H), 7.94-7.90 (m, 3H), 7.77 (d, 1H), 7.599 d, 1H), 3.13 (s, 3H)

Example 97) Preparation of 4-(5-chloro-3-(2-(trifluoromethyl)phenyl)-1H-indazol-1-yl)-3-cyano-N-(methylsulfonyl)benzamide

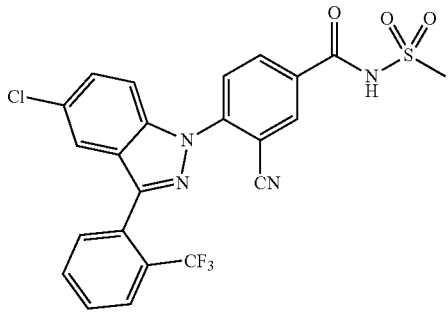 [SMILES: CS(=O)(=O)NC(=O)c1ccc(-n2nc(-c3ccccc3C(F)(F)F)c3cc(Cl)ccc32)c(C#N)c1]

1H NMR (500 MHz, MeOD) δ: 8.58 (s, 1H), 8.49 (d, 1H), 7.94-7.67 (m, 6H), 7.55 (d, 2H), 3.15 (s, 3H)

Example 98) Preparation of 4-(5-chloro-3-(3-(trifluoromethyl)phenyl)-1H-indazol-1-yl)-3-cyano-N-(methylsulfonyl)benzamide

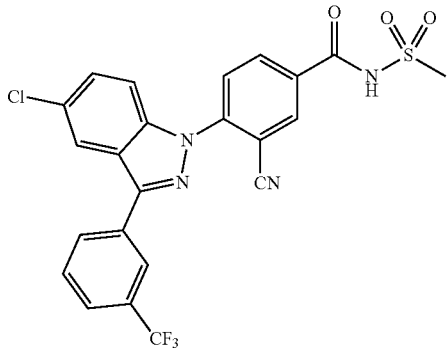 [SMILES: CS(=O)(=O)NC(=O)c1ccc(-n2nc(-c3cccc(C(F)(F)F)c3)c3cc(Cl)ccc32)c(C#N)c1]

1H NMR (500 MHz, MeOD) δ: 8.58 (s, 1H), 8.48 (d, 1H), 8.30 (d, 2H), 8.10 (s, 1H), 7.90 (d, 1H), 7.77-7.73 (m, 3H), 7.56 (d, 1H), 3.17 (s, 3H)

Example 99) Preparation of 4-(5-chloro-3-(4-(trifluoromethyl)phenyl)-1H-indazol-1-yl)-3-cyano-N-(methylsulfonyl)benzamide

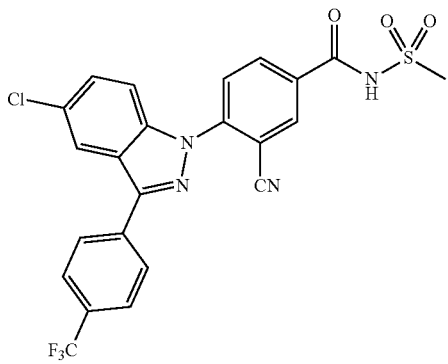 [SMILES: CS(=O)(=O)NC(=O)c1ccc(-n2nc(-c3ccc(C(F)(F)F)cc3)c3cc(Cl)ccc32)c(C#N)c1]

1H NMR (500 MHz, MeOD) δ: 8.57 (s, 1H), 8.46 (d, 1H), 8.22-8.14 (m, 3H), 7.88-7.71 (m, 4H), 7.52 (d, 1H), 3.15 (s, 3H)

Example 100) Preparation of 4-(5-chloro-3-(4-chloro-2-fluorophenyl)-1H-indazol-1-yl)-3-cyano-N-(methylsulfonyl)benzamide

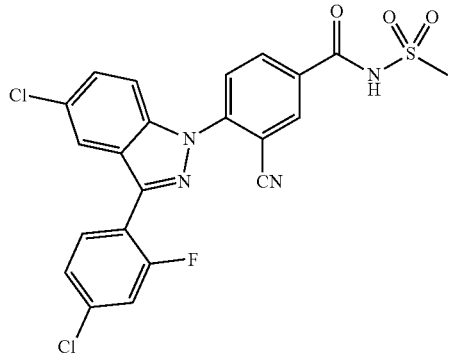 [SMILES: CS(=O)(=O)NC(=O)c1ccc(-n2nc(-c3ccc(Cl)cc3F)c3cc(Cl)ccc32)c(C#N)c1]

1H NMR (500 MHz, MeOD) δ: 8.60 (s, 1H), 8.50 (d, 1H), 7.94-7.89 (m, 3H), 7.72 (d, 1H), 7.56-7.41 (m, 3H), 3.13 (s, 3H)

Example 101) Preparation of 4-(5-chloro-3-(4-fluorophenyl)-1H-indazol-1-yl)-3-cyano-N-(methylsulfonyl)benzamide

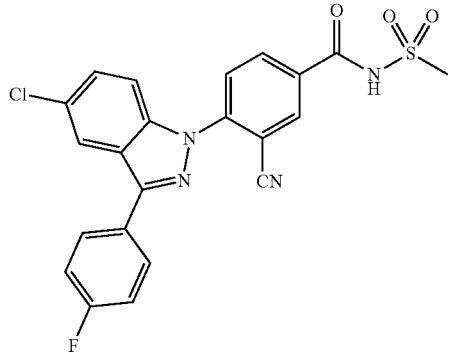 [SMILES: CS(=O)(=O)NC(=O)c1ccc(-n2nc(-c3ccc(F)cc3)c3cc(Cl)ccc32)c(C#N)c1]

1H NMR (500 MHz, MeOD) δ: 8.59 (s, 1H), 8.48 (d, 1H), 8.12-8.07 (m, 3H), 7.88 (d, 1H), 7.72 (d, 1H), 7.55 (d, 1H), 7.29 (t, 2H), 3.14 (s, 3H)

Example 102) Preparation of 4-(5-chloro-3-(2-fluorophenyl)-1H-indazol-1-yl)-3-cyano-N-(methylsulfonyl)benzamide

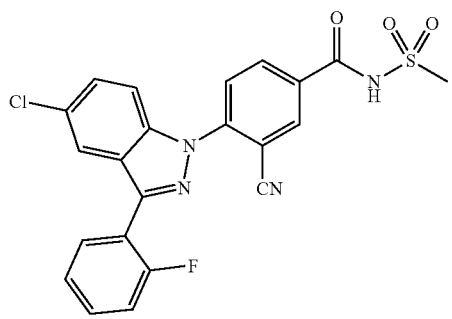 [SMILES: CS(=O)(=O)NC(=O)c1ccc(-n2nc(-c3ccccc3F)c3cc(Cl)ccc32)c(C#N)c1]

1H NMR (500 MHz, MeOD) δ: 8.60 (s, 1H), 8.50 (d, 1H), 7.95-7.87 (m, 3H), 7.72 (d, 1H), 7.55 (d, 2H), 7.37-7.34 (m, 2H), 3.13 (s, 3H)

Example 103) Preparation of 4-(5-chloro-3-(3-fluorophenyl)-1H-indazol-1-yl)-3-cyano-N-(methylsulfonyl)benzamide

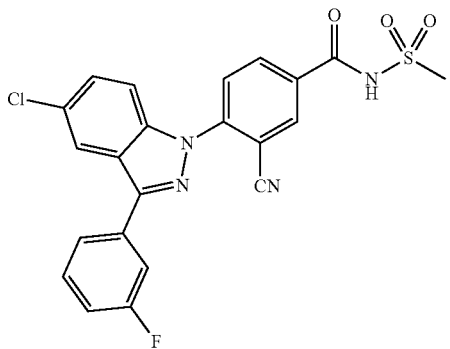 [SMILES: CS(=O)(=O)NC(=O)c1ccc(-n2nc(-c3cccc(F)c3)c3cc(Cl)ccc32)c(C#N)c1]

1H NMR (500 MHz, MeOD) δ: 8.60 (s, 1H), 8.49 (d, 1H), 8.13 (s, 1H), 7.89-7.86 (m, 2H), 7.77-7.72 (m, 2H), 7.60-7.54 (m, 2H), 7.21 (t, 1H), 3.13 (s, 3H)

Example 104) Preparation of 4-(5-chloro-3-(5-chloropyridin-3-yl)-1H-indazol-1-yl)-3-cyano-N-(methylsulfonyl)benzamide

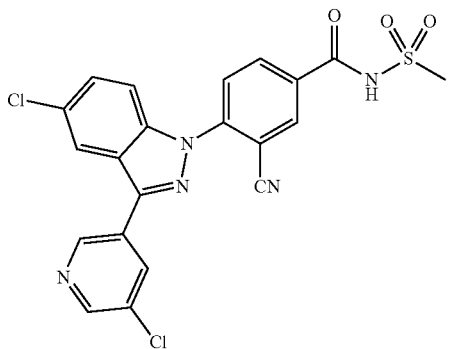 [SMILES: CS(=O)(=O)NC(=O)c1ccc(-n2nc(-c3cncc(Cl)c3)c3cc(Cl)ccc32)c(C#N)c1]

1H NMR (500 MHz, MeOD) δ: 9.17 (s, 1H), 8.66-8.50 (m, 4H), 8.20 (s, 1H), 7.91 (d, 1H), 7.77 (d, 1H), 7.60 (d, 1H), 3.13 (s, 3H)

Example 105) Preparation of 4-(5-chloro-3-(2,4-difluorophenyl)-1H-indazol-1-yl)-3-cyano-N-(methylsulfonyl)benzamide

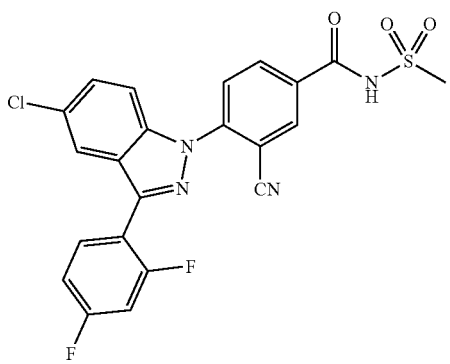 [SMILES: CS(=O)(=O)NC(=O)c1ccc(-n2nc(-c3ccc(F)cc3F)c3cc(Cl)ccc32)c(C#N)c1]

1H NMR (500 MHz, MeOD) δ: 8.59 (s, 1H), 8.49 (d, 1H), 7.99-7.87 (m, 3H), 7.72 (d, 1H), 7.55 (d, 1H), 7.25-7.16 (m, 2H), 3.14 (s, 3H)

Example 106) Preparation of 4-(5-chloro-3-(2-methoxypyridin-3-yl)-1H-indazol-1-yl)-3-cyano-N-(methylsulfonyl)benzamide

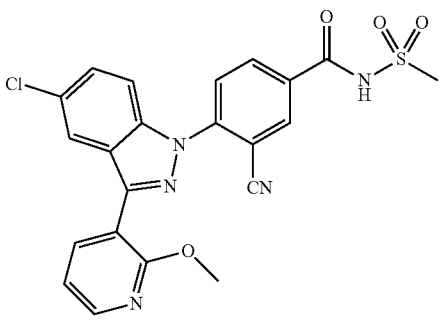 [SMILES: COc1ncccc1-c1nn(-c2ccc(C(=O)NS(C)(=O)=O)cc2C#N)c2ccc(Cl)cc12]

1H NMR (500 MHz, MeOD) δ: 8.59 (s, 1H), 8.49 (d, 1H), 8.30 (d, 1H), 8.14 (d, 1H), 7.89 (m, 2H), 7.70 (d, 1H), 7.50 (d, 1H), 7.12 (t, 1H), 4.14 (s, 3H), 3.13 (s, 3H)

Example 107) Preparation of 2-chloro-4-(5-chloro-3-(2-methoxyphenyl)-1H-indazol-1-yl)-5-fluoro-N-(methylsulfonyl)benzamide

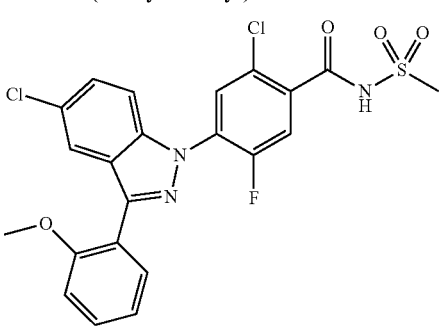

1H NMR (500 MHz, MeOD) δ: 7.80 (d, 1H), 7.70-7.61 (m, 3H), 7.51-7.46 (m, 3H), 7.21 (d, 1H), 7.10 (t, 1H), 3.88 (s, 3H), 3.21 (s, 3H)

Example 108) Preparation of 2-chloro-4-(5-chloro-3-(4-methoxyphenyl)-1H-indazol-1-yl)-5-fluoro-N-(methylsulfonyl)benzamide

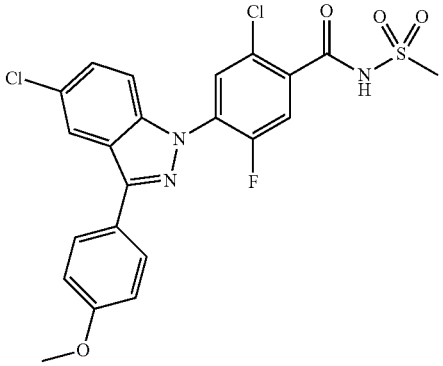 [SMILES: COc1ccc(-c2nn(-c3cc(Cl)c(C(=O)NS(C)(=O)=O)cc3F)c3ccc(Cl)cc23)cc1]

1H NMR (500 MHz, MeOD) δ: 8.05 (s, 1H), 7.92 (d, 2H), 7.77 (d, 1H), 7.61 (d, 1H), 7.50-7.47 (m, 2H), 7.12 (d, 2H), 3.88 (s, 3H), 3.18 (s, 3H)

Example 109) Preparation of 2-chloro-4-(5-chloro-3-(3-cyanophenyl)-1H-indazol-1-yl)-5-fluoro-N-(methylsulfonyl)benzamide

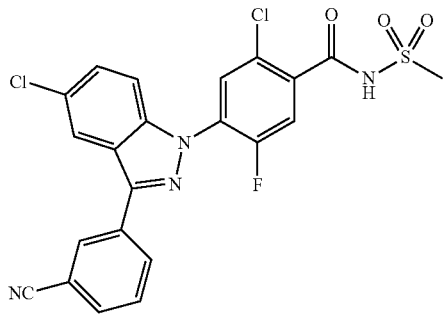 [SMILES: CS(=O)(=O)NC(=O)c1cc(F)c(-n2nc(-c3cccc(C#N)c3)c3cc(Cl)ccc32)cc1Cl]

1H NMR (500 MHz, MeOD) δ: 8.36-8.32 (m, 2H), 8.14 (s, 1H), 7.83-7.75 (m, 3H), 7.62-7.54 (m, 3H), 3.15 (s, 3H)

Example 110) Preparation of 2-chloro-4-(5-chloro-3-(3-(trifluoromethyl)phenyl)-1H-indazol-1-yl)-5-fluoro-N-(methylsulfonyl)benzamide

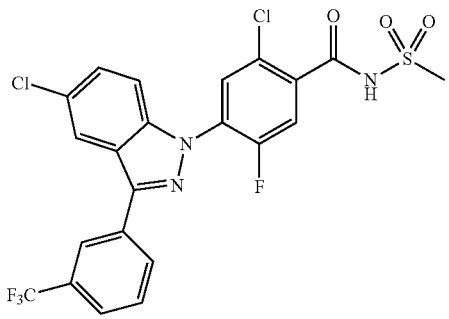 [SMILES: CS(=O)(=O)NC(=O)c1cc(F)c(-n2nc(-c3cccc(C(F)(F)F)c3)c3cc(Cl)ccc32)cc1Cl]

1H NMR (500 MHz, MeOD) δ: 8.26 (s, 2H), 8.08 (s, 1H), 7.81-7.77 (m, 3H), 7.63 (d, 1H), 7.53 (s, 2H), 3.17 (s, 3H)

Example 111) Preparation of 2-chloro-4-(5-chloro-3-(4-(trifluoromethyl)phenyl)-1H-indazol-1-yl)-5-fluoro-N-(methylsulfonyl)benzamide

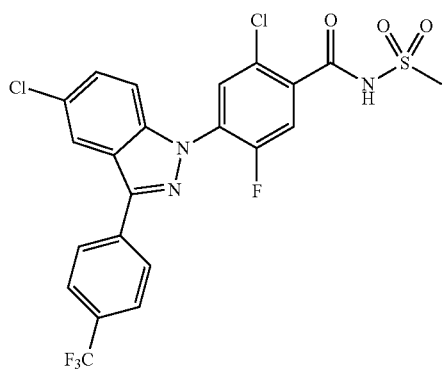 [SMILES: CS(=O)(=O)NC(=O)c1cc(F)c(-n2nc(-c3ccc(C(F)(F)F)cc3)c3cc(Cl)ccc32)cc1Cl]

1H NMR (500 MHz, MeOD) δ: 8.22 (d, 2H), 8.16 (s, 1H), 7.86-7.81 (m, 3H), 7.65 (d, 1H), 7.539 s, 2H), 3.20 (s, 3H)

Example 112) Preparation of 2-chloro-4-(5-chloro-3-(4-fluorophenyl)-1H-indazol-1-yl)-5-fluoro-N-(methylsulfonyl)benzamide

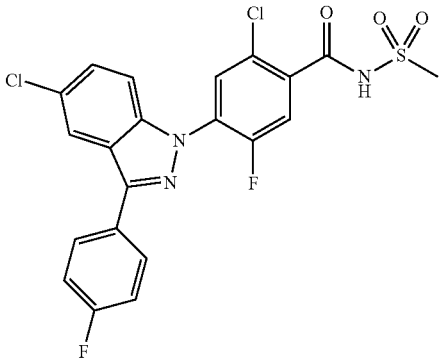 [SMILES: CS(=O)(=O)NC(=O)c1cc(F)c(-n2nc(-c3ccc(F)cc3)c3cc(Cl)ccc32)cc1Cl]

1H NMR (500 MHz, MeOD) δ: 8.08 (s, 1H), 8.03 (d, 2H), 7.78 (d, 1H), 7.63 (d, 1H), 7.51 (s, 2H), 7.32 (d, 2H), 3.19 (s, 3H)

Example 113) Preparation of 2-chloro-4-(5-chloro-3-(2-fluorophenyl)-1H-indazol-1-yl)-5-fluoro-N-(methylsulfonyl)benzamide

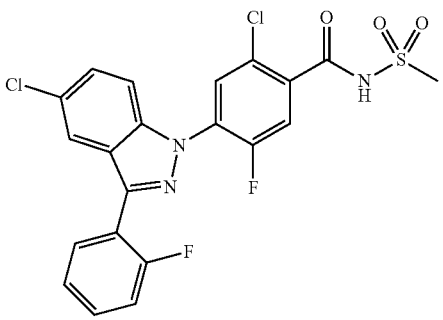 [SMILES: CS(=O)(=O)NC(=O)c1cc(F)c(-n2nc(-c3ccccc3F)c3cc(Cl)ccc32)cc1Cl]

1H NMR (500 MHz, MeOD) δ: 7.87-7.77 (m, 3H), 7.62 (d, 1H), 7.62-7.53 (m, 3H), 7.38-7.33 (m, 2H), 3.16 (s, 3H)

Example 114) Preparation of 2-chloro-4-(5-chloro-3-(3-fluorophenyl)-1H-indazol-1-yl)-5-fluoro-N-(methylsulfonyl)benzamide

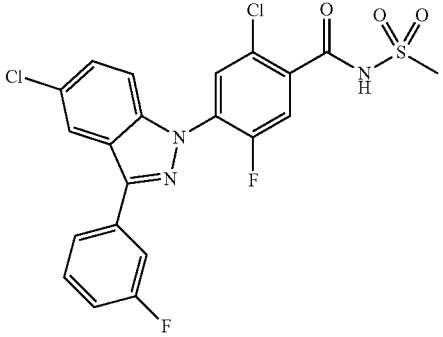 [SMILES: CS(=O)(=O)NC(=O)c1cc(F)c(-n2nc(-c3cccc(F)c3)c3cc(Cl)ccc32)cc1Cl]

1H NMR (500 MHz, MeOD) δ: 8.10 (s, 1H), 7.84-7.50 (m, 7H), 7.22 (t, 1H), 3.20 (s, 3H)

Example 115) Preparation of 2-chloro-4-(5-chloro-3-(2,4-difluorophenyl)-1H-indazol-1-yl)-5-fluoro-N-(methylsulfonyl)benzamide

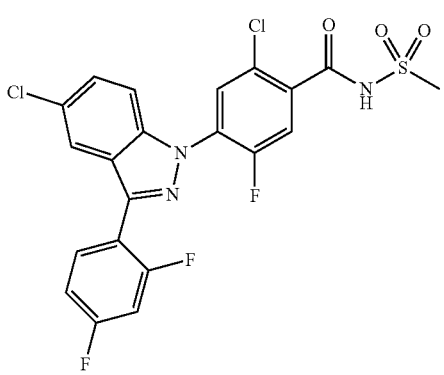 [SMILES: CS(=O)(=O)NC(=O)c1cc(F)c(-n2nc(-c3ccc(F)cc3F)c3cc(Cl)ccc32)cc1Cl]

1H NMR (500 MHz, MeOD) δ: 7.90-7.79 (m, 3H), 7.63 (d, 1H), 7.51 (s, 2H), 7.24-7.15 (m, 2H), 3.20 (s, 3H)

Example 116) Preparation of 2-chloro-4-(5-chloro-3-(2-methoxypyridin-3-yl)-1H-indazol-1-yl)-5-fluoro-N-(methylsulfonyl)benzamide

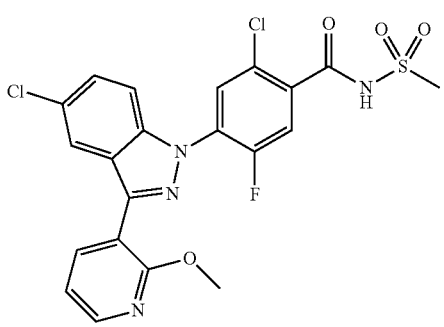 [SMILES: COc1ncccc1-c1nn(-c2cc(Cl)c(C(=O)NS(C)(=O)=O)cc2F)c2ccc(Cl)cc12]

1H NMR (500 MHz, MeOD) δ: 8.29 (s, 1H), 8.07 (d, 1H), 7.80-7.77 (m, 2H), 7.63 (d, 1H), 7.48 (s, 2H), 7.14-7.12 (m, 1H), 4.03 (s, 3H), 3.17 (s, 3H)

Example 117) Preparation of 4-(5-chloro-3-(2-methoxyphenyl)-1H-indazol-1-yl)-3-fluoro-N-(methylsulfonyl)benzamide

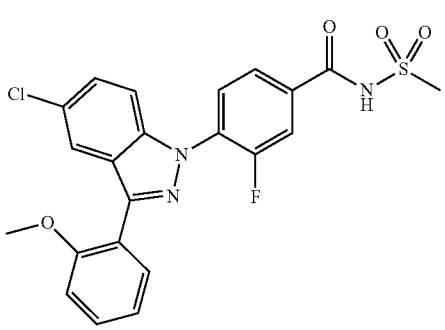

1H NMR (500 MHz, MeOD) δ: 8.04 (d, 2H), 7.75-7.62 (m, 3H), 7.51-7.45 (m, 3H), 7.21 (d, 1H), 7.10 (d, 1H), 3.17 (s, 3H)

Example 118) Preparation of 4-(5-chloro-3-(4-methoxyphenyl)-1H-indazol-1-yl)-3-fluoro-N-(methylsulfonyl)benzamide

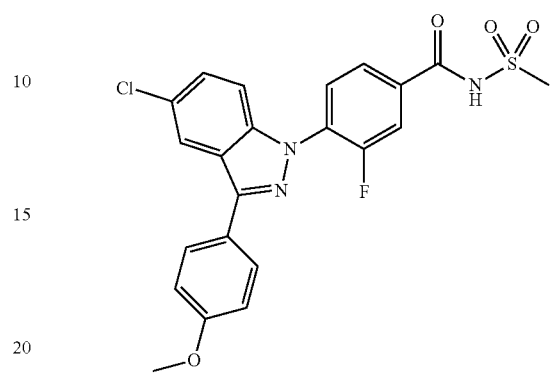

1H NMR (500 MHz, MeOD) δ: 8.06-8.02 (m, 3H), 7.93-7.73 (m, 3H), 7.48-7.46 (m, 2H), 7.12 (d, 2H), 3.19 (s, 3H)

Example 119) Preparation of 4-(5-chloro-3-(3-cyanophenyl)-1H-indazol-1-yl)-3-fluoro-N-(methylsulfonyl)benzamide

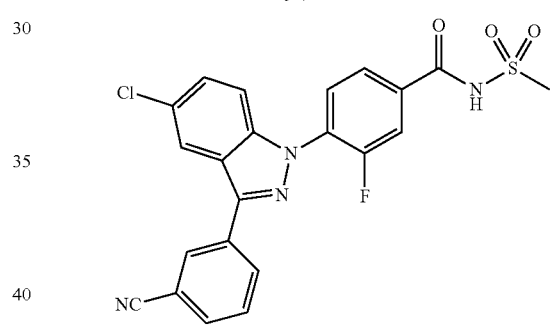

1H NMR (500 MHz, MeOD) δ: 8.36-8.33 (m, 2H), 8.15 (s, 1H), 8.07-8.03 (m, 2H), 7.83-7.75 (m, 3H), 7.52 (s, 2H), 3.17 (s, 3H)

Example 120) Preparation of 4-(5-chloro-3-(4-cyanophenyl)-1H-indazol-1-yl)-3-fluoro-N-(methylsulfonyl)benzamide

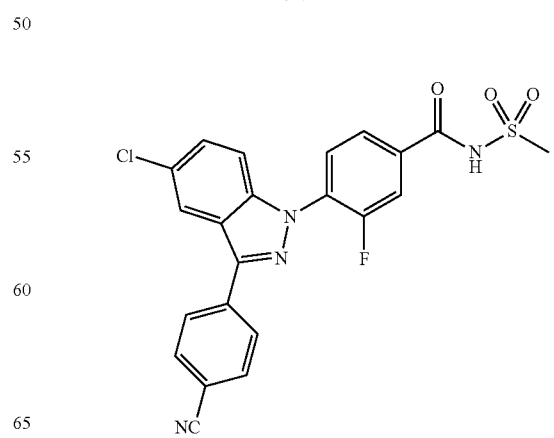

1H NMR (500 MHz, MeOD) δ: 8.23-8.18 (m, 3H), 8.05-8.03 (m, 2H), 7.91-7.90 (m, 2H), 7.77-7.73 (m, 1H), 7.53 (s, 2H), 3.17 (s, 3H)

Example 121) Preparation of 4-(5-chloro-3-(3-(trifluoromethyl)phenyl)-1H-indazol-1-yl)-3-fluoro-N-(methylsulfonyl)benzamide

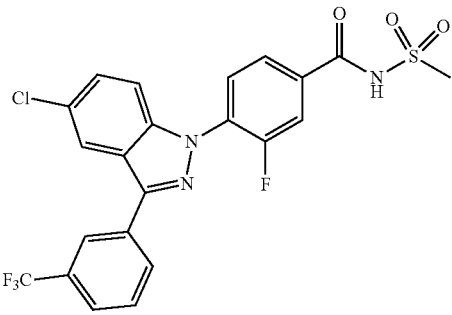 [SMILES: CS(=O)(=O)NC(=O)c1ccc(-n2nc(-c3cccc(C(F)(F)F)c3)c3cc(Cl)ccc32)c(F)c1]

1H NMR (500 MHz, MeOD) δ: 8.27 (s, 2H), 8.10-8.03 (m, 3H), 7.77 (s, 3H), 7.53 (s, 2H), 3.17 (s, 3H)

Example 122) Preparation of 4-(5-chloro-3-(4-(trifluoromethyl)phenyl)-1H-indazol-1-yl)-3-fluoro-N-(methylsulfonyl)benzamide

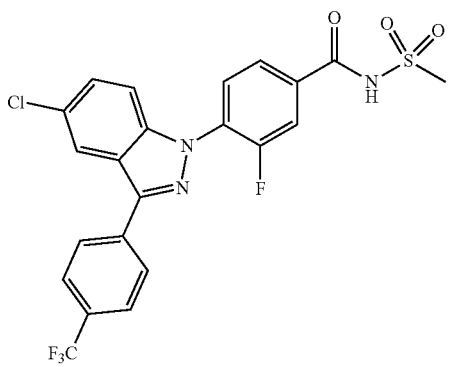 [SMILES: CS(=O)(=O)NC(=O)c1ccc(-n2nc(-c3ccc(C(F)(F)F)cc3)c3cc(Cl)ccc32)c(F)c1]

1H NMR (500 MHz, MeOD) δ: 8.23-8.17 (m, 3H), 8.05-8.03 (m, 2H), 7.87-7.75 (m, 3H), 7.52 (s, 2H), 3.17 (s, 3H)

Example 123) Preparation of 4-(5-chloro-3-(4-fluorophenyl)-1H-indazol-1-yl)-3-fluoro-N-(methylsulfonyl)benzamide

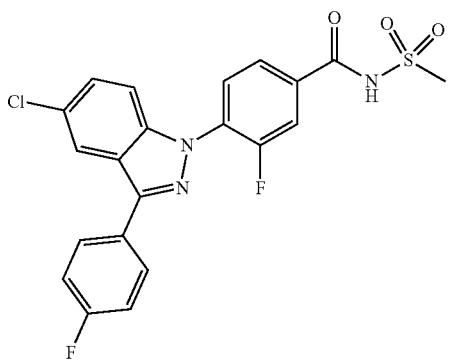 [SMILES: CS(=O)(=O)NC(=O)c1ccc(-n2nc(-c3ccc(F)cc3)c3cc(Cl)ccc32)c(F)c1]

1H NMR (500 MHz, MeOD) δ: 8.08-8.02 (m, 5H), 7.77-7.74 (m, 1H), 7.51-7.47 (m, 2H), 7.31-7.28 (m, 2H), 3.20 (s, 3H)

Example 124) Preparation of 4-(5-chloro-3-(2-fluorophenyl)-1H-indazol-1-yl)-3-fluoro-N-(methylsulfonyl)benzamide

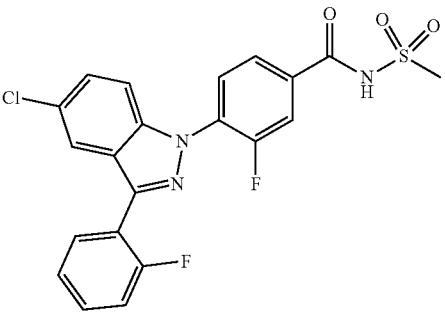 [SMILES: CS(=O)(=O)NC(=O)c1ccc(-n2nc(-c3ccccc3F)c3cc(Cl)ccc32)c(F)c1]

1H NMR (500 MHz, MeOD) δ: 8.04 (d, 2H), 7.86-7.75 (m, 3H), 7.54-7.49 (m, 3H), 7.36-7.33 (m, 2H), 3.20 (s, 3H)

Example 125) Preparation of 4-(5-chloro-3-(3-fluorophenyl)-1H-indazol-1-yl)-3-fluoro-N-(methylsulfonyl)benzamide

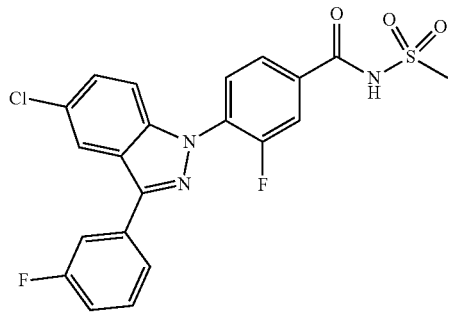 [SMILES: CS(=O)(=O)NC(=O)c1ccc(-n2nc(-c3cccc(F)c3)c3cc(Cl)ccc32)c(F)c1]

1H NMR (500 MHz, MeOD) δ: 8.10-8.03 (m, 3H), 7.84 (d, 1H), 7.78-7.72 (m, 2H), 7.76-7.48 (m, 3H), 7.21 (d, 1H), 3.19 (s, 3H)

Example 126) Preparation of 4-(5-chloro-3-(4-chlorophenyl)-1H-indazol-1-yl)-3-fluoro-N-(methylsulfonyl)benzamide

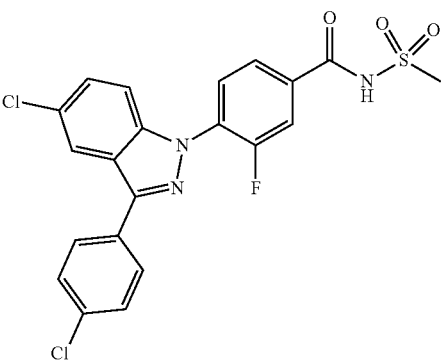 [SMILES: CS(=O)(=O)NC(=O)c1ccc(-n2nc(-c3ccc(Cl)cc3)c3cc(Cl)ccc32)c(F)c1]

1H NMR (500 MHz, MeOD) δ: 8.08 (s, 1H), 8.02 (d, 2H), 7.98 (d, 2H), 7.76 (t, 1H), 7.54 (d, 2H), 7.48 (d, 2H), 3.22 (s, 3H)

Example 127) Preparation of 4-(5-chloro-3-phenyl-1H-indazol-1-yl)-2-fluoro-N-(methylsulfonyl)benzamide

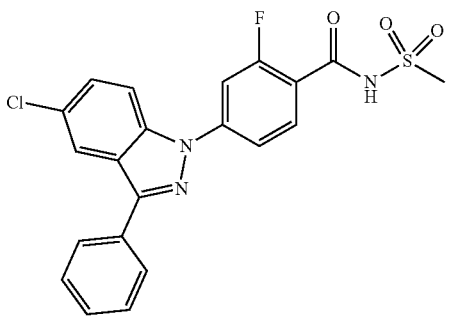 [SMILES: CS(=O)(=O)NC(=O)c1ccc(-n2nc(-c3ccccc3)c3cc(Cl)ccc32)cc1F]

1H NMR (500 MHz, MeOD) δ: 8.09 (s, 1H), 8.01-7.95 (m, 4H), 7.69-7.68 (d, 1H), 7.64-7.62 (d, 1H), 7.58-7.57 (m, 3H), 7.50-7.48 (m, 1H), 3.17 (s, 3H)

Example 128) Preparation of 6-(5-chloro-3-(4-chloro-2-fluorophenyl)-1H-indazol-1-yl)-N-(methylsulfonyl)nicotinamide

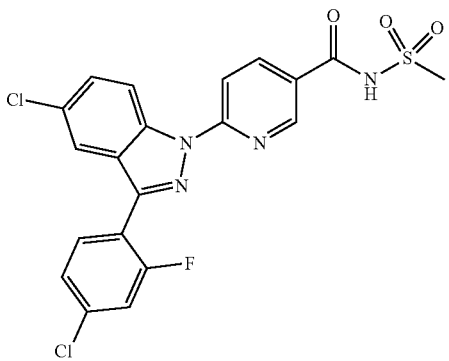 [SMILES: CS(=O)(=O)NC(=O)c1ccc(-n2nc(-c3ccc(Cl)cc3F)c3cc(Cl)ccc32)nc1]

1H NMR (500 MHz, MeOD) δ: 9.13 (d, 1H), 8.94 (d, 1H), 8.47 (dd, 1H), 8.14 (d, 1H), 7.90 (t, 1H), 7.81 (s, 1H), 7.57 (dd, 1H), 7.49 (d, 1H), 7.43 (d, 1H), 3.23 (s, 3H)

Example 130) Preparation of 5-chloro-4-(5-chloro-3-(1-methyl-6-oxo-1,6-dihydropyridin-3-yl)-1H-indazol-1-yl)-2-fluoro-N-(methylsulfonyl)benzamide

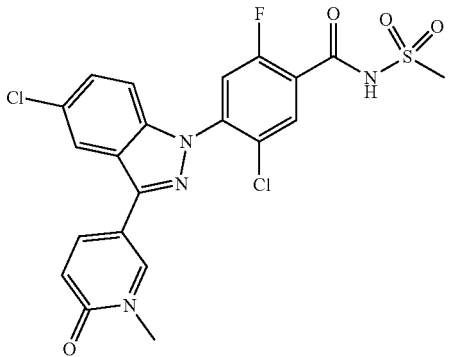

1H NMR (500 MHz, MeOD) δ: 8.36 (d, 1H), 8.18 (dd, 1H), 8.16 (d, 1H), 8.05 (d, 1H), 7.50 (d, 2H), 7.36 (d, 1H), 6.72 (d, 1H), 3.73 (s, 3H), 3.19 (s, 3H)

Example 131) Preparation of tert-butyl 4-(5-chloro-1-(2-chloro-5-fluoro-4-((methylsulfonyl)carbamoyl)phenyl)-1H-indazol-3-yl)-3,6-dihydropyridine-1(2H)-carboxylate

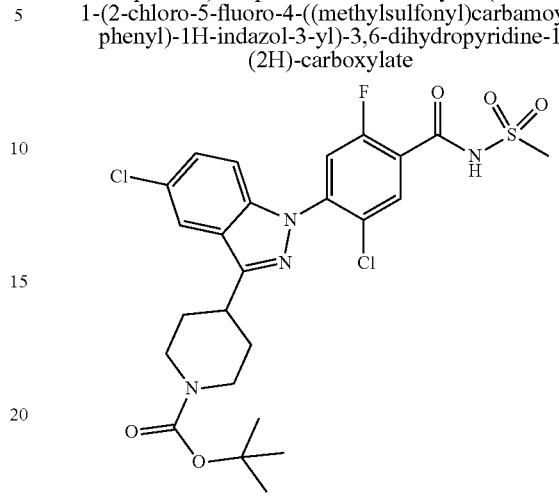

1H NMR (500 MHz, MeOD) δ: 8.06 (d, 1H), 8.02 (d, 1H), 7.45-7.42 (m, 2H), 7.29 (d, 2H), 6.16 (br, 1H), 4.20 (br, 2H), 3.67 (br, 2H), 3.17 (s, 3H), 2.76 (br, 2H), 1.50 (s, 9H)

Example 132) Preparation of 5-chloro-4-(5-chloro-3-(1,2,3,6-tetrahydropyridin-4-yl)-1H-indazol-1-yl)-2-fluoro-N-(methylsulfonyl)benzamide

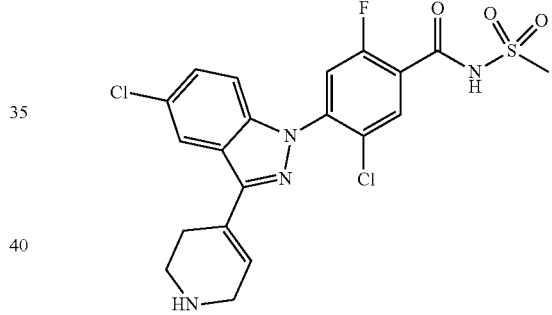

1H NMR (500 MHz, MeOD) δ: 8.13 (d, 1H), 8.02 (d, 1H), 7.52 (d, 1H), 7.45 (d, 1H), 7.40 (d, 1H), 6.66 (s, 1H), 4.59 (s, 2H), 3.63 (s, 2H), 3.14 (s, 3H), 3.10-3.08 (m, 2H), 2.15 (s, 1H)

Example 134) Preparation of (E)-5-chloro-4-(5-chloro-3-(2-(pyridin-2-yl)vinyl)-1H-indazol-1-yl)-2-fluoro-N-(methylsulfonyl)benzamide

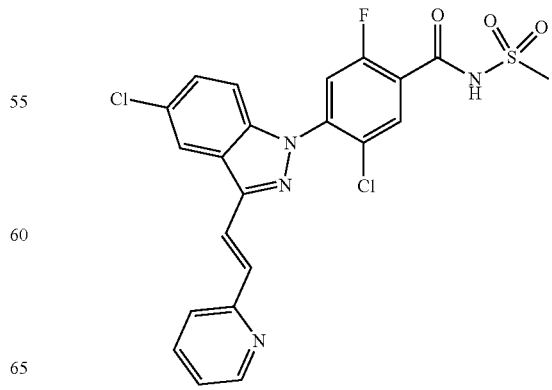

1H NMR (500 MHz, MeOD) δ: 8.57 (s, 1H), 8.23 (d, 1H), 8.04 (d, 1H), 7.97-7.85 (m, 2H), 7.76 (d, 1H), 7.68 (d, 1H), 7.51 (m, 2H), 7.34 (m, 2H), 3.17 (s, 3H)

Example 135) Preparation of (E)-5-chloro-4-(5-chloro-3-(2-fluorostyryl)-1H-indazol-1-yl)-2-fluoro-N-(methylsulfonyl)benzamide

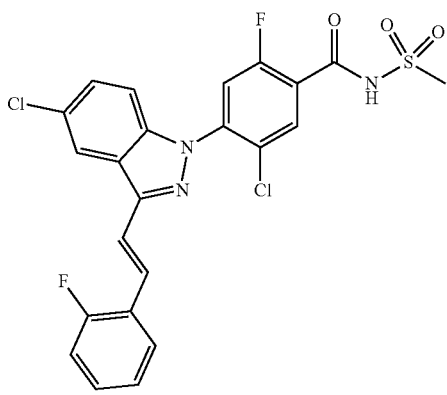 [SMILES: CS(=O)(=O)NC(=O)c1cc(Cl)c(-n2nc(/C=C/c3ccccc3F)c3cc(Cl)ccc32)cc1F]

1H NMR (500 MHz, MeOD) δ: 8.14 (s, 1H), 8.03 (d, 1H), 7.86 (td, 1H), 7.75-7.56 (dd, 2H), 7.49 (t, 2H), 7.34 (d, 2H), 7.14 (t, 2H), 3.17 (s, 3H)

Example 136) Preparation of (E)-5-chloro-4-(5-chloro-3-(2-chlorostyryl)-1H-indazol-1-yl)-2-fluoro-N-(methylsulfonyl)benzamide

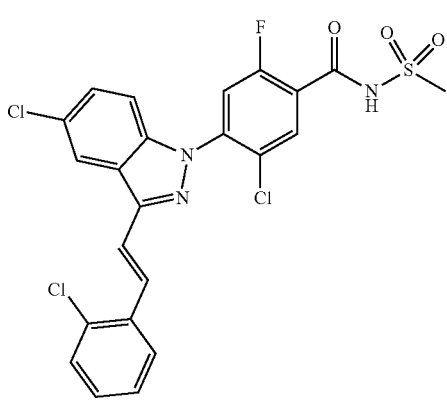 [SMILES: CS(=O)(=O)NC(=O)c1cc(Cl)c(-n2nc(/C=C/c3ccccc3Cl)c3cc(Cl)ccc32)cc1F]

1H NMR (500 MHz, MeOD) δ: 8.14 (s, 1H), 8.03 (d, 1H), 7.99-7.93 (m, 3H), 7.54-7.46 (m, 3H), 7.38-7.29 (m, 3H), 3.15 (s, 3H)

Example 137) Preparation of (E)-5-chloro-4-(5-chloro-3-(4-(trifluoromethyl)styryl)-1H-indazol-1-yl)-2-fluoro-N-(methylsulfonyl)benzamide

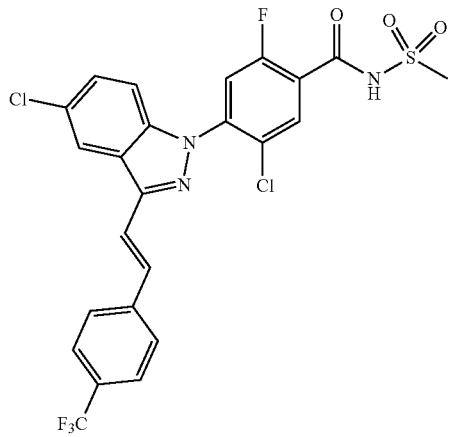 [SMILES: CS(=O)(=O)NC(=O)c1cc(Cl)c(-n2nc(/C=C/c3ccc(C(F)(F)F)cc3)c3cc(Cl)ccc32)cc1F]

1H NMR (500 MHz, MeOD) δ: 8.24 (s, 1H), 8.04 (d, 1H), 7.85 (d, 2H), 7.67 (m, 4H), 7.50 (m, 2H), 7.34 (d, 1H), 3.24 (s, 3H)

Example 138) Preparation of 5-chloro-4-(5-chloro-3-(4-chloro-2-fluorophenyl)-1H-indazol-1-yl)-N—(N,N-dimethylsulfamoyl)-2-fluorobenzamide

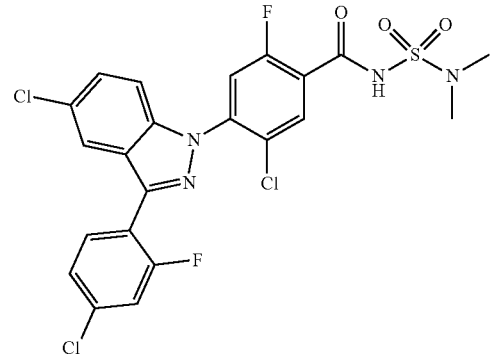 [SMILES: CN(C)S(=O)(=O)NC(=O)c1cc(Cl)c(-n2nc(-c3ccc(Cl)cc3F)c3cc(Cl)ccc32)cc1F]

1H NMR (500 MHz, MeOD) δ: 8.00 (d, 1H), 7.85 (t, 2H), 7.60 (d, 1H), 7.50 (d, 1H), 7.48 (d, 1H), 7.39 (m, 2H), 2.95 (s, 6H)

Example 139) Preparation of 5-chloro-4-(5-chloro-3-(4-chloro-2-fluorophenyl)-1H-indazol-1-yl)-2-fluoro-N-methyl-N-(methylsulfonyl)benzamide

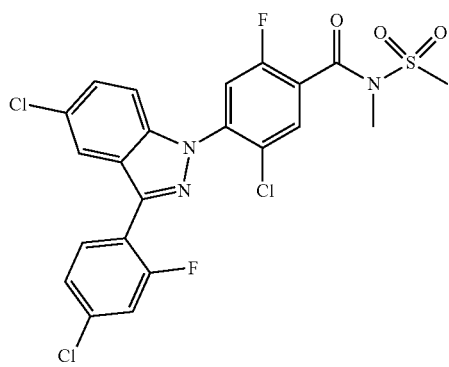 [SMILES: CN(C(=O)c1cc(Cl)c(-n2nc(-c3ccc(Cl)cc3F)c3cc(Cl)ccc32)cc1F)S(C)(=O)=O]

1H NMR (500 MHz, MeOD) δ: 8.05 (s, 1H), 7.86 (t, 2H), 7.50 (m, 3H), 7.40 (t, 2H), 4.00 (s, 3H), 3.40 (s, 3H)

Example 141) Preparation of 5-chloro-4-(3-chloro-5-hydroxy-1H-indazol-1-yl)-2-fluoro-N-(4-fluorobenzyl)-N-(methylsulfonyl)benzamide

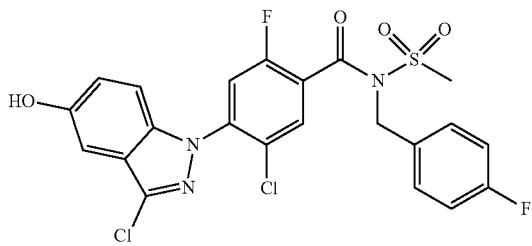 [SMILES: CS(=O)(=O)N(Cc1ccc(F)cc1)C(=O)c1cc(Cl)c(-n2nc(Cl)c3cc(O)ccc32)cc1F]

1H NMR (500 MHz, MeOD) δ: 8.20-8.18 (d, 1H), 7.54-7.51 (m, 3H), 723-7.21 (d, 1H), 7.15-7.10 (m, 3H), 6.99 (s, 1H), 5.10 (s, 2H), 3.30 (s, 3H)

Example 142) Preparation of 5-chloro-4-(3-(4-chloro-2-fluorophenyl)-5-fluoro-1H-indazol-1-yl)-2-fluoro-N-(methylsulfonyl)benzamide

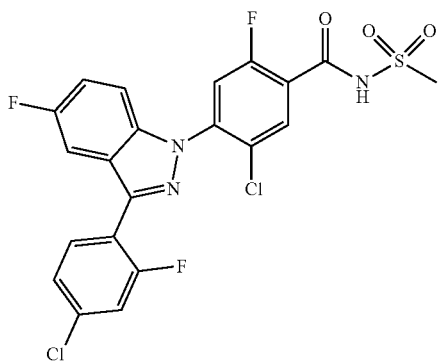 [SMILES: CS(=O)(=O)NC(=O)c1cc(Cl)c(-n2nc(-c3ccc(Cl)cc3F)c3cc(F)ccc32)cc1F]

1H NMR (500 MHz, MeOD) δ: 8.06 (d, 1H), 7.87-7.84 (m, 1H), 7.61-7.33 (m, 6H), 3.29 (s, 3H)

Example 143) Preparation of 5-chloro-2-fluoro-4-(5-fluoro-3-(2-fluorophenyl)-1H-indazol-1-yl)-N-(methylsulfonyl)benzamide

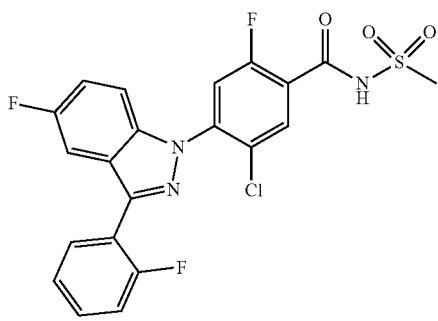 [SMILES: CS(=O)(=O)NC(=O)c1cc(Cl)c(-n2nc(-c3ccccc3F)c3cc(F)ccc32)cc1F]

1H NMR (500 MHz, MeOD) δ: 8.05 (d, 1H), 7.85 (t, 1H), 7.55-7.50 (m, 3H), 7.42-7.32 (m, 4H), 3.18 (s, 3H)

Example 144) Preparation of 5-chloro-4-(3-(2-chlorophenyl)-5-fluoro-1H-indazol-1-yl)-2-fluoro-N-(methylsulfonyl)benzamide

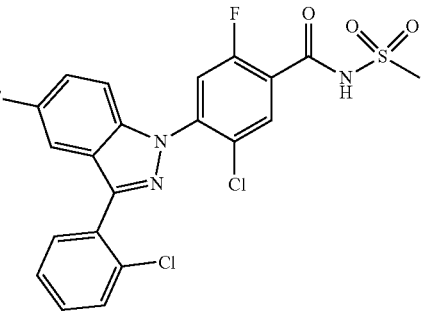

1H NMR (500 MHz, MeOD) δ: 7.97 (d, 1H), 7.77 (d, 1H), 7.60-7.58 (m, 2H), 7.49 (d, 1H), 7.31-7.17 (m, 4H), 3.13 (s, 3H)

Example 145) Preparation of 5-chloro-2-fluoro-4-(5-fluoro-3-(2-(trifluoromethyl)phenyl)-1H-indazol-1-yl)-N-(methylsulfonyl)benzamide

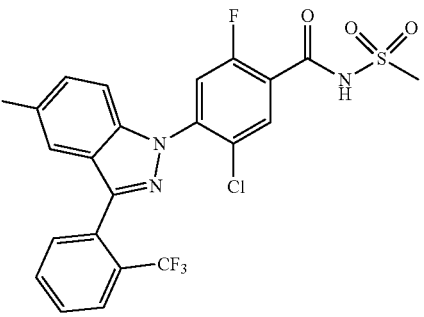

1H NMR (500 MHz, MeOD) δ: 8.05 (d, 1H), 7.93 (d, 1H), 7.81-7.70 (m, 3H), 7.49-7.32 (m, 3H), 7.22 (d, 1H), 3.22 (s, 3H)

Example 146) Preparation of 5-chloro-2-fluoro-4-(5-fluoro-3-(2-methoxyphenyl)-1H-indazol-1-yl)-N-(methylsulfonyl)benzamide

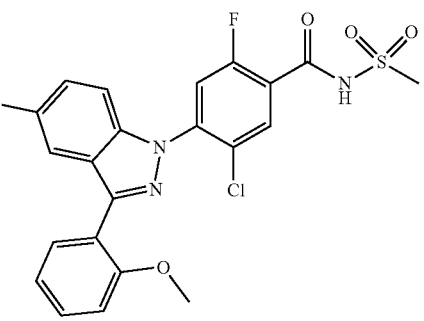

1H NMR (500 MHz, MeOD) δ: 8.05 (d, 1H), 7.63 (d, 1H), 7.51-7.08 (m, 7H), 3.88 (s, 3H), 3.18 (s, 3H)

Example 147) Preparation of 5-chloro-2-fluoro-4-(5-fluoro-3-(o-tolyl)-1H-indazol-1-yl)-N-(methylsulfonyl)benzamide

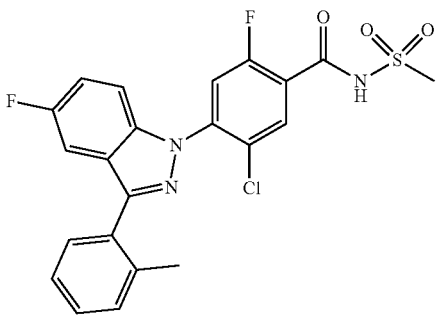 [SMILES: Cc1ccccc1-c1nn(-c2cc(F)c(C(=O)NS(C)(=O)=O)cc2Cl)c2ccc(F)cc12]

1H NMR (500 MHz, MeOD) δ: 8.05 (d, 1H), 7.54-7.48 (m, 2H), 7.42-7.31 (m, 6H), 3.17 (s, 3H), 2.41 (s, 3H)

Example 148) Preparation of 5-chloro-2-fluoro-4-(5-fluoro-3-(3-fluorophenyl)-1H-indazol-1-yl)-N-(methylsulfonyl)benzamide

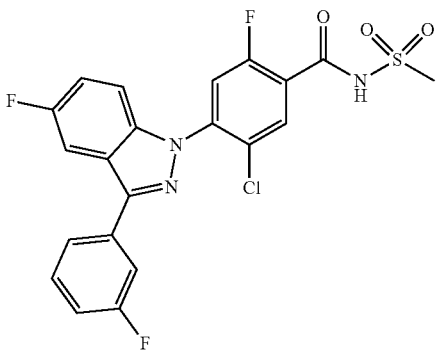 [SMILES: CS(=O)(=O)NC(=O)c1cc(Cl)c(-n2nc(-c3cccc(F)c3)c3cc(F)ccc32)cc1F]

1H NMR (500 MHz, MeOD) δ: 8.05 (d, 1H), 7.83-7.80 (m, 2H), 7.73-(d, 1H), 7.59-7.33 (m, 4H), 7.18 (t, 1H), 3.17 (s, 3H)

Example 149) Preparation of 5-chloro-4-(3-(3-chlorophenyl)-5-fluoro-1H-indazol-1-yl)-2-fluoro-N-(methylsulfonyl)benzamide

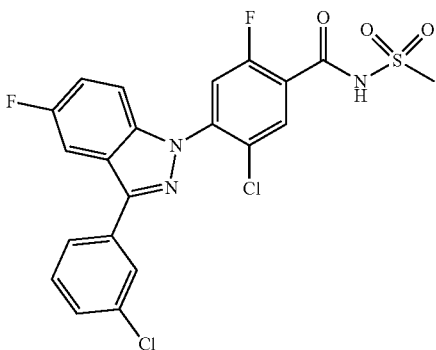 [SMILES: CS(=O)(=O)NC(=O)c1cc(Cl)c(-n2nc(-c3cccc(Cl)c3)c3cc(F)ccc32)cc1F]

1H NMR (500 MHz, MeOD) δ: 8.06-7.92 (m, 3H), 7.80-7.78 (m, 1H), 7.56-7.33 (m, 5H), 3.22 (s, 3H)

Example 150) Preparation of 5-chloro-2-fluoro-4-(5-fluoro-3-(3-(trifluoromethyl)phenyl)-1H-indazol-1-yl)-N-(methylsulfonyl)benzamide

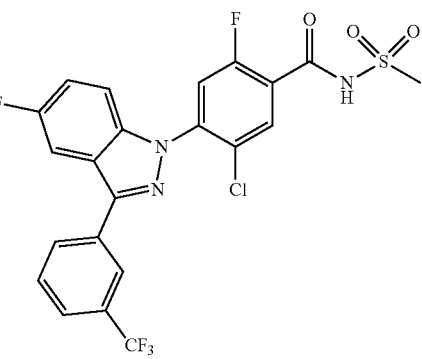

1H NMR (500 MHz, MeOD) δ: 8.26 (s, 2H), 8.06 (d, 1H), 7.80-7.75 (m, 3H), 7.56 (d, 1H), 7.44-7.34 (m, 2H), 3.22 (s, 3H)

Example 151) Preparation of 5-chloro-2-fluoro-4-(5-fluoro-3-(3-methoxyphenyl)-1H-indazol-1-yl)-N-(methylsulfonyl)benzamide

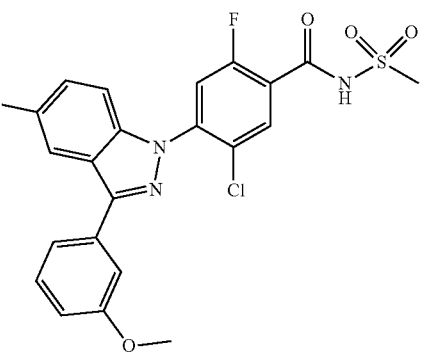

1H NMR (500 MHz, MeOD) δ: 8.05 (d, 1H), 7.79-7.75 (m, 3H), 7.52 (d, 1H), 7.44-7.28 (m, 4H), 3.19 (s, 3H), 2.46 (s, 3H)

Example 152) Preparation of 5-chloro-2-fluoro-4-(5-fluoro-3-(m-tolyl)-1H-indazol-1-yl)-N-(methylsulfonyl)benzamide

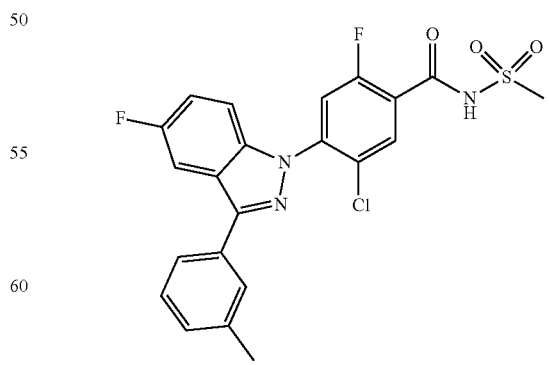

1H NMR (500 MHz, MeOD) δ: 8.05-8.01 (m, 3H), 7.79 (d, 1H), 7.50 (d, 1H), 7.41-7.27 (m, 4H), 3.30 (s, 3H), 3.17 (s, 3H)

Example 153) Preparation of 5-chloro-2-fluoro-4-(5-fluoro-3-(4-fluorophenyl)-1H-indazol-1-yl)-N-(methylsulfonyl)benzamide

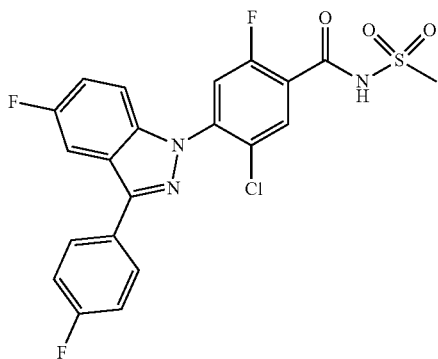 [SMILES: CS(=O)(=O)NC(=O)c1cc(Cl)c(-n2nc(-c3ccc(F)cc3)c3cc(F)ccc32)cc1F]

1H NMR (500 MHz, MeOD) δ: 8.04-7.98 (m, 3H), 7.79 (d, 1H), 7.55 (d, 2H), 7.47 (d, 1H), 7.38 (d, 1H), 7.33 (d, 1H), 3.14 (s, 3H)

Example 154) Preparation of 5-chloro-4-(3-(4-chlorophenyl)-5-fluoro-1H-indazol-1-yl)-2-fluoro-N-(methylsulfonyl)benzamide

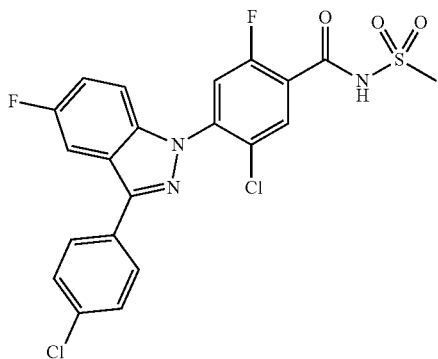 [SMILES: CS(=O)(=O)NC(=O)c1cc(Cl)c(-n2nc(-c3ccc(Cl)cc3)c3cc(F)ccc32)cc1F]

1H NMR (500 MHz, MeOD) δ: 8.22 (d, 2H), 8.06 (d, 1H), 7.88-7.84 (m, 3H), 7.55 (d, 1H), 7.44-7.35 (m, 2H), 3.21 (s, 3H)

Example 155) Preparation of 5-chloro-2-fluoro-4-(5-fluoro-3-(4-methoxyphenyl)-1H-indazol-1-yl)-N-(methylsulfonyl)benzamide

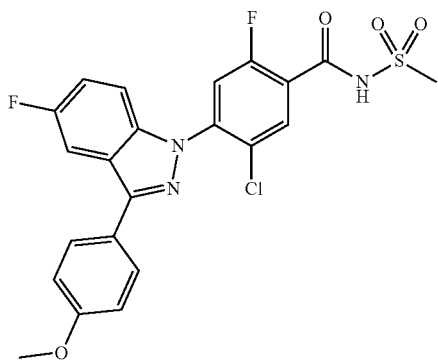 [SMILES: COc1ccc(-c2nn(-c3cc(F)c(C(=O)NS(C)(=O)=O)cc3Cl)c3ccc(F)cc23)cc1]

1H NMR (500 MHz, MeOD) δ: 8.05 (d, 1H), 7.98 (d, 2H), 7.79 (d, 1H), 7.56-7.31 (m, 6H), 3.16 (s, 3H)

Example 156) Preparation of 5-chloro-2-fluoro-4-(5-fluoro-3-(p-tolyl)-1H-indazol-1-yl)-N-(methylsulfonyl)benzamide

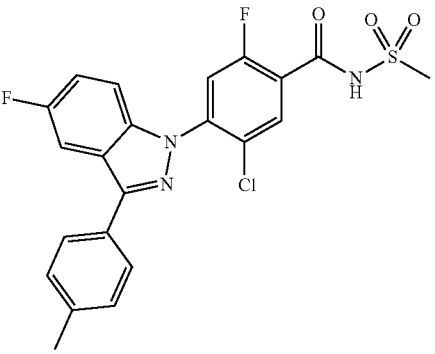 [SMILES: Cc1ccc(-c2nn(-c3cc(F)c(C(=O)NS(C)(=O)=O)cc3Cl)c3ccc(F)cc23)cc1]

1H NMR (500 MHz, MeOD) δ: 8.06 (d, 1H), 7.86 (d, 1H), 7.56-7.50 (m, 3H), 7.42-7.33 (m, 3H), 3.20 (s, 3H)

Example 157) Preparation of 5-chloro-4-(3-(3-chloro-5-fluorophenyl)-5-fluoro-1H-indazol-1-yl)-2-fluoro-N-(methylsulfonyl)benzamide

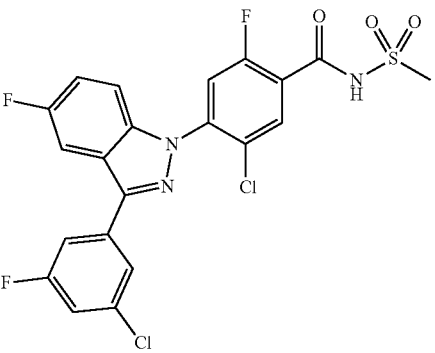 [SMILES: CS(=O)(=O)NC(=O)c1cc(Cl)c(-n2nc(-c3cc(F)cc(Cl)c3)c3cc(F)ccc32)cc1F]

1H NMR (500 MHz, MeOD) δ: 8.05 (d, 1H), 7.85 (s, 1H), 7.81 (d, 1H), 7.79 (d, 1H), 7.51 (d, 1H), 7.43-7.29 (m, 3H), 3.16 (s, 3H)

Example 158) Preparation of 5-chloro-4-(3-(2-chloro-4-fluorophenyl)-5-fluoro-1H-indazol-1-yl)-2-fluoro-N-(methylsulfonyl)benzamide

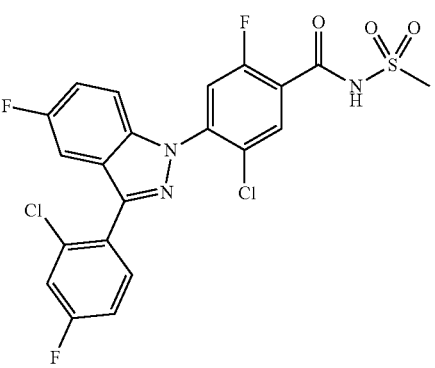 [SMILES: CS(=O)(=O)NC(=O)c1cc(Cl)c(-n2nc(-c3ccc(F)cc3Cl)c3cc(F)ccc32)cc1F]

1H NMR (500 MHz, MeOD) δ: 8.05 (d, 1H), 7.71 (d, 1H), 7.53-7.25 (m, 6H), 3.18 (s, 3H)

Example 159) Preparation of 5-chloro-4-(3-(2,4-difluorophenyl)-5-fluoro-1H-indazol-1-yl)-2-fluoro-N-(methylsulfonyl)benzamide

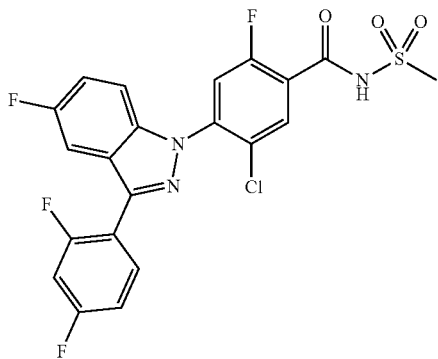 [SMILES: CS(=O)(=O)NC(=O)c1cc(Cl)c(-n2nc(-c3ccc(F)cc3F)c3cc(F)ccc32)cc1F]

1H NMR (500 MHz, MeOD) δ: 8.05 (d, 1H), 7.89 (q, 1H), 7.51 (m, 2H), 7.40 (m, 1H), 7.34 (m, 1H), 7.23-7.14 (m, 2H), 3.19 (s, 3H)

Example 160) Preparation of 5-chloro-4-(3-(2,5-difluorophenyl)-5-fluoro-1H-indazol-1-yl)-2-fluoro-N-(methylsulfonyl)benzamide

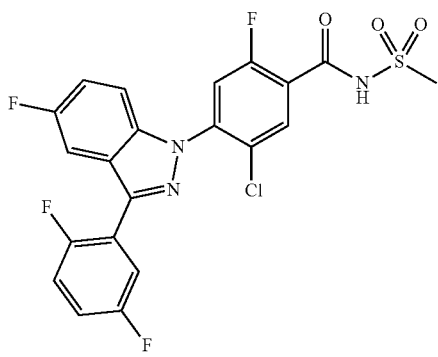 [SMILES: CS(=O)(=O)NC(=O)c1cc(Cl)c(-n2nc(-c3cc(F)ccc3F)c3cc(F)ccc32)cc1F]

1H NMR (500 MHz, MeOD) δ: 8.05 (d, 1H), 7.60 (m, 1H), 7.54 (d, 2H), 7.42-7.33 (m, 3H), 7.25 (m, 1H), 3.19 (s, 3H)

Example 161) Preparation of 5-chloro-4-(3-(3,4-difluorophenyl)-5-fluoro-1H-indazol-1-yl)-2-fluoro-N-(methylsulfonyl)benzamide

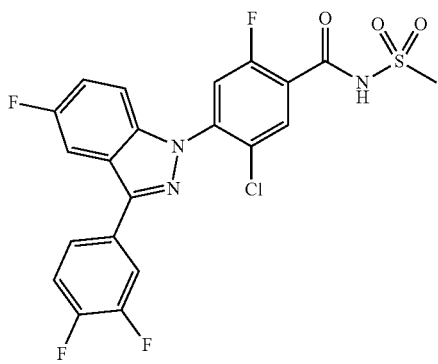 [SMILES: CS(=O)(=O)NC(=O)c1cc(Cl)c(-n2nc(-c3ccc(F)c(F)c3)c3cc(F)ccc32)cc1F]

1H NMR (500 MHz, MeOD) δ: 8.05 (d, 1H), 7.89 (m, 1H), 7.80 (m, 2H), 7.50 (d, 1H), 7.44 (m, 1H), 7.40-7.34 (m, 2H), 3.17 (s, 3H)

Example 162) Preparation of 5-chloro-4-(3-(2-chloro-6-fluorophenyl)-5-fluoro-1H-indazol-1-yl)-2-fluoro-N-(methylsulfonyl)benzamide

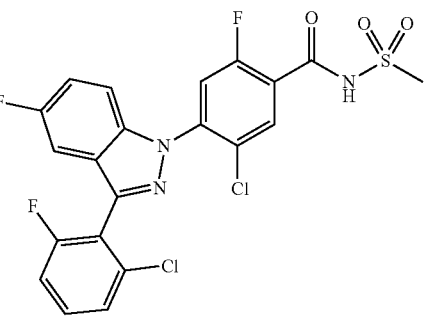

1H NMR (500 MHz, MeOD) δ: 8.04 (d, 1H), 7.56 (m, 1H), 7.47 (m, 3H), 7.37-7.29 (m, 2H), 7.22 (d, 1H), 3.15 (s, 3H)

Example 163) Preparation of 5-chloro-4-(3-(3-chloro-2-fluorophenyl)-5-fluoro-1H-indazol-1-yl)-2-fluoro-N-(methylsulfonyl)benzamide

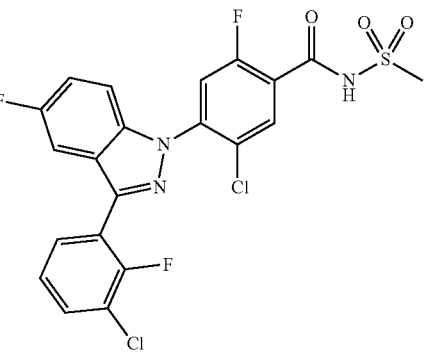

1H NMR (500 MHz, MeOD) δ: 8.05 (d, 1H), 7.79 (t, 1H), 7.62 (t, 1H), 7.50 (m 2H), 7.42 (m, 21H), 7.34 (m, 2H), 3.17 (s, 3H)

Example 164) Preparation of 5-chloro-4-(3-(4-chloro-3-fluorophenyl)-5-fluoro-1H-indazol-1-yl)-2-fluoro-N-(methylsulfonyl)benzamide

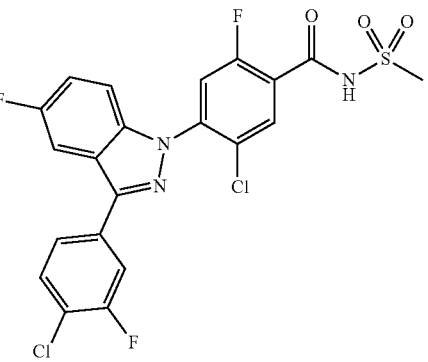

1H NMR (500 MHz, MeOD) δ: 8.05 (d, 1H), 7.89-7.82 (m, 3H), 7.65 (t, 1H), 7.52 (d, 1H), 7.42-7.33 (m, 2H), 3.19 (s, 3H)

Example 165) Preparation of 5-chloro-2-fluoro-4-(5-fluoro-3-(pyridin-3-yl)-1H-indazol-1-yl)-N-(methylsulfonyl)benzamide

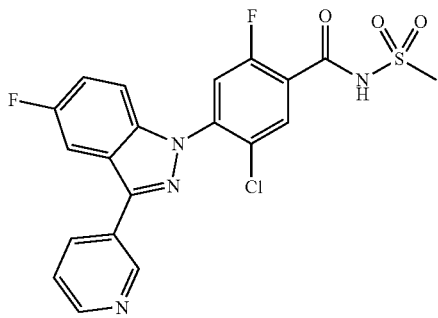 [SMILES: CS(=O)(=O)NC(=O)c1cc(Cl)c(-n2nc(-c3cccnc3)c3cc(F)ccc32)cc1F]

1H NMR (500 MHz, MeOD) δ: 9.18 (s, 1H), 8.73 (s, 1H), 8.63 (d, 1H), 8.05 (d, 1H), 7.85 (d, 1H)), 7.63 (d, 1H), 7.54-7.38 (m, 3H), 3.17 (s, 3H)

Example 166) Preparation of 5-chloro-4-(3-(3-cyanophenyl)-5-fluoro-1H-indazol-1-yl)-2-fluoro-N-(methylsulfonyl)benzamide

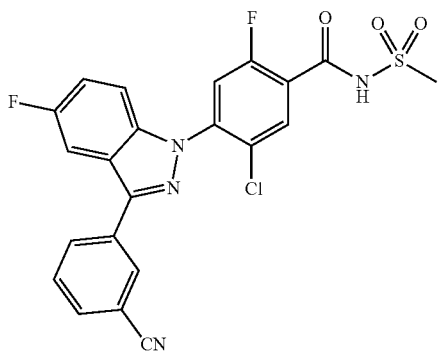 [SMILES: CS(=O)(=O)NC(=O)c1cc(Cl)c(-n2nc(-c3cccc(C#N)c3)c3cc(F)ccc32)cc1F]

1H NMR (500 MHz, MeOD) δ: 8.34 (d, 2H), 8.05 (d, 1H), 7.87-7.73 (m, 3H), 7.53 (d, 1H), 7.42-7.35 (m, 2H), 3.18 (s, 3H)

Example 167) Preparation of 3-cyano-4-(5-fluoro-3-(pyridin-3-yl)-1H-indazol-1-yl)-N-(methylsulfonyl)benzamide

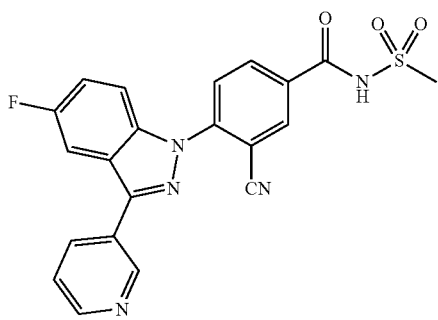 [SMILES: CS(=O)(=O)NC(=O)c1ccc(-n2nc(-c3cccnc3)c3cc(F)ccc32)c(C#N)c1]

1H NMR (500 MHz, MeOD) δ: 9.24 (s, 1H), 8.64 (d, 2H), 8.51 (d, 2H), 7.93-7.88 (m, 2H), 7.81 (d, 1H), 7.65 (d, 1H), 7.43 (t, 1H), 3.14 (s, 3H)

Example 168) Preparation of 3-cyano-4-(3-(3-cyanophenyl)-5-fluoro-1H-indazol-1-yl)-N-(methylsulfonyl)benzamide

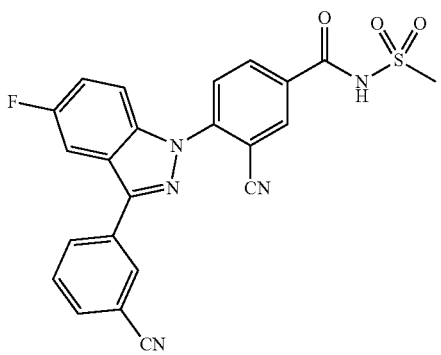 [SMILES: CS(=O)(=O)NC(=O)c1ccc(-n2nc(-c3cccc(C#N)c3)c3cc(F)ccc32)c(C#N)c1]

1H NMR (500 MHz, MeOD) δ: 8.60 (s, 1H), 8.50 (d, 1H), 8.38 (d, 2H), 7.92-7.74 (m, 5H), 7.42 (t, 1H), 3.14 (s, 3H)

Example 169) Preparation of 5-chloro-4-(3-(4-chloro-2-fluorophenyl)-5-methoxy-1H-indazol-1-yl)-2-fluoro-N-(methylsulfonyl)benzamide

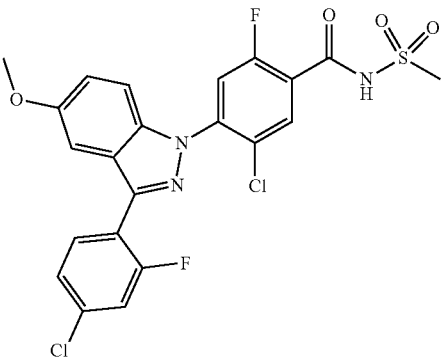

1H NMR (500 MHz, MeOD) δ: 8.04 (d, 1H), 7.84 (t, 1H), 7.53 (d, 1H), 7.45 (d, 1H), 7.39 (d, 1H), 7.30 (d, 1H), 7.18 (d, 2H), 3.86 (s, 3H), 3.24 (s, 3H)

Example 170) Preparation of 5-chloro-4-(3-(3-chlorophenyl)-1H-indazol-1-yl)-2-fluoro-N-(methylsulfonyl)benzamide

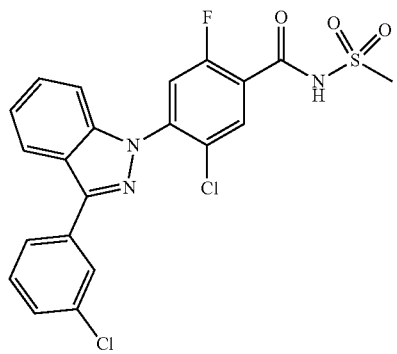 [SMILES: CS(=O)(=O)NC(=O)c1cc(Cl)c(-n2nc(-c3cccc(Cl)c3)c3ccccc32)cc1F]

1H NMR (500 MHz, MeOD) δ: 8.11 (d, 1H), 8.06 (d, 1H), 8.06 (s, 1H), 7.98 (d, 1H), 7.54 (t, 3H), 7.47 (d, 1H), 7.38 (d, 2H), 3.25 (s, 3H)

Example 171) Preparation of 5-chloro-2-fluoro-4-(3-(3-fluorophenyl)-1H-indazol-1-yl)-N-(methylsulfonyl)benzamide

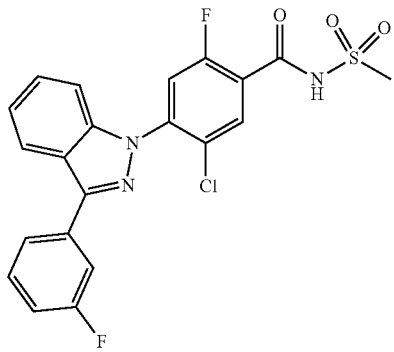

1H NMR (500 MHz, MeOD) δ: 8.13 (d, 1H), 8.06 (d, 1H), 7.87 (d, 1H), 7.75 (d, 1H), 7.58-7.50 (m, 3H), 7.38 (t, 2H), 7.21-7.17 (m, 1H), 3.19 (s, 3H)

Example 172) Preparation of 5-chloro-2-fluoro-N-(methylsulfonyl)-4-(3-(3-(trifluoromethyl)phenyl)-1H-indazol-1-yl)benzamide

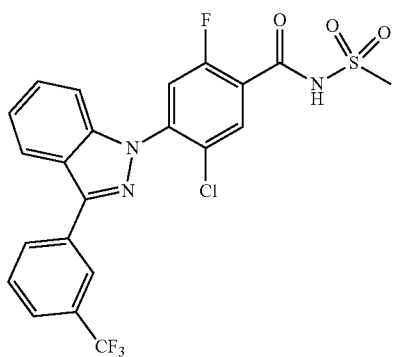 [SMILES: CS(=O)(=O)NC(=O)c1cc(Cl)c(-n2nc(-c3cccc(C(F)(F)F)c3)c3ccccc32)cc1F]

1H NMR (500 MHz, MeOD) δ: 8.31 (m, 2H), 8.12 (d, 1H), 8.06 (d, 1H), 7.76 (d, 2H), 7.55 (m, 2H), 7.40 (dd, 2H), 3.24 (s, 3H)

Example 173) Preparation of 5-chloro-2-fluoro-N-(methylsulfonyl)-4-(3-(o-tolyl)-1H-indazol-1-yl)benzamide

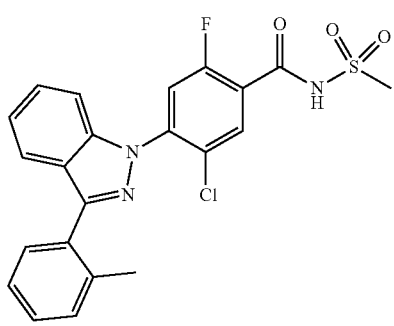 [SMILES: Cc1ccccc1-c1nn(-c2cc(F)c(C(=O)NS(C)(=O)=O)cc2Cl)c2ccccc12]

1H NMR (500 MHz, MeOD) δ: 8.05 (d, 1H), 7.68 (d, 1H), 7.56-7.51 (m, 3H), 7.41-7.35 (m, 4H), 7.31 (t, 1H), 3.26 (s, 3H), 2.41 (s, 3H)

Example 174) Preparation of 5-chloro-2-fluoro-4-(3-(2-methoxyphenyl)-1H-indazol-1-yl)-N-(methylsulfonyl)benzamide

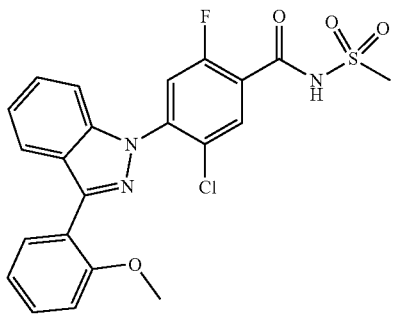 [SMILES: COc1ccccc1-c1nn(-c2cc(F)c(C(=O)NS(C)(=O)=O)cc2Cl)c2ccccc12]

1H NMR (500 MHz, MeOD) δ: 8.05 (d, 1H), 7.55 (d, 1H), 7.62 (d, 1H), 7.61 (d, 1H), 7.55-7.47 (m, 2H), 7.34 (d, 1H), 7.26 (t, 1H), 7.21 (d, 1H), 7.09 (t, 1H), 3.86 (s, 3H), 3.27 (s, 3H)

Example 175) Preparation of 5-chloro-4-(3-(2-chloro-4-fluorophenyl)-1H-indazol-1-yl)-2-fluoro-N-(methylsulfonyl)benzamide

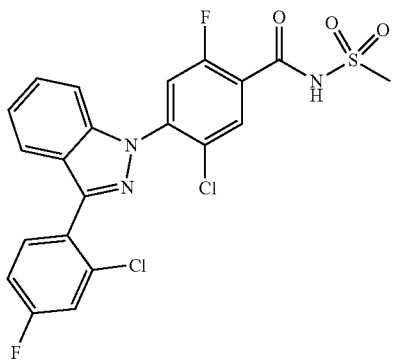 [SMILES: CS(=O)(=O)NC(=O)c1cc(Cl)c(-n2nc(-c3ccc(F)cc3Cl)c3ccccc32)cc1F]

1H NMR (500 MHz, MeOD) δ: 8.06 (d, 1H), 7.70 (t, 2H), 7.57 (d, 1H), 7.53 (t, 1H), 7.47 (m, 1H), 7.40 (d, 1H), 7.30-7.6 (m, 2H), 3.28 (s, 3H)

Example 176) Preparation of 5-chloro-4-(3-(2,4-difluorophenyl)-1H-indazol-1-yl)-2-fluoro-N-(methylsulfonyl)benzamide

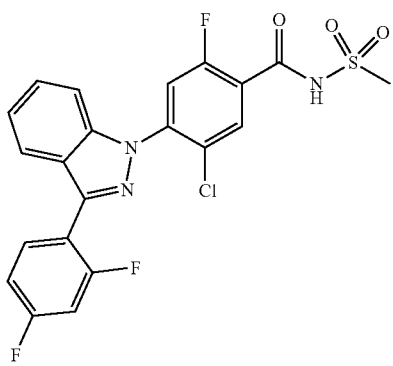 [SMILES: CS(=O)(=O)NC(=O)c1cc(Cl)c(-n2nc(-c3ccc(F)cc3F)c3ccccc32)cc1F]

1H NMR (500 MHz, MeOD) δ: 8.05 (d, 1H), 7.90-8.84 (m, 2H), 7.56 (d, 1H), 7.52 (t, 1H), 7.47 (d, 1H), 7.33 (t, 1H), 7.23-7.14 (m, 2H), 3.37 (s, 3H)

Example 177) Preparation of 5-chloro-2-fluoro-4-(3-(4-fluoropyridin-3-yl)-1H-indazol-1-yl)-N-(methylsulfonyl)benzamide

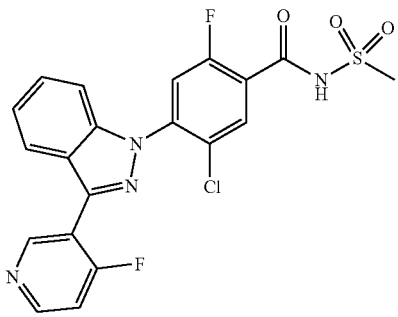 [SMILES: CS(=O)(=O)NC(=O)c1cc(Cl)c(-n2nc(-c3cnccc3F)c3ccccc32)cc1F]

1H NMR (500 MHz, MeOD) δ: 8.88 (s, 1H), 8.58 (t, 1H), 8.12 (d, 1H), 8.04 (d, 1H), 7.56 (t, 1H), 7.51 (d, 1H), 7.40 (t, 2H), 7.26 (d, 1H), 3.18 (s, 3H)

Example 178) Preparation of 5-chloro-2-fluoro-N-(methylsulfonyl)-4-(3-(4-(trifluoromethyl)phenyl)-1H-indazol-1-yl)benzamide

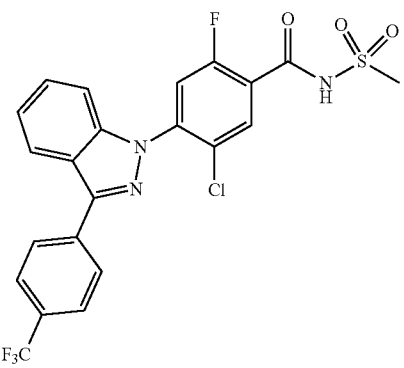 [SMILES: CS(=O)(=O)NC(=O)c1cc(Cl)c(-n2nc(-c3ccc(C(F)(F)F)cc3)c3ccccc32)cc1F]

1H NMR (500 MHz, MeOD) δ: 8.24 (d, 2H), 8.17 (d, 1H), 8.06 (d, 1H), 7.85 (d, 2H), 7.54 (m, 2H), 7.40 (m, 2H), 3.25 (s, 3H)

Example 179) Preparation of 5-chloro-2-fluoro-4-(3-(4-fluorophenyl)-1H-indazol-1-yl)-N-(methylsulfonyl)benzamide

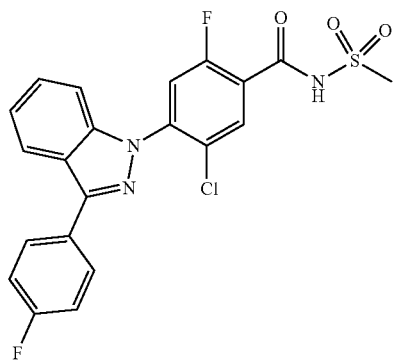 [SMILES: CS(=O)(=O)NC(=O)c1cc(Cl)c(-n2nc(-c3ccc(F)cc3)c3ccccc32)cc1F]

1H NMR (500 MHz, MeOD) δ: 8.09 (d, 1H), 8.06-8.03 (m, 3H), 7.52 (dd, 2H), 7.36 (t, 2H), 7.29 (t, 2H), 3.24 (s, 3H)

Example 180) Preparation of 5-chloro-2-fluoro-N-(methylsulfonyl)-4-(3-(pyridin-3-yl)-1H-indazol-1-yl)benzamide

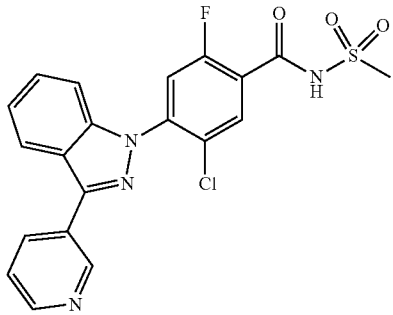 [SMILES: CS(=O)(=O)NC(=O)c1cc(Cl)c(-n2nc(-c3cccnc3)c3ccccc32)cc1F]

1H NMR (500 MHz, MeOD) δ: 9.21 (s, 1H), 8.62 (d, 1H), 8.50 (d, 1H), 8.13 (d, 1H), 8.06 (d, 1H), 7.63 (t, 1H), 7.53 (m, 2H), 7.40 (d, 2H), 3.22 (s, 3H)

Example 181) Preparation of 5-chloro-4-(3-(3-cyanophenyl)-1H-indazol-1-yl)-2-fluoro-N-(methylsulfonyl)benzamide

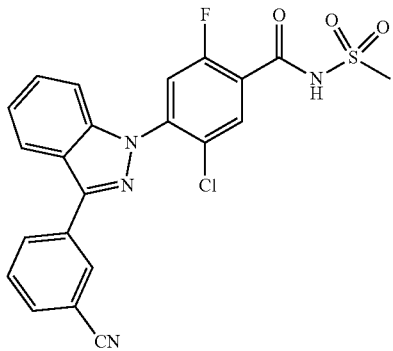 [SMILES: CS(=O)(=O)NC(=O)c1cc(Cl)c(-n2nc(-c3cccc(C#N)c3)c3ccccc32)cc1F]

1H NMR (500 MHz, MeOD) δ: 8.38 (d, 2H), 8.16 (d, 1H), 8.06 (d, 1H), 7.83-7.73 (m, 2H), 7.57-7.52 (m, 2H), 7.41 (d, 2H), 3.19 (s, 3H)

Example 182) Preparation of 3-cyano-N-(methylsulfonyl)-4-(3-(pyridin-3-yl)-1H-indazol-1-yl)benzamide

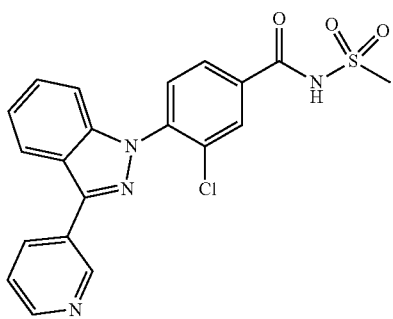 [SMILES: CS(=O)(=O)NC(=O)c1ccc(-n2nc(-c3cccnc3)c3ccccc32)c(Cl)c1]

1H NMR (500 MHz, MeOD) δ: 9.28 (s, 1H), 8.64-8.50 (m, 4H), 8.19 (d, 1H), 7.93 (d, 1H), 7.78 (d, 1H), 7.64-7.61 (m, 2H), 7.46 (t, 1H), 3.13 (s, 3H)

Example 183) Preparation of 3-cyano-4-(3-(3-cyanophenyl)-1H-indazol-1-yl)-N-(methylsulfonyl)benzamide

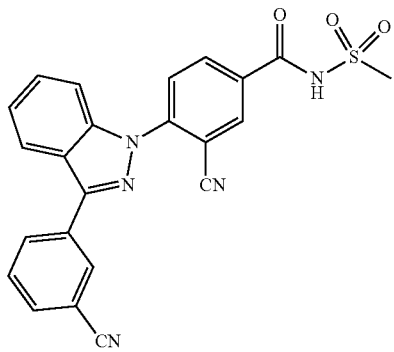 [SMILES: CS(=O)(=O)NC(=O)c1ccc(-n2nc(-c3cccc(C#N)c3)c3ccccc32)c(C#N)c1]

1H NMR (500 MHz, MeOD) δ: 8.59 (s, 1H), 8.48-8.41 (m, 3H), 8.20 (d, 1H), 7.95 (d, 1H), 7.84-7.76 (m, 3H), 7.62 (t, 1H), 7.46 (t, 1H), 3.20 (s, 3H)

Example 184) Preparation of 5-chloro-4-(3-(4-chloro-2-fluorophenyl)-1H-indazol-1-yl)-2-fluoro-N-(methylsulfonyl)benzamide

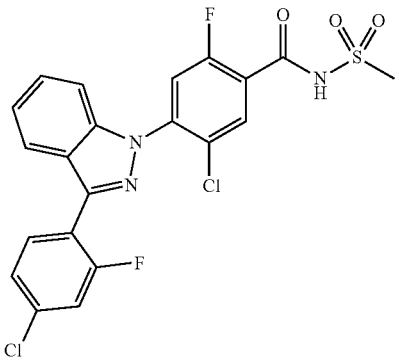 [SMILES: CS(=O)(=O)NC(=O)c1cc(Cl)c(-n2nc(-c3ccc(Cl)cc3F)c3ccccc32)cc1F]

1H NMR (500 MHz, MeOD) δ: 8.07 (d, 1H), 7.88-7.84 (m, 2H), 7.61-7.33 (m, 6H), 3.30 (s, 3H)

Example 186) Preparation of 5-chloro-4-(5-chloro-3-(2,4-difluorophenyl)-1H-pyrrolo[2,3-b]pyridin-1-yl)-2-fluoro-N-(methylsulfonyl)benzamide

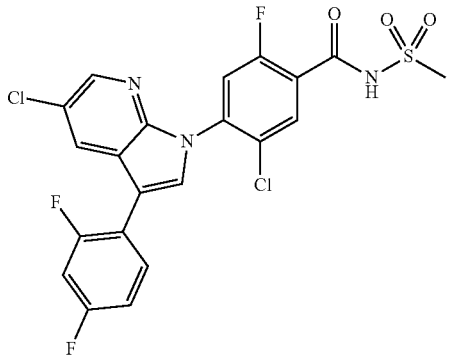

1H NMR (500 MHz, MeOD) δ: 8.28 (m, 1H), 8.17 (m, 1H), 8.02 (d, 1H), 7.91 (s, 1H), 7.74 (q, 1H), 7.59 (d, 1H), 7.13 (m, 2H), 3.27 (s, 3H)

Example 187) Preparation of 5-chloro-4-(5-chloro-3-(4-cyanophenyl)-1H-pyrrolo[2,3-b]pyridin-1-yl)-2-fluoro-N-(methylsulfonyl)benzamide

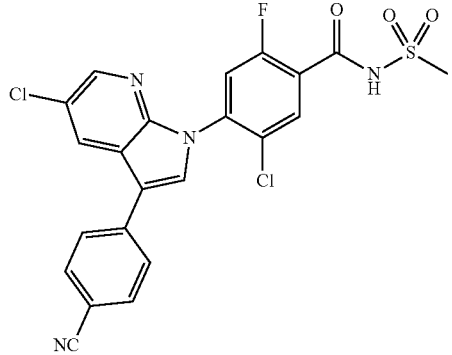 [SMILES: CS(=O)(=O)NC(=O)c1cc(Cl)c(-n2cc(-c3ccc(C#N)cc3)c3cc(Cl)cnc32)cc1F]

1H NMR (500 MHz, MeOD) δ: 8.45 (m, 1H), 8.30 (m, 1H), 8.15 (s, 1H), 8.03 (d, 1H), 7.93 (d, 2H), 7.83 (d, 2H), 7.56 (d, 1H), 3.22 (s, 3H)

Example 188) Preparation of 5-chloro-4-(5-chloro-3-(4-(trifluoromethyl)phenyl)-1H-pyrrolo[2,3-b]pyridin-1-yl)-2-fluoro-N-(methylsulfonyl)benzamide

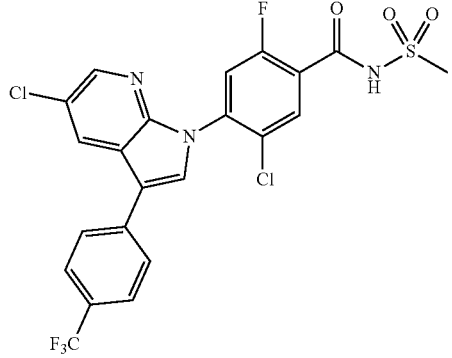 [SMILES: CS(=O)(=O)NC(=O)c1cc(Cl)c(-n2cc(-c3ccc(C(F)(F)F)cc3)c3cc(Cl)cnc32)cc1F]

1H NMR (500 MHz, MeOD) δ: 8.44 (s, 1H), 8.30 (s, 1H), 8.10 (s, 1H), 8.03 (m, 1H), 7.94 (d, 2H), 7.78 (d, 2H), 7.57 (d, 1H), 3.24 (s, 3H)

Example 189) Preparation of 5-chloro-4-(5-chloro-3-(4-chloro-2-fluorophenyl)-1H-pyrrolo[2,3-b]pyridin-1-yl)-2-fluoro-N-(methylsulfonyl)benzamide

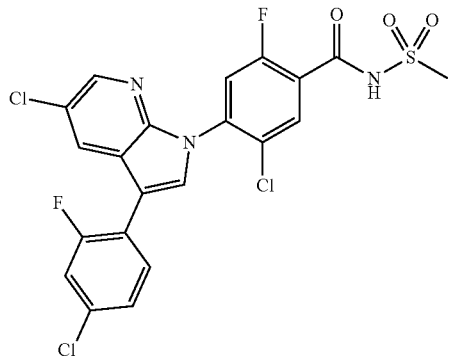 [SMILES: CS(=O)(=O)NC(=O)c1cc(Cl)c(-n2cc(-c3ccc(Cl)cc3F)c3cc(Cl)cnc32)cc1F]

1H NMR (500 MHz, MeOD) δ: 8.29 (m, 1H), 8.21 (m, 1H), 8.03 (d, 1H), 7.96 (s, 1H), 7.73 (t, 1H), 7.58 (d, 1H), 7.39 (m, 2H), 3.26 (s, 3H)

Example 190) Preparation of 5-chloro-4-(5-chloro-3-(3-fluorophenyl)-1H-pyrrolo[2,3-b]pyridin-1-yl)-2-fluoro-N-(methylsulfonyl)benzamide

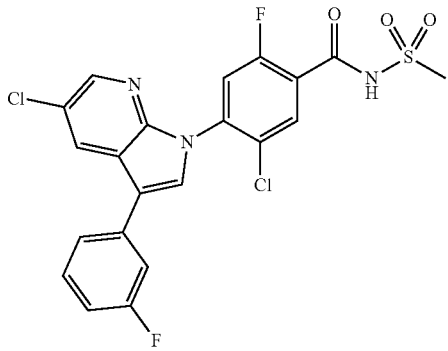 [SMILES: CS(=O)(=O)NC(=O)c1cc(Cl)c(-n2cc(-c3cccc(F)c3)c3cc(Cl)cnc32)cc1F]

1H NMR (500 MHz, MeOD) δ: 8.36 (s, 1H), 8.28 (s, 1H), 8.03 (d, 1H), 7.99 (s, 1H), \.52 (m, 4H), 7.08 (m, 1H), 3.24 (s, 3H)

Example 191) Preparation of 5-chloro-4-(5-chloro-3-(2-fluorophenyl)-1H-pyrrolo[2,3-b]pyridin-1-yl)-2-fluoro-N-(methylsulfonyl)benzamide

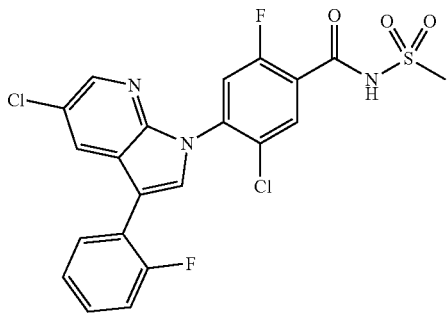 [SMILES: CS(=O)(=O)NC(=O)c1cc(Cl)c(-n2cc(-c3ccccc3F)c3cc(Cl)cnc32)cc1F]

1H NMR (500 MHz, MeOD) δ: 8.58 (s, 1H), 8.28 (s, 1H), 8.05 (m, 1H), 7.75 (s, 1H), 7.51 (m, 4H), 7.14 (m, 1H), 3.23 (s, 3H)

Example 192) 5 Preparation of 5-chloro-4-(5-chloro-3-(3-(trifluoromethyl)phenyl)-1H-pyrrolo[2,3-b]pyridin-1-yl)-2-fluoro-N-(methylsulfonyl)benzamide

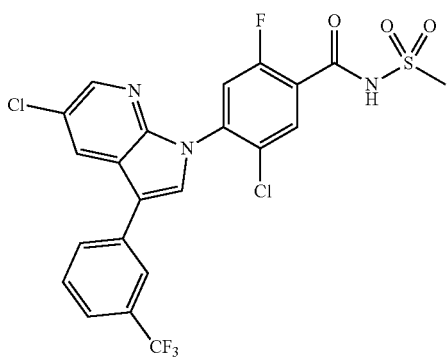 [SMILES: CS(=O)(=O)NC(=O)c1cc(Cl)c(-n2cc(-c3cccc(C(F)(F)F)c3)c3cc(Cl)cnc32)cc1F]

1H NMR (500 MHz, MeOD) δ: 8.27 (s, 1H), 8.03 (d, 1H), 7.88 (m, 1H), 7.83 (m, 1H), 7.74 (m, 1H), 7.70 (s, 1H), 7.60 (m, 3H), 3.26 (s, 3H)

Example 193) Preparation of 5-chloro-4-(5-chloro-3-(2-(trifluoromethyl)phenyl)-1H-pyrrolo[2,3-b]pyridin-1-yl)-2-fluoro-N-(methylsulfonyl)benzamide

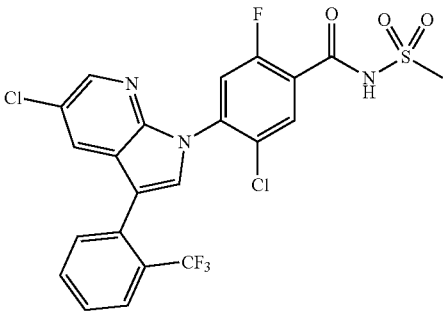 [SMILES: CS(=O)(=O)NC(=O)c1cc(Cl)c(-n2cc(-c3ccccc3C(F)(F)F)c3cc(Cl)cnc32)cc1F]

1H NMR (500 MHz, MeOD) δ: 8.33 (s, 1H), 8.29 (m, 1H), 8.07 (s, 1H), 8.01 (m, 2H), 7.96 (s, 1H), 7.70 (m, 1H), 7.65 (m, 1H), 7.58 (m, 1H), 3.26 (s, 3H)

Example 194) Preparation of 5-chloro-4-(5-chloro-3-(3-cyanophenyl)-1H-pyrrolo[2,3-b]pyridin-1-yl)-2-fluoro-N-(methylsulfonyl)benzamide

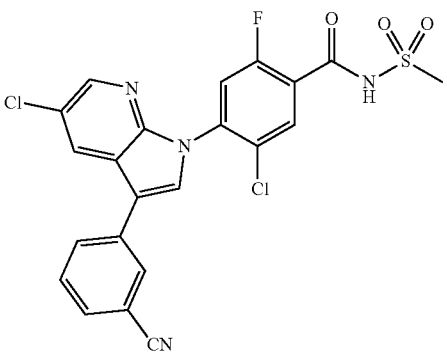 [SMILES: CS(=O)(=O)NC(=O)c1cc(Cl)c(-n2cc(-c3cccc(C#N)c3)c3cc(Cl)cnc32)cc1F]

1H NMR (500 MHz, MeOD) δ: 8.41 (s, 1H), 7.80 (m, 1H), 8.06 (m, 4H), 7.68 (m, 2H), 7.56 (m, 1H), 3.23 (s, 3H)

Example 195) Preparation of 5-chloro-4-(5-chloro-3-(4-chlorophenyl)-1H-pyrrolo[2,3-b]pyridin-1-yl)-2-fluoro-N-(methylsulfonyl)benzamide

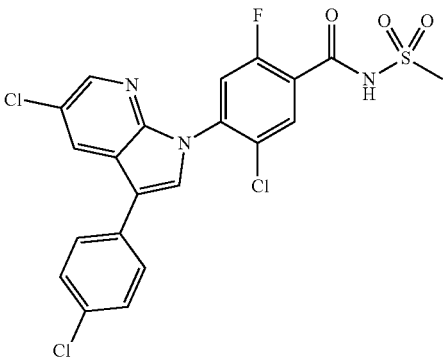

1H NMR (500 MHz, MeOD) δ: 8.35 (s, 1H), 8.27 (m, 1H), 8.02 (d, 1H), 7.95 (s, 1H), 7.71 (d, 2H), 7.50 (m, 3H), 3.19 (s, 3H)

Example 196) Preparation of 5-chloro-4-(5-chloro-3-(4-methoxyphenyl)-1H-pyrrolo[2,3-b]pyridin-1-yl)-2-fluoro-N-(methylsulfonyl)benzamide

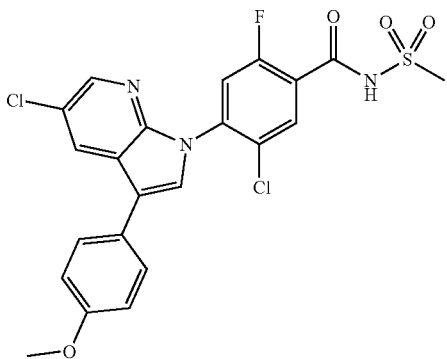

1H NMR (500 MHz, MeOD) δ: 8.30 (s, 1H), 8.24 (s, 1H), 8.02 (d, 1H), 7.84 (s, 1H), 7.62 (s, 2H), 7.55 (m, 1H), 7.06 (m, 2H), 3.85 (s, 3H), 3.24 (s, 3H)

Example 197) Preparation of 5-chloro-4-(5-chloro-3-(2-chloro-4-fluorophenyl)-1H-pyrrolo[2,3-b]pyridin-1-yl)-2-fluoro-N-(methylsulfonyl)benzamide

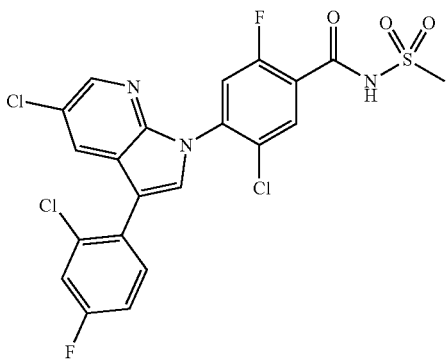 [SMILES: CS(=O)(=O)NC(=O)c1cc(Cl)c(-n2cc(-c3ccc(F)cc3Cl)c3cc(Cl)cnc32)cc1F]

1H NMR (500 MHz, MeOD) δ: 8.27 (m, 1H), 8.03 (d, 1H), 7.98 (m, 1H), 7.85 (s, 1H), 7.61 (m, 2H), 7.43 (dd, 1H), 7.23 (m, 1H), 3.25 (s, 3H)

Example 198) Preparation of 5-chloro-4-(5-chloro-3-(2-chlorophenyl)-1H-pyrrolo[2,3-b]pyridin-1-yl)-2-fluoro-N-(methylsulfonyl)benzamide

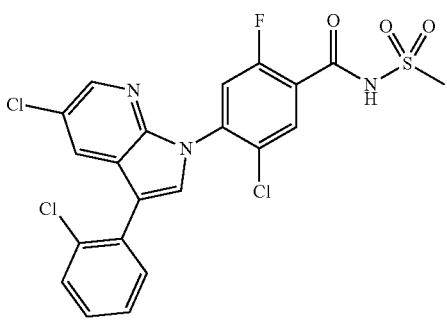 [SMILES: CS(=O)(=O)NC(=O)c1cc(Cl)c(-n2cc(-c3ccccc3Cl)c3cc(Cl)cnc32)cc1F]

1H NMR (500 MHz, MeOD) δ: 8.26 (s, 1H), 8.03-8.02 (d, 1H), 7.99-7.98 (d, 1H), 7.86 (s, 1H), 7.63-7.58 (m, 3H), 7.44-7.39 (m, 2H)

Example 199) Preparation of 5-chloro-4-(5-chloro-3-(4-fluoro-2-methoxyphenyl)-1H-pyrrolo[2,3-b]pyridin-1-yl)-2-fluoro-N-(methylsulfonyl)benzamide

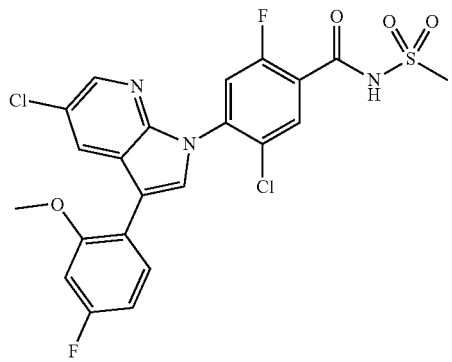

1H NMR (500 MHz, MeOD) δ: 8.23 (m, 1H), 8.07 (m, 1H), 8.02 (d, 1H), 7.82 (s, 1H), 7.60 (d, 1H), 7.53 (m, 1H), 6.95 (dd, 1H), 6.82 (m, 1H), 3.88 (s, 3H), 3.26 (s, 3H)

Example 200) Preparation of 5-chloro-4-(5-chloro-3-(4-fluoro-2-methylphenyl)-1H-pyrrolo[2,3-b]pyridin-1-yl)-2-fluoro-N-(methylsulfonyl)benzamide

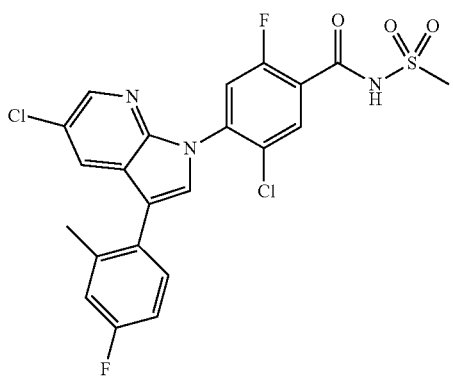 [SMILES: Cc1cc(F)ccc1-c1cn(-c2cc(F)c(C(=O)NS(C)(=O)=O)cc2Cl)c2ncc(Cl)cc12]

1H NMR (500 MHz, MeOD) δ: 8.26 (s, 1H), 8.02 (d, 1H), 7.88 (t, 1H), 7.69 (s, 1H), 7.62 (d, 1H), 7.41 (m 1H), 7.18 (m, 1H), 7.08 (m, 1H), 3.25 (s, 3H), 2.35 (s, 3H)

Example 201) Preparation of 5-chloro-4-(3-(4-chloro-2-fluorophenyl)-5-fluoro-1H-pyrrolo[2,3-b]pyridin-1-yl)-2-fluoro-N-(methylsulfonyl)benzamide

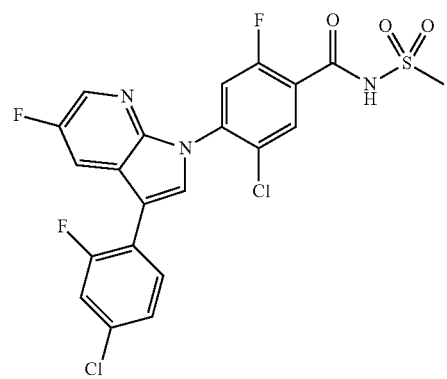

1H NMR (500 MHz, MeOD) δ: 8.24 (s, 1H), 8.03-8.02 (d, 1H), 7.99-7.97 (m, 2H), 7.74-7.71 (t, 1H), 7.63-7.61 (d, 1H), 7.39-7.34 (m, 2H), 3.27 (s, 3H)

Example 202) Preparation of 5-chloro-4-(3-(2-chloro-4-fluorophenyl)-5-fluoro-1H-pyrrolo[2,3-b]pyridin-1-yl)-2-fluoro-N-(methylsulfonyl)benzamide

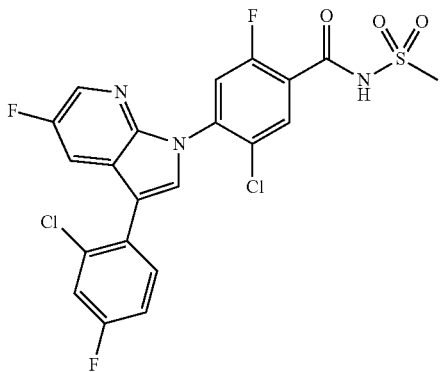 [SMILES: CS(=O)(=O)NC(=O)c1cc(Cl)c(-n2cc(-c3ccc(F)cc3Cl)c3cc(F)cnc32)cc1F]

1H NMR (500 MHz, MeOD) δ: 8.21 (s, 1H), 8.02 (d, 1H), 7.86 (s, 1H), 7.74 (m, 1H), 7.61 (m, 2H), 7.42 (m, 1H), 7.22 (m, 1H), 3.26 (s, 3H)

Example 203) Preparation of 5-chloro-4-(3-(2,4-difluorophenyl)-5-fluoro-1H-pyrrolo[2,3-b]pyridin-1-yl)-2-fluoro-N-(methylsulfonyl)benzamide

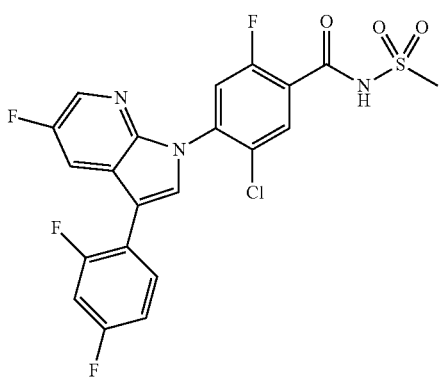 [SMILES: CS(=O)(=O)NC(=O)c1cc(Cl)c(-n2cc(-c3ccc(F)cc3F)c3cc(F)cnc32)cc1F]

1H NMR (500 MHz, MeOD) δ: 8.21 (s, 1H), 8.03-8.02 (d, 1H), 7.96-7.93 (m, 1H), 7.76-7.71 (m, 2H), 7.62-7.60 (d, 1H), 7.17-7.09 (m, 2H), 3.30 (s, 3H)

Example 204) Preparation of 5-chloro-4-(3-(4-chlorophenyl)-5-fluoro-1H-pyrrolo[2,3-b]pyridin-1-yl)-2-fluoro-N-(methylsulfonyl)benzamide

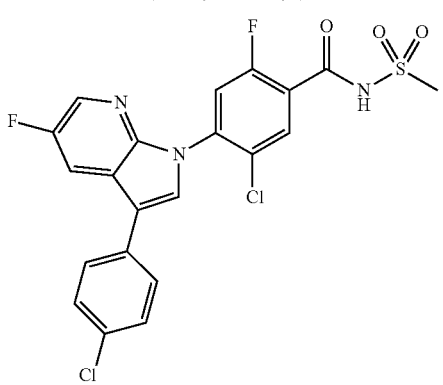

1H NMR (500 MHz, MeOD) δ: 8.23 (s, 1H), 8.15-8.13 (dd, 1H), 8.03-8.01 (d, 1H), 7.98 (s, 1H), 7.72-7.70 (d, 2H), 7.62-7.60 (d, 1H), 7.49-7.48 (d, 1H), 3.30 (s, 3H)

Example 205) Preparation of 5-chloro-2-fluoro-4-(5-fluoro-3-(4-(trifluoromethyl)phenyl)-1H-pyrrolo[2,3-b]pyridin-1-yl)-N-(methylsulfonyl)benzamide

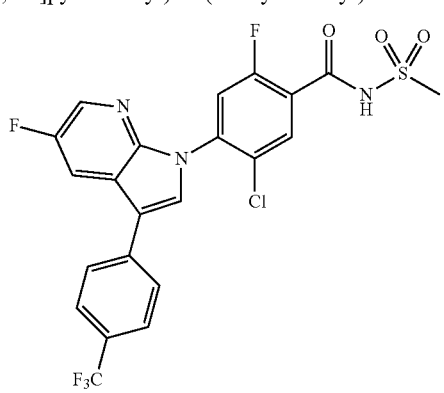

1H NMR (500 MHz, MeOD) δ: 8.25 (s, 1H), 8.23-8.20 (dd, 1H), 8.12 (s, 1H), 8.04-8.03 (d, 1H), 7.94-7.92 (d, 2H), 7.79-7.77 (d, 2H), 7.62-7.60 (d, 1H), 3.29 (s, 3H)

Example 206) Preparation of 5-chloro-2-fluoro-4-(5-fluoro-3-(4-fluorophenyl)-1H-pyrrolo[2,3-b]pyridin-1-yl)-N-(methylsulfonyl)benzamide

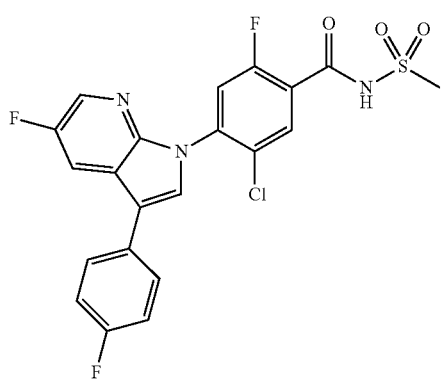 [SMILES: CS(=O)(=O)NC(=O)c1cc(Cl)c(-n2cc(-c3ccc(F)cc3)c3cc(F)cnc32)cc1F]

1H NMR (500 MHz, MeOD) δ: 8.22 (s, 1H), 8.12-8.10 (dd, 1H), 8.03-8.01 (d, 1H), 7.92 (s, 1H), 7.74-7.71 (m, 2H), 7.61-7.59 (d, 1H), 7.28-7.21 (m, 2H), 3.26 (s, 3H)

Example 207) Preparation of 5-chloro-4-(3-(2-chlorophenyl)-5-fluoro-1H-pyrrolo[2,3-b]pyridin-1-yl)-2-fluoro-N-(methylsulfonyl)benzamide

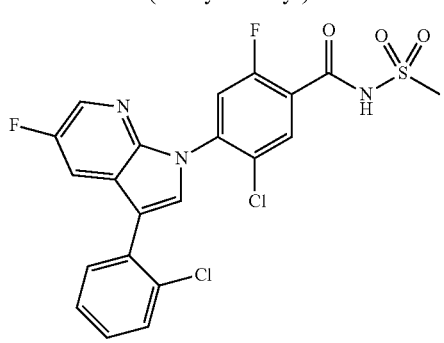

1H NMR (500 MHz, MeOD) δ: 8.23 (s, 1H), 8.02 (d, 1H), 7.90 (s, 1H), 7.77 (dd, 1H), 7.70 (d, 1H), 7.59 (m, 2H), 7.42 (m, 2H), 3.38 (s, 3H)

Example 208) Preparation of 5-chloro-4-(3-(3-chlorophenyl)-5-fluoro-1H-pyrrolo[2,3-b]pyridin-1-yl)-2-fluoro-N-(methylsulfonyl)benzamide

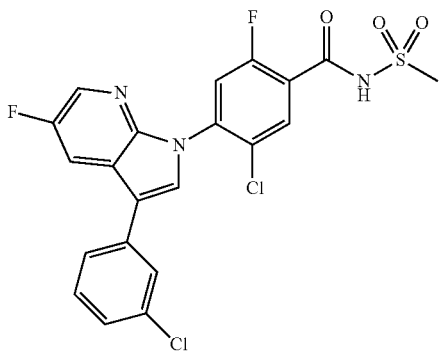 [SMILES: CS(=O)(=O)NC(=O)c1cc(Cl)c(-n2cc(-c3cccc(Cl)c3)c3cc(F)cnc32)cc1F]

1H NMR (500 MHz, MeOD) δ: 8.25 (s, 1H), 8.14 (dd, 1H), 8.03 (m, 2H), 8.02 (s, 1H), 7.72 (m, 1H), 7.68 (m, 2H), 7.48 (tm 1H), 7.35 (m, 1H), 3.40 (s, 3H)

Example 209) Preparation of 5-chloro-4-(3-(2,4-dichlorophenyl)-5-fluoro-1H-pyrrolo[2,3-b]pyridin-1-yl)-2-fluoro-N-(methylsulfonyl)benzamide

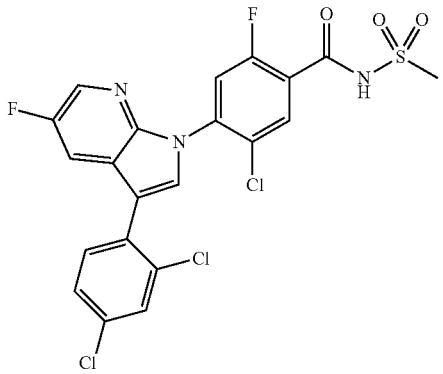 [SMILES: CS(=O)(=O)NC(=O)c1cc(Cl)c(-n2cc(-c3ccc(Cl)cc3Cl)c3cc(F)cnc32)cc1F]

1H NMR (500 MHz, MeOD) δ: 8.24 (s, 1H), 8.02 (d, 1H), 7.93 (s, 1H), 7.79 (dd, 1H), 7.65 (m, 2H), 7.60 (m, 1H), 7.47 (dd, 1H), 3.28 (s, 3H)

Example 210) Preparation of 5-chloro-4-(3-(4-chloro-3-fluorophenyl)-5-fluoro-1H-pyrrolo[2,3-b]pyridin-1-yl)-2-fluoro-N-(methylsulfonyl)benzamide

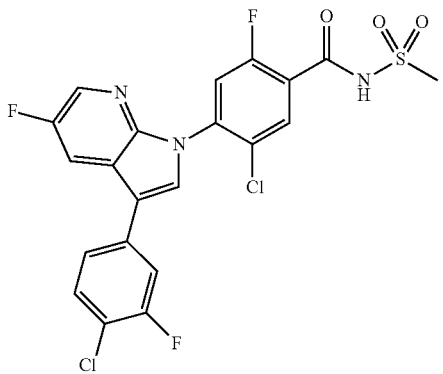 [SMILES: CS(=O)(=O)NC(=O)c1cc(Cl)c(-n2cc(-c3ccc(Cl)c(F)c3)c3cc(F)cnc32)cc1F]

1H NMR (500 MHz, MeOD) δ: 8.25 (s, 1H), 8.19 (dd, 1H), 8.08 (s, 1H), 8.03 (d, 1H), 7.68 (d, 1H), 7.63 (m, 1H), 7.58 (m, 2H), 3.39 (s, 3H)

Example 211) Preparation of 5-chloro-4-(3-(3-chloro-2-fluorophenyl)-5-fluoro-1H-pyrrolo[2,3-b]pyridin-1-yl)-2-fluoro-N-(methylsulfonyl)benzamide

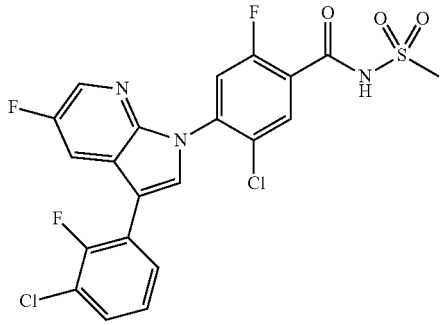 [SMILES: CS(=O)(=O)NC(=O)c1cc(Cl)c(-n2cc(-c3cccc(Cl)c3F)c3cc(F)cnc32)cc1F]

1H NMR (500 MHz, MeOD) δ: 8.26 (s, 1H), 8.03 (m, 2H), 7.99 (d, 1H), 7.69 (m, 2H), 7.49 (t, 1H), 7.31 (t, 1H), 3.40 (s, 3H)

Example 212) Preparation of 5-chloro-2-fluoro-4-(5-fluoro-3-(4-fluoro-2-methylphenyl)-1H-pyrrolo[2,3-b]pyridin-1-yl)-N-(methylsulfonyl)benzamide

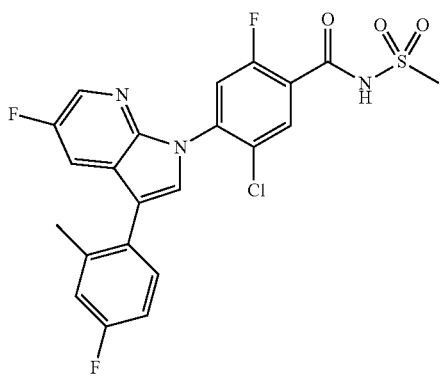 [SMILES: Cc1cc(F)ccc1-c1cn(-c2cc(F)c(C(=O)NS(C)(=O)=O)cc2Cl)c2ncc(F)cc12]

1H NMR (500 MHz, MeOD) δ: 8.21 (s, 1H), 8.03-8.01 (d, 1H), 7.71 (s, 1H), 7.66-7.62 (m, 2H), 7.43-7.40 (q, 1H), 7.13-7.11 (dd, 1H), 7.05-7.02 (m, 1H), 3.30 (s, 3H), 2.36 (s, 3H)

Example 213) Preparation of 5-chloro-2-fluoro-4-(3-(2-fluorophenyl)-1H-pyrrolo[2,3-b]pyridin-1-yl)-N-(methylsulfonyl)benzamide

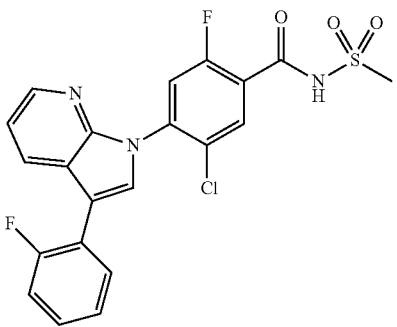 [SMILES: CS(=O)(=O)NC(=O)c1cc(Cl)c(-n2cc(-c3ccccc3F)c3cccnc32)cc1F]

1H NMR (500 MHz, MeOD) δ: 8.31 (dd, 1H), 8.26 (d, 1H), 8.03 (d, 1H), 8.56 (s, 1H), 7.75 (td, 1H), 7.64 (d, 1H), 7.38 (m, 1H), 7.34 (m, 3H), 3.34 (s, 3H)

Example 214) Preparation of 5-chloro-2-fluoro-4-(3-(3-fluorophenyl)-1H-pyrrolo[2,3-b]pyridin-1-yl)-N-(methylsulfonyl)benzamide

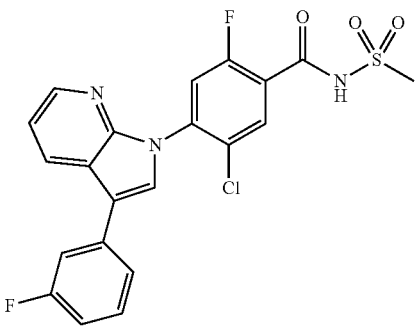 [SMILES: CS(=O)(=O)NC(=O)c1cc(Cl)c(-n2cc(-c3cccc(F)c3)c3cccnc32)cc1F]

1H NMR (500 MHz, MeOD) δ: 8.42-8.40 (d, 1H), 8.31-8.30 (d, 1H), 8.03-8.02 (d, 1H), 7.92 (s, 1H), 7.63-7.61 (d, 1H), 7.58-7.56 (d, 1H), 7.51-7.46 (m, 2H), 7.36-7.33 (m, 1H), 7.08-7.06 (m, 1H), 3.30 (s, 3H)

Example 215) Preparation of 5-chloro-2-fluoro-N-(methylsulfonyl)-4-(3-(m-tolyl)-1H-pyrrolo[2,3-b]pyridin-1-yl)benzamide

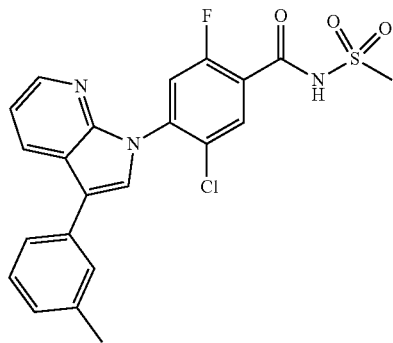 [SMILES: Cc1cccc(-c2cn(-c3cc(F)c(C(=O)NS(C)(=O)=O)cc3Cl)c3ncccc23)c1]

1H NMR (500 MHz, MeOD) δ: 8.38 (s, 1H), 8.29-8.28 (d, 1H), 8.03-8.02 (d, 1H), 7.81 (s, 1H), 7.62-7.60 (d, 1H), 7.54-7.51 (m, 2H), 7.38-7.28 (m, 2H), 7.17-7.15 (d, 1H), 3.34 (s, 3H), 2.43 (s, 3H)

Example 216) Preparation of 5-chloro-2-fluoro-N-(methylsulfonyl)-4-(3-(2-(trifluoromethyl)phenyl)-1H-pyrrolo[2,3-b]pyridin-1-yl)benzamide

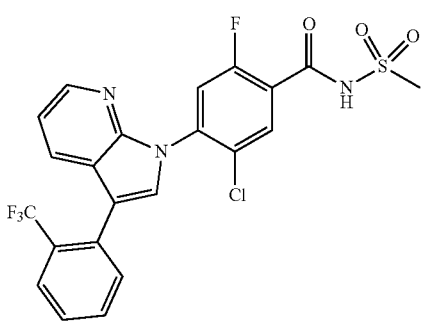 [SMILES: CS(=O)(=O)NC(=O)c1cc(Cl)c(-n2cc(-c3ccccc3C(F)(F)F)c3cccnc32)cc1F]

1H NMR (500 MHz, MeOD) δ: 8.29 (d, 1H), 8.05-8.04 (d, 1H), 7.88-7.86 (m, 2H), 7.74-7.71 (t, 1H), 7.63-7.58 (m, 3H), 7.54-7.52 (d, 1H), 7.27-7.25 (d, 1H), 3.22 (s, 3H)

Example 217) Preparation of 5-chloro-2-fluoro-N-(methylsulfonyl)-4-(3-(3-(trifluoromethyl)phenyl)-1H-pyrrolo[2,3-b]pyridin-1-yl)benzamide

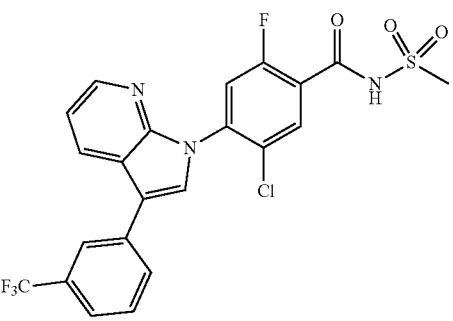 [SMILES: CS(=O)(=O)NC(=O)c1cc(Cl)c(-n2cc(-c3cccc(C(F)(F)F)c3)c3cccnc32)cc1F]

1H NMR (500 MHz, MeOD) δ: 8.38-8.36 (d, 1H), 8.32-8.31 (d, 1H), 8.06-7.98 (m, 4H), 7.70-7.67 (t, 1H), 7.63-7.62 (d, 1H), 7.54-7.52 (d, 1H), 7.36-7.33 (m, 1H), 3.20 (s, 3H)

Example 218) Preparation of 5-chloro-2-fluoro-N-(methylsulfonyl)-4-(3-(4-(trifluoromethyl)phenyl)-1H-pyrrolo[2,3-b]pyridin-1-yl)benzamide

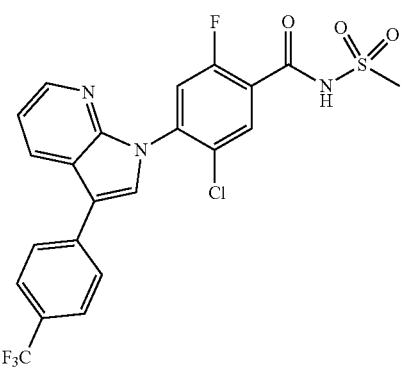 [SMILES: CS(=O)(=O)NC(=O)c1cc(Cl)c(-n2cc(-c3ccc(C(F)(F)F)cc3)c3cccnc32)cc1F]

1H NMR (500 MHz, MeOD) δ: 8.46-8.44 (d, 1H), 8.32-8.31 (d, 1H), 8.06-8.04 (d, 1H), 8.00 (s, 1H), 7.96-7.94 (d, 2H), 7.78-7.76 (d, 2H), 7.55-7.53 (d, 1H), 7.36-7.34 (m, 1H), 3.22 (s, 3H)

Example 219) Preparation of 5-chloro-4-(3-(5-chloro-2-fluorophenyl)-1H-pyrrolo[2,3-b]pyridin-1-yl)-2-fluoro-N-(methylsulfonyl)benzamide

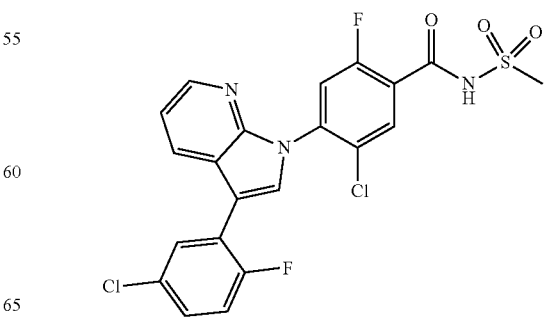

1H NMR (500 MHz, MeOD) δ: 8.31-8.30 (d, 1H), 8.22-8.21 (d, 1H), 8.05-8.04 (d, 1H), 7.88 (s, 1H), 7.74-7.72 (m, 1H), 7.52-7.50 (d, 1H), 7.38-7.26 (m, 3H), 3.19 (s, 3H)

Example 220) Preparation of 5-chloro-4-(3-(3-chloro-5-fluorophenyl)-1H-pyrrolo[2,3-b]pyridin-1-yl)-2-fluoro-N-(methylsulfonyl)benzamide

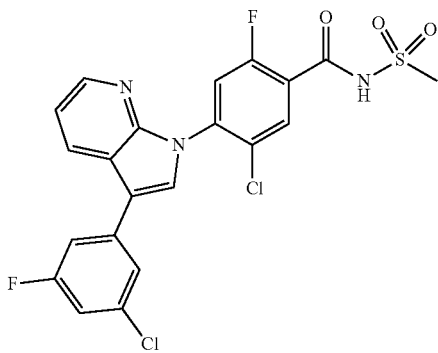 [SMILES: CS(=O)(=O)NC(=O)c1cc(Cl)c(-n2cc(-c3cc(F)cc(Cl)c3)c3cccnc32)cc1F]

1H NMR (500 MHz, MeOD) δ: 8.39-8.38 (d, 1H), 8.31-8.30 (d, 1H), 8.05-8.04 (d, 1H), 7.98 (s, 1H), 7.60 (s, 1H), 7.52-7.46 (m, 2H), 7.36-7.33 (m, 1H), 7.16-7.14 (d, 1H), 3.19 (s, 3H)

Example 221) Preparation of 5-chloro-4-(3-(3-chlorophenyl)-1H-pyrrolo[2,3-b]pyridin-1-yl)-2-fluoro-N-(methylsulfonyl)benzamide

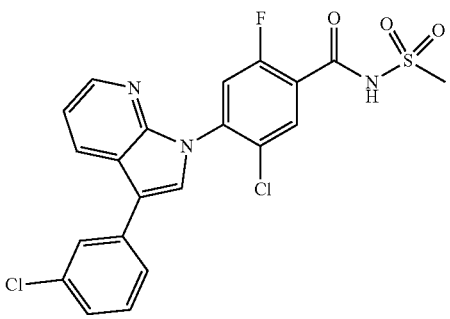 [SMILES: CS(=O)(=O)NC(=O)c1cc(Cl)c(-n2cc(-c3cccc(Cl)c3)c3cccnc32)cc1F]

1H NMR (500 MHz, MeOD) δ: 8.38-8.36 (d, 1H), 8.30-8.29 (d, 1H), 8.05-8.04 (d, 1H), 7.90 (s, 1H), 7.74 (s, 1H), 7.69-7.67 (d, 1H), 7.50-7.44 (m, 2H), 7.34-7.31 (m, 2H), 3.18 (s, 3H)

Example 222) Preparation of 5-chloro-4-(3-(3-chloro-2-fluorophenyl)-1H-pyrrolo[2,3-b]pyridin-1-yl)-2-fluoro-N-(methylsulfonyl)benzamide

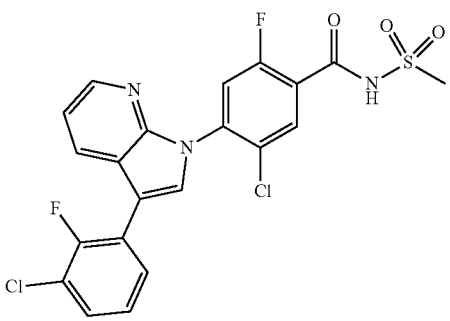 [SMILES: CS(=O)(=O)NC(=O)c1cc(Cl)c(-n2cc(-c3cccc(Cl)c3F)c3cccnc32)cc1F]

1H NMR (500 MHz, MeOD) δ: 8.32-8.31 (d, 1H), 8.24-8.22 (d, 1H), 8.05-8.04 (d, 1H), 7.89 (s, 1H), 7.71-7.68 (t, 1H), 7.57-7.55 (d, 1H), 7.48-7.45 (t, 1H), 7.34-7.27 (m, 2H), 3.24 (s, 3H)

Example 223) Preparation of 5-chloro-4-(3-(4-chloro-3-fluorophenyl)-1H-pyrrolo[2,3-b]pyridin-1-yl)-2-fluoro-N-(methylsulfonyl)benzamide

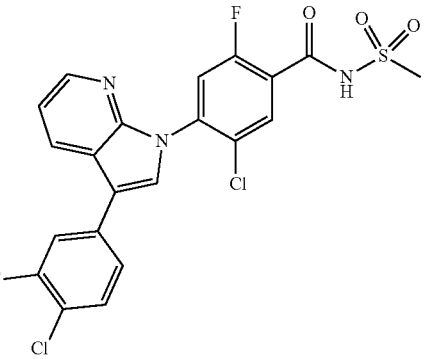

1H NMR (500 MHz, MeOD) δ: 8.41-8.40 (d, 1H), 8.31-8.30 (d, 1H), 8.05-8.03 (d, 1H), 7.95 (s, 1H), 7.65-7.62 (d, 1H), 7.59-7.52 (m, 3H), 7.35-7.33 (m, 1H), 3.22 (s, 3H)

Example 224) Preparation of 5-chloro-4-(3-(4-chlorophenyl)-1H-pyrrolo[2,3-b]pyridin-1-yl)-2-fluoro-N-(methylsulfonyl)benzamide

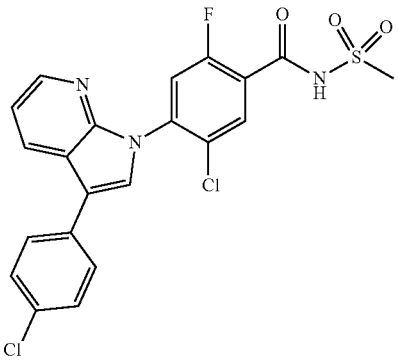 [SMILES: CS(=O)(=O)NC(=O)c1cc(Cl)c(-n2cc(-c3ccc(Cl)cc3)c3cccnc32)cc1F]

1H NMR (500 MHz, MeOD) δ: 8.29 (s, 1H), 8.04 (m, 2H), 7.77 (s, 1H), 7.57 (m, 3H), 7.40 (m, 2H), 7.28 (m, 1H), 3.19 (s, 3H)

Example 225) Preparation of 5-chloro-4-(3-(2-chlorophenyl)-1H-pyrrolo[2,3-b]pyridin-1-yl)-2-fluoro-N-(methylsulfonyl)benzamide

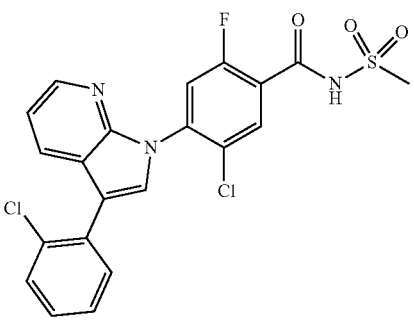 [SMILES: CS(=O)(=O)NC(=O)c1cc(Cl)c(-n2cc(-c3ccccc3Cl)c3cccnc32)cc1F]

1H NMR (500 MHz, MeOD) δ: 8.38 (m, 1H), 8.30 (d, 1H), 8.03 (d, 1H), 7.82 (s, 1H), 7.74 (m, 2H), 7.60 (d, 1H), 7.32 (m, 1H), 7.22 (m, 2H), 3.30 (s, 3H)

Example 226) Preparation of 5-chloro-2-fluoro-4-(3-(4-fluorophenyl)-1H-pyrrolo[2,3-b]pyridin-1-yl)-N-(methylsulfonyl)benzamide

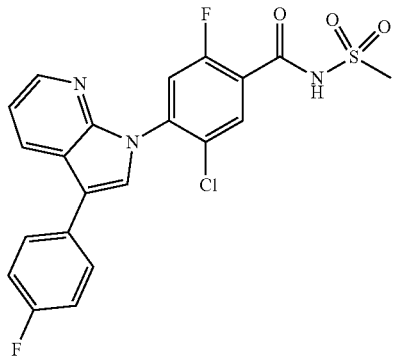 [SMILES: CS(=O)(=O)NC(=O)c1cc(Cl)c(-n2cc(-c3ccc(F)cc3)c3cccnc32)cc1F]

1H NMR (500 MHz, MeOD) δ: 8.31 (m, 1H), 8.25 (m, 1H), 8.03 (d, 1H), 7.88 (s, 1H), 7.75 (t, 1H), 7.61 (m, 1H), 7.35 (m, 3H), 3.27 (s, 3H)

Example 227) Preparation of 5-chloro-4-(3-(4-chloro-2-fluorophenyl)-1H-pyrrolo[2,3-b]pyridin-1-yl)-2-fluoro-N-(methylsulfonyl)benzamide

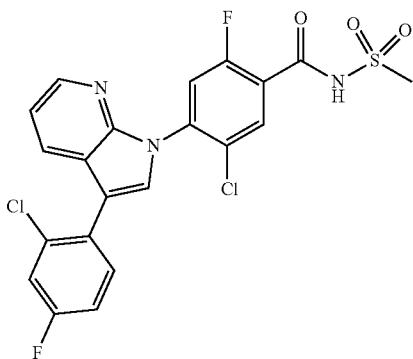 [SMILES: CS(=O)(=O)NC(=O)c1cc(Cl)c(-n2cc(-c3ccc(F)cc3Cl)c3cccnc32)cc1F]

1H NMR (500 MHz, MeOD) δ: 8.30 (m, 1H), 8.03 (m, 2H), 7.78 (s, 1H), 7.63 (m, 2H), 7.42 (m, 1H), 7.30 (dd, 1H), 7.22 (m, 1H), 3.27 (s, 3H)

Example 228) Preparation of 5-chloro-4-(3-(2-chloro-4-fluorophenyl)-1H-pyrrolo[2,3-b]pyridin-1-yl)-2-fluoro-N-(methylsulfonyl)benzamide

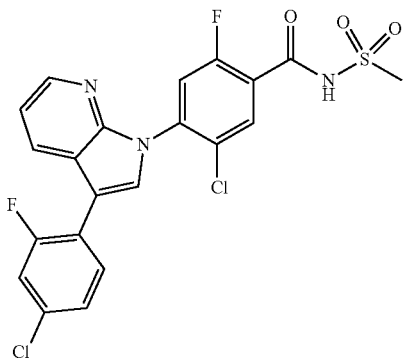 [SMILES: CS(=O)(=O)NC(=O)c1cc(Cl)c(-n2cc(-c3ccc(Cl)cc3F)c3cccnc32)cc1F]

1H NMR (500 MHz, MeOD) δ: 8.32 (d, 1H), 7.22 (d, 1H), 8.03 (d, 1H), 7.84 (s, 1H), 7.77 (m, 1H), 7.63 (d, 1H), 7.32 (m, 1H), 7.12 (m, 2H), 3.34 (s, 3H)

Example 229) Preparation of 5-chloro-4-(3-(2,4-difluorophenyl)-1H-pyrrolo[2,3-b]pyridin-1-yl)-2-fluoro-N-(methylsulfonyl)benzamide

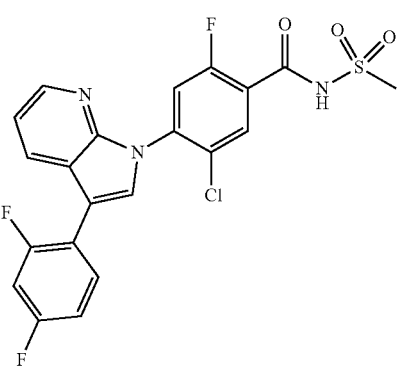

1H NMR (500 MHz, MeOD) δ: 8.04 (d, 1H), 7.94 (s, 1H), 7.84 (d, 1H), 7.69 (d, 2H), 7.50-7.43 (m, 4H), 7.38 (t, 1H), 3.21 (s, 3H)

Example 230) Preparation of 5-chloro-4-(3-chloro-5-phenyl-1H-indazol-1-yl)-2-fluoro-N-(methylsulfonyl)benzamide

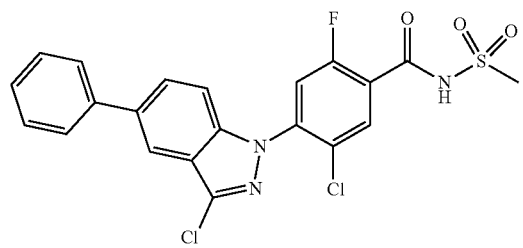 [SMILES: CS(=O)(=O)NC(=O)c1cc(Cl)c(-n2nc(Cl)c3cc(-c4ccccc4)ccc32)cc1F]

1H NMR (500 MHz, MeOD) δ: 8.89 (s, 1H), 8.22 (d, 1H), 8.18 (d, 1H), 8.04 (sd, 2H), 7.86 (d, 1H), 7.55 (m, 1H), 7.48 (m, 2H), 3.19 (s, 3H)

Example 231) Preparation of 5-chloro-4-(3-chloro-5-(pyridin-3-yl)-1H-indazol-1-yl)-2-fluoro-N-(methylsulfonyl)benzamide

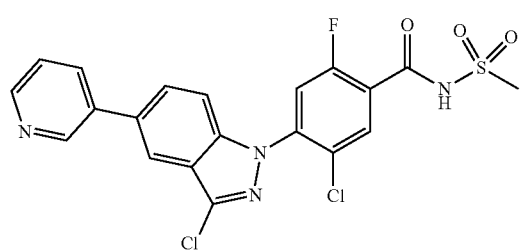 [SMILES: CS(=O)(=O)NC(=O)c1cc(Cl)c(-n2nc(Cl)c3cc(-c4cccnc4)ccc32)cc1F]

1H NMR (500 MHz, MeOD) δ: 8.63 (d, 2H), 8.19 (s, 1H), 8.04 (d, 1H), 7.97 (d, 1H), 7.84 (d, 2H), 7.51 (d, 1H), 3.20 (s, 3H)

Example 232) Preparation of 5-chloro-4-(3-chloro-5-(pyridin-4-yl)-1H-indazol-1-yl)-2-fluoro-N-(methylsulfonyl)benzamide

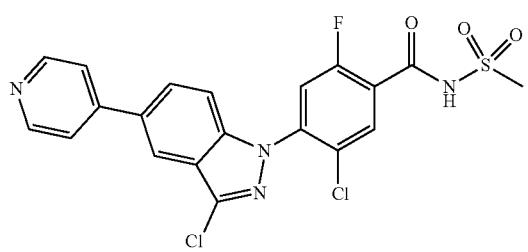 [SMILES: CS(=O)(=O)NC(=O)c1cc(Cl)c(-n2nc(Cl)c3cc(-c4ccncc4)ccc32)cc1F]

1H NMR (500 MHz, MeOD) δ: 8.04 (d, 1H), 7.91 (s, 1H), 7.83 (d, 1H), 7.50-7.46 (m, 3H), 7.41 (d, 1H), 7.35 (t, 1H), 7.19 (d, 1H), 3.18 (s, 3H), 2.43 (s, 3H)

Example 233) Preparation of 5-chloro-4-(3-chloro-5-(m-tolyl)-1H-indazol-1-yl)-2-fluoro-N-(methylsulfonyl)benzamide

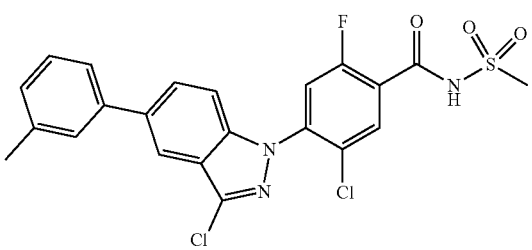

1H NMR (500 MHz, MeOD) δ: 8.06-8.04 (d, 1H), 7.91 (s, 1H), 7.77-7.75 (d, 1H), 7.59-7.56 (m, 2H), 7.46-7.45 (d, 1H), 7.42-7.40 (m, 1H), 7.32-7.29 (t, 1H), 7.26-7.22 (m, 1H), 3.30 (s, 3H)

Example 235) Preparation of 5-chloro-4-(3-chloro-5-(3-fluorophenyl)-1H-indazol-1-yl)-2-fluoro-N-(methylsulfonyl)benzamide

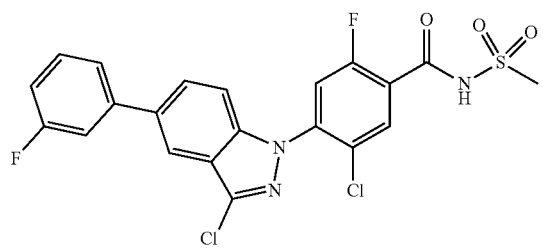 [SMILES: CS(=O)(=O)NC(=O)c1cc(Cl)c(-n2nc(Cl)c3cc(-c4cccc(F)c4)ccc32)cc1F]

1H NMR (500 MHz, MeOD) δ: 8.06-8.05 (d, 1H), 8.00 (s, 1H), 7.88-7.86 (d, 1H), 7.59-7.46 (m, 5H), 7.13-7.10 (t, 1H), 3.30 (s, 3H)

Example 236) Preparation of 5-chloro-4-(3-chloro-5-(4-fluorophenyl)-1H-indazol-1-yl)-2-fluoro-N-(methylsulfonyl)benzamide

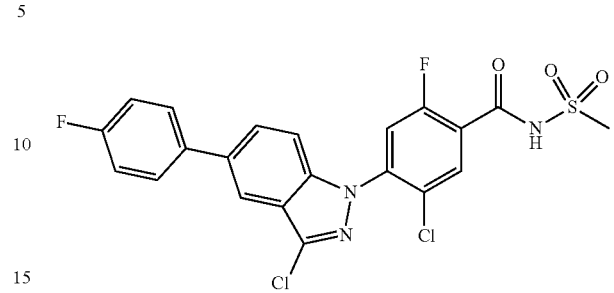

1H NMR (500 MHz, DMSO) δ: 8.12 (d, 1H), 8.01 (s, 1H), 7.91 (m, 2H), 7.82 (m, 2H), 7.51 (d, 1H), 7.32 (t, 2H), 3.36 (s, 3H)

Example 237) Preparation of 5-chloro-4-(3-chloro-5-(2-cyanophenyl)-1H-indazol-1-yl)-2-fluoro-N-(methylsulfonyl)benzamide

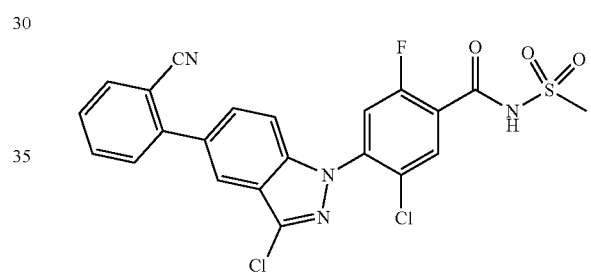

1H NMR (500 MHz, MeOD) δ: 8.02 (d, 1H), 7.84 (s, 1H), 7.65 (d, 1H), 7.56 (m, 2H), 7.51-7.43 (m, 3H), 7.39 (d, 1H), 3.15 (s, 3H)

Example 238) Preparation of 5-chloro-4-(3-chloro-5-(5-cyano-2-fluorophenyl)-1H-indazol-1-yl)-2-fluoro-N-(methylsulfonyl)benzamide

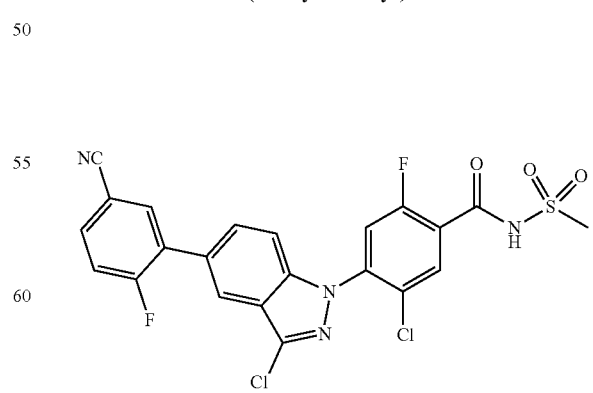

1H NMR (500 MHz, MeOD) δ: 8.03 (t, 2H), 7.97 (s, 1H), 7.81 (s, 1H), 7.75 (d, 1H), 7.46 (m, 3H), 3.14 (s, 3H)

Example 239) Preparation of 5-chloro-4-(3-chloro-5-(3-cyano-4-fluorophenyl)-1H-indazol-1-yl)-2-fluoro-N-(methylsulfonyl)benzamide

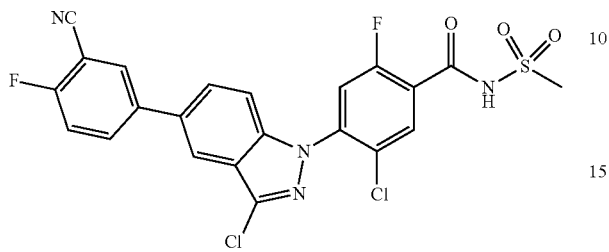

1H NMR (500 MHz, MeOD) δ: 8.11 (s, 1H), 8.02 (m, 2H), 8.00 (s, 1H), 7.82 (d, 1H), 7.47 (t, 3H), 3.18 (s, 3H)

Example 240) Preparation of 5-chloro-4-(3-chloro-5-(4-cyanophenyl)-1H-indazol-1-yl)-2-fluoro-N-(methylsulfonyl)benzamide

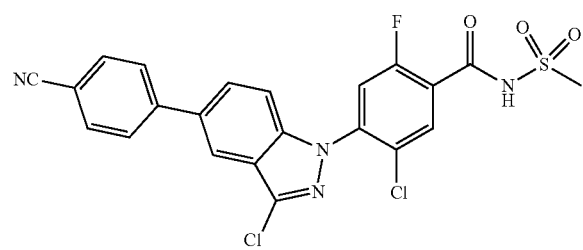 [SMILES: CS(=O)(=O)NC(=O)c1cc(Cl)c(-n2nc(Cl)c3cc(-c4ccc(C#N)cc4)ccc32)cc1F]

1H NMR (500 MHz, MeOD) δ: 8.04 (m, 2H), 7.90 (m, 3H), 7.83 (d, 2H), 7.47 (d, 2H), 3.17 (s, 3H)

Example 241) Preparation of 5-chloro-4-(3-chloro-5-(pyrimidin-5-yl)-1H-indazol-1-yl)-2-fluoro-N-(methylsulfonyl)benzamide

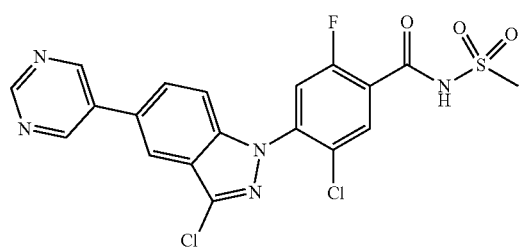 [SMILES: CS(=O)(=O)NC(=O)c1cc(Cl)c(-n2nc(Cl)c3cc(-c4cncnc4)ccc32)cc1F]

1H NMR (500 MHz, MeOD) δ: 9.17 (m, 3H), 8.17 (s, 1H), 8.04 (d, 1H), 7.66 (d, 1H), 7.54 (d, 1H), 7.50 (d, 1H), 3.17 (s, 3H)

Example 242) Preparation of 5-chloro-4-(3-chloro-5-(5-chloropyridin-3-yl)-1H-indazol-1-yl)-2-fluoro-N-(methylsulfonyl)benzamide 1H NMR (500 MHz, MeOD) δ: 8.86 (s, 1H), 8.57 (s, 1H), 8.27 (s, 1H), 8.11 (s, 1H), 8.04 (d, 1H), 7.90 (d, 1H), 7.52 (d, 2H), 3.20 (s, 3H)

Example 243) Preparation of 5-chloro-4-(3-chloro-5-(2,4-difluorophenyl)-1H-indazol-1-yl)-2-fluoro-N-(methylsulfonyl)benzamide 1H NMR (500 MHz, MeOD) δ: 8.19 (m, 1H), 8.16 (m, 1H), 8.05 (m, 1H), 8.01 (s, 1H), 7.81 (m, 1H), 7.54 (m, 1H), 7.48 (m, 2H), 3.23 (s, 3H)

Example 244) Preparation of 5-chloro-4-(3-chloro-5-(2-fluoropyridin-3-yl)-1H-indazol-1-yl)-2-fluoro-N-(methylsulfonyl)benzamide

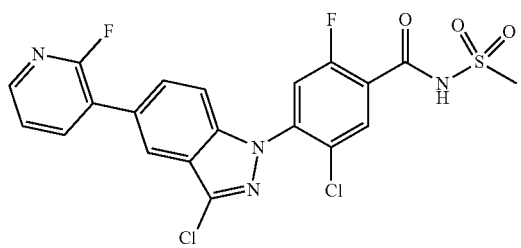 [SMILES: CS(=O)(=O)NC(=O)c1cc(Cl)c(-n2nc(Cl)c3cc(-c4cccnc4F)ccc32)cc1F]

1H NMR (500 MHz, MeOD) δ: 8.22 (m, 1H), 8.17 (t, 1H), 8.05 (d, 1H), 8.01 (s, 1H), 7.81 (m, 1H), 7.54 (d, 1H), 7.48 (m, 2H), 3.31 (s, 3H)

Example 245) Preparation of 5-chloro-4-(3-chloro-5-(6-fluoropyridin-3-yl)-1H-indazol-1-yl)-2-fluoro-N-(methylsulfonyl)benzamide

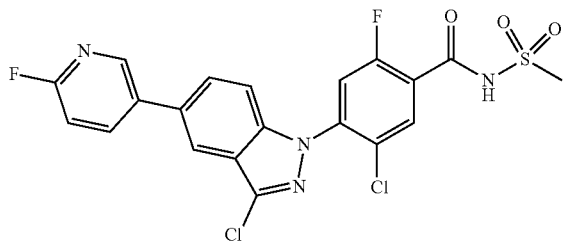 [SMILES: CS(=O)(=O)NC(=O)c1cc(Cl)c(-n2nc(Cl)c3cc(-c4ccc(F)nc4)ccc32)cc1F]

1H NMR (500 MHz, MeOD) δ: 8.55 (s, 1H), 8.30 (m, 1H), 8.05 (m, 2H), 7.86 (m, 1H), 7.56 (d, 1H), 7.50 (d, 1H), 7.50 (dd, 1H), 3.30 (s, 3H)

Example 246) Preparation of 5-chloro-4-(3-chloro-5-(2,6-difluoropyridin-3-yl)-1H-indazol-1-yl)-2-fluoro-N-(methylsulfonyl)benzamide

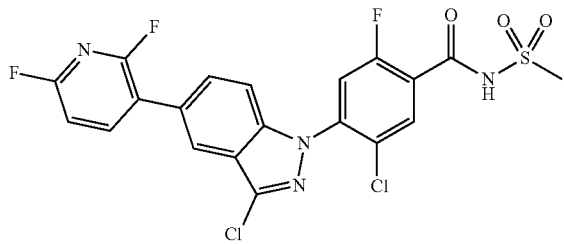 [SMILES: CS(=O)(=O)NC(=O)c1cc(Cl)c(-n2nc(Cl)c3cc(-c4ccc(F)nc4F)ccc32)cc1F]

1H NMR (500 MHz, MeOD) δ: 8.28 9 m, 1H), 8.05 (m, 1H), 7.97 (m 1H), 7.77 (m, 1H), 7.56 (m, 1H), 7.49 (m, 1H), 7.13 (m, 1H), 3.30 (s, 3H)

Example 247) Preparation of 5-chloro-4-(3-chloro-5-(4-chloro-2-fluorophenyl)-1H-indazol-1-yl)-2-fluoro-N-(methylsulfonyl)benzamide

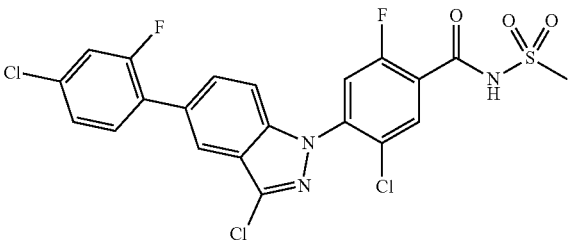

1H NMR (500 MHz, MeOD) δ: 8.04 (d, 1H), 7.91 (s, 1H), 7.74 (m, 1H), 7.59 (t, 1H), 7.51 (m, 1H), 7.46 (m, 1H), 7.35 (m, 2H), 3.20 (s, 3H)

Example 248) Preparation of 5-chloro-4-(3-chloro-5-(4-methoxyphenyl)-1H-indazol-1-yl)-2-fluoro-N-(methylsulfonyl)benzamide

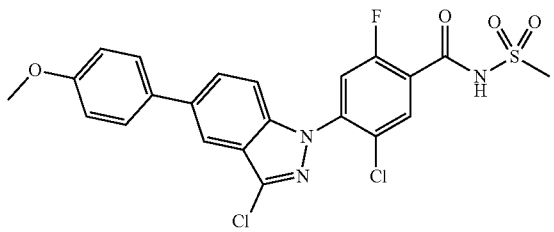

1H NMR (500 MHz, MeOD) δ: 8.04 (d, 1H), 7.87 (s, 1H), 7.79 (d, 1H), 7.61 (d, 2H), 7.48 (d, 1H), 7.38 (d, 1H), 7.02 (d, 2H), 3.84 (s, 3H), 3.21 (s, 3H)

Example 249) Preparation of 5-chloro-4-(3-chloro-5-(3-(trifluoromethyl)phenyl)-1H-indazol-1-yl)-2-fluoro-N-(methylsulfonyl)benzamide

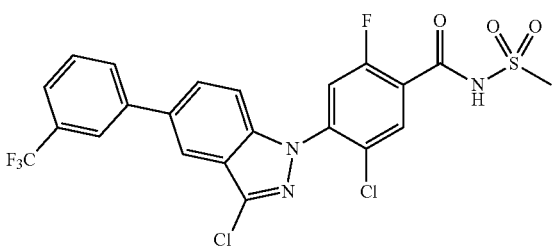 [SMILES: CS(=O)(=O)NC(=O)c1cc(Cl)c(-n2nc(Cl)c3cc(-c4cccc(C(F)(F)F)c4)ccc32)cc1F]

1H NMR (500 MHz, MeOD) δ: 8.04 (d, 1H), 8.01 (s, 1H), 7.96 (s, 2H), 7.87 (d, 1H), 7.69 (s, 2H), 7.51 (d, 1H), 7.47 (d, 1H), 3.22 (s, 3H)

Example 250) Preparation of 5-chloro-4-(3-chloro-5-(2-(trifluoromethyl)phenyl)-1H-indazol-1-yl)-2-fluoro-N-(methylsulfonyl)benzamide

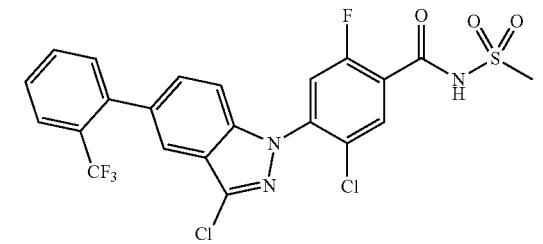

1H NMR (500 MHz, MeOD) δ: 8.05 (d, 1H), 7.81 (d, 1H), 7.67 (s, 2H), 7.59 (t, 1H), 7.55-7.50 (m, 3H), 7.44 (d, 1H), 7.40 (d, 1H), 3.24 (s, 3H)

Example 251) Preparation of 5-chloro-4-(3-chloro-5-(4-(trifluoromethyl)phenyl)-1H-indazol-1-yl)-2-fluoro-N-(methylsulfonyl)benzamide

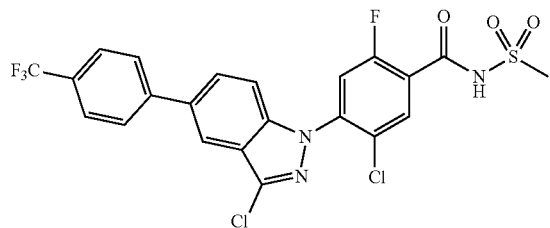 [SMILES: CS(=O)(=O)NC(=O)c1cc(Cl)c(-n2nc(Cl)c3cc(-c4ccc(C(F)(F)F)cc4)ccc32)cc1F]

1H NMR (500 MHz, MeOD) δ: 8.05 (s, 2H), 7.90 (d, 3H), 7.78 (d, 2H), 7.52 (d, 1H), 7.47 (d, 1H), 3.24 (s, 3H)

Example 252) Preparation of 5-chloro-4-(3-chloro-5-(2-chlorophenyl)-1H-indazol-1-yl)-2-fluoro-N-(methylsulfonyl)benzamide

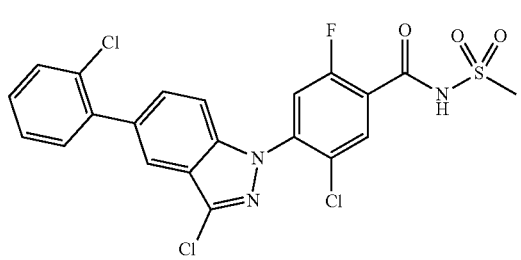 [SMILES: CS(=O)(=O)NC(=O)c1cc(Cl)c(-n2nc(Cl)c3cc(-c4ccccc4Cl)ccc32)cc1F]

1H NMR (500 MHz, MeOD) δ: 8.04 (d, 1H), 7.77 (s, 1H), 7.63 (d, 1H), 7.61-7.49 (m, 2H), 7.47-7.38 (m, 4H), 3.20 (s, 3H)

Example 253) Preparation of 5-chloro-4-(3-chloro-5-(4-chloro-2-methylphenyl)-1H-indazol-1-yl)-2-fluoro-N-(methylsulfonyl)benzamide

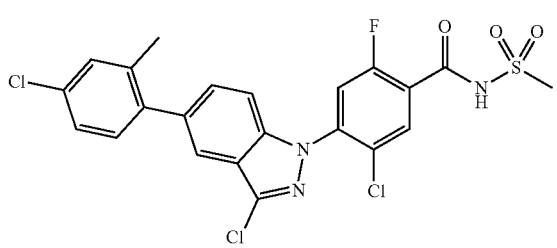 [SMILES: Cc1cc(Cl)ccc1-c1ccc2c(c1)c(Cl)nn2-c1cc(F)c(C(=O)NS(C)(=O)=O)cc1Cl]

1H NMR (500 MHz, MeOD) δ: 8.05 (d, 1H), 7.66 (s, 1H), 7.51 (t, 2H), 7.42 (d, 1H), 7.34 (s, 1H), 7.26 (s, 2H), 3.19 (s, 3H), 2.26 (s, 3H)

Example 254) Preparation of 5-chloro-4-(3-chloro-5-(5-chloro-2-fluorophenyl)-1H-indazol-1-yl)-2-fluoro-N-(methylsulfonyl)benzamide

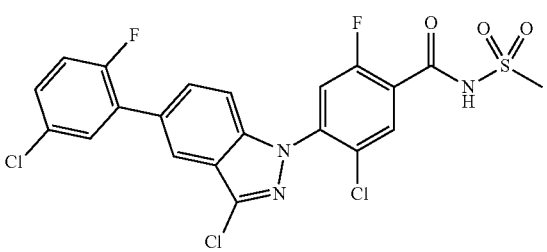 [SMILES: CS(=O)(=O)NC(=O)c1cc(Cl)c(-n2nc(Cl)c3cc(-c4cc(Cl)ccc4F)ccc32)cc1F]

1H NMR (500 MHz, MeOD) δ: 8.04 (d, 1H), 7.92 (s, 1H), 7.73 (d, 1H), 7.59 (dd, 1H), 7.50 (d, 1H), 7.45 (d, 1H), 7.40 (d, 1H), 7.25 (t, 1H), 3.20) s, 3H)

Example 255) Preparation of 5-chloro-4-(3-chloro-5-(4-chlorophenyl)-1H-indazol-1-yl)-2-fluoro-N-(methylsulfonyl)benzamide

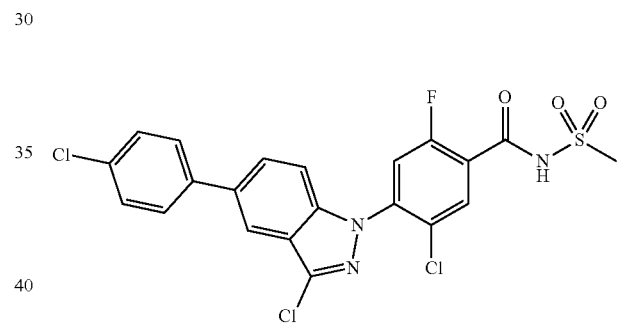

1H NMR (500 MHz, MeOD) δ: 8.04 (d, 1H), 7.97 (s, 2H), 7.84 (d, 1H), 7.70 (d, 2H), 7.54 (d, 1H), 7.46 (m, 3H), 3.26 (s, 3H)

Example 256) Preparation of 5-chloro-4-(3-chloro-5-(1-methyl-1H-pyrazol-5-yl)-1H-indazol-1-yl)-2-fluoro-N-(methylsulfonyl)benzamide

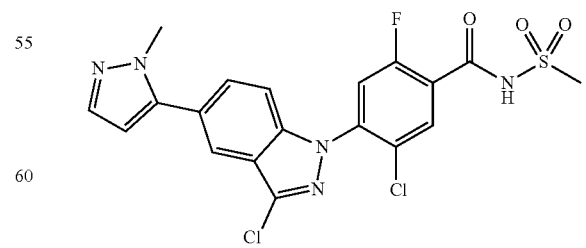

1H NMR (500 MHz, MeOD) δ: 8.05-8.04 (d, 1H), 7.88 (s, 1H), 7.68-7.66 (d, 1H), 7.53 (s, 1H), 7.48-7.46 (d, 2H), 6.45 (s, 1H), 3.91 (s, 3H), 3.14 (s, 3H)

Example 258) Preparation of 5-chloro-4-(3-chloro-5-(4-cyanophenyl)-1H-pyrrolo[2,3-b]pyridin-1-yl)-2-fluoro-N-(methylsulfonyl)benzamide

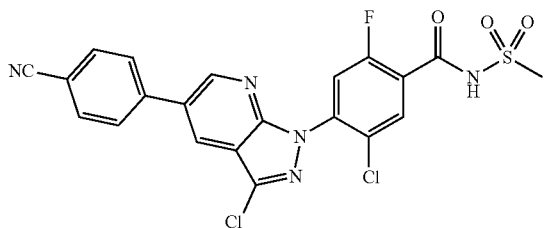 [SMILES: CS(=O)(=O)NC(=O)c1cc(Cl)c(-n2nc(Cl)c3cc(-c4ccc(C#N)cc4)cnc32)cc1F]

1H NMR (500 MHz, MeOD) δ: 8.63 (d, 1H), 8.35 (d, 1H), 8.02 (d, 1H), 7.93 (d, 2H), 7.89 (d, 2H), 7.54 (d, 1H), 3.22 (s, 3H)

Example 259) Preparation of 5-chloro-4-(3-chloro-5-(4-chlorophenyl)-1H-pyrrolo[2,3-b]pyridin-1-yl)-2-fluoro-N-(methylsulfonyl)benzamide

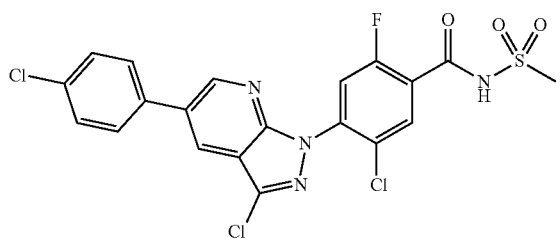 [SMILES: CS(=O)(=O)NC(=O)c1cc(Cl)c(-n2nc(Cl)c3cc(-c4ccc(Cl)cc4)cnc32)cc1F]

1H NMR (500 MHz, MeOD) δ: 8.56 (m, 1H), 8.26 (m, 1H), 8.02 (m, 1H), 7.75 (s, 1H), 7.70 (d, 2H), 7.58 (d, 1H), 7.50 (d, 2H), 3.25 (s, 3H)

Example 260) Preparation of 5-chloro-4-(3-chloro-5-(4-methoxyphenyl)-1H-pyrrolo[2,3-b]pyridin-1-yl)-2-fluoro-N-(methylsulfonyl)benzamide

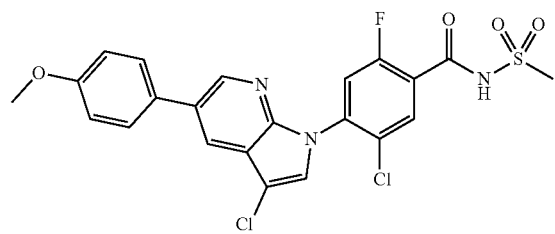

1H NMR (500 MHz, MeOD) δ: 8.51 (m, 1H), 8.17 (m, 1H), 8.03 (d, 1H), 7.69 (s, 1H), 7.62 (d, 2H), 7.48 (d, 1H), 7.06 (d, 2H), 4.86 (s, 3H), 3.16 (d, 3H)

Example 261) Preparation of 5-chloro-4-(3-chloro-5-(4-(trifluoromethyl)phenyl)-1H-pyrrolo[2,3-b]pyridin-1-yl)-2-fluoro-N-(methylsulfonyl)benzamide

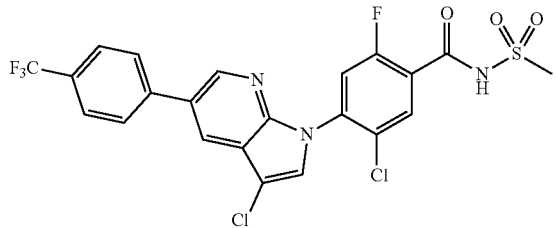 [SMILES: CS(=O)(=O)NC(=O)c1cc(Cl)c(-n2cc(Cl)c3cc(-c4ccc(C(F)(F)F)cc4)cnc32)cc1F]

1H NMR (500 MHz, MeOD) δ: 8.63 (m, 1H), 8.34 (m, 1H), 8.03 (d, 1H), 7.93 (d, 2H), 7.80 (d, 2H). 7.67 (s, 1H), 7.53 (m, 1H), 3.21 (s, 3H)

Example 262) Preparation of 5-chloro-4-(3-chloro-5-(3-fluorophenyl)-1H-pyrrolo[2,3-b]pyridin-1-yl)-2-fluoro-N-(methylsulfonyl)benzamide

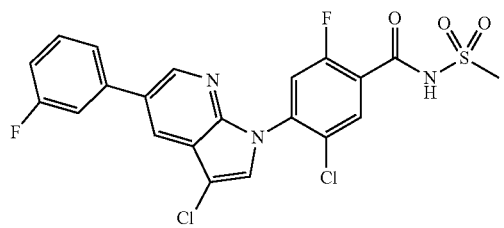 [SMILES: CS(=O)(=O)NC(=O)c1cc(Cl)c(-n2cc(Cl)c3cc(-c4cccc(F)c4)cnc32)cc1F]

1H NMR (500 MHz, MeOD) δ: 8.30 (s, 1H), 8.18 (s, 1H), 8.03 (d, 1H), 7.92 (s, 1H), 7.72 (m, 1H), 7.58 (d, 1H), 7.39 (m, 1H), 7.30 (m, 2H), 2015 (s, 3H)

Example 263) Preparation of 5-chloro-4-(3-chloro-6-phenyl-1H-indazol-1-yl)-2-fluoro-N-(methylsulfonyl)benzamide

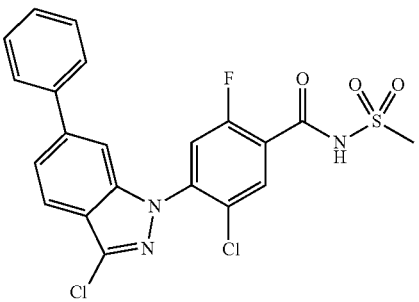 [SMILES: CS(=O)(=O)NC(=O)c1cc(Cl)c(-n2nc(Cl)c3ccc(-c4ccccc4)cc32)cc1F]

1H NMR (500 MHz, CDCl₃) δ: 8.29 (d, 1H), 7.77 (d, 1H), 7.54 (d, 3H), 7.43-7.26 (m, 5H), 3.38 (s, 3H)

Example 264) Preparation of 5-chloro-4-(3,5-diphenyl-1H-indazol-1-yl)-2-fluoro-N-(methylsulfonyl)benzamide

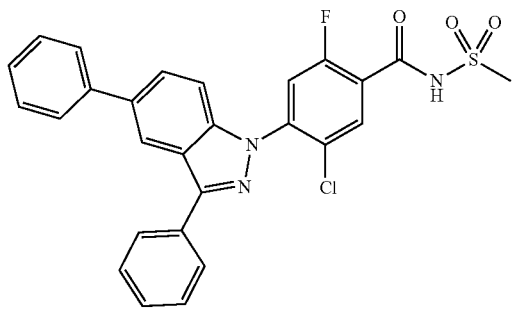 [SMILES: CS(=O)(=O)NC(=O)c1cc(Cl)c(-n2nc(-c3ccccc3)c3cc(-c4ccccc4)ccc32)cc1F]

1H NMR (500 MHz, MeOD) δ: 8.13 (s, 1H), 8.06 (d, 1H), 7.97 (d, 2H), 7.67 (d, 1H), 7.59 (d, 2H), 7.50 (t, 2H), 7.43-7.38 (m, 4H), 7.31 (d, 2H) 3.18 (s, 3H)

Example 265) Preparation of 5-chloro-1-(2-chloro-5-fluoro-4-((methylsulfonyl)carbamoyl)phenyl)-1H-indole-3-carboxylic acid

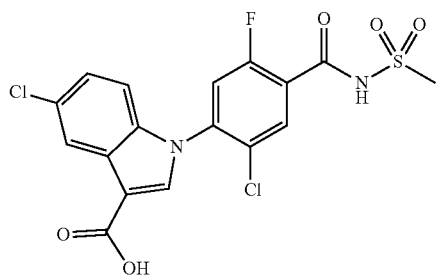 [SMILES: CS(=O)(=O)NC(=O)c1cc(Cl)c(-n2cc(C(=O)O)c3cc(Cl)ccc32)cc1F]

1H NMR (500 MHz, DMSO) δ: 8.00 (m, 1H), 7.95 (s, 1H), 7.72 (m, 1H), 7.62 (m, 1H), 7.30 (m, 1H), 7.18 (m, 1H), 3.14 (s, 3H)

Example 266) Preparation of 5-chloro-4-(3,5-dichloro-1H-indol-1-yl)-2-fluoro-N-(methylsulfonyl)benzamide

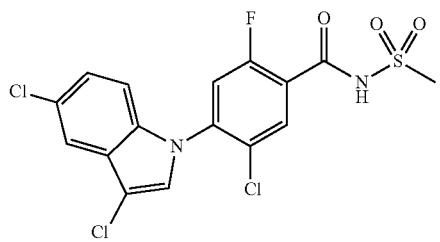 [SMILES: CS(=O)(=O)NC(=O)c1cc(Cl)c(-n2cc(Cl)c3cc(Cl)ccc32)cc1F]

1H NMR (500 MHz, DMSO) δ: 8.00 (m, 1H), 7.95 (s, 1H), 7.87 (d, 1H), 7.62 (m, 1H), 7.30 (m, 1H), 7.08 (s, 1H), 3.14 (s, 3H)

Example 267) Preparation of 5-chloro-4-(3,4-dichloro-5-hydroxy-1H-indol-1-yl)-2-fluoro-N-(methylsulfonyl)benzamide

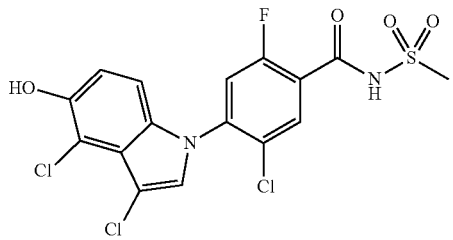 [SMILES: CS(=O)(=O)NC(=O)c1cc(Cl)c(-n2cc(Cl)c3c(Cl)c(O)ccc32)cc1F]

1H NMR (500 MHz, MeOD) δ: 7.87 (d, 1H), 7.08 (s, 1H), 6.97 (m, 2H), 6.59 (d, 1H), 3.27 (s, 3H)

Example 268) Preparation of 5-chloro-4-(3-chloro-5-methoxy-1H-indol-1-yl)-2-fluoro-N-(methylsulfonyl)benzamide

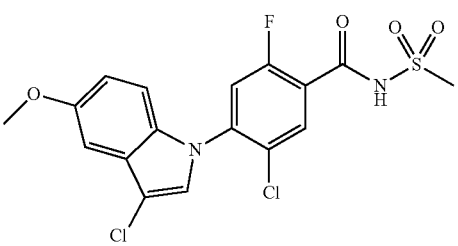

1H NMR (500 MHz, MeOD) δ: 8.05-8.04 (d, 1H), 7.40-7.39 (d, 1H), 7.38 (s, 1H), 7.05-7.04 (m, 2H), 6.89-6.87 (m 1H), 3.85 (s, 3H), 3.22 (s, 3H)

Example 269) Preparation of 4-(5-(benzyloxy)-3-chloro-1H-indol-1-yl)-5-chloro-2-fluoro-N-(methylsulfonyl)benzamide

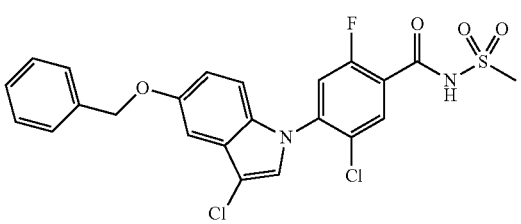 [SMILES: CS(=O)(=O)NC(=O)c1cc(Cl)c(-n2cc(Cl)c3cc(OCc4ccccc4)ccc32)cc1F]

1H NMR (500 MHz, MeOD) δ: 8.02 (d, 1H), 7.44 (m, 4H), 7.37 (m, 2H), 7.30 (m, 1H), 7.14 (m, 1H), 7.08 (m, 1H), 6.98 (m, 1H), 5.13 (s, 2H), 3.27 (s, 3H)

Example 270) Preparation of 4-(4-(benzyloxy)-3-chloro-1H-indol-1-yl)-5-chloro-2-fluoro-N-(methylsulfonyl)benzamide

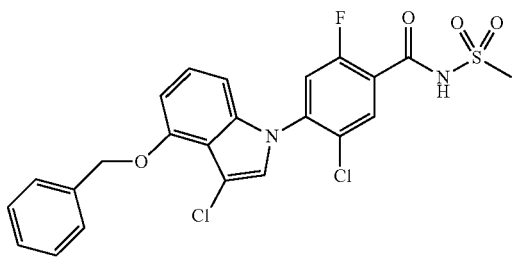 [SMILES: CS(=O)(=O)NC(=O)c1cc(Cl)c(-n2cc(Cl)c3c(OCc4ccccc4)cccc32)cc1F]

1H NMR (500 MHz, MeOD) δ: 8.00-7.99 (d, 1H), 7.58-7.57 (d, 2H), 7.44-7.42 (d, 1H), 7.39-7.36 (m, 2H), 7.31-7.30 (m, 2H), 7.15-7.12 (t, 1H), 6.76-7.72 (m, 2H), 5.23 (s, 2H), 3.30 (s, 3H)

Example 271) Preparation of 4-(6-(benzyloxy)-3-chloro-1H-indol-1-yl)-5-chloro-2-fluoro-N-(methylsulfonyl)benzamide

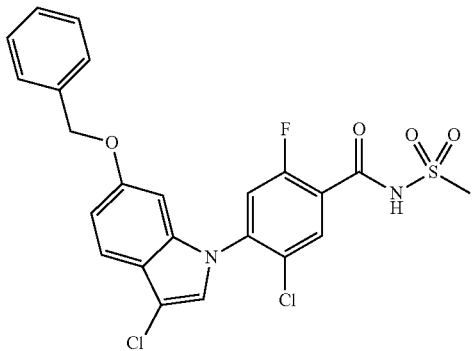 [SMILES: CS(=O)(=O)NC(=O)c1cc(Cl)c(-n2cc(Cl)c3ccc(OCc4ccccc4)cc32)cc1F]

1H NMR (500 MHz, MeOD) δ: 8.00-7.99 (d, 1H), 7.49-7.47 (d, 1H), 7.40-7.28 (m, 7H), 6.98-6.96 (m, 1H), 6.70 (s, 1H), 5.03 (s, 2H), 3.30 (s, 3H)

Example 272) Preparation of 5-chloro-4-(5-chloro-3-(4-chlorophenyl)-1H-indol-1-yl)-2-fluoro-N-(methylsulfonyl)benzamide

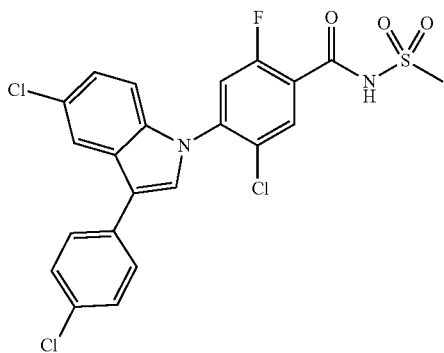 [SMILES: CS(=O)(=O)NC(=O)c1cc(Cl)c(-n2cc(-c3ccc(Cl)cc3)c3cc(Cl)ccc32)cc1F]

1H NMR (500 MHz, MeOD) δ: 8.04-8.03 (d, 1H), 7.85 (s, 1H), 7.69-7.66 (m, 3H), 7.50-7.46 (m, 3H), 7.25-7.23 (d, 1H), 7.19-7.17 (d, 1H), 3.26 (s, 3H)

Example 273) Preparation of 5-chloro-4-(5-chloro-3-(6-chloropyridin-3-yl)-1H-indol-1-yl)-2-fluoro-N-(methylsulfonyl)benzamide

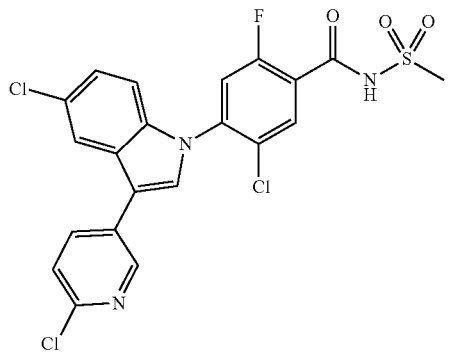 [SMILES: CS(=O)(=O)NC(=O)c1cc(Cl)c(-n2cc(-c3ccc(Cl)nc3)c3cc(Cl)ccc32)cc1F]

1H NMR (500 MHz, MeOD) δ: 8.04-8.03 (d, 1H), 7.71-7.68 (m, 3H), 7.51-7.49 (d, 1H), 7.37-7.32 (m, 2H), 7.26 (d, 1H), 7.24-7.18 (d, 1H), 3.27 (s, 3H)

Example 275) Preparation of 6-(5-chloro-3-(4-fluorophenyl)-1H-indol-1-yl)-N-(methylsulfonyl)nicotinamide

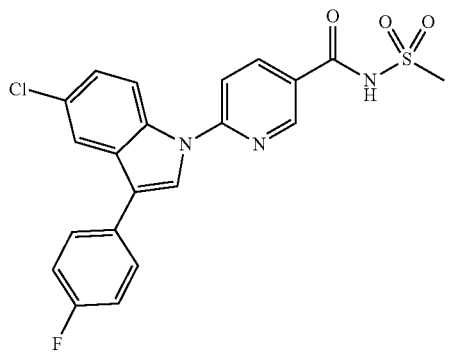 [SMILES: CS(=O)(=O)NC(=O)c1ccc(-n2cc(-c3ccc(F)cc3)c3cc(Cl)ccc32)nc1]

1H NMR (500 MHz, MeOD) δ: 9.13 (m, 1H), 8.54 (d, 1H), 8.48 (d, 1H), 8.15 (s, 1H), 7.79 (m, 1H), 7.73 (m, 3H), 7.32 (dd, 1H), 7.24 (t, 2H), 3.20 (s, 3H)

Example 276) Preparation of 5-chloro-4-(3-chloro-5-phenyl-1H-indazol-1-yl)-2-fluoro-N-(thiazol-4-yl)benzenesulfonamide

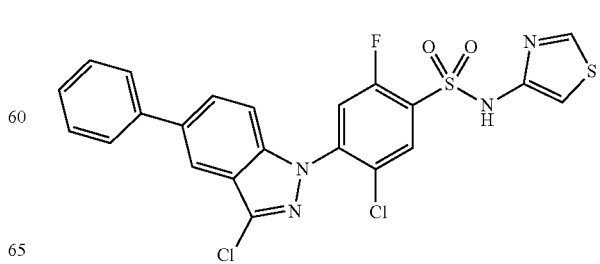

1H NMR (500 MHz, MeOD) δ: 8.78 (s, 1H), 8.19-8.18 (d, 1H), 7.95 (s, 1H), 7.86-7.85 (d, 1H), 7.69-7.68 (m, 3H), 7.49-7.44 (m, 3H), 7.39-7.37 (d, 1H), 7.16 (s, 1H)

Example 277) Preparation of 5-chloro-4-(5-chloro-3-methyl-1H-indazol-1-yl)-2-fluoro-N-(thiazol-4-yl)benzenesulfonamide

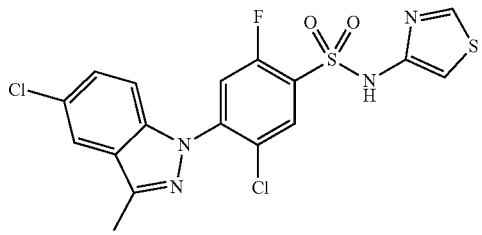 [SMILES: Cc1nn(-c2cc(F)c(S(=O)(=O)Nc3cscn3)cc2Cl)c2ccc(Cl)cc12]

1H NMR (500 MHz, MeOD) δ: 8.76 (d, 1H), 8.14-8.12 (d, 1H), 7.81 (s, 1H), 7.56-7.54 (d, 1H), 7.43-7.41 (d, 1H), 7.27-7.25 (d, 1H), 7.14 (d, 1H), 2.57 (s, 3H)

Example 278) Preparation of 4-(3-chloro-5-(trifluoromethyl)-1H-indazol-1-yl)-3-cyano-N-(thiazol-4-yl)benzenesulfonamide

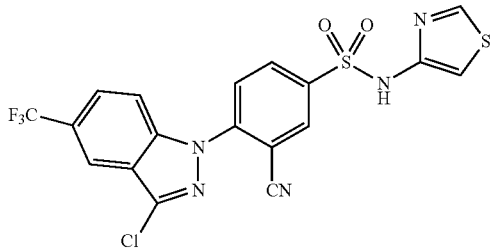 [SMILES: N#Cc1cc(S(=O)(=O)Nc2cscn2)ccc1-n1nc(Cl)c2cc(C(F)(F)F)ccc21]

1H NMR (500 MHz, MeOD) δ: 8.77 (d, 1H), 8.46 (d, 1H), 8.31-8.29 (dd, 1H), 8.18 (s, 1H), 8.00-7.98 (d, 1H), 7.86 (s, 2H), 7.21 (d, 1H)

Example 279) Preparation of 4-(3-chloro-5-(trifluoromethyl)-1H-indazol-1-yl)-2,5-difluoro-N-(thiazol-4-yl)benzenesulfonamide

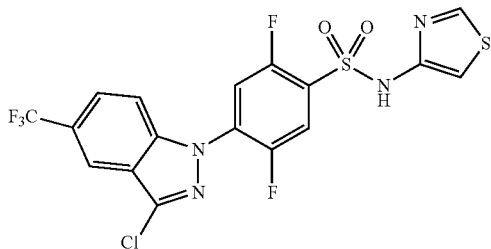 [SMILES: O=S(=O)(Nc1cscn1)c1cc(F)c(-n2nc(Cl)c3cc(C(F)(F)F)ccc32)cc1F]

1H NMR (500 MHz, MeOD) δ: 8.77-8.76 (d, 1H), 8.15 (s, 1H), 8.00-7.97 (m, 1H), 7.86-7.84 (d, 1H), 7.76-7.69 (m, 2H), 7.16 (d, 1H)

Example 280) Preparation of 5-chloro-4-(3-chloro-5-(trifluoromethyl)-1H-indazol-1-yl)-2-fluoro-N-(thiazol-4-yl)benzenesulfonamide

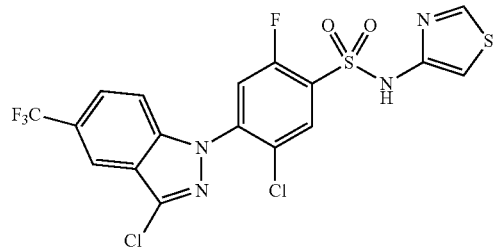 [SMILES: O=S(=O)(Nc1cscn1)c1cc(Cl)c(-n2nc(Cl)c3cc(C(F)(F)F)ccc32)cc1F]

1H NMR (500 MHz, MeOD) δ: 8.78 (d, 1H), 8.20-8.18 (d, 1H), 8.16 (s, 1H), 7.83-7.81 (d, 1H), 7.72-7.70 (d, 1H), 7.58-7.56 (d, 1H), 7.17 (d, 1H)

Example 281) Preparation of 4-(3-chloro-5-(trifluoromethyl)-1H-indazol-1-yl)-2,5-difluoro-N-(1,2,4-thiadiazol-5-yl)benzenesulfonamide

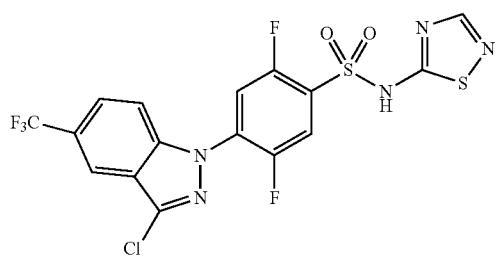 [SMILES: O=S(=O)(Nc1ncns1)c1cc(F)c(-n2nc(Cl)c3cc(C(F)(F)F)ccc32)cc1F]

1H NMR (500 MHz, MeOD) δ: 8.13 (s, 1H), 8.03 (s, 1H), 7.96-7.93 (m, 1H), 7.83-7.82 (d, 1H), 7.72-7.69 (m, 1H), 7.65-7.62 (m, 1H)

Example 282) Preparation of 5-chloro-4-(5-chloro-3-(1-methyl-1H-pyrazol-5-yl)-1H-indazol-1-yl)-2-fluoro-N-(thiazol-4-yl)benzenesulfonamide

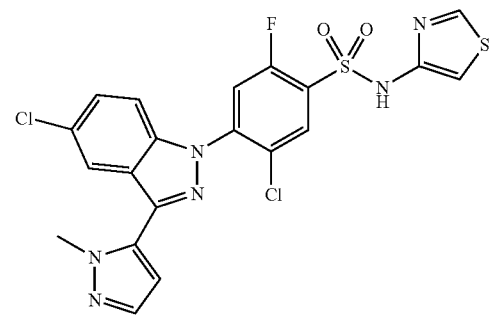 [SMILES: Cn1nccc1-c1nn(-c2cc(F)c(S(=O)(=O)Nc3cscn3)cc2Cl)c2ccc(Cl)cc12]

1H NMR (500 MHz, MeOD) δ: 8.77 (s, 1H), 8.21-8.20 (d, 1H), 8.02 (s, 1H), 7.76-7.74 (d, 1H), 7.65 (s, 1H), 7.56-7.54 (d, 1H), 7.47-7.45 (d, 1H), 7.12 (s, 1H), 6.98 (s, 1H)

Example 283) Preparation of 5-chloro-4-(5-chloro-3-(1-methyl-1H-pyrazol-5-yl)-1H-indazol-1-yl)-2-fluoro-N-(1,2,4-thiadiazol-5-yl)benzenesulfonamide

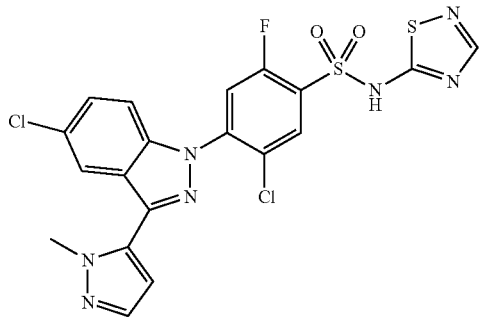 [SMILES: Cn1nccc1-c1nn(-c2cc(F)c(S(=O)(=O)Nc3ncns3)cc2Cl)c2ccc(Cl)cc12]

1H NMR (500 MHz, MeOD) δ: 8.08 (s, 1H), 8.00-7.94 (m, 2H), 7.74-7.71 (m, 1H), 7.64 (d, 1H), 7.60-7.54 (m, 2H), 6.97 (d, 1H)

Example 284) Preparation of 5-chloro-4-(5-chloro-3-(1H-pyrazol-4-yl)-1H-indazol-1-yl)-2-fluoro-N-(thiazol-4-yl)benzenesulfonamide

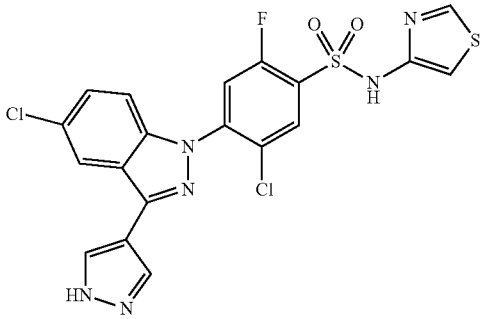 [SMILES: O=S(=O)(Nc1cscn1)c1cc(Cl)c(-n2nc(-c3cn[nH]c3)c3cc(Cl)ccc32)cc1F]

1H NMR (500 MHz, MeOD) δ: 8.78 (d, 1H), 8.27 (s, 1H), 8.18-8.17 (d, 1H), 8.10 (s, 1H), 7.68-7.66 (d, 1H), 7.49-7.48 (d, 1H), 7.35-7.33 (d, 1H), 7.16-7.15 (d, 1H)

Example 285) Preparation of 5-chloro-2-fluoro-4-(5-(1-methyl-1H-pyrazol-5-yl)-1H-indazol-1-yl)-N-(thiazol-4-yl)benzenesulfonamide

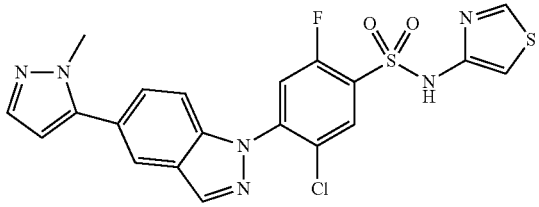 [SMILES: Cn1nccc1-c1ccc2c(cnn2-c2cc(F)c(S(=O)(=O)Nc3cscn3)cc2Cl)c1]

1H NMR (500 MHz, MeOD) δ: 8.81 (s, 1H), 8.76 (d, 1H), 8.19-8.18 (d, 1H), 7.93 (s, 1H), 7.84-7.80 (t, 2H), 7.52-7.49 (m, 2H), 7.13 (d, 1H), 6.43 (d, 1H), 3.92 (s, 3H)

Example 286) Preparation of 5-chloro-4-(3-chloro-5-(1-methyl-1H-pyrazol-5-yl)-1H-indazol-1-yl)-2-fluoro-N-(thiazol-4-yl)benzenesulfonamide

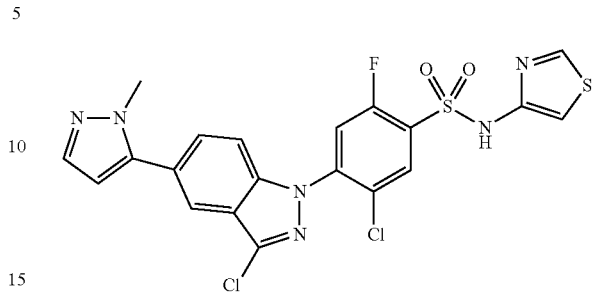

1H NMR (500 MHz, MeOD) δ: 8.77-8.76 (d, 1H), 8.17-8.16 (d, 1H), 7.85 (s, 1H), 7.66-7.64 (d, 2H), 7.52-7.51 (d, 1H), 7.47-7.45 (d, 1H), 7.16-7.15 (d, 1H), 6.42 (d, 1H), 3.88 (s, 3H)

Example 287) Preparation of 5-chloro-4-(5-chloro-3-(4-chloro-2-fluorophenyl)-1H-indazol-1-yl)-2-fluoro-N-(thiazol-4-yl)benzenesulfonamide

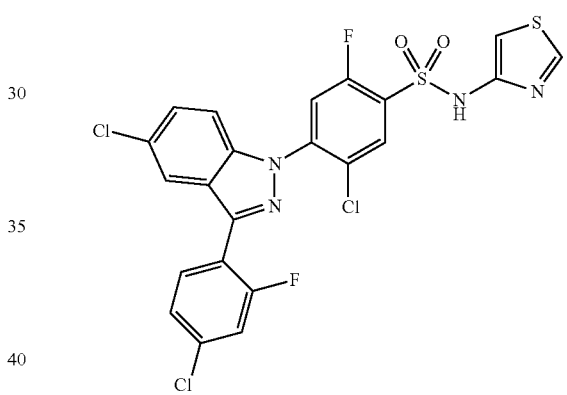

1H NMR (500 MHz, MeOD) δ: 8.78 (d, 1H), 8.20-8.18 (d, 1H), 7.85-7.82 (m, 2H), 7.73-7.72 (d, 1H), 7.52-7.50 (m, 2H), 7.45-7.18 (m, 2H), 7.17 (s, 1H)

Example 288) Preparation of 5-chloro-4-(5-chloro-3-(4-chloro-2-fluorophenyl)-1H-indazol-1-yl)-2-fluorobenzonitrile

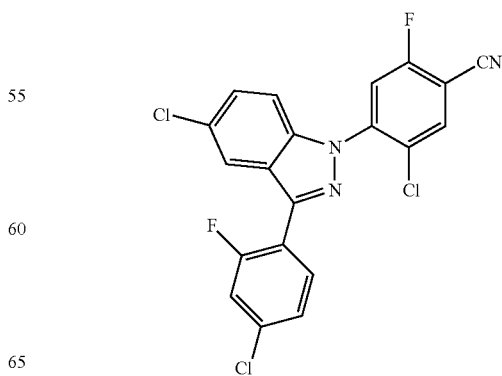

1H NMR (500 MHz, MeOD) δ: 8.00 (d, 1H), 7.93-7.88 (m, 3H), 7.71 (d, 1H), 7.56 (d, 1H), 7.48 (d, 2H)

Example 289) Preparation of 5-chloro-3-(4-chloro-2-fluorophenyl)-1-(2-chloro-5-fluoro-4-(1H-tetrazol-5-yl)phenyl)-1H-indazole

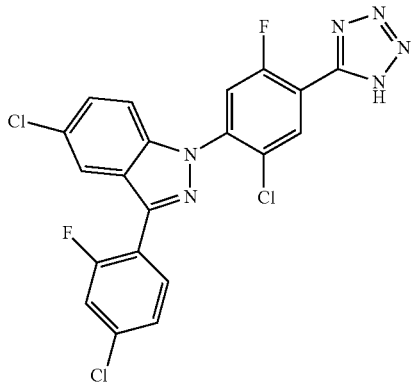 [SMILES: Fc1cc(-n2nc(-c3ccc(Cl)cc3F)c3cc(Cl)ccc32)c(Cl)cc1-c1nnn[nH]1]

1H NMR (500 MHz, MeOD) δ: 8.26 (d, 1H), 7.90-7.86 (m, 3H), 7.71 (d, 1H), 7.56 (d, 1H), 7.30 (d, 2H)

Example 295) Preparation of 5-chloro-4-(5-chloro-3-(4-chloro-2-fluorophenyl)-1H-indazol-1-yl)-2-fluoro-N-(5-methylthiazol-2-yl)benzamide

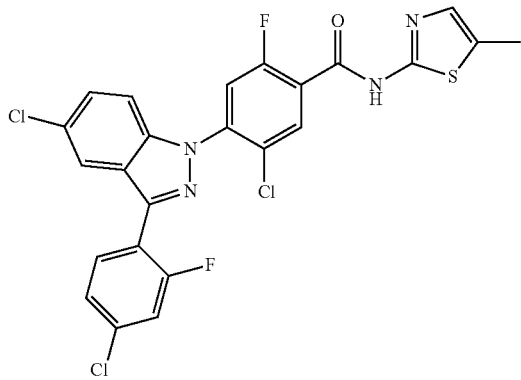 [SMILES: Cc1cnc(NC(=O)c2cc(Cl)c(-n3nc(-c4ccc(Cl)cc4F)c4cc(Cl)ccc43)cc2F)s1]

1H NMR (500 MHz, DMSO) δ: 8.18 (d, 1H), 7.97-7.91 (m, 3H), 7.71 (d, 1H), 7.58 (d, 1H), 7.51 (m, 2H), 7.21 (s, 1H), 2.37 (s, 3H)

Example 296) Preparation of ethyl 2-(5-chloro-4-(5-chloro-3-(4-chloro-2-fluorophenyl)-1H-indazol-1-yl)-2-fluorobenzamido)thiazole-5-carboxylate

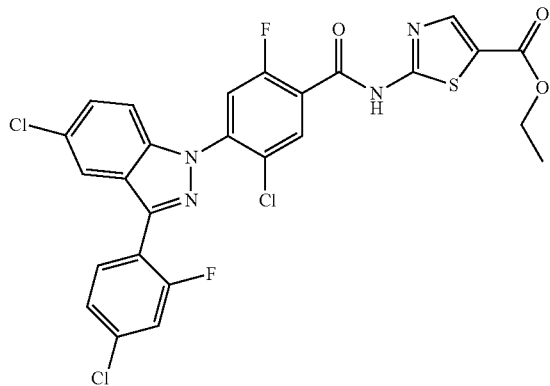 [SMILES: CCOC(=O)c1cnc(NC(=O)c2cc(Cl)c(-n3nc(-c4ccc(Cl)cc4F)c4cc(Cl)ccc43)cc2F)s1]

1H NMR (500 MHz, DMSO) δ: 8.25 (t, 1H), 7.91 (m, 2H), 7.71 (d, 1H), 7.58 (t, 1H), 7.53-7.49 (m, 2H), 4.28 (m, 2H), 1.29 (t, 3H)

Experimental Example: Experiment on Blocking Effects Against Sodium Ion Channel (Nav1.7)

In order to measure the activities of the compounds of the invention as antagonist, an experiment on a blocking effect against the sodium ion channel Nav 1.7 was carried out as follows:

1) Cell Culture

The hNav1.7 HEK293 cell line used was a cell line where human sodium ion channel 1.7 gene (type IX voltage-gated sodium channel alpha subunit) was stably expressed in human embryonic kidney (HEK) 293 cells, and was purchased from Millipore. The culture medium was prepared by adding 1% 100XNEAA and 10% heat inactivated FBS to DMEM F-12, and adding 1% P/S as an antibiotic thereto. G-418 as a restriction enzyme was added during subculture, and the hNav1.7 HEK293 cells were cultured to a confluence of about 80% in a T75 flask in a 5% CO2 incubator at 37° C. for 2 or 3 days, and detached from the flask by treatment of 0.05% trypsin solution. Then, the cells were collected by centrifugation and used for the experiment.

2) Preparation of Compound Samples

The compounds prepared in Examples of the present invention were dissolved in dimethyl sulfoxide (DMSO) and used in the experiment. 90 mM and 10 mM DMSO stock solutions were prepared from each of the compounds and diluted in an extracellular solution (4 mM KCl, 138 mM NaCl, 1 mM MgCl$_2$, 1.8 mM CaCl$_2$, 5.6 mM Glucose, 10 mM HEPES, pH7.45) at various concentrations so that the final concentration of each compound in DMSO was 0.3% or less.

3) Measurement on Blocking Effects Against Sodium Ion Channels

In order to measure the inhibitory effects of sodium ion channels, an IonFlux16 Auto patch clamp system (Fluxion, Inc.) and a plate for exclusive use were used. The cells were distributed in an extracellular solution (4 mM KCl, 138 mM NaCl, 1 mM MgCl$_2$, 1.8 mM CaCl$_2$, 5.6 mM Glucose, 10 mM HEPES, pH 7.45) and then dispensed in the specified region of the plate. Each of the prepared compound samples were diluted at various concentrations and then dispensed in the specified region of the plate. After the dispensation of the cells, the compound samples and an intracellular solution (100 mM CsF, 45 mM CsCl, 5 mM NaCl, 5 mM EGTA, 10 mM HEPES, pH 7.2) in the plate has been completed, the plate was attached to the patch clamp system, and whether the compounds inhibited the ion channel was determined according to a setting program and pulse protocol.

Specifically, eight concentrations per compound were set, and percent inhibition was determined by calculating the percentage of inhibition of the peak current, generated after treating the cells with each concentration of the compound for 50 seconds, relative to the peak current generated before treatment with the compound, and the IC$_{50}$ value was calculated using Sigma Plot program. The results are shown in the following tables 2 to 4.

TABLE 2

| Ex. No. | IC$_{50}$ (μM) |
|---|---|
| 1 | >10 |
| 2 | 5.389 |

TABLE 2-continued

| Ex. No. | IC$_{50}$ (μM) |
|---|---|
| 3 | 1.13 |
| 4 | >10 |
| 5 | >10 |
| 6 | >10 |
| 7 | 0.227 |
| 8 | 0.88 |
| 9 | 0.117 |
| 10 | >10 |
| 11 | >10 |
| 12 | >10 |
| 13 | >10 |
| 14 | 3~10 |
| 15 | 3.089 |
| 16 | >10 |
| 17 | 0.476 |
| 18 | 0.587 |
| 19 | 0.216 |
| 20 | 0.185 |
| 21 | 0.175 |
| 22 | 0.966 |
| 23 | 0.365 |
| 24 | 0.28 |
| 25 | 0.38 |
| 26 | 0.1 |
| 27 | 7.71 |
| 28 | 0.049 |
| 29 | 0.786 |
| 30 | 0.247 |
| 31 | 1.508 |
| 32 | 0.158 |
| 33 | 0.214 |
| 34 | 0.211 |
| 35 | 0.076 |
| 36 | 0.087 |
| 37 | 0.159 |
| 38 | 0.098 |
| 39 | 0.28 |
| 40 | 0.19 |
| 41 | 6.341 |
| 42 | 0.181 |
| 43 | 0.2 |
| 44 | 0.166 |
| 45 | 0.134 |
| 46 | >10 |
| 47 | 0.437 |
| 48 | 0.048 |
| 49 | 2.218 |
| 50 | 0.913 |
| 51 | 0.187 |
| 52 | 0.039 |
| 53 | 0.033 |
| 54 | 0.026 |
| 55 | 0.051 |
| 56 | 0.04 |
| 57 | 0.123 |
| 58 | 0.098 |
| 59 | 0.108 |
| 60 | >10 |
| 61 | 0.096 |
| 62 | 0.554 |
| 63 | 0.041 |
| 64 | 0.094 |
| 65 | 0.028 |
| 66 | 0.016 |
| 67 | 0.033 |
| 68 | 0.59 |
| 69 | 0.037 |
| 70 | 0.142 |
| 71 | 0.048 |
| 72 | 0.061 |
| 73 | 0.03 |
| 74 | 0.02 |
| 75 | 0.18 |
| 76 | 0.09 |
| 77 | 0.02 |
| 78 | 0.13 |
| 79 | 0.07 |
| 80 | 0.08 |
| 81 | 0.24 |
| 82 | 7.91 |
| 83 | 0.08 |
| 84 | 0.11 |
| 85 | 0.6 |
| 86 | >10 |
| 87 | >3 |
| 88 | >10 |
| 89 | >10 |
| 90 | 11.181 |
| 91 | 1.929 |
| 92 | 5.286 |
| 93 | 0.226 |
| 94 | >10 |
| 95 | >10 |
| 96 | >10 |
| 97 | 0.17 |
| 98 | 0.887 |
| 99 | 1.342 |
| 100 | 0.279 |

TABLE 3

| Ex. No. | IC$_{50}$ (μM) |
|---|---|
| 101 | 3.021 |
| 102 | 1.211 |
| 103 | 2.174 |
| 104 | >10 |
| 105 | 0.957 |
| 106 | 6.024 |
| 107 | 0.811 |
| 108 | 1.483 |
| 109 | 0.45 |
| 110 | 0.267 |
| 111 | 0.552 |
| 112 | 0.789 |
| 113 | 0.752 |
| 114 | 1.44 |
| 115 | 0.727 |
| 116 | 3 |
| 117 | 0.64 |
| 118 | 0.36 |
| 119 | 1.79 |
| 120 | 3.89 |
| 121 | 1.09 |
| 122 | 0.31 |
| 123 | 0.35 |
| 124 | 0.29 |
| 125 | 0.56 |
| 126 | 0.99 |
| 127 | 3.935 |
| 128 | 1.33 |
| 129 | 1.74 |
| 130 | >10 |
| 131 | 2.6 |
| 132 | >10 |
| 133 | 0.12 |
| 134 | 2.17 |
| 135 | 0.37 |
| 136 | 1.01 |
| 137 | 0.68 |
| 138 | 0.1 |
| 139 | 1.43 |
| 140 | >10 |
| 141 | >10 |
| 142 | 0.03 |
| 143 | 0.12 |
| 144 | 0.54 |
| 145 | 0.11 |
| 146 | 0.2 |
| 147 | 0.06 |
| 148 | 0.09 |
| 149 | 0.04 |
| 150 | 0.18 |

TABLE 3-continued

| Ex. No. | IC$_{50}$ (μM) |
|---|---|
| 151 | 0.08 |
| 152 | 0.08 |
| 153 | 0.2 |
| 154 | 0.06 |
| 155 | 0.11 |
| 156 | 0.1 |
| 157 | 0.1 |
| 158 | 0.08 |
| 159 | 0.1 |
| 160 | 0.21 |
| 161 | 0.12 |
| 162 | 0.64 |
| 163 | 0.12 |
| 164 | 0.22 |
| 165 | 5.495 |
| 166 | 0.228 |
| 167 | >10 |
| 168 | >10 |
| 169 | 0.18 |
| 170 | 0.07 |
| 171 | 0.19 |
| 172 | 0.14 |
| 173 | 0.21 |
| 174 | 0.85 |
| 175 | 0.08 |
| 176 | 0.2 |
| 177 | 0.97 |
| 178 | 0.33 |
| 179 | 0.39 |
| 180 | >10 |
| 181 | 0.837 |
| 182 | >10 |
| 183 | >10 |
| 184 | 0.07 |
| 185 | 0.08 |
| 186 | 0.08 |
| 187 | 0.62 |
| 188 | 0.05 |
| 189 | 0.11 |
| 190 | 0.17 |
| 191 | 0.11 |
| 192 | 0.27 |
| 193 | 0.1 |
| 194 | 0.48 |
| 195 | 0.08 |
| 196 | 0.13 |
| 197 | 0.04 |
| 198 | 0.17 |
| 199 | 0.2 |
| 200 | 0.09 |

TABLE 4

| Ex. No. | IC$_{50}$ (μM) |
|---|---|
| 201 | 0.07 |
| 202 | 0.05 |
| 203 | 0.08 |
| 204 | 0.1 |
| 205 | 0.05 |
| 206 | 0.21 |
| 207 | 0.14 |
| 208 | 0.05 |
| 209 | 0.04 |
| 210 | 0.06 |
| 211 | 0.04 |
| 212 | 0.18 |
| 213 | 0.72 |
| 214 | 0.34 |
| 215 | 0.21 |
| 216 | 0.37 |
| 217 | 0.53 |
| 218 | 0.29 |
| 219 | 0.3 |
| 220 | 0.54 |

TABLE 4-continued

| Ex. No. | IC$_{50}$ (μM) |
|---|---|
| 221 | 0.97 |
| 222 | 0.41 |
| 223 | 0.23 |
| 224 | 0.28 |
| 225 | 0.46 |
| 226 | 0.4 |
| 227 | 0.08 |
| 228 | 0.11 |
| 229 | 0.18 |
| 230 | 0.144 |
| 231 | 3~10 |
| 232 | 1~3 |
| 233 | 0.068 |
| 234 | 0.111 |
| 235 | 0.089 |
| 236 | 0.071 |
| 237 | >10 |
| 238 | 0.341 |
| 239 | 0.283 |
| 240 | 0.752 |
| 241 | >10 |
| 242 | 0.809 |
| 243 | 0.175 |
| 244 | 2.318 |
| 245 | 1.667 |
| 246 | 1.049 |
| 247 | 0.304 |
| 248 | 0.088 |
| 249 | 0.074 |
| 250 | 0.067 |
| 251 | 0.113 |
| 252 | 0.24 |
| 253 | 0.48 |
| 254 | 0.42 |
| 255 | 0.83 |
| 256 | 3.986 |
| 257 | 0.36 |
| 258 | 2.07 |
| 259 | 0.52 |
| 260 | 0.47 |
| 261 | 0.18 |
| 262 | 0.21 |
| 263 | >10 |
| 264 | 0.164 |
| 265 | 0.3~1 |
| 266 | 0.133 |
| 267 | >10 |
| 268 | 0.608 |
| 269 | 0.142 |
| 270 | 0.187 |
| 271 | 2.133 |
| 272 | 0.37 |
| 273 | 0.18 |
| 274 | 5.96 |
| 275 | 1.23 |
| 276 | >10 |
| 277 | 0.33 |
| 278 | 8.914 |
| 279 | >10 |
| 280 | 1.084 |
| 281 | 3~10 |
| 282 | 1.653 |
| 283 | >3 |
| 284 | >10 |
| 285 | >10 |
| 286 | 3~10 |
| 287 | 8.25 |
| 288 | >10 |
| 289 | >10 |
| 290 | 11.2 |
| 291 | 10.85 |
| 292 | >10 |
| 293 | >10 |
| 294 | >10 |
| 295 | >10 |
| 296 | >10 |

What is claimed is:

1. A compound represented by the following Chemical Formula 1 or a pharmaceutically acceptable salt thereof:

[Chemical Formula 1]

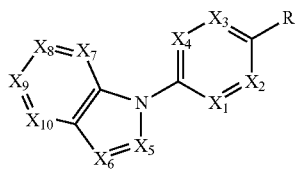

In the above Formula,
$X_1$ is C—$R_a$ or N, $X_2$ is C—$R_b$ or N, $X_3$ is C—$R_c$ or N, $X_4$ is C—$R_d$ or N,
$R_a$, $R_b$, $R_c$ and $R_d$ are each independently hydrogen, $C_{1-4}$ alkyl, $C_{3-6}$ cycloalkyl, $C_{1-4}$ alkoxy, $C_{6-10}$ aryl, 5-membered or 6-membered heteroaryl, halogen or cyano,
$X_5$ is CH, or N, $X_6$ is C—$R_e$ or N, $X_7$ is CH or N, $X_8$ is C—$R_f$ or N,
$R_e$ is hydrogen; $C_{1-4}$ alkyl; $C_{2-4}$ alkynyl which is unsubstituted or substituted with $C_{1-4}$ hydorxyalkyl; $C_{3-6}$ cycloalkyl; —COO—($C_{1-4}$ alkyl); —NHCO—($C_{1-4}$ alkyl); —CH═CH-(pyridinyl); amino; carboxy; cyano; halogen; morpholino; 5-membered or 6-membered heteroaryl which is unsubstituted or substituted with a substituent selected from the group consisting of $C_{1-4}$ alkyl, $C_{1-4}$ alkoxy, amino and halogen; phenyl which is unsubstituted or substituted with one to three substituents independently selected from the group consisting of $C_{1-4}$ alkyl, $C_{1-4}$ alkoxy, $C_{1-4}$ haloalkyl, $C_{1-4}$ haloalkoxy, halogen, amino, cyano and nitro; pyridin-2-onyl which is unsubstituted or substituted with $C_{1-4}$ alkyl; styryl which is unsubstituted or substituted with a substituent selected from the group consisting of $C_{1-4}$ halolkyl and halogen; or tetrahydropyridinyl which is unsubstituted or substituted with —COO—($C_{1-4}$ alkyl),
$R_f$ is hydrogen, benzyloxy or phenyl,
$X_9$ is C—$R_g$ or N,
$R_g$ is hydrogen; $C_{1-4}$ alkyl; $C_{1-4}$ alkoxy which is unsubstituted or substituted with a substituent selected from the group consisting of $C_{3-6}$ cycloalkyl, phenyl, phenyl substituted with halogen, and naphthyl; $C_{1-4}$ haloalkyl; $C_{3-6}$ cycloalkyl; amino; halogen; hydroxy; nitro; phenylamino; benzyloxy which is unsubstituted or substituted with halogen; phenyl which is unsubstituted or substituted with one to three substituents independently selected from the group consisting of $C_{1-4}$ alkyl, $C_{1-4}$ alkoxy, $C_{1-4}$ haloalkyl, cyano, amino, nitro and halogen; 5-membered or 6-membered heteroaryl which is unsubstituted or substituted with a substituent independently selected from the group consisting of $C_{1-4}$ alkyl and halogen; or pyridinyloxy which is unsubstituted or substituted with halogen,
$X_{10}$ is C—$R_h$ or N,
$R_h$ is hydrogen, halogen or benzyloxy,
R is —CO—N($R_i$)—$SO_2$—$R_{ii}$, —$SO_2$—NH—$R_{iii}$, —CONH—$R_{iv}$, dihydrotriazolonyl, or tetrazolyl,
$R_i$ is hydrogen; $C_{1-4}$ alkyl; naphthylmethyl; or benzyl which is unsubstituted or substituted with halogen;
$R_{ii}$ is $C_{1-4}$ alkyl or N($C_{1-4}$ alkyl)$_2$,
$R_{iii}$ is 5-membered or 6-membered heteroaryl which is unsubstituted or substituted with a substituent selected from the group consisting of $C_{1-4}$ alkyl and halogen; and
$R_{iv}$ is —CO—($C_{1-4}$ alkyl); —NHCO—NH$_2$; or thiazolyl which is unsubstituted or substituted with a substituent selected from the group consisting of $C_{1-4}$ alkyl and —COO—($C_{1-4}$ alkyl).

2. The compound or a pharmaceutically acceptable salt thereof according to claim 1 wherein $X_1$ is C—$R_a$ or N, $X_2$ is CH, $X_3$ is C—$R_c$, and $X_4$ is CH.

3. The compound or a pharmaceutically acceptable salt thereof according to claim 1 wherein $R_a$, $R_b$, $R_c$, and $R_d$ are each independently hydrogen, fluoro, chloro or cyano.

4. The compound or a pharmaceutically acceptable salt thereof according to claim 1 wherein $X_1$ is C—Cl, $X_2$ is CH, $X_3$ is C—F, and $X_4$ is CH.

5. The compound or a pharmaceutically acceptable salt thereof according to claim 1 wherein the 5-membered or 6-membered heteroaryl of $R_e$ is pyrazolyl unsubstituted or substituted with $C_{1-4}$ alkyl; pyridinyl unsubstituted or substituted with a substituent selected from the group consisting of $C_{1-4}$ alkoxy and halogen; or thiazolyl unsubstituted or substituted with $C_{1-4}$ alkyl.

6. The compound or a pharmaceutically acceptable salt thereof according to claim 1 wherein $R_e$ is hydrogen; methyl; ethynyl substituted with hydroxyisopropyl; cyclopropyl; —COO-(methyl); —NHCO-(methyl); —CH═CH-(pyridinyl); amino; carboxy; cyano; bromo; chloro; morpholino; pyrazolyl unsubstituted or substituted with methyl; pyridinyl unsubstituted or substituted with a substituent selected from the group consisting of methoxy, fluoro and chloro; thiazolyl unsubstituted or substituted with methyl; phenyl unsubstituted or substituted with one to three substituents independently selected from the group consisting of methyl, methoxy, trifluoromethyl, trifluoromethoxy, fluoro, chloro, amino, cyano and nitro; pyridin-2-onyl unsubstituted or substituted with methyl; styryl unsubstituted or substituted with a substituent selected from the group consisting of trifluoromethyl, fluoro and chloro; or tetrahydropyridinyl unsubstituted or substituted with —COO-(tert-butyl).

7. The compound or a pharmaceutically acceptable salt thereof according to claim 1 wherein $R_i$ is hydrogen; methyl; naphthylmethyl; or benzyl substituted with fluoro, and $R_{ii}$ is methyl or dimethylamino.

8. The compound or a pharmaceutically acceptable salt thereof according to claim 1 wherein $R_{iv}$ —CO-(methyl); —NHCO—NH$_2$; or thiazolyl unsubstituted or substituted with one or substituents selected from the group consisting of methyl and —COO-(ethyl).

9. The compound or a pharmaceutically acceptable salt thereof according to claim 1 wherein $X_9$ is C—$R_g$ and $X_{10}$ is C—$R_h$.

10. The compound or a pharmaceutically acceptable salt thereof according to claim 1 wherein
$X_9$ is C—$R_g$, and
$R_g$ is hydrogen; isobutyl; methoxy, ethoxy or isobutoxy, which is unsubstituted or substituted with a substituent selected from the group consisting of cyclohexyl, phenyl, phenyl substituted with fluoro, and naphthyl; trifluoromethyl; cyclopropyl; amino; fluoro; chloro; bromo; hydroxy; nitro; phenylamino; benzyloxy unsubstituted or substituted with fluoro; phenyl unsubstituted or substituted with one or two substituents independently selected from the group consisting of methyl, methoxy, trifluoromethyl, cyano, fluoro and chloro; pyrazolyl substituted with methyl; pyridinyl unsubstituted or substituted with one or two substituents selected from the group consisting of fluoro and chloro; pyridinyloxy unsubstituted or substituted with fluoro; or pyrimidinyl.

11. The compound or a pharmaceutically acceptable salt thereof according to claim 1 wherein $X_{10}$ is C—$R_h$ and $R_h$ is hydrogen, chloro or benzyloxy.

12. The compound or a pharmaceutically acceptable salt thereof according to claim 1 wherein
$X_5$ is N, $X_6$ is C—$R_e$, $X_7$ is CH, and $X_8$ is C—$R_f$, or
$X_5$ is CH, $X_6$ is C—$R_e$, $X_7$ is N, and $X_8$ is C—$R_f$, or
$X_5$ is CH, $X_6$ is C—$R_e$, $X_7$ is CH, and $X_8$ is C—$R_f$, or
$X_5$ is N, $X_6$ is C—$R_e$, $X_7$ is N, $X_8$ is C—$R_f$, or
$X_5$ is N, $X_6$ is C—$R_e$, $X_7$ is CH, and $X_8$ is N.

13. The compound or a pharmaceutically acceptable salt thereof according to claim 1 wherein
$X_1$ is C—$R_a$ or N, $X_2$ is C—$R_b$, $X_3$ is C—$R_c$, $X_4$ is C—$R_d$,
$X_5$ is N, $X_6$ is C—$R_e$, $X_7$ is CH, $X_8$ is C—$R_f$,
$R_e$ is hydrogen; $C_{1-4}$ alkyl; $C_{2-4}$ alkynyl unsubstituted or substituted with $C_{1-4}$ hydroxyalkyl; $C_{3-6}$ cycloalkyl; —COO—($C_{1-4}$ alkyl); —NHCO—($C_{1-4}$ alkyl); —CH=CH-(pyridinyl); amino; cyano; halogen; morpholino; 5-membered or 6-membered heteroaryl unsubstituted or substituted with a substituent selected from the group consisting of $C_{1-4}$ alkyl, $C_{1-4}$ alkoxy and halogen; phenyl unsubstituted or substituted with one to three substituents independently selected from the group consisting of $C_{1-4}$ alkyl, $C_{1-4}$ alkoxy, $C_{1-4}$ haloalkyl, $C_{1-4}$ haloalkoxy, halogen, amino, cyano and nitro; pyridin-2-onyl unsubstituted or substituted with $C_{1-4}$ alkyl; styryl unsubstituted or substituted with a substituent selected from the group consisting of $C_{1-4}$ haloalkyl and halogen; or tetrahydro-pyridinyl unsubstituted or substituted with —COO—($C_{1-4}$ alkyl),
$X_9$ is C—$R_g$,
$X_{10}$ is C—$R_h$, and
$R_h$ is hydrogen or halogen.

14. The compound or a pharmaceutically acceptable salt thereof according to claim 1 wherein
$X_1$ is C—$R_a$, $X_2$ is C—$R_b$, $X_3$ is C—$R_c$, and $X_4$ is C—$R_d$,
$R_a$, $R_b$, $R_c$ and $R_d$ are each independently hydrogen or halogen,
$X_5$ is CH, $X_6$ is C—$R_e$, $X_7$ is N, and $X_8$ is C—$R_f$,
$R_e$ is halogen; or phenyl unsubstituted or substituted with one to three substituents independently selected from the group consisting of $C_{1-4}$ alkyl, $C_{1-4}$ alkoxy, $C_{1-4}$ haloalkyl, $C_{1-4}$ haloalkoxy, halogen, amino, cyano and nitro,
$R_f$ is hydrogen,
$X_9$ is C—$R_g$,
$R_g$ is hydrogen, halogen, or phenyl unsubstituted or substituted with a substituent selected from the group consisting of $C_{1-4}$ alkoxy, $C_{1-4}$ haloalkyl, cyano and halogen,
$X_{10}$ is C—$R_h$,
$R_h$ is hydrogen,
R is —CO—N($R_i$)—SO$_2$—$R_{ii}$,
$R_i$ is hydrogen, and
$R_{ii}$ is $C_{1-4}$ alkyl.

15. The compound or a pharmaceutically acceptable salt thereof according to claim 1 wherein
$X_1$ is C—$R_a$ or N, $X_2$ is C—$R_b$, $X_3$ is C—$R_c$, and $X_4$ is C—$R_d$,
$R_a$, $R_b$, $R_c$ and $R_d$ are each independently hydrogen or halogen,
$X_5$ is CH, $X_6$ is C—$R_e$, $X_7$ is CH, and $X_8$ is C—$R_f$,
$R_e$ is carboxy; halogen; 5-membered or 6-membered heteroaryl unsubstituted or substituted with a substituent selected from the group consisting of $C_{1-4}$ alkyl, $C_{1-4}$ alkoxy and halogen; or phenyl unsubstituted or substituted with one to three substituents independently selected from the group consisting of $C_{1-4}$ alkyl, $C_{1-4}$ alkoxy, $C_{1-4}$ haloalkyl, $C_{1-4}$ haloalkoxy, halogen, amino, cyano and nitro,
$R_f$ is hydrogen or benzyloxy,
$X_9$ is C—$R_g$,
$R_g$ is hydrogen; $C_{1-4}$ alkoxy unsubstituted or substituted with a substituent selected from the group consisting of $C_{3-6}$ cycloalkyl, phenyl, phenyl substituted with halogen, and naphthyl; halogen; hydroxy; or benzyloxy unsubstituted or substituted with halogen,
$X_{10}$ is C—$R_h$,
R is —CO—N($R_i$)—SO$_2$—$R_{ii}$,
$R_i$ is hydrogen, and
$R_{ii}$ is $C_{1-4}$ alkyl.

16. The compound or a pharmaceutically acceptable salt thereof according to claim 1 wherein
$X_1$ is C—$R_a$, $X_2$ is C—$R_b$, $X_3$ is C—$R_c$, and $X_4$ is C—$R_d$,
$R_a$, $R_b$, $R_c$ and $R_d$ are each independently hydrogen or halogen,
$X_5$ is N, $X_6$ is C—$R_e$, $X_7$ is N, $X_8$ is C—$R_f$,
$R_e$ is halogen,
$R_f$ is hydrogen,
$X_9$ is C—$R_g$,
$R_g$ is halogen,
$X_{10}$ is C—$R_h$,
$R_h$ is hydrogen,
R is —CO—N($R_i$)—SO$_2$—$R_{ii}$,
$R_i$ is hydrogen, and
$R_{ii}$ is $C_{1-4}$ alkyl.

17. The compound or a pharmaceutically acceptable salt thereof according to claim 1 wherein
X, is C—$R_a$, $X_2$ is C—$R_b$, $X_3$ is C—$R_c$, and $X_4$ is C—$R_d$,
$R_a$, $R_b$, $R_c$ and $R_d$ are each independently hydrogen or halogen,
$X_5$ is N, $X_6$ is C—$R_e$, $X_7$ is CH, $X_8$ is N,
$R_e$ is hydrogen or halogen;
$X_9$ is C—$R_g$,
$R_g$ is halogen,
$X_{10}$ is C—$R_h$,
$R_h$ is hydrogen,
R is —CO—N($R_i$)—SO$_2$—$R_{ii}$,
$R_i$ is hydrogen, and
$R_{ii}$ is $C_{1-4}$ alkyl.

18. A compound or a pharmaceutically acceptable salt thereof, wherein the compound is selected from the group consisting of
1) 5-chloro-4-(5-chloro-3-methyl-1H-indazol-1-yl)-2-fluoro-N-(methylsulfonyl)benzamide,
2) 5-chloro-4-(5-chloro-1H-indazol-1-yl)-2-fluoro-N-(methylsulfonyl)benzamide,
3) 5-chloro-4-(3,5-dichloro-1H-pyrazolo[3,4-b]pyridin-1-yl)-2-fluoro-N-(methylsulfonyl)benzamide,
4) 4-(3,5-dichloro-1H-indazol-1-yl)-2-fluoro-N-(methylsulfonyl)benzamide,
5) 4-(3-amino-5-chloro-1H-indazol-1-yl)-5-chloro-2-fluoro-N-(methylsulfonyl)benzamide,
6) 4-(3-acetamido-5-chloro-1H-indazol-1-yl)-5-chloro-2-fluoro-N-(methylsulfonyl)benzamide,
7) 5-chloro-4-(3,5-dichloro-1H-indazol-1-yl)-N—(N,N-dimethylsulfamoyl)-2-fluorobenzamide, 8) 3-chloro-4-(3,5-dichloro-1H-indazol-1-yl)-N-(methylsulfonyl)benzamide,
9) 5-chloro-4-(3,5-dichloro-1H-indazol-1-yl)-2-fluoro-N-(methylsulfonyl)benzamide,
10) 5-chloro-4-(5-chloro-1H-pyrazolo[3,4-c]pyridin-1-yl)-2-fluoro-N-(methylsulfonyl)benzamide,
11) 5-chloro-4-(3,5-dichloro-1H-pyrazolo[3,4-c]pyridin-1-yl)-2-fluoro-N-(methylsulfonyl)benzamide,
12) 4-(3-chloro-5-hydroxy-1H-indazol-1-yl)-N-(methylsulfonyl)benzamide,
13) 4-(5-amino-1H-indazol-1-yl)-5-chloro-2-fluoro-N-(methylsulfonyl)benzamide,
14) 5-chloro-2-fluoro-4-(3-methyl-5-nitro-1H-indazol-1-yl)-N-(methylsulfonyl)benzamide,
15) 5-chloro-4-(4-chloro-5-fluoro-1H-indazol-1-yl)-2-fluoro-N-(methylsulfonyl)benzamide,
16) 5-chloro-4-(3-chloro-5-hydroxy-1H-indazol-1-yl)-2-fluoro-N-(methylsulfonyl)benzamide,
17) 5-chloro-4-(3-chloro-5-fluoro-1H-indazol-1-yl)-2-fluoro-N-(methylsulfonyl)benzamide,
18) 5-chloro-4-(3-chloro-5-(trifluoromethyl)-1H-indazol-1-yl)-2-fluoro-N-(methylsulfonyl)benzamide,
19) 4-(3-bromo-5-chloro-1H-indazol-1-yl)-5-chloro-2-fluoro-N-(methylsulfonyl)benzamide,
20) 5-chloro-4-(3,5-dichloro-1H-pyrrolo[2,3-b]pyridin-1-yl)-2-fluoro-N-(methylsulfonyl)benzamide,
21) 4-(5-bromo-3-chloro-1H-indazol-1-yl)-5-chloro-2-fluoro-N-(methylsulfonyl)benzamide,
22) 4-(5-bromo-3-cyano-1H-indazol-1-yl)-5-chloro-2-fluoro-N-(methylsulfonyl)benzamide,
23) 5-chloro-4-(3-chloro-5-nitro-1H-indazol-1-yl)-2-fluoro-N-(methylsulfonyl)benzamide,
24) 5-chloro-4-(3-chloro-5-cyclopropyl-1H-indazol-1-yl)-2-fluoro-N-(methylsulfonyl)benzamide,
25) 5-chloro-4-(5-chloro-3-cyclopropyl-1H-indazol-1-yl)-2-fluoro-N-(methylsulfonyl)benzamide,
26) 5-chloro-4-(5-cyclopropyl-3-phenyl-1H-indazol-1-yl)-2-fluoro-N-(methylsulfonyl)benzamide,
27) 5-chloro-4-(3-chloro-5-(phenylamino)-1H-indazol-1-yl)-2-fluoro-N-(methylsulfonyl)benzamide,
28) 4-(5-(benzyloxy)-3-chloro-1H-indazol-1-yl)-5-chloro-2-fluoro-N-(methylsulfonyl)benzamide,
29) 4-(5-(benzyloxy)-4-chloro-1H-indazol-1-yl)-5-chloro-2-fluoro-N-(methylsulfonyl)benzamide,
30) 4-(5-(benzyloxy)-3-methyl-1H-indazol-1-yl)-5-chloro-2-fluoro-N-(methylsulfonyl)benzamide,
31) 5-chloro-4-(3,4-dichloro-5-((4-fluorobenzyl)oxy)-1H-indazol-1-yl)-2-fluoro-N-(methylsulfonyl)benzamide,
32) 5-chloro-4-(3,4-dichloro-5-((2-fluorobenzyl)oxy)-1H-indazol-1-yl)-2-fluoro-N-(methylsulfonyl)benzamide,
33) 5-chloro-4-(3-chloro-5-(1-phenylethoxy)-1H-indazol-1-yl)-2-fluoro-N-(methylsulfonyl)benzamide,
34) 5-chloro-4-(3-chloro-5-(cyclohexylmethoxy)-1H-indazol-1-yl)-2-fluoro-N-(methylsulfonyl)benzamide,
35) 5-chloro-4-(3-chloro-5-(naphthalen-2-ylmethoxy)-1H-indazol-1-yl)-2-fluoro-N-(methylsulfonyl)benzamide,
36) 5-chloro-4-(3-chloro-5-((4-fluorobenzyl)oxy)-1H-indazol-1-yl)-2-fluoro-N-(methylsulfonyl)benzamide,
37) 5-chloro-4-(3-chloro-5-((2-fluorobenzyl)oxy)-1H-indazol-1-yl)-2-fluoro-N-(methylsulfonyl)benzamide,
38) 5-chloro-4-(3-chloro-5-((3-fluorobenzyl)oxy)-1H-indazol-1-yl)-2-fluoro-N-(methylsulfonyl)benzamide,
39) 5-chloro-4-(3-chloro-5-(1-(4-fluorophenyl)ethoxy)-1H-indazol-1-yl)-2-fluoro-N-(methylsulfonyl)benzamide,
40) 5-chloro-4-(3-chloro-5-phenethoxy-1H-indazol-1-yl)-2-fluoro-N-(methylsulfonyl)benzamide,
41) 5-chloro-2-fluoro-4-(5-isobutoxy-1H-indazol-1-yl)-N-(methylsulfonyl)benzamide,
42) 5-chloro-4-(3-chloro-5-isobutoxy-1H-indazol-1-yl)-2-fluoro-N-(methylsulfonyl)benzamide,
43) 4-(5-(benzyloxy)-3-chloro-1H-indazol-1-yl)-5-chloro-N—(N,N-dimethylsulfamoyl)-2-fluorobenzamide,
44) 4-(5-(benzyloxy)-3-chloro-1H-indazol-1-yl)-3-chloro-N-(methylsulfonyl)benzamide,
45) 4-(6-(benzyloxy)-3-chloro-1H-indazol-1-yl)-5-chloro-2-fluoro-N-(methylsulfonyl)benzamide,
46) methyl 6-(benzyloxy)-1-(2-chloro-5-fluoro-4-((methylsulfonyl)carbamoyl)phenyl)-1H-indazole-3-carboxylate,
47) 5-chloro-4-(3-chloro-5-((6-fluoropyridin-3-yl)oxy)-1H-indazol-1-yl)-2-fluoro-N-(methylsulfonyl)benzamide,
48) 5-chloro-4-(5-chloro-3-phenyl-1H-indazol-1-yl)-2-fluoro-N-(methylsulfonyl)benzamide,
49) 5-chloro-4-(5-chloro-3-(pyridin-4-yl)-1H-indazol-1-yl)-2-fluoro-N-(methylsulfonyl)benzamide,
50) 5-chloro-4-(5-chloro-3-(pyridin-3-yl)-1H-indazol-1-yl)-2-fluoro-N-(methylsulfonyl)benzamide,
51) 5-chloro-4-(5-chloro-3-(5-chloropyridin-3-yl)-1H-indazol-1-yl)-2-fluoro-N-(methylsulfonyl)benzamide,
52) 5-chloro-4-(5-chloro-3-(m-tolyl)-1H-indazol-1-yl)-2-fluoro-N-(methylsulfonyl)benzamide,
53) 5-chloro-4-(5-chloro-3-(2-fluorophenyl)-1H-indazol-1-yl)-2-fluoro-N-(methylsulfonyl)benzamide,
54) 5-chloro-4-(5-chloro-3-(3-fluorophenyl)-1H-indazol-1-yl)-2-fluoro-N-(methylsulfonyl)benzamide,
55) 5-chloro-4-(5-chloro-3-(4-fluorophenyl)-1H-indazol-1-yl)-2-fluoro-N-(methylsulfonyl)benzamide,
56) 5-chloro-4-(5-chloro-3-(2,4-difluorophenyl)-1H-indazol-1-yl)-2-fluoro-N-(methylsulfonyl)benzamide,
57) 5-chloro-4-(5-chloro-3-(2-methoxypyridin-3-yl)-1H-indazol-1-yl)-2-fluoro-N-(methylsulfonyl)benzamide,
58) 5-chloro-4-(5-chloro-3-(2-methoxyphenyl)-1H-indazol-1-yl)-2-fluoro-N-(methylsulfonyl)benzamide,
59) 5-chloro-4-(5-chloro-3-(4-methoxyphenyl)-1H-indazol-1-yl)-2-fluoro-N-(methylsulfonyl)benzamide,
60) 5-chloro-4-(5-chloro-3-(2-cyanophenyl)-1H-indazol-1-yl)-2-fluoro-N-(methylsulfonyl)benzamide,
61) 5-chloro-4-(5-chloro-3-(3-cyanophenyl)-1H-indazol-1-yl)-2-fluoro-N-(methylsulfonyl)benzamide,
62) 5-chloro-4-(5-chloro-3-(4-cyanophenyl)-1H-indazol-1-yl)-2-fluoro-N-(methylsulfonyl)benzamide,
63) 5-chloro-4-(5-chloro-3-(2-(trifluoromethyl)phenyl)-1H-indazol-1-yl)-2-fluoro-N-(methylsulfonyl)benzamide,
64) 5-chloro-4-(5-chloro-3-(3-(trifluoromethyl)phenyl)-1H-indazol-1-yl)-2-fluoro-N-(methylsulfonyl)benzamide,
65) 5-chloro-4-(5-chloro-3-(4-(trifluoromethyl)phenyl)-1H-indazol-1-yl)-2-fluoro-N-(methylsulfonyl)benzamide,
66) 5-chloro-4-(5-chloro-3-(4-chloro-2-fluorophenyl)-1H-indazol-1-yl)-2-fluoro-N-(methylsulfonyl)benzamide,
67) 5-chloro-4-(5-chloro-3-(4-chlorophenyl)-1H-indazol-1-yl)-2-fluoro-N-(methylsulfonyl)benzamide, 68) 5-chloro-4-(5-chloro-3-(2-fluoropyridin-4-yl)-1H-indazol-1-yl)-2-fluoro-N-(methylsulfonyl)benzamide,
69) 5-chloro-4-(5-chloro-3-(5-chloro-2-fluorophenyl)-1H-indazol-1-yl)-2-fluoro-N-(methylsulfonyl)benzamide,
70) 5-chloro-4-(5-chloro-3-(3-cyano-4-fluorophenyl)-1H-indazol-1-yl)-2-fluoro-N-(methylsulfonyl)benzamide,
71) 5-chloro-4-(5-chloro-3-(2-chlorophenyl)-1H-indazol-1-yl)-2-fluoro-N-(methylsulfonyl)benzamide,
72) 5-chloro-4-(5-chloro-3-(3-chlorophenyl)-1H-indazol-1-yl)-2-fluoro-N-(methylsulfonyl)benzamide,
73) 5-chloro-4-(5-chloro-3-(3-chloro-5-fluorophenyl)-1H-indazol-1-yl)-2-fluoro-N-(methylsulfonyl)benzamide,
74) 5-chloro-4-(5-chloro-3-(2-chloro-4-fluorophenyl)-1H-indazol-1-yl)-2-fluoro-N-(methylsulfonyl)benzamide,
75) 5-chloro-4-(5-chloro-3-(3,4-difluorophenyl)-1H-indazol-1-yl)-2-fluoro-N-(methylsulfonyl)benzamide,
76) 5-chloro-4-(5-chloro-3-(2,5-difluorophenyl)-1H-indazol-1-yl)-2-fluoro-N-(methylsulfonyl)benzamide,
77) 5-chloro-4-(5-chloro-3-(3,4,5-trifluorophenyl)-1H-indazol-1-yl)-2-fluoro-N-(methylsulfonyl)benzamide,
78) 5-chloro-4-(5-chloro-3-(2-chloro-6-fluorophenyl)-1H-indazol-1-yl)-2-fluoro-N-(methylsulfonyl)benzamide,
79) 5-chloro-4-(5-chloro-3-(3-chloro-2-fluorophenyl)-1H-indazol-1-yl)-2-fluoro-N-(methylsulfonyl)benzamide,
80) 5-chloro-4-(5-chloro-3-(4-chloro-3-fluorophenyl)-1H-indazol-1-yl)-2-fluoro-N-(methylsulfonyl)benzamide,
81) 5-chloro-4-(5-chloro-3-(4-nitrophenyl)-1H-indazol-1-yl)-2-fluoro-N-(methylsulfonyl)benzamide,
82) 4-(3-(4-aminophenyl)-5-chloro-1H-indazol-1-yl)-5-chloro-2-fluoro-N-(methylsulfonyl)benzamide,
83) 5-chloro-4-(5-chloro-3-(4-(trifluoromethoxy)phenyl)-1H-indazol-1-yl)-2-fluoro-N-(methylsulfonyl)benzamide,
84) 5-chloro-2-fluoro-4-(5-isobutyl-3-phenyl-1H-indazol-1-yl)-N-(methylsulfonyl)benzamide,
85) 5-chloro-4-(3-(4-chlorophenyl)-5-cyclopropyl-1H-indazol-1-yl)-2-fluoro-N-(methylsulfonyl)benzamide,
86) 5-chloro-4-(5-chloro-3-morpholino-1H-indazol-1-yl)-2-fluoro-N-(methylsulfonyl)benzamide,
87) 5-chloro-4-(5-chloro-3-(1-methyl-1H-pyrazol-5-yl)-1H-indazol-1-yl)-2-fluoro-N-(methylsulfonyl)benzamide,
88) 5-chloro-4-(5-chloro-3-(1-methyl-1H-pyrazol-4-yl)-1H-indazol-1-yl)-2-fluoro-N-(methylsulfonyl)benzamide,
89) 5-chloro-4-(5-chloro-3-(1H-pyrazol-4-yl)-1H-indazol-1-yl)-2-fluoro-N-(methylsulfonyl)benzamide,
90) 5-chloro-4-(5-chloro-3-(1H-pyrazol-3-yl)-1H-indazol-1-yl)-2-fluoro-N-(methylsulfonyl)benzamide,
91) 5-chloro-4-(5-chloro-3-(2-methylthiazol-5-yl)-1H-indazol-1-yl)-2-fluoro-N-(methylsulfonyl)benzamide,
92) 4-(5-chloro-3-(2-methoxyphenyl)-1H-indazol-1-yl)-3-cyano-N-(methylsulfonyl)benzamide,
93) 4-(5-chloro-3-(4-methoxyphenyl)-1H-indazol-1-yl)-3-cyano-N-(methylsulfonyl)benzamide,
94) 4-(5-chloro-3-(2-cyanophenyl)-1H-indazol-1-yl)-3-cyano-N-(methylsulfonyl)benzamide,
95) 4-(5-chloro-3-(3-cyanophenyl)-1H-indazol-1-yl)-3-cyano-N-(methylsulfonyl)benzamide,
96) 4-(5-chloro-3-(4-cyanophenyl)-1H-indazol-1-yl)-3-cyano-N-(methylsulfonyl)benzamide,
97) 4-(5-chloro-3-(2-(trifluoromethyl)phenyl)-1H-indazol-1-yl)-3-cyano-N-(methylsulfonyl)benzamide,
98) 4-(5-chloro-3-(3-(trifluoromethyl)phenyl)-1H-indazol-1-yl)-3-cyano-N-(methylsulfonyl)benzamide,
99) 4-(5-chloro-3-(4-(trifluoromethyl)phenyl)-1H-indazol-1-yl)-3-cyano-N-(methylsulfonyl)benzamide,
100) 4-(5-chloro-3-(4-chloro-2-fluorophenyl)-1H-indazol-1-yl)-3-cyano-N-(methylsulfonyl)benzamide,
101) 4-(5-chloro-3-(4-fluorophenyl)-1H-indazol-1-yl)-3-cyano-N-(methylsulfonyl)benzamide,
102) 4-(5-chloro-3-(2-fluorophenyl)-1H-indazol-1-yl)-3-cyano-N-(methylsulfonyl)benzamide,
103) 4-(5-chloro-3-(3-fluorophenyl)-1H-indazol-1-yl)-3-cyano-N-(methylsulfonyl)benzamide,
104) 4-(5-chloro-3-(5-chloropyridin-3-yl)-1H-indazol-1-yl)-3-cyano-N-(methylsulfonyl)benzamide,
105) 4-(5-chloro-3-(2,4-difluorophenyl)-1H-indazol-1-yl)-3-cyano-N-(methylsulfonyl)benzamide,
106) 4-(5-chloro-3-(2-methoxypyridin-3-yl)-1H-indazol-1-yl)-3-cyano-N-(methylsulfonyl)benzamide,
107) 2-chloro-4-(5-chloro-3-(2-methoxyphenyl)-1H-indazol-1-yl)-5-fluoro-N-(methylsulfonyl)benzamide,
108) 2-chloro-4-(5-chloro-3-(4-methoxyphenyl)-1H-indazol-1-yl)-5-fluoro-N-(methylsulfonyl)benzamide,
109) 2-chloro-4-(5-chloro-3-(3-cyanophenyl)-1H-indazol-1-yl)-5-fluoro-N-(methylsulfonyl)benzamide,
110) 2-chloro-4-(5-chloro-3-(3-(trifluoromethyl)phenyl)-1H-indazol-1-yl)-5-fluoro-N-(methylsulfonyl)benzamide,
111) 2-chloro-4-(5-chloro-3-(4-(trifluoromethyl)phenyl)-1H-indazol-1-yl)-5-fluoro-N-(methylsulfonyl)benzamide,
112) 2-chloro-4-(5-chloro-3-(4-fluorophenyl)-1H-indazol-1-yl)-5-fluoro-N-(methylsulfonyl)benzamide,
113) 2-chloro-4-(5-chloro-3-(2-fluorophenyl)-1H-indazol-1-yl)-5-fluoro-N-(methylsulfonyl)benzamide,
114) 2-chloro-4-(5-chloro-3-(3-fluorophenyl)-1H-indazol-1-yl)-5-fluoro-N-(methylsulfonyl)benzamide,
115) 2-chloro-4-(5-chloro-3-(2,4-difluorophenyl)-1H-indazol-1-yl)-5-fluoro-N-(methylsulfonyl)benzamide,
116) 2-chloro-4-(5-chloro-3-(2-methoxypyridin-3-yl)-1H-indazol-1-yl)-5-fluoro-N-(methylsulfonyl)benzamide,
117) 4-(5-chloro-3-(2-methoxyphenyl)-1H-indazol-1-yl)-3-fluoro-N-(methylsulfonyl)benzamide,
118) 4-(5-chloro-3-(4-methoxyphenyl)-1H-indazol-1-yl)-3-fluoro-N-(methylsulfonyl)benzamide,
119) 4-(5-chloro-3-(3-cyanophenyl)-1H-indazol-1-yl)-3-fluoro-N-(methylsulfonyl)benzamide,
120) 4-(5-chloro-3-(4-cyanophenyl)-1H-indazol-1-yl)-3-fluoro-N-(methylsulfonyl)benzamide,
121) 4-(5-chloro-3-(3-(trifluoromethyl)phenyl)-1H-indazol-1-yl)-3-fluoro-N-(methylsulfonyl)benzamide,
122) 4-(5-chloro-3-(4-(trifluoromethyl)phenyl)-1H-indazol-1-yl)-3-fluoro-N-(methylsulfonyl)benzamide,
123) 4-(5-chloro-3-(4-fluorophenyl)-1H-indazol-1-yl)-3-fluoro-N-(methylsulfonyl)benzamide,
124) 4-(5-chloro-3-(2-fluorophenyl)-1H-indazol-1-yl)-3-fluoro-N-(methylsulfonyl)benzamide,
125) 4-(5-chloro-3-(3-fluorophenyl)-1H-indazol-1-yl)-3-fluoro-N-(methylsulfonyl)benzamide,
126) 4-(5-chloro-3-(4-chlorophenyl)-1H-indazol-1-yl)-3-fluoro-N-(methylsulfonyl)benzamide,
127) 4-(5-chloro-3-phenyl-1H-indazol-1-yl)-2-fluoro-N-(methylsulfonyl)benzamide, 128) 6-(5-chloro-3-(4-chloro-2-fluorophenyl)-1H-indazol-1-yl)-N-(methylsulfonyl)nicotinamide,
129) 5-chloro-4-(5-chloro-3-(3-hydroxy-3-methylbut-1-yn-1-yl)-1H-indazol-1-yl)-2-fluoro-N-(methylsulfonyl)benzamide,
130) 5-chloro-4-(5-chloro-3-(1-methyl-6-oxo-1,6-dihydropyridin-3-yl)-1H-indazol-1-yl)-2-fluoro-N-(methylsulfonyl)benzamide,
131) tert-butyl 4-(5-chloro-1-(2-chloro-5-fluoro-4-((methylsulfonyl)carbamoyl)phenyl)-1H-indazol-3-yl)-3,6-dihydropyridine-1(2H)-carboxylate,
132) 5-chloro-4-(5-chloro-3-(1,2,3,6-tetrahydropyridin-4-yl)-1H-indazol-1-yl)-2-fluoro-N-(methylsulfonyl)benzamide,
133) (E)-5-chloro-4-(5-chloro-3-styryl-1H-indazol-1-yl)-2-fluoro-N-(methylsulfonyl)benzamide,
134) (E)-5-chloro-4-(5-chloro-3-(2-(pyridin-2H)vinyl)-1H-indazol-1-yl)-2-fluoro-N-(methylsulfonyl)benzamide,
135) (E)-5-chloro-4-(5-chloro-3-(2-fluorostyryl)-1H-indazol-1-yl)-2-fluoro-N-(methylsulfonyl)benzamide,
136) (E)-5-chloro-4-(5-chloro-3-(2-chlorostyryl)-1H-indazol-1-yl)-2-fluoro-N-(methylsulfonyl)benzamide,
137) (E)-5-chloro-4-(5-chloro-3-(4-(trifluoromethyl)styryl)-1H-indazol-1-yl)-2-fluoro-N-(methylsulfonyl)benzamide,
138) 5-chloro-4-(5-chloro-3-(4-chloro-2-fluorophenyl)-1H-indazol-1-yl)-N—(N,N-dimethylsulfamoyl)-2-fluorobenzamide,
139) 5-chloro-4-(5-chloro-3-(4-chloro-2-fluorophenyl)-1H-indazol-1-yl)-2-fluoro-N-methyl-N-(methylsulfonyl)benzamide,
140) 5-chloro-4-(3-chloro-5-hydroxy-1H-indazol-1-yl)-2-fluoro-N-(methylsulfonyl)-N-(naphthalen-2-ylmethyl)benzamide,
141) 5-chloro-4-(3-chloro-5-hydroxy-1H-indazol-1-yl)-2-fluoro-N-(4-fluorobenzyl)-N-(methylsulfonyl)benzamide,
142) 5-chloro-4-(3-(4-chloro-2-fluorophenyl)-5-fluoro-1H-indazol-1-yl)-2-fluoro-N-(methylsulfonyl)benzamide,
143) 5-chloro-2-fluoro-4-(5-fluoro-3-(2-fluorophenyl)-1H-indazol-1-yl)-N-(methylsulfonyl)benzamide,
144) 5-chloro-4-(3-(2-chlorophenyl)-5-fluoro-1H-indazol-1-yl)-2-fluoro-N-(methylsulfonyl)benzamide,
145) 5-chloro-2-fluoro-4-(5-fluoro-3-(2-(trifluoromethyl)phenyl)-1H-indazol-1-yl)-N-(methylsulfonyl)benzamide,
146) 5-chloro-2-fluoro-4-(5-fluoro-3-(2-methoxyphenyl)-1H-indazol-1-yl)-N-(methylsulfonyl)benzamide,
147) 5-chloro-2-fluoro-4-(5-fluoro-3-(o-tolyl)-1H-indazol-1-yl)-N-(methylsulfonyl)benzamide,
148) 5-chloro-2-fluoro-4-(5-fluoro-3-(3-fluorophenyl)-1H-indazol-1-yl)-N-(methylsulfonyl)benzamide,
149) 5-chloro-4-(3-(3-chlorophenyl)-5-fluoro-1H-indazol-1-yl)-2-fluoro-N-(methylsulfonyl)benzamide,
150) 5-chloro-2-fluoro-4-(5-fluoro-3-(3-(trifluoromethyl)phenyl)-1H-indazol-1-yl)-N-(methylsulfonyl)benzamide,
151) 5-chloro-2-fluoro-4-(5-fluoro-3-(3-methoxyphenyl)-1H-indazol-1-yl)-N-(methylsulfonyl)benzamide,
152) 5-chloro-2-fluoro-4-(5-fluoro-3-(m-tolyl)-1H-indazol-1-yl)-N-(methylsulfonyl)benzamide,
153) 5-chloro-2-fluoro-4-(5-fluoro-3-(4-fluorophenyl)-1H-indazol-1-yl)-N-(methylsulfonyl)benzamide,
154) 5-chloro-4-(3-(4-chlorophenyl)-5-fluoro-1H-indazol-1-yl)-2-fluoro-N-(methylsulfonyl)benzamide,
155) 5-chloro-2-fluoro-4-(5-fluoro-3-(4-methoxyphenyl)-1H-indazol-1-yl)-N-(methylsulfonyl)benzamide,
156) 5-chloro-2-fluoro-4-(5-fluoro-3-(p-tolyl)-1H-indazol-1-yl)-N-(methylsulfonyl)benzamide,
157) 5-chloro-4-(3-(3-chloro-5-fluorophenyl)-5-fluoro-1H-indazol-1-yl)-2-fluoro-N-(methylsulfonyl)benzamide,
158) 5-chloro-4-(3-(2-chloro-4-fluorophenyl)-5-fluoro-1H-indazol-1-yl)-2-fluoro-N-(methylsulfonyl)benzamide,
159) 5-chloro-4-(3-(2,4-difluorophenyl)-5-fluoro-1H-indazol-1-yl)-2-fluoro-N-(methylsulfonyl)benzamide,
160) 5-chloro-4-(3-(2,5-difluorophenyl)-5-fluoro-1H-indazol-1-yl)-2-fluoro-N-(methylsulfonyl)benzamide,
161) 5-chloro-4-(3-(3,4-difluorophenyl)-5-fluoro-1H-indazol-1-yl)-2-fluoro-N-(methylsulfonyl)benzamide,
162) 5-chloro-4-(3-(2-chloro-6-fluorophenyl)-5-fluoro-1H-indazol-1-yl)-2-fluoro-N-(methylsulfonyl)benzamide,
163) 5-chloro-4-(3-(3-chloro-2-fluorophenyl)-5-fluoro-1H-indazol-1-yl)-2-fluoro-N-(methylsulfonyl)benzamide,
164) 5-chloro-4-(3-(4-chloro-3-fluorophenyl)-5-fluoro-1H-indazol-1-yl)-2-fluoro-N-(methylsulfonyl)benzamide,
165) 5-chloro-2-fluoro-4-(5-fluoro-3-(pyridin-3-yl)-1H-indazol-1-yl)-N-(methylsulfonyl)benzamide,
166) 5-chloro-4-(3-(3-cyanophenyl)-5-fluoro-1H-indazol-1-yl)-2-fluoro-N-(methylsulfonyl)benzamide,
167) 3-cyano-4-(5-fluoro-3-(pyridin-3-yl)-1H-indazol-1-yl)-N-(methylsulfonyl)benzamide,
168) 3-cyano-4-(3-(3-cyanophenyl)-5-fluoro-1H-indazol-1-yl)-N-(methylsulfonyl)benzamide,
169) 5-chloro-4-(3-(4-chloro-2-fluorophenyl)-5-methoxy-1H-indazol-1-yl)-2-fluoro-N-(methylsulfonyl)benzamide,
170) 5-chloro-4-(3-(3-chlorophenyl)-1H-indazol-1-yl)-2-fluoro-N-(methylsulfonyl)benzamide,
171) 5-chloro-2-fluoro-4-(3-(3-fluorophenyl)-1H-indazol-1-yl)-N-(methylsulfonyl)benzamide,
172) 5-chloro-2-fluoro-N-(methylsulfonyl)-4-(3-(3-(trifluoromethyl)phenyl)-1H-indazol-1-yl)benzamide,
173) 5-chloro-2-fluoro-N-(methylsulfonyl)-4-(3-(o-tolyl)-1H-indazol-1-yl)benzamide,
174) 5-chloro-2-fluoro-4-(3-(2-methoxyphenyl)-1H-indazol-1-yl)-N-(methylsulfonyl)benzamide,
175) 5-chloro-4-(3-(2-chloro-4-fluorophenyl)-1H-indazol-1-yl)-2-fluoro-N-(methylsulfonyl)benzamide,
176) 5-chloro-4-(3-(2,4-difluorophenyl)-1H-indazol-1-yl)-2-fluoro-N-(methylsulfonyl)benzamide,
177) 5-chloro-2-fluoro-4-(3-(4-fluoropyridin-3-yl)-1H-indazol-1-yl)-N-(methylsulfonyl)benzamide,
178) 5-chloro-2-fluoro-N-(methylsulfonyl)-4-(3-(4-(trifluoromethyl)phenyl)-1H-indazol-1-yl)benzamide,
179) 5-chloro-2-fluoro-4-(3-(4-fluorophenyl)-1H-indazol-1-yl)-N-(methylsulfonyl)benzamide,
180) 5-chloro-2-fluoro-N-(methylsulfonyl)-4-(3-(pyridin-3-yl)-1H-indazol-1-yl)benzamide,
181) 5-chloro-4-(3-(3-cyanophenyl)-1H-indazol-1-yl)-2-fluoro-N-(methylsulfonyl)benzamide,
182) 3-cyano-N-(methylsulfonyl)-4-(3-(pyridin-3-yl)-1H-indazol-1-yl)benzamide,
183) 3-cyano-4-(3-(3-cyanophenyl)-1H-indazol-1-yl)-N-(methylsulfonyl)benzamide,
184) 5-chloro-4-(3-(4-chloro-2-fluorophenyl)-1H-indazol-1-yl)-2-fluoro-N-(methylsulfonyl)benzamide, 185) 5-chloro-4-(5-chloro-3-(4-fluorophenyl)-1H-pyrrolo[2,3-b]pyridin-1-yl)-2-fluoro-N-(methylsulfonyl)benzamide,
186) 5-chloro-4-(5-chloro-3-(2,4-difluorophenyl)-1H-pyrrolo[2,3-b]pyridin-1-yl)-2-fluoro-N-(methylsulfonyl)benzamide,
187) 5-chloro-4-(5-chloro-3-(4-cyanophenyl)-1H-pyrrolo[2,3-b]pyridin-1-yl)-2-fluoro-N-(methylsulfonyl)benzamide,
188) 5-chloro-4-(5-chloro-3-(4-(trifluoromethyl)phenyl)-1H-pyrrolo[2,3-b]pyridin-1-yl)-2-fluoro-N-(methylsulfonyl)benzamide,
189) 5-chloro-4-(5-chloro-3-(4-chloro-2-fluorophenyl)-1H-pyrrolo[2,3-b]pyridin-1-yl)-2-fluoro-N-(methylsulfonyl)benzamide,
190) 5-chloro-4-(5-chloro-3-(3-fluorophenyl)-1H-pyrrolo[2,3-b]pyridin-1-yl)-2-fluoro-N-(methylsulfonyl)benzamide,
191) 5-chloro-4-(5-chloro-3-(2-fluorophenyl)-1H-pyrrolo[2,3-b]pyridin-1-yl)-2-fluoro-N-(methylsulfonyl)benzamide,
192) 5-chloro-4-(5-chloro-3-(3-(trifluoromethyl)phenyl)-1H-pyrrolo[2,3-b]pyridin-1-yl)-2-fluoro-N-(methylsulfonyl)benzamide,
193) 5-chloro-4-(5-chloro-3-(2-(trifluoromethyl)phenyl)-1H-pyrrolo[2,3-b]pyridin-1-yl)-2-fluoro-N-(methylsulfonyl)benzamide,
194) 5-chloro-4-(5-chloro-3-(3-cyanophenyl)-1H-pyrrolo[2,3-b]pyridin-1-yl)-2-fluoro-N-(methylsulfonyl)benzamide,
195) 5-chloro-4-(5-chloro-3-(4-chlorophenyl)-1H-pyrrolo[2,3-b]pyridin-1-yl)-2-fluoro-N-(methylsulfonyl)benzamide,
196) 5-chloro-4-(5-chloro-3-(4-methoxyphenyl)-1H-pyrrolo[2,3-b]pyridin-1-yl)-2-fluoro-N-(methylsulfonyl)benzamide,
197) 5-chloro-4-(5-chloro-3-(2-chloro-4-fluorophenyl)-1H-pyrrolo[2,3-b]pyridin-1-yl)-2-fluoro-N-(methylsulfonyl)benzamide,
198) 5-chloro-4-(5-chloro-3-(2-chlorophenyl)-1H-pyrrolo[2,3-b]pyridin-1-yl)-2-fluoro-N-(methylsulfonyl)benzamide,
199) 5-chloro-4-(5-chloro-3-(4-fluoro-2-methoxyphenyl)-1H-pyrrolo[2,3-b]pyridin-1-yl)-2-fluoro-N-(methylsulfonyl)benzamide,
200) 5-chloro-4-(5-chloro-3-(4-fluoro-2-methylphenyl)-1H-pyrrolo[2,3-b]pyridin-1-yl)-2-fluoro-N-(methylsulfonyl)benzamide,
201) 5-chloro-4-(3-(4-chloro-2-fluorophenyl)-5-fluoro-1H-pyrrolo[2,3-b]pyridin-1-yl)-2-fluoro-N-(methylsulfonyl)benzamide,
202) 5-chloro-4-(3-(2-chloro-4-fluorophenyl)-5-fluoro-1H-pyrrolo[2,3-b]pyridin-1-yl)-2-fluoro-N-(methylsulfonyl)benzamide,
203) 5-chloro-4-(3-(2,4-difluorophenyl)-5-fluoro-1H-pyrrolo[2,3-b]pyridin-1-yl)-2-fluoro-N-(methylsulfonyl)benzamide,
204) 5-chloro-4-(3-(4-chlorophenyl)-5-fluoro-1H-pyrrolo[2,3-b]pyridin-1-yl)-2-fluoro-N-(methylsulfonyl)benzamide,
205) 5-chloro-2-fluoro-4-(5-fluoro-3-(4-(trifluoromethyl)phenyl)-1H-pyrrolo[2,3-b]pyridin-1-yl)-N-(methylsulfonyl)benzamide,
206) 5-chloro-2-fluoro-4-(5-fluoro-3-(4-fluorophenyl)-1H-pyrrolo[2,3-b]pyridin-1-yl)-N-(methylsulfonyl)benzamide,
207) 5-chloro-4-(3-(2-chlorophenyl)-5-fluoro-1H-pyrrolo[2,3-b]pyridin-1-yl)-2-fluoro-N-(methylsulfonyl)benzamide,
208) 5-chloro-4-(3-(3-chlorophenyl)-5-fluoro-1H-pyrrolo[2,3-b]pyridin-1-yl)-2-fluoro-N-(methylsulfonyl)benzamide,
209) 5-chloro-4-(3-(2,4-dichlorophenyl)-5-fluoro-1H-pyrrolo[2,3-b]pyridin-1-yl)-2-fluoro-N-(methylsulfonyl)benzamide,
210) 5-chloro-4-(3-(4-chloro-3-fluorophenyl)-5-fluoro-1H-pyrrolo[2,3-b]pyridin-1-yl)-2-fluoro-N-(methylsulfonyl)benzamide,
211) 5-chloro-4-(3-(3-chloro-2-fluorophenyl)-5-fluoro-1H-pyrrolo[2,3-b]pyridin-1-yl)-2-fluoro-N-(methylsulfonyl)benzamide,
212) 5-chloro-2-fluoro-4-(5-fluoro-3-(4-fluoro-2-methylphenyl)-1H-pyrrolo[2,3-b]pyridin-1-yl)-N-(methylsulfonyl)benzamide,
213) 5-chloro-2-fluoro-4-(3-(2-fluorophenyl)-1H-pyrrolo[2,3-b]pyridin-1-A-N-(methylsulfonyl)benzamide,
214) 5-chloro-2-fluoro-4-(3-(3-fluorophenyl)-1H-pyrrolo[2,3-b]pyridin-1-A-N-(methylsulfonyl)benzamide,
215) 5-chloro-2-fluoro-N-(methylsulfonyl)-4-(3-(m-tolyl)-1H-pyrrolo[2,3-b]pyridin-1-yl)benzamide,
216) 5-chloro-2-fluoro-N-(methylsulfonyl)-4-(3-(2-(trifluoromethyl)phenyl)-1H-pyrrolo[2,3-b]pyridin-1-yl)benzamide,
217) 5-chloro-2-fluoro-N-(methylsulfonyl)-4-(3-(3-(trifluoromethyl)phenyl)-1H-pyrrolo[2,3-b]pyridin-1-yl)benzamide,
218) 5-chloro-2-fluoro-N-(methylsulfonyl)-4-(3-(4-(trifluoromethyl)phenyl)-1H-pyrrolo[2,3-b]pyridin-1-yl)benzamide,
219) 5-chloro-4-(3-(5-chloro-2-fluorophenyl)-1H-pyrrolo[2,3-b]pyridin-1-yl)-2-fluoro-N-(methylsulfonyl)benzamide,
220) 5-chloro-4-(3-(3-chloro-5-fluorophenyl)-1H-pyrrolo[2,3-b]pyridin-1-yl)-2-fluoro-N-(methylsulfonyl)benzamide,
221) 5-chloro-4-(3-(3-chlorophenyl)-1H-pyrrolo[2,3-b]pyridin-1-yl)-2-fluoro-N-(methylsulfonyl)benzamide,
222) 5-chloro-4-(3-(3-chloro-2-fluorophenyl)-1H-pyrrolo[2,3-b]pyridin-1-yl)-2-fluoro-N-(methylsulfonyl)benzamide,
223) 5-chloro-4-(3-(4-chloro-3-fluorophenyl)-1H-pyrrolo[2,3-b]pyridin-1-yl)-2-fluoro-N-(methylsulfonyl)benzamide,
224) 5-chloro-4-(3-(4-chlorophenyl)-1H-pyrrolo[2,3-b]pyridin-1-yl)-2-fluoro-N-(methylsulfonyl)benzamide,
225) 5-chloro-4-(3-(2-chlorophenyl)-1H-pyrrolo[2,3-b]pyridin-1-yl)-2-fluoro-N-(methylsulfonyl)benzamide,
226) 5-chloro-2-fluoro-4-(3-(4-fluorophenyl)-1H-pyrrolo[2,3-b]pyridin-1-yl)-N-(methylsulfonyl)benzamide,
227) 5-chloro-4-(3-(4-chloro-2-fluorophenyl)-1H-pyrrolo[2,3-b]pyridin-1-yl)-2-fluoro-N-(methylsulfonyl)benzamide,
228) 5-chloro-4-(3-(2-chloro-4-fluorophenyl)-1H-pyrrolo[2,3-b]pyridin-1-yl)-2-fluoro-N-(methylsulfonyl)benzamide,
229) 5-chloro-4-(3-(2,4-difluorophenyl)-1H-pyrrolo[2,3-b]pyridin-1-yl)-2-fluoro-N-(methylsulfonyl)benzamide,
230) 5-chloro-4-(3-chloro-5-phenyl-1H-indazol-1-yl)-2-fluoro-N-(methylsulfonyl)benzamide,
231) 5-chloro-4-(3-chloro-5-(pyridin-3-yl)-1H-indazol-1-yl)-2-fluoro-N-(methylsulfonyl)benzamide, 232) 5-chloro-4-(3-chloro-5-(pyridin-4-yl)-1H-indazol-1-yl)-2-fluoro-N-(methylsulfonyl)benzamide,
233) 5-chloro-4-(3-chloro-5-(m-tolyl)-1H-indazol-1-yl)-2-fluoro-N-(methylsulfonyl)benzamide,
234) 5-chloro-4-(3-chloro-5-(2-fluorophenyl)-1H-indazol-1-yl)-2-fluoro-N-(methylsulfonyl)benzamide,
235) 5-chloro-4-(3-chloro-5-(3-fluorophenyl)-1H-indazol-1-yl)-2-fluoro-N-(methylsulfonyl)benzamide,
236) 5-chloro-4-(3-chloro-5-(4-fluorophenyl)-1H-indazol-1-yl)-2-fluoro-N-(methylsulfonyl)benzamide,
237) 5-chloro-4-(3-chloro-5-(2-cyanophenyl)-1H-indazol-1-yl)-2-fluoro-N-(methylsulfonyl)benzamide,
238) 5-chloro-4-(3-chloro-5-(5-cyano-2-fluorophenyl)-1H-indazol-1-yl)-2-fluoro-N-(methylsulfonyl)benzamide,
239) 5-chloro-4-(3-chloro-5-(3-cyano-4-fluorophenyl)-1H-indazol-1-yl)-2-fluoro-N-(methylsulfonyl)benzamide,
240) 5-chloro-4-(3-chloro-5-(4-cyanophenyl)-1H-indazol-1-yl)-2-fluoro-N-(methylsulfonyl)benzamide,
241) 5-chloro-4-(3-chloro-5-(pyrimidin-5-yl)-1H-indazol-1-yl)-2-fluoro-N-(methylsulfonyl)benzamide,
242) 5-chloro-4-(3-chloro-5-(5-chloropyridin-3-yl)-1H-indazol-1-yl)-2-fluoro-N-(methylsulfonyl)benzamide,
243) 5-chloro-4-(3-chloro-5-(2,4-difluorophenyl)-1H-indazol-1-yl)-2-fluoro-N-(methylsulfonyl)benzamide,
244) 5-chloro-4-(3-chloro-5-(2-fluoropyridin-3-yl)-1H-indazol-1-yl)-2-fluoro-N-(methylsulfonyl)benzamide,
245) 5-chloro-4-(3-chloro-5-(6-fluoropyridin-3-yl)-1H-indazol-1-yl)-2-fluoro-N-(methylsulfonyl)benzamide,
246) 5-chloro-4-(3-chloro-5-(2,6-difluoropyridin-3-yl)-1H-indazol-1-yl)-2-fluoro-N-(methylsulfonyl)benzamide,
247) 5-chloro-4-(3-chloro-5-(4-chloro-2-fluorophenyl)-1H-indazol-1-yl)-2-fluoro-N-(methylsulfonyl)benzamide,
248) 5-chloro-4-(3-chloro-5-(4-methoxyphenyl)-1H-indazol-1-yl)-2-fluoro-N-(methylsulfonyl)benzamide,
249) 5-chloro-4-(3-chloro-5-(3-(trifluoromethyl)phenyl)-1H-indazol-1-yl)-2-fluoro-N-(methylsulfonyl)benzamide,
250) 5-chloro-4-(3-chloro-5-(2-(trifluoromethyl)phenyl)-1H-indazol-1-yl)-2-fluoro-N-(methylsulfonyl)benzamide,
251) 5-chloro-4-(3-chloro-5-(4-(trifluoromethyl)phenyl)-1H-indazol-1-yl)-2-fluoro-N-(methylsulfonyl)benzamide,
252) 5-chloro-4-(3-chloro-5-(2-chlorophenyl)-1H-indazol-1-yl)-2-fluoro-N-(methylsulfonyl)benzamide,
253) 5-chloro-4-(3-chloro-5-(4-chloro-2-methylphenyl)-1H-indazol-1-yl)-2-fluoro-N-(methylsulfonyl)benzamide,
254) 5-chloro-4-(3-chloro-5-(5-chloro-2-fluorophenyl)-1H-indazol-1-yl)-2-fluoro-N-(methylsulfonyl)benzamide,
255) 5-chloro-4-(3-chloro-5-(4-chlorophenyl)-1H-indazol-1-yl)-2-fluoro-N-(methylsulfonyl)benzamide,
256) 5-chloro-4-(3-chloro-5-(1-methyl-1H-pyrazol-5-yl)-1H-indazol-1-yl)-2-fluoro-N-(methylsulfonyl)benzamide,
257) 5-chloro-4-(3-chloro-5-(4-fluorophenyl)-1H-pyrrolo[2,3-b]pyridin-1-yl)-2-fluoro-N-(methylsulfonyl)benzamide,
258) 5-chloro-4-(3-chloro-5-(4-cyanophenyl)-1H-pyrrolo[2,3-b]pyridin-1-yl)-2-fluoro-N-(methylsulfonyl)benzamide,
259) 5-chloro-4-(3-chloro-5-(4-chlorophenyl)-1H-pyrrolo[2,3-b]pyridin-1-yl)-2-fluoro-N-(methylsulfonyl)benzamide,
260) 5-chloro-4-(3-chloro-5-(4-methoxyphenyl)-1H-pyrrolo[2,3-b]pyridin-1-yl)-2-fluoro-N-(methylsulfonyl)benzamide,
261) 5-chloro-4-(3-chloro-5-(4-(trifluoromethyl)phenyl)-1H-pyrrolo[2,3-b]pyridin-1-yl)-2-fluoro-N-(methylsulfonyl)benzamide,
262) 5-chloro-4-(3-chloro-5-(3-fluorophenyl)-1H-pyrrolo[2,3-b]pyridin-1-yl)-2-fluoro-N-(methylsulfonyl)benzamide,
263) 5-chloro-4-(3-chloro-6-phenyl-1H-indazol-1-yl)-2-fluoro-N-(methylsulfonyl)benzamide,
264) 5-chloro-4-(3,5-diphenyl-1H-indazol-1-yl)-2-fluoro-N-(methylsulfonyl)benzamide,
265) 5-chloro-1-(2-chloro-5-fluoro-4-((methylsulfonyl)carbamoyl)phenyl)-1H-indole-3-carboxylic acid,
266) 5-chloro-4-(3,5-dichloro-1H-indol-1-yl)-2-fluoro-N-(methylsulfonyl)benzamide,
267) 5-chloro-4-(3,4-dichloro-5-hydroxy-1H-indol-1-yl)-2-fluoro-N-(methylsulfonyl)benzamide,
268) 5-chloro-4-(3-chloro-5-methoxy-1H-indol-1-yl)-2-fluoro-N-(methylsulfonyl)benzamide,
269) 4-(5-(benzyloxy)-3-chloro-1H-indol-1-yl)-5-chloro-2-fluoro-N-(methylsulfonyl)benzamide,
270) 4-(4-(benzyloxy)-3-chloro-1H-indol-1-yl)-5-chloro-2-fluoro-N-(methylsulfonyl)benzamide,
271) 4-(6-(benzyloxy)-3-chloro-1H-indol-1-yl)-5-chloro-2-fluoro-N-(methylsulfonyl)benzamide,
272) 5-chloro-4-(5-chloro-3-(4-chlorophenyl)-1H-indol-1-yl)-2-fluoro-N-(methylsulfonyl)benzamide,
273) 5-chloro-4-(5-chloro-3-(6-chloropyridin-3-yl)-1H-indol-1-yl)-2-fluoro-N-(methylsulfonyl)benzamide,
274) 6-(5-chloro-3-(4-chlorophenyl)-1H-indol-1-yl)-N-(methylsulfonyl)nicotinamide,
275) 6-(5-chloro-3-(4-fluorophenyl)-1H-indol-1-yl)-N-(methylsulfonyl)nicotinamide,
276) 5-chloro-4-(3-chloro-5-phenyl-1H-indazol-1-yl)-2-fluoro-N-(thiazol-4-yl)benzenesulfonamide,
277) 5-chloro-4-(5-chloro-3-methyl-1H-indazol-1-yl)-2-fluoro-N-(thiazol-4-yl)benzenesulfonamide,
278) 4-(3-chloro-5-(trifluoromethyl)-1H-indazol-1-yl)-3-cyano-N-(thiazol-4-yl)benzenesulfonamide,
279) 4-(3-chloro-5-(trifluoromethyl)-1H-indazol-1-yl)-2,5-difluoro-N-(thiazol-4-yl)benzenesulfonamide,
280) 5-chloro-4-(3-chloro-5-(trifluoromethyl)-1H-indazol-1-yl)-2-fluoro-N-(thiazol-4-yl)benzenesulfonamide,
281) 4-(3-chloro-5-(trifluoromethyl)-1H-indazol-1-yl)-2,5-difluoro-N-(1,2,4-thiadiazol-5-yl)benzenesulfonamide,
282) 5-chloro-4-(5-chloro-3-(1-methyl-1H-pyrazol-5-yl)-1H-indazol-1-yl)-2-fluoro-N-(thiazol-4-yl)benzenesulfonamide,
283) 5-chloro-4-(5-chloro-3-(1-methyl-1H-pyrazol-5-yl)-1H-indazol-1-yl)-2-fluoro-N-(1,2,4-thiadiazol-5-yl)benzenesulfonamide,
284) 5-chloro-4-(5-chloro-3-(1H-pyrazol-4-yl)-1H-indazol-1-yl)-2-fluoro-N-(thiazol-4-yl)benzenesulfonamide,
285) 5-chloro-2-fluoro-4-(5-(1-methyl-1H-pyrazol-5-yl)-1H-indazol-1-yl)-N-(thiazol-4-yl)benzenesulfonamide,
286) 5-chloro-4-(3-chloro-5-(1-methyl-1H-pyrazol-5-yl)-1H-indazol-1-yl)-2-fluoro-N-(thiazol-4-yl)benzenesulfonamide, 287) 5-chloro-4-(5-chloro-3-(4-chloro-2-fluorophenyl)-1H-indazol-1-yl)-2-fluoro-N-(thiazol-4-yl)benzenesulfonamide,
288) 5-chloro-3-(4-chloro-2-fluorophenyl)-1-(2-chloro-5-fluoro-4-(1H-tetrazol-5-yl)phenyl)-1H-indazole,
289) 2-(5-chloro-4-(5-chloro-3-(4-chloro-2-fluorophenyl)-1H-indazol-1-yl)-2-fluorobenzoyl)hydrazine-1-carboxamide,
290) 5-(5-chloro-4-(5-chloro-3-(4-chloro-2-fluorophenyl)-1H-indazol-1-yl)-2-fluorophenyl)-2,4-dihydro-3H-1,2,4-triazol-3-one,
291) 5-chloro-4-(5-chloro-3-(4-chloro-2-fluorophenyl)-1H-indazol-1-yl)-2-fluorobenzamide,
292) N-acetyl-5-chloro-4-(5-chloro-3-(4-chloro-2-fluorophenyl)-1H-indazol-1-yl)-2-fluorobenzamide,
293) 5-chloro-4-(5-chloro-3-(4-chloro-2-fluorophenyl)-1H-indazol-1-yl)-2-fluoro-N-(thiazol-2-yl)benzamide,
294) 5-chloro-4-(5-chloro-3-(4-chloro-2-fluorophenyl)-1H-indazol-1-yl)-2-fluoro-N-(5-methylthiazol-2-yl)benzamide, and
295) ethyl 2-(5-chloro-4-(5-chloro-3-(4-chloro-2-fluorophenyl)-1H-indazol-1-yl)-2-fluorobenzamido)thiazole-5-carboxylate.

19. A pharmaceutical composition for treating sodium channel blocker-related diseases, comprising the compound according to claim 1 or a pharmaceutically acceptable salt thereof as an active ingredient.

20. The pharmaceutical composition according to claim 19, wherein the sodium channel blocker-related diseases is selected from the group consisting of acute pain, chronic pain, neuropathic pain, postoperative pain, migraine, arthralgia, neuropathy, nerve injury, diabetic neuropathy, neuropathic disease, epilepsy, arrhythmia, myotonia, ataxia, multiple sclerosis, irritable bowel syndrome, urinary incontinence, visceral pain, depression, erythromelalgia, and paroxysmal extreme pain disorder (PEPD).

* * * * *